(12) United States Patent
Argade et al.

(10) Patent No.: US 7,700,628 B2
(45) Date of Patent: Apr. 20, 2010

(54) AROMATIC ETHER DERIVATIVES USEFUL AS THROMBIN INHIBITORS

(75) Inventors: Ankush Baburao Argade, South San Francisco, CA (US); Theodore Goodson, Jr., Indianapolis, IN (US); David Kent Herron, Indianapolis, IN (US); Sajan Joseph, Indianapolis, IN (US); Salvatore Donato Lepore, Del Ray Beach, FL (US); Angela Lynn Marquart, Greenwood, IN (US); John Joseph Masters, Fishers, IN (US); David Mendel, Indianapolis, IN (US); Leander Merritt, Indianapolis, IN (US); Andrew Michael Ratz, Zionsville, IN (US); Gerald Floyd Smith, Greenwood, IN (US); Anne Louise Tebbe, Spartanburg, SC (US); Michael Robert Wiley, Zionsville, IN (US); Ying Kwong Yee, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 397 days.

(21) Appl. No.: 11/719,415

(22) PCT Filed: Nov. 10, 2005

(86) PCT No.: PCT/US2005/041161
§ 371 (c)(1),
(2), (4) Date: May 16, 2007

(87) PCT Pub. No.: WO2006/057845
PCT Pub. Date: Jun. 1, 2006

(65) Prior Publication Data
US 2009/0227566 A1 Sep. 10, 2009

Related U.S. Application Data

(60) Provisional application No. 60/630,984, filed on Nov. 24, 2004.

(51) Int. Cl.
| | |
|---|---|
| C07D 413/10 | (2006.01) |
| C07D 413/14 | (2006.01) |
| C07D 401/10 | (2006.01) |
| C07D 401/02 | (2006.01) |
| C07D 401/14 | (2006.01) |
| C07D 401/12 | (2006.01) |
| C07D 409/10 | (2006.01) |
| C07D 243/08 | (2006.01) |
| C07D 213/75 | (2006.01) |
| A61K 31/381 | (2006.01) |
| A61K 31/4402 | (2006.01) |
| A61K 31/4436 | (2006.01) |
| A61K 31/4439 | (2006.01) |
| A61K 31/444 | (2006.01) |
| A61K 31/4545 | (2006.01) |
| A61K 31/5377 | (2006.01) |
| A61K 31/551 | (2006.01) |

(52) U.S. Cl. ............... 514/327; 514/235.5; 514/316; 514/253.12; 514/343; 514/352; 514/218; 514/336; 514/217.04; 544/130; 544/131; 544/364; 546/194; 546/187; 546/276.4; 546/309; 546/281.4; 540/597

(58) Field of Classification Search ............... 544/129, 544/124, 360, 364, 130, 131; 546/268.1, 546/309, 194, 187, 276.04, 281.4; 514/327, 514/235.5, 316, 253.12, 343, 352, 218, 33, 514/217.04; 540/597
See application file for complete search history.

(56) References Cited

U.S. PATENT DOCUMENTS 6,140,351 A 10/2000 Arnaiz et al.

(Continued)

FOREIGN PATENT DOCUMENTS

AU 2001-29827 10/2001

(Continued)

OTHER PUBLICATIONS

Kaiser, B. Drugs of the Future 1998, 23, 423-436.*

(Continued)

*Primary Examiner*—Rebecca L Anderson
*Assistant Examiner*—Matthew P Coughlin
(74) *Attorney, Agent, or Firm*—R. Craig Tucker

(57) ABSTRACT

This application relates to a compound of formula (I) (or a pharmaceutically acceptable salt of the compound or prodrug thereof) as defined herein, pharmaceutical compositions thereof, and its use as an inhibitor of factor Xa and/or thrombin, as well as a process for its preparation and intermediates therefor. An example of a compound of formula (I) is (a).

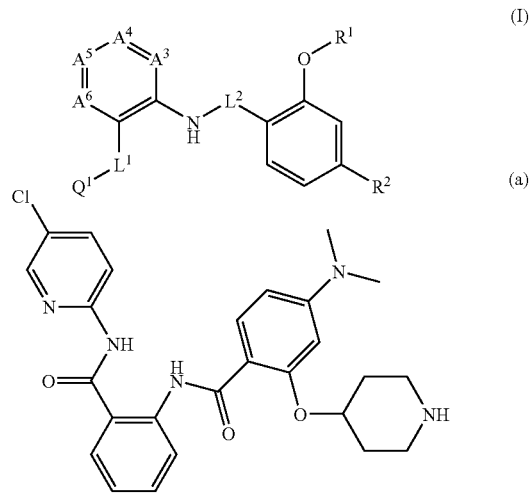

21 Claims, No Drawings

U.S. PATENT DOCUMENTS

| | | |
|---|---|---|
| 6,313,122 B1 | 11/2001 | Beight et al. |
| 6,313,151 B1 | 11/2001 | Beight et al. |
| 6,372,759 B1 | 4/2002 | Beight et al. |
| 6,376,515 B2 | 4/2002 | Zhu et al. |
| 6,417,200 B1 | 7/2002 | Beight et al. |
| 6,610,704 B1 | 8/2003 | Beight et al. |
| 6,635,657 B1 | 10/2003 | Beight et al. |
| 6,689,780 B1 | 2/2004 | Beight et al. |
| 6,844,367 B1 | 1/2005 | Zhu et al. |
| 7,160,878 B2 | 1/2007 | Herron et al. |
| 7,163,938 B2 | 1/2007 | Herron et al. |
| 2004/0242581 A1 | 12/2004 | Herron et al. |
| 2007/0027185 A1 | 2/2007 | Franciskovich et al. |

FOREIGN PATENT DOCUMENTS

| | | |
|---|---|---|
| EP | 1 273 575 | 1/2003 |
| JP | 2000-302765 | 10/2000 |
| WO | WO 2004/108677 | 12/2004 |
| WO | WO 2006/057868 | 6/2006 |

OTHER PUBLICATIONS

Hauptmann et al. Thrombosis Research 1999, 93, 203-241.*

Zhu, et al. : "Factor Xa Inhibitors: Recent Advances in Anticoagulant Agents" Annual Reports in Medicinal Chemistry, (2000), 35, 83-102.

* cited by examiner

AROMATIC ETHER DERIVATIVES USEFUL AS THROMBIN INHIBITORS

CROSS-REFERENCE TO RELATED APPLICATIONS

This application is a U.S. national stage entry of international application serial No. PCT/US2005/041161 filed Nov. 10, 2005, which claims priority to U.S. Provisional Application No. 60/630,984, filed Nov. 24, 2004.

This invention relates to aromatic ethers which demonstrate activity as inhibitors of thrombin and/or factor Xa and, accordingly, which are useful antithrombotics in mammals. In particular it relates to aromatic ethers having high anticoagulant activity, good oral exposure and antithrombotic activity. Thus, this invention relates to new aromatic ethers which are inhibitors of thrombin and/or factor Xa, pharmaceutical compositions containing the aromatic ethers as active ingredients, and the use of the aromatic ethers as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process. In addition, the aromatic ethers are useful as anticoagulants in vitro applications.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation. The formation of thrombin from prothrombin is catalyzed by factor Xa.

Anticoagulation currently is achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because clot-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6-24 hours after administration. Further, they are not selective anticoagulants. Coumarins also require monitoring with coagulation assays (particularly the prothrombin time (PT) assay).

Recently, interest has grown in small synthetic molecules which demonstrate potent direct inhibition of thrombin and factor Xa. See, for example, B. Y. Zhu and R. M. Scarborough, *Annual Reports in Medicinal Chemistry*, (2000), 35, 83-102, Factor Xa Inhibitors: Recent Advances in Anticoagulant Agents.

Although the heparins and coumarins are effective anticoagulants, there still exists a need for anticoagulants which act selectively on factor Xa and/or thrombin, and which, independent of antithrombin III, exert inhibitory action shortly after administration, preferably by an oral route, and do not interfere with lysis of blood clots, as required to maintain hemostasis.

The present invention is directed to the discovery that the aromatic ethers of the present invention, as defined below, are potent inhibitors of thrombin and/or factor Xa which may have high bioavailability following oral administration.

According to the invention there is provided a compound of formula I,

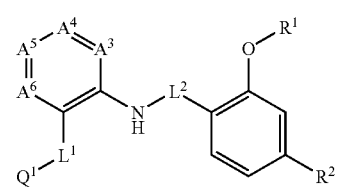

or a pharmaceutically acceptable salt thereof, wherein:

$A^3$, $A^4$, $A^5$ and $A^6$, together with the two carbons to which they are attached, complete a substituted benzene in which $A^3$ is $CR^3$, $A^4$ is $CR^4$, $A^5$ is $CR^5$, and $A^6$ is $CR^6$; wherein $R^3$ is hydrogen, methyl, fluoro, chloro or carboxy;

one of $R^4$ and $R^5$ is hydrogen, (1-4C)alkyl, halo, cyano, trifluoromethyl, trifluoro-methoxy, $R^fO$—, $R^fO_2CCH_2O$—, $HO(CH_2)_aO$— (in which a is 2, 3 or 4), $R^fO_2C$—, $R^fO_2CCH_2$—, nitro or $R^gNH$—;

the other of $R^4$ and $R^5$ is hydrogen; and $R^6$ is hydrogen, methyl, fluoro, chloro or methoxy;

in which $R^f$ is hydrogen, (1-4C)alkyl or benzyl; $R^g$ is hydrogen or $R^hSO_2$—; and $R^h$ is (1-4C)alkyl or dimethylamino;

$L^1$ is —CO—NH— or —SO$_2$—NH— such that -$L^1$-$Q^1$ is —CO—NH-$Q^1$ or —SO$_2$—NH-$Q^1$;

$Q^1$ is $Q^{1A}$, $Q^{1B}$, or $Q^{1C}$ wherein $Q^{1A}$ is phenyl (in which the phenyl may bear one, two or three substituents at the 3-, 4- or 5-position(s) independently selected from halo, trifluoromethyl, cyano, carbamoyl, aminomethyl, methyl, methoxy, difluoromethoxy, hydroxymethyl, methylthio, formyl, acetyl, vinyl, nitro, amino, hydroxy and 3,4-methylenedioxy; and in addition the phenyl may bear a chloro, fluoro, methyl, methoxy, or nitro substituent at the 2- and/or 6-position), $Q^{1B}$ is 5-membered ring heteroaryl (which 5-membered ring heteroaryl is a 5-membered aromatic ring which includes one to three heteroatoms selected from sulfur, oxygen and nitrogen and which is attached to $L^1$ at a carbon atom and further which may bear one or more methyl substituents on carbon or nitrogen and may bear one or more halo substituents on carbon which is not bonded to a ring nitrogen), and $Q^{1C}$ is 6-membered ring heteroaryl (which 6-membered ring heteroaryl is a 6-membered aromatic ring which includes one or two nitrogens and further which may bear one or more amino, nitro, methoxy, methylthio, trifluoromethyl or methyl substituents and may bear one or more halo substituents on carbon which is not bonded to a ring nitrogen); or -$L^1$-$Q^1$ is piperazinocarbonyl (in which the piperazino may bear a 4-methyl substituent);

$L^2$ is carbonyl or methylene;

$R^1$ is —(CH$_2$)$_i$-Q-(CH$_2$)$_j$—NR$^a$R$^b$ wherein:

a) Q is a single bond; the sum of i and j is 2, 3 or 4;

b) Q is oxy; i is 2; and j is 2;

c) Q is —CH(CH$_3$)—, —C(CH$_3$)$_2$—, or —CH(OH)—; i is 1; and j is 1;

d) Q is cyclohexane-1,4-diyl; i is 0; and j is 0;
e) Q is —CH{(CH$_2$)$_2$—SCH$_3$}—; i is 1; and j is 0;
f) Q is —CHR$^c$; i is 0 or 1; j is 1; and R$^b$ and R$^c$ together are —(CH$_2$)$_k$— wherein k is 2 or 3;
g) Q is —CHR$^c$; i is 1 or 2; j is 0; and R$^b$ and R$^c$ together are —(CH$_2$)$_4$—;
h) Q is —CHR$^c$; i is 0; j is 2; and R$^b$ and R$^c$ together are —(CH$_2$)$_2$— or —C(CH$_3$)$_2$—CH$_2$— (wherein the CH$_2$ carbon is bonded to the nitrogen); or
i) Q is —CHR$^c$; i is 1; j is 2; and R$^b$ and R$^c$ together are —(CH$_2$)$_2$—;

wherein, unless defined above,

R$^a$ is hydrogen or R$^d$; and R$^b$ is hydrogen or (1-3C) normal alkyl;

or NR$^a$R$^b$ is a cyclic amino group selected from azetidin-1-yl, pyrrolidin-1-yl, 3,4-didehydropyrrolidin-1-yl, thiazolidin-3-yl, piperidin-1-yl, 3,4-didehydropiperidin-1-yl, morpholin-4-yl, thiomorpholin-4-yl, piperazin-1-yl, hexahydroazepin-1-yl, hexahydro-1,4-diazepin-1-yl and octahydroazocin-1-yl (which cyclic group may bear one or more {for example, one to three} methyl substituents on carbon, or may bear a carbamoyl, hydroxymethyl, methoxymethyl, 2-hydroxyethyl, pyrrolidin-1-ylmethyl or 2-(pyrrolidin-1-yl)ethyl substituent on carbon, or may bear a hydroxy, amino, methylamino, dimethylamino, pyrrolidin-1-yl, piperidin-1-yl, {(1-2C)acyl}amino, or {(1-4C)alkoxy}carbonylamino substituent on a carbon which is not attached to a ring nitrogen, oxygen or sulfur nor double bonded to another carbon, or may bear a (1-3C)alkyl, cyclopentyl, pyrrolidin-1-ylcarbonylmethyl, 2-hydroxyethyl, acetyl, furanylcarbonyl, phenyl {which phenyl may bear a chloro, methyl or methoxy substituent}, pyridinyl, pyrimidinyl or pyrazinyl substituent on a ring nitrogen at the 4-position); or NR$^a$R$^b$ is 1,3,3-trimethyl-6-azabicyclo[3.2.1]octan-6-yl or N(CH$_2$R$^w$)$_2$;

R$^d$ is (1-7C)alkyl (which alkyl may bear one or more {for example, one or two} substituents R$^e$ on a carbon which is not otherwise directly bonded to a nitrogen or oxygen wherein each R$^e$ is independently hydroxy, (1-3C)alkoxy, (1-3C)alkylthio, amino {which amino may bear an acetyl or one or two (1-3C)alkyl groups which may be the same or different} or cyclic amino {which cyclic amino is selected from azetidin-1-yl, pyrrolidin-1-yl, piperidin-1-yl, morpholin-4-yl, thiomorpholin-4-yl and piperazin-1-yl}), or R$^d$ is (3-8C)cycloalkyl (which cycloalkyl may bear one or more {for example, one to three} methyl substituents and/or may bear one or more {for example, one or two} hydroxy substituents on a carbon, including a methyl carbon, which is not otherwise directly bonded to a nitrogen or oxygen), or R$^d$ is 3-phenylpropyl, hexahydro-2-oxo-azepin-3-yl, —CH$_2$R$^w$, —CH(CH$_3$)R$^w$, —CH$_2$ CH(OH)R$^w$, —CH$_2$ CH=CHR$^w$, —(CH$_2$)$_2$ R$^w$, —CH$_2$ CH(CH$_3$)R$^w$, α-(hydroxymethyl)benzyl, {(1-4C)alkoxy}carbonyl, trifluoroacetyl, —COCH$_2$R$^X$, —COYR$^y$ (in which Y is a single bond, carbonyl or 1,2-ethenediyl) or —CZNH—(CH$_2$)$_z$R$^z$ (in which z is 0, 1, 2 or 3; and Z is O or S); and in which R$^w$ is (1-4C)alkyl, ethynyl, trifluoromethyl, (3-7C)cycloalkyl (which cycloalkyl may bear one or more {for example, one to three} methyl substituents and/or may bear one or more {for example, one or two} hydroxy substituents on a carbon, including a methyl carbon, which is not otherwise directly bonded to a nitrogen or oxygen), tetrahydrofuran-2-yl, phenyl (which is unsubstituted or bears one to three substituents independently selected from halo, methyl, trifluoromethyl, methoxy, ethoxy, hydroxy, methylenedioxy, nitro, carboxy, methoxycarbonyl and cyano), or heteroaryl (which heteroaryl is a 5-membered aromatic ring which includes one to three heteroatoms selected from sulfur, oxygen and nitrogen or is a 6-membered aromatic ring which includes one to three nitrogen atoms, wherein the heteroaryl is attached at carbon and may bear one or more methyl substituents on carbon or nitrogen);

R$^x$ is carboxymethyl, dimethylamino, thienyl, pyridinyl or 1-tetrazolyl;

R$^y$ is methyl, phenyl (which may bear a fluoro or methyl substituent), or heteroaryl (which heteroaryl is a 5-membered aromatic ring which includes one to three heteroatoms selected from sulfur, oxygen and nitrogen or is a 6-membered aromatic ring which includes one to three nitrogen atoms, wherein the heteroaryl is attached at carbon and may bear one or more methyl substituents on carbon or nitrogen); and R$^z$ is phenyl (which may bear a fluoro or methyl substituent), thienyl or pyridinyl or (provided z is 2 or 3) R$^z$ is (1-2C)alkoxy, di(1-2C)alkylamino or cyclic amino (which cyclic amino is selected from pyrrolidin-1-yl, piperidin-1-yl, morpholin-4-yl and thiomorpholin-4-yl); or R$^1$ is 4-oxocyclohexyl; and R$^2$ is fluoro, chloro, aminomethyl, 1-aminoethyl, 1-amino-1-methylethyl, —S(O)$_n$—R'' (wherein n is 0, 1 or 2), (1-6C)alkyl, phenyl (which may bear a chloro or methoxy substituent at the 4-position), thienyl, —O—R$^q$ or —NR$^S$R$^t$ wherein R'' is (1-2C)alkyl;

R$^q$ is (1-6C)alkyl (which alkyl may bear a fluoro or methoxy substituent on a carbon not bound to oxygen), (3-7C)cycloalkyl or —CH$_2$—R$^r$ (in which R$^r$ is ethynyl, cyano, carbamoyl, {(1-2C)alkoxy}carbonyl, phenyl or 1,2,4-triazol-3-yl); and wherein R$^s$ is hydrogen or (1-6C)alkyl and R$^t$ is hydrogen or methyl, or —NR$^S$R$^t$ is a cyclic amino group selected from azetidin-1-yl, pyrrolidin-1-yl, 3,4-didehydropyrrolidin-1-yl, piperidin-1-yl, 3,4-didehydropiperidin-1-yl, morpholin-4-yl, thiomorpholin-4-yl, piperazin-1-yl, and hexahydro-1,4-diazepin-1-yl (which cyclic group may bear one or more methyl substituents on carbon, or may bear a carbamoyl, hydroxymethyl, methoxymethyl, or 2-hydroxyethyl substituent on carbon, or may bear a hydroxy, amino, methylamino, dimethylamino, (1-2C)acylamino, or {(1-4C)alkoxy}carbonylamino substituent on a carbon which is not attached to a ring nitrogen, oxygen or sulfur nor double bonded to another carbon, or may bear a (1-3C)alkyl, acetyl, hydroxyacetyl or acetoxyacetyl substituent on a ring nitrogen at the 4-position);

or —OR$^1$ represents 1-(4-pyridyl)piperidin-4-ylcarbonylamino and R$^2$ is hydrogen.

As used herein, the expression a compound of formula I or the expression a compound of the invention includes the compound and any conventional prodrug thereof, as well as a pharmaceutically acceptable salt of said compound or prodrug.

In this specification, the following definitions are used, unless otherwise described: Halo is fluoro, chloro, bromo or iodo. Alkyl, alkoxy, etc. denote both straight and branched groups; but reference to an individual radical such as "propyl" embraces only the straight chain ("normal") radical, a branched chain isomer such as "isopropyl" being specifically denoted.

Particular values for the groups and ranges defined herein include the following: halo is fluoro, chloro, bromo or iodo; (1-2C)acyl is formyl or acetyl; for an alkyl group or the alkyl portion of an alkoxy or alkylthio group: (1-2C)alkyl is methyl or ethyl; (1-3C) normal alkyl is methyl, ethyl or propyl; (1-3C)alkyl is methyl, ethyl, propyl or isopropyl; (1-4C)alkyl is methyl, ethyl, propyl, isopropyl, butyl, isobutyl, or t-butyl; (1-6C)alkyl is methyl, ethyl, propyl, isopropyl, butyl, t-butyl, pentyl or hexyl; (1-7C)alkyl is methyl, ethyl, propyl, isopropyl, butyl, t-butyl, 1-methylpropyl, 2-methylpropyl, pentyl, 2-methyl-butyl, 3-methylbutyl, 1,2-dimethylpropyl, 2,2-dimethylpropyl, hexyl, 3,3-dimethylbutyl, 1,3-dimethylbutyl, 1,2,2-trimethylpropyl, 1-(1-methylethyl)-2-methylpropyl or heptyl; (3-6C)cycloalkyl is cyclopropyl, cyclobutyl, cyclopenylyl or cyclohexyl; (3-7C)cycloalkyl is cyclopropyl, cyclobutyl, cyclopentyl, cyclohexyl or cycloheptyl; (3-8C)cycloalkyl is cyclopropyl, cyclobutyl, cyclopenylyl, cyclohexyl, cycloheptyl or cyclooctyl.

It will be appreciated that certain compounds of formula I (or salts or prodrugs, etc.) may exist in, and be isolated in, isomeric forms, including tautomeric forms, cis- or trans-isomers, as well as optically active, racemic, or diastereomeric forms. It is to be understood that the present invention encompasses a compound of formula I in any of the tautomeric forms or as an a mixture thereof; or as a mixture of diastereomers, as well as in the form of an individual diastereomer, and that the present invention encompasses a compound of formula I as a mixture of enantiomers, as well as in the form of an individual enantiomer, any of which mixtures or form possesses inhibitory properties against thrombin and/or factor Xa, it being well known in the art how to prepare or isolate particular forms and how to determine inhibitory properties against thrombin and/or factor Xa by standard tests including those described below.

In addition, a compound of formula I (or salt or prodrug, etc.) may exhibit polymorphism or may form a solvate with water or an organic solvent. The present invention also encompasses any such polymorphic form, any solvate or any mixture thereof.

A prodrug of a compound of formula I may be one formed in a conventional manner with a functional group of the compound, such as with an amino, hydroxy or carboxy group.

One particular compound of formula I is one wherein
$R^3$ is hydrogen;
$R^4$ is fluoro, chloro, methoxycarbonyl, carboxy, nitro or amino, and $R^5$ is hydrogen; or
$R^4$ is hydrogen, and $R^5$ is hydrogen, fluoro, chloro, iodo or cyano; and
$R^6$ is hydrogen.

Another particular compound, or salt thereof, as described above is one wherein
$L^1$ is —CO—NH— such that -$L^1$-$Q^1$ is —CO—NH-$Q^1$;
$Q^{1A}$ is 2-fluorophenyl, 2-methoxyphenyl, 4-acetylphenyl, 4-chlorophenyl, 4-methoxyphenyl, 4-methylthiophenyl, 4-nitrophenyl, 2,4-dichlorophenyl, 3,4-dichlorophenyl, 4-bromo-2-chlorophenyl, 4-chloro-2-methylphenyl, 2-chloro-4-nitrophenyl, 4-methoxy-2-nitrophenyl or 2,4,6-trichlorophenyl;
$Q^{1B}$ is 2-thiazolyl, 4-methylthiazol-2-yl, 5-methylisoxazol-3-yl or 1-methylpyrazol-4-yl; and
$Q^{1C}$ is 2-pyridinyl, 5-fluoropyridin-2-yl, 5-chloropyridin-2-yl, 5-methylpyridin-2-yl, 5-trifluoromethylpyridin-2-yl, 3-methylpyridin-2-yl, 3-nitropyridin-2-yl, 3,5-dichloropyridin-2-yl, 4,6-dimethylpyridin-2-yl or 5-chloropyrimidin-2-yl.

A further particular compound, or salt thereof, as described above is one wherein
$R^1$ is —(CH$_2$)$_2$—NR$^a$R$^b$, —(CH$_2$)$_3$—NR$^a$R$^b$, —(CH$_2$)$_4$—NR$^a$R$^b$, —(CH$_2$)$_2$—O—(CH$_2$)$_2$—NR$^a$R$^b$, —CH$_2$—CH(CH$_3$)—CH$_2$—NR$^a$R$^b$, —CH$_2$—C(CH$_3$)$_2$—CH$_2$—NR$^a$R$^b$, —CH$_2$—CH(OH)—CH$_2$—NR$^a$R$^b$, 1,4-cyclohexyl-NR$^a$R$^b$, —CH$_2$—CH{(CH$_2$)$_2$—SCH$_3$}CH$_2$—NR$^a$R$^b$, 3-pyrrolidinyl bearing R$^a$ on the nitrogen, 3-pyrrolidinylmethyl bearing R$^a$ on the nitrogen, 3-piperidinyl bearing a group R$^a$ on the nitrogen, 3-piperidinylmethyl bearing R$^a$ on the nitrogen, 2-piperidinylmethyl bearing R$^a$ on the nitrogen, 2-(2-piperidinyl)ethyl bearing R$^a$ group on the nitrogen, 4-piperidinyl bearing R$^a$ on the nitrogen, 3,3-dimethylpiperidin-4-yl bearing R$^a$ on the nitrogen, or 4-piperidinylmethyl bearing R$^a$ on the nitrogen;

R$^a$ is hydrogen or R$^d$; and R$^b$ is hydrogen, methyl, ethyl or propyl;

or NR$^a$R$^b$ is azetidin-1-yl, pyrrolidin-1-yl, 2-methylpyrrolidin-1-yl, 2-(hydroxymethyl)pyrrolidin-1-yl, 2-(methoxymethyl)pyrrolidin-1-yl, 2-(2-hydroxyethyl)pyrrolidin-1-yl, 2-(pyrrolidin-1-ylmethyl)pyrrolidin-1-yl, 3-hydroxypyrrolidin-1-yl, 2-(dimethylamino)pyrrolidin-1-yl, 3-(acetylamino)pyrrolidin-1-yl, thiazolidin-3-yl, piperidin-1-yl, 2-methylpiperidin-1-yl, 4-methylpiperidin-1-yl, 2,6-dimethylpiperidin-1-yl, 3,5-dimethylpiperidin-1-yl, 3-carbamoylpiperidin-1-yl, 4-carbamoylpiperidin-1-yl, 2-(hydroxymethyl)piperidin-1-yl, 3-(hydroxymethyl)-piperidin-1-yl, 4-(hydroxymethyl)piperidin-1-yl, 2-(2-hydroxyethyl)piperidin-1-yl, 4-(2-hydroxyethyl)piperidin-1-yl, 2-(2-pyrrolidin-1-ylethyl)piperidin-1-yl, 4-hydroxypiperidin-1-yl, 4-(pyrrolidin-1-yl)piperidin-1-yl, 4-(piperidin-1-yl)piperidin-1-yl, 3,4-didehydropiperidin-1-yl, morpholin-4-yl, 3,5-dimethylmorpholin-4-yl, thiomorpholin-4-yl, piperazin-1-yl, 4-methylpiperazin-1-yl, 4-cyclopentylpiperazin-1-yl, 4-(pyrrolidin-1-ylcarbonylmethyl)piperazin-1-yl, 4-(2-hydroxyethyl)piperazin-1-yl, 4-acetylpiperazin-1-yl, 4-(furan-1-ylcarbonyl)piperazin-1-yl, 4-phenylpiperazin-1-yl, 4-(2-chlorophenyl)piperazin-1-yl, 4-(3-chlorophenyl)piperazin-1-yl, 4-(3-methylphenyl)-piperazin-1-yl, 4-(2-methoxyphenyl)piperazin-1-yl, 4-(pyridin-2-yl)piperazin-1-yl, 4-(pyridin-2-yl)piperazin-1-yl, 4-(pyrimidin-2-yl)piperazin-1-yl, 4-(pyrazin-2-yl)-piperazin-1-yl, hexahydroazepin-1-yl, 2,2,5-trimethylhexahydroazepin-1-yl, 3,3,5-trimethylhexahydroazepin-1-yl, 4-methylhexahydro-1,4-diazepin-1-yl, octahydroazocin-1-yl, 1,3,3-trimethyl-6-azabicyclo[3.2.1]octan-6-yl, di(thiophen-2-ylmethyl)amino, di(2-methylbenzyl)amino or di(cyclopropylmethyl)amino; and R$^d$ is methyl, propyl, isopropyl, butyl, t-butyl, pentyl, 2-methylbutyl, 3-methyl-butyl, hexyl, 3,3-dimethylbutyl, 1-(1-methylethyl)-2-methylpropyl, 2-hydroxyethyl, 2-hydroxy-1-methylethyl, 2-hydroxy-1,1-dimethylethyl, 1-hydroxymethyl-2-hydroxyethyl, 3-hydroxypropyl, 3-hydroxy-2-methylpropyl, 4-hydroxybutyl, 1-hydroxymethylpropyl, 3-hydroxy-2,2-dimethylpropyl, 1-hydroxymethyl-2-methylpropyl, 1-hydroxymethyl-2,2-dimethylpropyl, 1-hydroxymethyl-3-methylthiopropyl, 1-hydroxymethyl-3-methylbutyl, 2-methoxyethyl, 2-methylthioethyl, 2-(dimethylamino)ethyl, 1-methyl-2-(dimethylamino)ethyl, 2,2-dimethyl-3-(dimethylamino)propyl, 2-(acetylamino)ethyl, 2-(pyrrolidin-1-yl)ethyl, 2-(piperidin-1-yl)ethyl, cyclopropyl, cyclobutyl, cyclopenylyl, cyclohexyl, cycloheptyl, cyclooctyl, 3-methylcyclohexyl, 4-methylcyclohexyl, trans-4-hydroxycyclohexyl, 1-(hydroxymethyl)cyclopenylyl, 3-phenylpropyl or hexahydro-2-oxoazepin-3-yl, or R$^d$ is —CH$_2$R$^w$, in which R$^w$ is ethynyl, cyclopropyl, tetrahydrofuran-2-yl, phenyl, 2-fluorophenyl, 2-chlorophenyl, 2-methylphenyl, 3-methylphenyl, 4-methylphenyl, 2-methoxyphenyl, 3-methoxyphenyl, 4-methoxyphenyl, 2,3-dimethoxyphenyl, 2,6-dimethoxyphenyl, 2-ethoxyphenyl, 2-hydroxyphenyl, 2-hydroxy-3-methoxyphenyl, 2,3-methylenedioxyphenyl, 2-nitrophenyl, 2-carboxyphenyl, 2-methoxycarbonylphenyl, 2-cyanophenyl, 2-furanyl, 2-thienyl, 3-methylthien-2-yl, 3-thienyl, 2-imidazolyl, 5-methylimidazol-4-yl, 2-thiazolyl, 2-pyridinyl, 3-pyridinyl or 4-pyridinyl, or R$^d$ is —CH(CH$_3$)R$^w$, in which R$^w$ is phenyl or 2-pyridinyl, or R$^d$ is —CH$_2$CH(OH)R$^w$, in which R$^w$ is methyl, t-butyl or trifluoromethyl, or R$^d$ is —$CH_2CH=CHR^w$, in which $R^w$ is phenyl or 2-furanyl, or $R^d$ is —$(CH_2)_2R^w$, in which $R^w$ is phenyl or 2-thienyl, or $R^d$ is —$CH_2CH(CH_3)R^w$, in which $R^W$ is phenyl, or $R^d$ is α-(hydroxymethyl)benzyl, t-butoxycarbonyl, trifluoroacetyl, or $R^d$ is —$COCH_2R^x$, in which $R^x$ is carboxymethyl, dimethylamino, 2-thienyl, 3-thienyl, 2-pyridinyl or 1-tetrazolyl, or $R^d$ is —$COR^y$ in which $R^y$ is methyl, phenyl, 2-fluorophenyl, 3-fluorophenyl, 4-fluorophenyl, 2-methylphenyl, 3-methylphenyl, 4-methylphenyl, 2-thienyl, 3-methylthien-2-yl, 3-thienyl, 1-methylpyrrol-2-yl or 1-methylpyrazol-5-yl, or $R^d$ is —CO—CO—$R^y$ in which $R^y$ is methyl, 2-furanyl or 2-thienyl, or $R^d$ is —$CONHR^z$ in which $R^z$ is 2-fluorophenyl or 4-fluoro-phenyl, or $R^d$ is —$CONH$—$(CH_2)_2R^z$ in which $R^z$ is 2-thienyl, or $R^d$ is —$CSNHR^z$ in which $R^z$ is 2-fluorophenyl, or $R^d$ is —$CSNH$—$CH_2$—$R^z$ in which $R^z$ is 3-pyridinyl, or $R^d$ is —$CSNH$—$(CH_2)_2R^z$ in which $R^z$ is methoxy, or $R^d$ is —$CSNH$—$(CH_2)_3R^z$ in which $R^z$ is methoxy, dimethylamino, diethylamino or morpholin-4-yl;

or $R^1$ is 4-oxocyclohexyl.

A more particular compound according to the above definitions is a one wherein $R^2$ is fluoro, chloro, 1-aminoethyl, 1-amino-1-methylethyl, methylthio, methylsulfinyl, methylsulfonyl, ethylsulfonyl, isopropyl, t-butyl, 4-chlorophenyl, 4-methoxyphenyl, 3-thienyl, methoxy, 2-fluoroethoxy, 2-methoxyethoxy, isopropoxy, 1-ethylpropoxy, 3-methylbutoxy, cyclopentyloxy, cycloheptyloxy, propargyloxy, 2-amino-2-oxoethoxy, 2-ethoxy-2-oxoethoxy, benzyloxy, 1,2,4-oxadiazol-3-ylmethoxy, dimethylamino, azetidin-1-yl, pyrrolidin-1-yl, (R)-2-carbamoylpyrrolidin-1-yl, (S)-2-(methoxymethyl)pyrrolidin-1-yl, 3-hydroxypyrrolidin-1-yl, 3-aminopyrrolidin-1-yl, (S)-3-aminopyrrolidin-1-yl, (S)-3-(dimethylamino)pyrrolidin-1-yl, 3-(t-butoxycarbonylamino)pyrrolidin-1-yl, (S)-3-(acetylamino)pyrrolidin-1-yl, piperidin-1-yl, 3-methylpiperidin-1-yl, 3-carbamoylpiperidin-1-yl, 4-carbamoylpiperidin-1-yl, 4-(2-hydroxyethyl)piperidin-1-yl, 3-hydroxypiperidin-1-yl, 4-hydroxypiperidin-1-yl, 3,4-didehydropiperidin-1-yl, morpholin-4-yl, thiomorpholin-4-yl, 4-methylpiperazin-1-yl, 4-acetylpiperazin-1-yl, hexahydro-1,4-diazepin-1-yl or 4-methylhexahydro-1,4-diazepin-1-yl.

A further more particular compound according to the above definition is one wherein:

each of $R^3$, $R^5$ and $R^6$ is hydrogen and $R^4$ is methoxycarbonyl; or each of $R^3$, $R^4$ and $R^6$ is hydrogen and $R^5$ is hydrogen, fluoro or chloro;

$L^1$ is —CO—NH— such that -$L^1$-$Q^1$ is —CO—NH-$Q^1$; and $Q^1$ is 5-chloropyridin-2-yl, 5-fluoropyridin-2-yl, or 6-chloropyridazin-3-yl; and, more particularly, wherein:

each of $R^3$, $R^4$ and $R^6$ is hydrogen and $R^5$ is hydrogen or fluoro; and $Q^1$ is 5-chloropyridin-2-yl.

One aromatic ether according to the above definitions is one wherein $R^a$ is hydrogen or methyl, and $R^b$ is hydrogen or methyl; or $R^a$ is hydrogen or methyl, and $R^b$ and $R^c$ together are —$(CH_2)_2$—, —$(CH_2)_3$—, —$(CH_2)_4$— or —$C(CH_3)_2$—$CH_2$—; particularly wherein $R^1$ is 2-aminoethyl, 3-aminopropyl, 4-piperidinyl, 1-methylpiperidin-4-yl or 1-isopropylpiperidin-4-yl; and more particularly, wherein $R^1$ is 3-aminopropyl or 4-piperidinyl.

Another aromatic ether according to the above definitions is one wherein $R^2$ is 1-amino-1-methylethyl.

A further aromatic ether according to the above definitions is one wherein $R^2$ is methylthio, methylsulfinyl, methylsulfonyl or ethylsulfonyl; particularly, wherein $R^2$ is methylsulfinyl or methylsulfonyl.

Another aromatic ether according to the above definitions is one wherein $R^2$ is methoxy, 2-fluoroethoxy, 2-methoxyethoxy, isopropoxy or propargyloxy; particularly, wherein $R^2$ is 2-fluoroethoxy.

Another particular compound or salt according to the above definitions is one wherein $R^2$ is dimethylamino, azetidin-1-yl, pyrrolidin-1-yl, 3-carbamoylpiperidin-1-yl, 4-hydroxypiperidin-1-yl, morpholin-4-yl or 4-methylhexahydro-1,4-diazepin-1-yl; particularly wherein $R^2$ is dimethylamino, pyrrolidin-1-yl or 4-methylhexahydro-1,4-diazepin-1-yl.

Another particular compound or salt according to the above definitions is one wherein $R^1$ is 4-oxocyclohexyl and $R^2$ is 1-amino-1-methylethyl or 4-methylhexahydro-1,4-diazepin-1-yl.

A specific compound, or pharmaceutically acceptable salt thereof, is any one of those provided in the Examples, particularly the compound provided in one of Examples 2, 5, 89, 107, 109 and 1509, or a pharmaceutically acceptable salt thereof.

A pharmaceutically acceptable salt of a compound of formula I of the instant invention is an acid-addition salt made from a basic compound of formula I and an acid which provides a pharmaceutically acceptable anion or a salt which is made from an acidic compound of formula I and a base which provides a pharmaceutically acceptable cation.

As an additional aspect of the invention there is provided a pharmaceutical composition comprising in association with a pharmaceutically acceptable carrier, diluent or excipient, a compound of formula I, or a pharmaceutically acceptable salt thereof, as provided in any of the descriptions herein.

Further, there is provided a pharmaceutical composition for treating a thromboembolic disorder containing as an active ingredient a compound of formula I, or a pharmaceutically acceptable salt thereof, as provided in any of the descriptions herein.

In addition, there is provided the use of a compound of formula I, or a pharmaceutically acceptable salt thereof, as described herein as an active ingredient in the manufacture of a medicament for use in producing an anticoagulant or antithrombotic effect.

The present invention also provides a method of inhibiting coagulation in a mammal, particularly a human, comprising administering to a mammal in need of treatment, a coagulation inhibiting dose of a compound of formula I, or a pharmaceutically acceptable salt thereof, having any of the definitions herein.

The present invention further provides a method of inhibiting thrombin and/or factor Xa comprising administering to a mammal, particularly a human, in need of treatment, a thrombin and/or factor Xa inhibiting dose of compound of formula I having any of the definitions herein.

Further, the present invention provides a method of treating a thromboembolic disorder comprising administering to a mammal, particularly a human, in need of treatment, an effective amount of a compound of formula I, or a pharmaceutically acceptable salt thereof, having any of the definitions herein.

Also, there is provided a compound of formula I, or a pharmaceutically acceptable salt thereof, having any of the definitions herein for use as an antithrombotic agent.

In addition, there is provided the use of a compound of formula I, or a pharmaceutically acceptable salt thereof, having any of the definitions herein for the manufacture of a medicament for treatment of a thromboembolic disorder.

A compound of formula I may be prepared by processes which include processes known in the chemical art for the production of structurally analogous compounds or by a novel process described herein. A novel process described herein provides another aspect of the invention. A process for the preparation of a compound of formula I (or a pharmaceutically acceptable salt thereof) and novel intermediates for the manufacture of a compound of formula I provide further features of the invention and are illustrated by the following procedures in which the meanings of the generic radicals are as defined above, unless otherwise specified. It will be recognized that it may be preferred or necessary to prepare a compound of formula I in which a functional group is protected using a conventional protecting group, then to remove the protecting group to provide the compound of formula I.

Thus, there is provided a process for preparing a compound of formula I, or a pharmaceutically acceptable salt thereof, as provided in any of the above descriptions, comprising the step selected from (A) for a compound in which $L^2$ is carbonyl, acylating an amine of formula II,

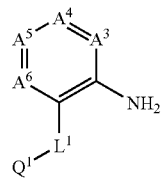

II using an acid of formula III,

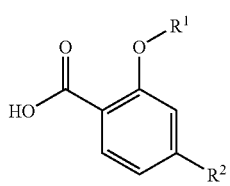

III or an activated derivative thereof;

(B) for a compound in which $L^1$ is —CO—NH—, acylating an amine of formula $Q^1$-$NH_2$ using an acid of formula IV,

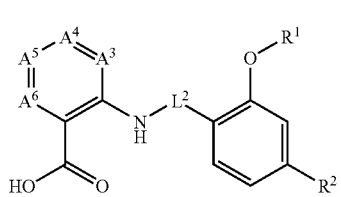

IV or an activated derivative thereof;

(C) for a compound of formula I in which $L^2$ is methylene, substituting the group $Y^a$ of a compound of formula VI

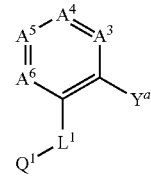

VI in which $Y^a$ is a leaving group for nucleophilic aromatic substitution with an amine of formula VII; or

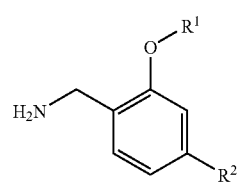

VII alkylating an amine of formula II directly, using a compound of formula VIII,

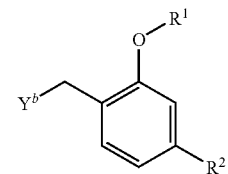

VIII in which $Y^b$ is a leaving group for nucleophilic substitution, or indirectly, by reductive alkylation using an aldehyde of formula IX;

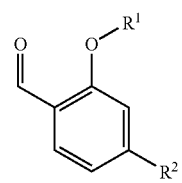

IX (D) for a compound of formula I in which each of $R^a$ and $R^b$ is (1-3C) normal alkyl, or $NR^aR^b$ is 1-pyrrolidinyl or 4-morpholinyl, or $NR^aR^b$ is $N(CH_2R^w)_2$, alkylating a corresponding compound of formula I in which each of $R^a$ and $R^b$ is hydrogen;

(E) for a compound of formula I in which $R^a$ is $R^d$ and $R^d$ is (1-7C)alkyl, (3-8C)cycloalkyl, 3-phenylpropyl, —$CH_2R^w$, —$CH(CH_3)R^w$, —$CH_2$ $CH(OH)R^w$, —$CH_2$ CH=$CHR^w$, —$(CH_2)_2R^w$, —$CH_2$ $CH(CH_3)R^w$ or α-(hydroxymethyl)benzyl, alkylating a corresponding compound of formula I in which $R^a$ is hydrogen;

(F) for a compound of formula I in which $R^a$ is $R^d$ and $R^d$ is {(1-4C)alkoxy}-carbonyl, trifluoroacetyl, —$COCH_2R^x$, —$COYR^y$ or —$CZNH$—$(CH_2)_zR^z$, acylating a corresponding compound of formula I in which $R^a$ is hydrogen;

(G) alkylating the phenolic oxygen of a compound of formula X,

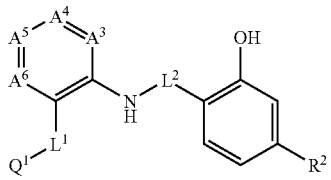

using a corresponding compound of formula Y—R$^1$, wherein Y is a conventional leaving group for nucleophilic substitution and wherein, for a compound of formula I in which i is 0, the stereochemistry of the carbon to which Y is attached is inverted from that of the product;

(H) for a compound of formula I in which L$^2$ is carbonyl and R$^2$ is —NR$^s$R$^t$, —OR$^f$ or —SR$^n$, substitution of the group Y$^c$ of a compound of formula XI,

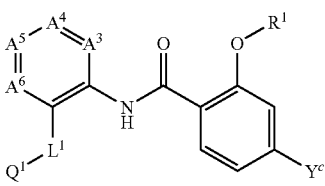

wherein Y$^c$ is a leaving group for nucleophilic aromatic substitution, using H—NR$^s$R$^t$, H—OR$^f$ or H—SR$^n$, or the deprotonated form thereof;

(I) for a compound of formula I in which R$^2$ is —OR$^f$, alkylating the phenolic oxygen of a compound of formula XII,

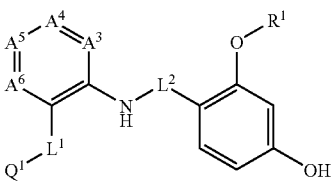

using a corresponding compound of formula Y—R$^f$ in which Y is a conventional leaving group for nucleophilic substitution;

(J) for a compound of formula I in which R$^2$ is —S(O)$_n$—R$^n$ and n is 1, oxidizing the corresponding compound of formula I in which n is 0;

(K) for a compound of formula I in which R$^2$ is —S(O)$_n$—R$^n$ and n is 2, oxidizing the corresponding compound of formula I in which n is 0 or 1;

(L) for a compound of formula I in which NR$^a$R$^b$ is a basic moiety, other than one in which R$^b$ and R$^c$ together are —(CH$_2$)$_2$—, —(CH$_2$)$_3$—, —(CH$_2$)$_4$— or —C(CH$_3$)$_2$—CH$_2$—, alkylation of a compound of formula H—NR$^a$R$^b$;

(M) for a compound of formula I in which R$^4$ or R$^5$ is amino, reducing the nitro group of a compound corresponding to a compound of formula I in which R$^4$ or R$^5$ is nitro;

(N) for a compound of formula I in which R$^4$ or R$^5$ is R$^g$NH— and R$^g$ is R$^h$SO$_2$—, substituting the amino group of a corresponding compound of formula I in which R$^4$ or R$^5$ is amino using an activated derivative of the sulfonic acid R$^h$SO$_2$—OH;

(O) for a compound of formula I in which R$^4$ or R$^5$ is R$^f$O$_2$CCH$_2$O—, R$^f$O$_2$C— or R$^f$O$_2$CCH$_2$— and R$^f$ is H, decomposing the ester of a corresponding compound in which R$^f$ is (1-4C)alkyl or benzyl;

(P) for a compound of formula I in which R$^4$ or R$^5$ is cyano, substituting the iodo or bromo group of a compound corresponding to a compound of formula I in which R$^4$ or R$^5$ is iodo or bromo;

wherein, for any of the above procedures, a functional group which is present and not involved in the indicated procedure may be protected using a protecting group, including a nitrogen protecting group R$^p$ in place of an amino hydrogen or an ethylene ketal in place of an oxo group;

whereafter, for any of the above procedures, when a functional group is protected using a protecting group, removing the protecting group;

whereafter, for any of the above procedures, when a pharmaceutically acceptable salt of a compound of formula I is required, it is obtained by reacting the basic form of a basic compound of formula I with an acid affording a physiologically acceptable counterion or by any other conventional procedure; and wherein, unless otherwise specified above in this claim, A$^3$-A$^6$, L$^1$, L$^2$, R$^1$, R$^2$, and Q$^1$, and the values therein have any of the values defined hereinabove.

As used herein, a nitrogen protecting group RP includes any conventional nitrogen protecting group which is appropriate for the relevant transformation(s) and compounds in terms of stability and removal. It may be preferred to introduce or change the nitrogen protecting group RP during the preparation of a compound. A typical value for RP is one which forms a urethane, such as for example a t-butoxycarbonyl or benzyloxycarbonyl group; however, RP will be other than a urethane when the intramolecular formation of a (cyclic) urethane is favorable, for example, RP may be a trifluoroacetyl or a phenylsulfonyl group. In addition, RP includes resin based protecting groups, such as the urethane formed with Wang-p-nitrophenyl carbonate (Wang-PNP) resin, as described in the examples, for example at Example 113-H, at General Procedure H at Example 1301 and at General Procedure K at Example 1602.

For a carboxylic acid herein, a typical activated derivative includes an ester (particularly a lower alkyl ester such as the methyl or ethyl ester), an acid halide (particularly the acid chloride), and an activated ester or anhydride (including the 4-nitrophenyl ester and an activated ester or mixed anhydride derived from a coupling reagent).

As used herein, a leaving group "Y$^a$" or "Y$^c$" is a moiety which is displaced in an aromatic nucleophilic substitution reaction, for example a halo group (such as fluoro or chloro) or a sulfonate ester group (such as methylsulfonyloxy, p-toluoylsulfonyloxy or trifluoromethylsulfonyloxy). The substitution may be carried out by heating a mixture of the reagents, optionally in a polar solvent, and optionally in the presence of a base, for example as described at Examples 4-F, 35-C, 168-D and 1401-B.

As used herein, a leaving group "Y$^b$" is a moiety which is displaced in a nucleophilic substitution reaction, for example a halo group (such as chloro, bromo or iodo), a sulfonate ester group (such as methylsulfonyloxy, p-toluoyl-sulfonyloxy or trifluoromethylsulfonyloxy), or the reactive species derived from treating an alcohol with triphenyl-phospine, diethyl azodicarboxylate and triethyl amine (in a Mitsunobu reaction).

Reductive alkylations are described, for example, at Examples 3, 56-C, 92, 94-E and 147, as well as in General Procedure A prior to Example 202 and in General Procedure G prior to Example 313.

As used herein, a leaving group "Y" is a moiety which is displaced in a nucleophilic substitution reaction, for example a halo group (such as bromo or iodo), a sulfonate ester group (such as methylsulfonyloxy, p-toluoylsulfonyloxy or trifluoromethylsulfonyloxy), or the reactive species derived from treating an alcohol with triphenylphospine, diethyl azodicarboxylate and triethyl amine (in a Mitsunobu reaction). In addition, an epoxy group may provide the leaving group for the preparation of a compound in which the —CH(OH)— group is adjacent to the substituted carbon. Direct alkylation at nitrogen with an alkyl halide is described, for example, at General Procedure E prior to Example 402; and direct alkylation at nitrogen using an epoxide is described, for example, at Example 36, as well as at General Procedure D prior to Example 231 and GeneralProcedure F prior to Example 601. Direct alkylation at oxygen is described, for example, at Example 113-I, as well as in General Procedure H at Example 1301-B and at General Procedure K prior to Example 1602.

Acylating the amino nitrogen of a compound of formula I in which $R^a$ is hydrogen is conveniently carried out using an activated derivative of the corresponding acid, for example the acyl chloride, an anhydride or an activated ester or mixed anhydride derived from a coupling reagent, optionally in the presense of a base. When $R^d$ is —CZNH—$(CH_2)_z R^z$, the acylating agent is conveniently the corresponding isocyanate or isothiocyanate of formula ZCN—$(CH_2)_z R^z$. Acylations are described, for example, at Example 58, Example 139-A, General Procedure B prior to Example 206, General Procedure C prior to Example 228, and at Example 244.

Oxidizing a compound in which n is 0 to afford a compound in which n is 1 is conveniently carried out in a manner as described in Example 23 or by using one equivalent of meta-choloroperbenzoic acid. Oxidizing a compound in which n is 1 to afford a compound in which n is 2 is conveniently carried out using at least one equivalent of meta-choloroperbenzoic acid. When a compound in which n is 2 is required, it is conveniently obtained from the compound in which n is 0 as described in Example 25, in which the intermediate compound in which n is 1 is not isolated but oxidized directly in situ into the compound in which n is 2.

If not commercially available, a necessary starting material for the preparation of a compound of formula I may be prepared by a novel process described herein or one analogous thereto or by a procedure which is selected from standard techniques of organic chemistry, including aromatic substitution and transformation, from techniques which are analogous to the syntheses of known, structurally similar compounds, and techniques which are analogous to the above described procedures or procedures described in the Examples. It will be clear to one skilled in the art that a variety of sequences is available for the preparation of the starting materials. A novel intermediate or starting material compound provides a further aspect of the invention.

Selective methods of substitution, protection and deprotection are well known in the art for preparation of a compound such as one of formulae II-XIII.

Thus, one particular intermediate is an acid of formula III, or a salt thereof, or an activated derivative thereof,

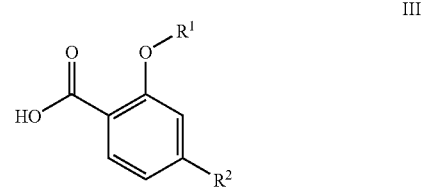

wherein $R^1$ and $R^2$ have any of the values defined herein above (and in which $R^a$ as hydrogen may be replaced by a nitrogen protecting group RP and/or an amino group in $R^2$ may bear a nitrogen protecting group RP). Conveniently, the salt of a carboxylic acid herein may be the lithium, sodium or potassium salt. A particular acid of formula III is one in which $R^1$ has any of the values defined herein above and $R^2$ is aminomethyl, 1-aminoethyl or 1-amino-1-methylethyl, (and in which $R^a$ as hydrogen may be replaced by a nitrogen protecting group RP and/or the amino group in $R^2$ may bear a nitrogen protecting group RP).

Another aspect is an acid of formula IV

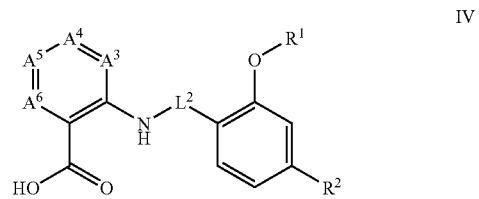

(in which $R^a$ as hydrogen may be replaced by a nitrogen protecting group RP and/or an amino group in $R^2$ may bear a nitrogen protecting group RP), or an activated derivative thereof, wherein $A^3$-$A^6$, $L^2$, $R^1$ and $R^2$ have any of the values defined herein. In addition, for an acid of formula IV, in which $L^2$ is carbonyl, a particular activated derivative is a compound of formula V,

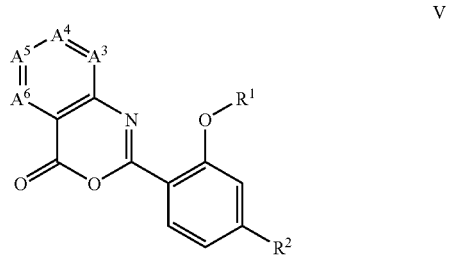

or a salt of the active derivative, in which $A^3$-$A^6$, $R^1$ and $R^2$ have any of the values defined herein, or a derivative thereof in which a functional group other than the activated derivative of the carboxy group is protected using a protecting group.

Further, for an acid of formula IV, in which $L^2$ is methylene, a particular activated derivative is a compound of formula Va,

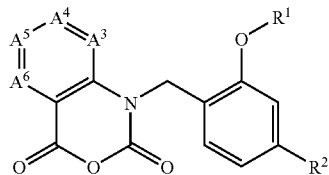

or a salt of the active derivative, in which $A^3$-$A^6$, $R^1$ and $R^2$ have any of the values defined herein, or a derivative thereof in which a functional group other than the activated derivative of the carboxy group is protected using a protecting group.

A compound of formula X or a salt thereof,

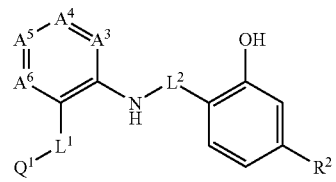

in which $R^2$ is aminomethyl, 1-aminoethyl, 1-amino-1-methylethyl (in which the amino group in $R^2$ may bear a nitrogen protecting group RP), wherein $A^3$-$A^6$, $L^1$, $L^2$ and $Q^1$ have any of the values defined herein is another particular intermediate.

An additional intermediate, beyond a compound of formula I in which $R^2$ is chloro or fluoro, is a compound of formula XI

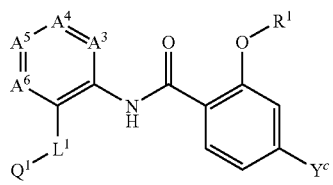

(in which $R^a$ as hydrogen may be replaced by a nitrogen protecting group RP or an oxo group may be replaced by a ketal) wherein $Y^c$ is a leaving group for nucleophilic aromatic substitution other than fluoro or chloro and $A^3$-$A^6$, -$L^1$-$Q^1$ and $R^1$ have any of the values defined hereinabove.

A further intermediate is a compound of formula XII

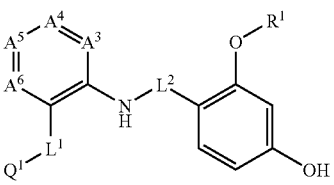

(in which $R^a$ as hydrogen may be replaced by a nitrogen protecting group RP or an oxo group may be replaced by a ketal) wherein $A^3$-$A^6$, -$L^1$-$Q^1$ and $R^1$ have any of the values defined hereinabove.

As an another aspect of the invention there is provided compound of formula I as disclosed herein, but in which $R^a$ as hydrogen is replaced by a nitrogen protecting group RP and/or an amino group in $R^2$ bears a nitrogen protecting group RP and/or an oxo group is replaced by a ketal, wherein $A^3$-$A^6$, $L^1$, $L^2$, $Q^1$, $R^1$ and $R^2$, otherwise, have any of the values defined herein.

As mentioned above, the invention includes a pharmaceutically acceptable salt of the thrombin and/or factor Xa inhibiting compound defined by the above formula I. A basic compound of this invention possesses one or more functional groups sufficiently basic to react with any of a number of inorganic and organic acids affording a physiologically acceptable counterion to form a pharmaceutically acceptable salt.

Generally, a basic compound of the invention is isolated best in the form of an acid addition salt. A salt of a compound of formula I formed with an acid such as mentioned above is useful as a pharmaceutically acceptable salt for administration of the antithrombotic agent and for preparation of a pharmaceutical composition of the agent. Other acid addition salts may be prepared and used in the isolation and purification of the compounds.

As noted above, the optically active isomers and diastereomers of the compounds of formula I are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors.

The compounds of the invention are believed to selectively inhibit thrombin and/or factor Xa over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis.

The invention in one of its aspects provides a method of inhibiting thrombin and/or factor Xa in a mammal comprising administering to a mammal in need of treatment an effective (thrombin and/or factor Xa inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in a mammal comprising administering to a mammal in need of treatment an effective (coagulation inhibiting) dose of a compound of formula I.

The thrombin and/or factor Xa inhibition, coagulation inhibition and thromboembolic disorder treatment contemplated by the present method includes both medical therapeutic and/or prophylactic treatment as appropriate.

In a further embodiment, the invention relates to treatment, in a human or animal, of a condition where inhibition of thrombin and/or factor Xa is required. The compounds of the invention are expected to be useful in mammals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs, including joint replacement, and cardiac valves. Further, the compounds have expected utility in anticoagulant treatment in hemodialysis and disseminated intravascular coagulation. Further, the compounds may be useful in reducing the increased thrombin generation which occurs in the airways of patients with asthma; see, E. C. Gabazza, et al., Lung, (1999), 177(4), 253-262. A further expected utility is in rinsing or coating of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anti-coagulant compound is administered orally or parenterally, e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides a pharmaceutical composition for use in the above described therapeutic method. A pharmaceutical composition of the invention comprises a compound of formula I, or a pharmaceutically acceptable salt thereof, in association with a pharmaceutically acceptable carrier, diluent or excipient.

The active ingredient in such formulations comprises from 0.1 percent to 99.9 percent by weight of the formulation. By "pharmaceutically acceptable" it is meant the carrier, diluent or excipient must be compatible with the other ingredients of the formulation and not deleterious to the recipient thereof.

The present pharmaceutical compositions are prepared by known procedures using well known and readily available ingredients. The compositions of this invention may be formulated so as to provide quick, sustained, or delayed release of the active ingredient after administration to the patient by employing procedures well known in the art.

The ability of a compound of the present invention to be an effective and orally active thrombin and/or factor Xa inhibitor may be evaluated in one or more of the following assays or in other standard assays known to those in the art.

The inhibition by a compound of the invention of a serine protease of the human blood coagulation system or of the fibrinolytic system, as well as of trypsin, is determined in vitro for the particular enzyme by measuring its inhibitor binding affinity in an assay in which the enzyme hydrolyzes a particular chromogenic substrate, for example as described in Smith, G. F.; Gifford-Moore, D.; Craft, T. J.; Chirgadze, N.; Ruterbories, K. J.; Lindstrom, T. D.; Satterwhite, J. H. Efegatran: A New Cardiovascular Anticoagulant. *New Anticoagulants for the Cardiovascular Patient*; Pifarre, R., Ed.; Hanley & Belfus, Inc.: Philadelphia, 1997; pp. 265-300. The inhibitor binding affinity is measured as apparent association constant Kass which is the hypothetical equilibrium constant for the reaction between enzyme and the test inhibitor compound (I).

$$\text{Enzyme} + I \rightleftharpoons \text{Enzyme} - I$$

$$Kass = \frac{[\text{Enzyme} - I]}{([\text{Enzyme}] \times [I])}$$

Conveniently, enzyme inhibition kinetics are performed in a high-volume protocol using automated dilutions of inhibitors (n=3 for each of four to eight inhibitor concentrations) into 96-well polystyrene plates and reaction rates are determined from the rate of hydrolysis of appropriate p-nitroanilide substrates at 405 nm using a Thermomax plate reader from Molecular Devices (San Francisco, Calif.). The same general protocol is followed for all enzymes studied: In each well is placed 50 µL buffer (0.06 M Tris, 0.3 M NaCl, pH 7.4), followed by 25 µL of inhibitor solution (in 100 % methanol) and 25 µL enzyme solution (e.g., human factor Xa, 32 nM in 0.03 M Tris, 0.15 M NaCl, 1 mg/mL HAS); finally, within two minutes, 150 µL aqueous solution of chromogenic substrate (e.g., 0.3 mM BzIle-Glu-Gly-Arg-pNA) is added to start the enzymatic reaction. Final factor Xa concentration is 3.2 nM.

The rates of chromogenic substrate hydrolysis reactions provide a linear relationship with the enzymes studied such that free enzyme can be quantitated in reaction mixtures. Data is analyzed directly as rates by the Softmax program to produce [free enzyme] calculations for tight-binding Kass determinations. For apparent Kass determinations, human factor Xa is used to hydrolyze BzIle-Glu-Gly-Arg-pNA (SEQ ID NO: 1); 5.9 nM human thrombin is used to hydrolyze 0.2 mM BzPhe-Val-Arg-pNA; 3.4 nM human plasmin is used with 0.5 mM HD-Val-Leu-Lys-pNA; 1.2 nM human nt-PA is used with 0.8 mM HD-Ile-Pro-Arg-pNA; and 0.4 nM urokinase is used with 0.4 mM pyro-Glu-Gly-Arg-pNA.

Kass is calculated for a range of concentrations of test compounds which produce hydrolysis inhibition of between 20% and 80% of control and the mean value reported in units of liter per mole. In general, a compound of formula I of the instant invention, as exemplified hereinbelow in the working examples, exhibits a Kass for factor Xa of $0.1\text{-}1{,}000 \times 10^6$ L/mole or greater. Most of the examples also exhibit a Kass for thrombin (factor IIa) of $0.3\text{-}100 \times 10^6$ L/mole or greater. For example, the respective Kass values as to factor Xa/thrombin for Examples 41, 60, 106, 115, 1403 and 1414 are 407/16.9, 430/4.2, 3630/308, 3013/40 and $3630/308 \times 10^6$ L/mole.

The thrombin and/or factor Xa inhibitor preferably should spare fibrinolysis induced by urokinase, tissue plasminogen activator (t-PA) and streptokinase. This would be important to the therapeutic use of such an agent as an adjunct to streptokinase, tp-PA or urokinase thrombolytic therapy and to the use of such an agent as an endogenous fibrinolysis-sparing (with respect to t-PA and urokinase) antithrombotic agent. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Butler Farms, Clyde, N.Y., U.S.A.) by venipuncture into 3.8 percent citrate. Fibrinogen is prepared from fresh dog plasma and human fibrinogen is prepared from in-date ACD human blood at the fraction I-2 according to previous procedures and specification. Smith, *Biochem. J.*, 185, 1-11 (1980; and Smith, et al., *Biochemistry*, 11, 2958-2967, (1972). Human fibrinogen (98 percent pure/plasmin free) is from American Diagnostica, Greenwich, Conn. Radiolabeling of fibrinogen I-2 preparations is performed as previously reported. Smith, et al., *Biochemistry*, 11, 2958-2967, (1972). Urokinase is purchased from Leo Pharmaceuticals, Denmark, as 2200 Ploug units/vial. Streptokinase is purchased from Hoechst-Roussel Pharmaceuticals, Somerville, N.J.

Anticoagulant Activity

Materials

Dog plasma and rat plasma are obtained from conscious mixed-breed hounds (either sex, Butler Farms, Clyde, N.Y., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1-11 (1980); and Smith, et al., *Biochemistry*, 11, 2958-2967 (1972). Human fibrinogen is also purchased as 98 percent pure/plasmin free from American Diagnostica, Greenwich, Connecticut. Coagulation reagents Actin, Thromboplastin, Innovin and Human plasma are from Baxter Healthcare Corp., Dade Division, Miami, Fla. Bovine thrombin from Parke-Davis (Detroit, Mich.) is used for coagulation assays in plasma.

Methods

Anticoagulation Determinations

Coagulation assay procedures are as previously described. Smith, et al., *Thrombosis Research*, 50, 163-174 (1988). A CoAScreener coagulation instrument (American LABor, Inc.) is used for all coagulation assay measurements. The prothrombin time (PT) is measured by adding 0.05 mL saline and 0.05 mL Thromboplastin-C reagent or recombinant human tissue factor reagent (Innovin) to 0.05 mL test plasma. The activated partial thromboplastin time (APTT) is measured by incubation of 0.05 mL test plasma with 0.05 mL Actin reagent for 120 seconds followed by 0.05 mL $CaCl_2$ (0.02 M). The thrombin time (TT) is measured by adding 0.05 mL saline and 0.05 mL thrombin (10 NIH units/mL) to 0.05 mL test plasma. Thus, the plasma concentrations are three times the assay concentrations. The compounds of formula I are added to human or animal plasma over a wide range of concentrations to determine prolongation effects on the APTT, PT, and TT assays. Linear extrapolations are performed to estimate the concentrations required to double the clotting time for each assay. Compounds of the instant invention potently extended the prolongation times in the APTT and PT assays, for example in some cases, with assay concentrations necessary to double the APPT or PT of less than 1 μM.

Animals

Male Sprague Dawley rats (350-425 gm, Harlan Sprague Dawley Inc., Indianapolis, Ind.) are anesthetized with xylazine (20 mg/kg, s.c.) and ketamine (120 mg/kg, s.c.) or preferably are anesthetized using isoflurane anesthesia (2-3%, conveniently 2.5%, for surgery; 1.5-2.5%, conveniently 2.5%, for maintenance; flow rate kept at 0.5% throughout) and maintained on a heated water blanket (37° C.). The jugular vein(s) is cannulated to allow for infusions.

Arterio-Venous Shunt Model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol*, 77:29, 1982).

$FeCl_3$ Model of Arterial Injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. $FeCl_3$ hexahydrate is dissolved in water and the concentration (20 percent) is expressed in terms of the actual weight of $FeCl_3$ only. To injure the artery and induce thrombosis, 2.85 μL is pipetted into the cuff to bathe the artery above the thermocouple probe. Arterial occlusion is indicated by a rapid drop in temperature. The time to occlusion is reported in minutes and represents the elapsed time between application of $FeCl_3$ and the rapid drop in vessel temperature (see K. D. Kurz, *Thromb. Res.*, 60:269, 1990).

Ex Vivo Coagulation Parameters

Ex vivo plasma thrombin time (TT), prothrombin time (PT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 mL) is mixed with isotonic saline (0.1 mL) and bovine thrombin (0.1 mL, 30 U/mL in TRIS buffer; Parke Davis) at 37° C. For PT, to plasma (0.1 mL) mixed with isotonic saline (0.1 mL) is added PT reagent (0.1 mL, Dade, Thromboplastin-C); and the fibrometer started immediately after the addition of the final reagent. For APTT, plasma (0.1 mL) and APTT solution (0.1 mL, Organon Teknika) are incubated for 5 minutes (37° C.); and $CaCl_2$ (0.1 mL, 0.025 M) is added to start coagulation. Assays are done in duplicate and averaged.

Index of Bioavailability

Bioavailability studies may be conducted as follows. Compounds are administered as aqueous solutions, or as solutions in 5% PEG 200, to male Fisher rats, intravenously (iv) at 5 mg/kg via tail vein injection and orally (po) as aqueous solutions, or as a suspension in 5% acacia, to fasted animals at 20 mg/kg by gavage. Serial blood samples are obtained at 5, 30, 120, and 240 minutes postdose following intravenous administration and at 1, 2, 4, and 6 hours after oral dosing. Plasma is analyzed for drug concentration using an HPLC procedure involving C8 Bond Elute (Varian) cartridges for sample preparation and a methanol/30 nM ammonium acetate buffer (pH 4) gradient optimized for each compound. % Oral bioavailability is calculated by the following equation:

$$\% \text{ Oral bioavailability} = \frac{AUC\ po}{AUC\ iv} \times \frac{\text{Dose } iv}{\text{Dose } po} \times 100$$

where AUC is area under the curve calculated from the plasma level of compound over the time course of the experiment following oral (AUC po) and intravenous (AUC iv) dosing.

Compounds

For oral determinations, the compound may be administered orally, by gavage, as a suspension in 5% acaia to conscious fasted rats. The pretreatment time before flow is established through the shunt is selected based upon the peak apparent plasma concentration recorded in preliminary time course experiments that track apparent drug concentration in plasma following oral administration to conscious fasted rats, and typically varies between 1 to 5 hours. Animals used in antithrombotic efficacy experiments are anesthetized as described 15 minutes before the predetermined pretreatment time to allow for surgical preparation of the animals. Compound solutions are prepared fresh daily in normal saline or in 5% PEG200 in water for iv determinations and are injected as a bolus or are infused starting 15 minutes before and continuing throughout the experimental perturbation which is 15 minutes in the arteriovenous shunt model and 60 minutes in the $FeCl_3$ model of arterial injury and in the spontaneous thrombolysis model. Typically, bolus injection volume is 1 mL/kg for iv, and 5 mL/kg for po, and infusion volume is 3 mL/h. For a similar procedure run in the anesthesized rabbit, for example an infusion rate of 6.8 mL/h was used for one compound infused in 5% PEG200 in water.

Statistics

Results are expressed as means +/−SEM. One-way analysis of variance is used to detect statistically significant differences and then Dunnett's test is applied to determine which means are different. Significance level for rejection of the null hypothesis of equal means is P<0.05.

Animals

Male dogs (Beagles; 18 months-2 years; 12-13 kg, Marshall Farms, North Rose, New York 14516) are fasted overnight and fed Purina certified Prescription Diet (Purina Mills, St. Louis, Mo.) 240 minutes after dosing. Water is available ad libitum. The room temperature is maintained between 66-74° F.; 45-50 percent relative humidity; and lighted from 0600-1800 hours.

Pharmacokinetic Model.

Test compound is formulated immediately prior to dosing by making a suspension in a "wet granulaion" (povidone, 0.85 mg/mL; lactose, 15.0 mg/mL; and polysorbate 80, 65 µL in 250 mL water). Dogs are given a single 20 mg/kg (in 25 mL of wet granulation) dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are analyzed by HPLC MS. Plasma concentration of test compound is recorded and used to calculate the pharmacokinetic parameters: elimination rate constant, Ke; total clearance, Clt; volume of distribution, $V_D$; time of maximum plasma test compound concentration, Tmax; maximum concentration of test compound of Tmax, Cmax; plasma half-life, t0.5; and area under the curve, A.U.C.; fraction of test compound absorbed, F.

Canine Model of Coronary Artery Thrombosis

Male dogs (Beagles, as described above) are fasted overnight and dosed with test compound that is fomulated immediately prior to dosing by making a suspension in a "wet granulation" as described above. Dogs are given a single dose of 5, 10 or 20 mg/kg (in 25 mL of wet granulation) of test compound by oral gavage. Based on the pharmacokinetics of the test compound, dogs are dosed either 1 or 2 hours prior to anesthesia. Dogs are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3-4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40-50 percent inhibition of the hyperemic blood flow response observed after 10-s mechanical occlusion of the LCX. All hemodynamic and ECG measurements are recorded and analyzed with a data acquisition system (Notochord HEM data analysis system, Croissy, France).

Thrombus Formation and Compound Administration Regimens

Electrolytic injury of the intima of the LCX is produced by applying 100-µA direct current (DC) to the anode. The current is maintained for 60 min and then discontinued whether the vessel has occluded or not. Thrombus formation proceeds spontaneously until the LCX is totally occluded (determined as zero CBF and an increase in the S-T segment for a minimum of 30 minutes). The preparation is followed for 4 hours at which time the animal is euthanized and the thrombus is dissected from the LCX and weighed.

Hematology, Coagulation and Template Bleeding Time Determinations

Citrated blood (3 mL, 1 part 3.8% citrate:9 parts blood) is drawn before drug administration, at 60 min after administration, at 60 min after initiation of vessel injury and just prior to the end of the experiment. Whole blood cell counts, hemoglobin, and hematocrit values are determined on a 40-µL sample of the citrated whole blood with a hematology analyzer (Cell-Dyn 900, Sequoia-Turner, Mount View, Calif., U.S.A.). The remaining blood was cetrifuged at 3,000 g for 5 min to prepare cell-free plasma. Plasma clotting times, prothrombin time (PT) and activated partial thromoplastin times (APTT) were performed using standard Dade reagents and the Coa-Screener coagulation device (American Labor, Largo, Fla.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Dunnet's post hoc t test to determine the level of significance. Repeated-measures ANOVA are used to determine significant differences between time points during the experiments. Values are determined to be statistically different at least at the level of $p<0.05$. All values are mean±SEM. All studies are conducted in accordance with the guiding principles of the American Physiological Society. Further details regarding the procedures are described in Jackson, et al., *J. Cardiovasc. Pharmacol.*, (1993), 21, 587-599.

Compounds of the instant invention are potent anticoagulant and antithrombotic agents which exhibit particularly good plasma exposure following oral administration, as evidenced by standard pharmacokinetic/pharmcodynamic assays.

The following Examples are provided to further describe the invention and are not to be construed as limitations thereof. Resin based reagents used in the examples are commercially available or well described in the literature. The term "aldehyde resin" refers to a formylpolystyrene resin. See, for example, X. Beebe et at., *J. Amer. Chem. Soc.*, 114, 10061 (1992); J. M. Frechet and C. Schuerch, *J. Amer. Chem. Soc.*, 93, 492 (1971). Generally, see S. W. Kaldor and M. G. Siegel, *Current Opinion in Chem. Biol.*, 1, 101-106 (1997).

The abbreviations, symbols and terms used in the examples have the following meanings.

Ac=acetyl
Analysis=elemental analysis
aq=aqueous
Boc=t-butyloxycarbonyl
t-Bu=tert-butyl
Calcd=calculated
conc=concentrated
satd=saturated
DMF=dimethylformamide
DMSO=dimethylsulfoxide
EtOAc=ethyl acetate
Et$_2$O=diethyl ether
HOAc=acetic acid
EtOH=ethanol
Hex=hexanes
MeOH=methanol
NMP=N-methylpyrrolidone
TFA=trifluoroacetic acid
THF=tetrahydrofuran
Et$_3$N=triethyl amine
mCPBA=meta-chloroperbenzoic acid
SCX=strong cation exchange
HPLC=High Performance Liquid Chromatography (including RPHPLC, reversed phase HPLC)
IR=Infrared Spectrum
$^1$NMR=(proton) nuclear magnetic resonance spectrum
ES-MS=electron spray mass spectrum
IS-MS=ion spray mass spectrum
FD-MS=field desorption mass spectrum When indicated without data, $^1$NMR, IR or MS means a satisfactory spectrum was obtained.

EXAMPLE 1

Preparation of N-(4-Chlorophenyl)-2-[4-(N,N-dimethylamino)-2-(piperidin-4-yloxy)-benzoylamino] benzamide A. Methyl 2-hydroxy-4-(N,N-dimethylamino)benzoate To a solution of 2-hydroxy-4-(N,N-dimethylamino)benzoic acid (9.05 g, 50 mmol) and MeOH (100 mL) at 0° C. was added thionyl chloride (5.34 mL, 75 mmol) dropwise. The reaction was warmed to room temperature and refluxed for 14 hours. After cooling, ether was added to the mixture and the reaction was carefully quenched with satd NaHCO$_3$. The mixture was diluted with ether (200 mL) and partitioned. The organic layer was dried over MgSO$_4$ and the crude product was adsorbed onto silica gel. The crude product was chromatographed on silica gel (5% CH$_2$Cl$_2$/hexane to 25% CH$_2$Cl$_2$/hexane) and triturated with ether/hexane to give the desired product as a white solid (7.1 g, 73%).

$^1$NMR (300 MHz, DMSO-d$_6$): δ 10.90 (s, 1H), 7.65 (d, J=9.0 Hz, 1H), 6.23 (dd, J=2.3, 9.0 Hz, 1H), 6.15 (d, J=2.3 Hz, 1H), 3.88 (s, 3H), 3.02 (s, 6H). IS-MS, m/e: 196.2 (m+1). Analysis for C$_{10}$H$_{13}$NO$_3$: Calcd: C, 61.53; H, 6.71; N, 7.18; Found: C, 61.31; H, 6.62; N, 7.30.

B. 4-Hydroxy-1-tert-butoxycarbonylpiperidine

To a mixture of 4-hydroxypiperidine (60.69 g, 0.6 mol), 4-(dimethylamino)-pyridine (74 mg, 0.6 mmol), CH$_2$Cl$_2$ (150 mL), and THF (150 mL) was added di-tert-butyl dicarbonate (130.95 g, 0.6 mol). After stirring for 6 hours, the reaction was heated to 35° C. for 16 hours. More di-tert-butyl dicarbonate (13.09 g, 0.06 mol) in THF (20 mL) was added and the reaction was heated for 10 hours. After cooling, water and ether (1 L) were added and the mixture was stirred for 2 hours. The organic layer was partitioned, dried (MgSO$_4$), and concentrated in vacuo. The residue was crystallized from ether to give the desired product as a white solid (105 g, 87%).

$^1$NMR (300 MHz, DMSO-d$_6$): δ 3.85 (m, 3H), 3.04 (m, 2H), 1.88 (m, 2H), 1.56 (m, 2H), 1.25 (s, 9H). IS-MS, m/e: 202.0 (m+1).

C. Methyl 2-(1-tert-butoxycarbonylpiperidin-4-yloxy)-4-(N,N-dimethylamino)-benzoate To a mixture of methyl 2-hydroxy-4-(N,N-dimethylamino)benzoate (7.809 g, 40 mmol), 4-hydroxy-1-tert-butoxycarbonylpiperidine (8.048 g, 40 mmol), triphenylphosphine (11.02 g, 42 mmol), and THF (250 mL) at 0° C. was added diethyl azodicarboxylate (7.1 mL, 45.1 mmol), dropwise. The reaction was warmed to room temperature and stirred overnight. The reaction was concentrated, chromatographed (hexane to 30% EtOAc/hexane), and triturated with ether/hexane to give the desired product as a white solid (5.55 g, 37%).

$^1$NMR (300 MHz, DMSO-d$_6$): δ 8.60 (d, J=8.7 Hz, 1H), 6.85 (br s, 1H), 6.60 (d, J=8.7 Hz, 1H), 4.63 (m, 1H), 3.85 (s, 3H), 3.70-3.43 (m, 4H), 3.07 (s, 6H), 1.90 (m, 4H), 1.46 (s, 9H). IS-MS, m/e: 379 (m+1).

D. 2-(1-tert-Butoxycarbonylpiperidin-4-yloxy)-4-(N,N-dimethylamino)benzoic acid Potassium hydroxide (3.79 g, 67.5 mmol) in water (135 mL) was added to a mixture of methyl 2-(1-tert-butoxycarbonylpiperidin-4-yloxy)-4-(N,N-dimethylamino)-benzoate (5.11 g, 13.5 mmol) and ethanol. The reaction was heated to 70° C. for 14 hours. The ethanol was removed in vacuo. The resulting aqueous mixture was cooled to 5° C., acidified with satd citric acid, filtered with water wash, and vacuum dried to give the desired product as a white solid (4.65 g, 95%).

$^1$NMR (300 MHz, DMSO-d$_6$): δ 7.60 (d, J=6.6 Hz, 1H), 6.29 (dd, J=1.6, 6.6 Hz, 1H), 6.24 (s, 1H), 4.68 (br s, 1H), 3.48 (m, 4H), 2.93 (s, 6H), 1.76 (m, 2H), 1.63 (m, 2H), 1.37 (s, 9H). IS-MS, m/e: 365 (m+1).

E. N-(4-chlorophenyl)-2-aminobenzamide

A mixture of 20 g (123 mmol) isatoic anhydride (formed by treating anthranilic acid with phosgene) and 15.64 g (123 mmol) 4-chloroaniline was heated at 120° C. for 2 hours. The reaction was cooled to room temperature, mixed with CH$_2$Cl$_2$ and filtered.

The filtrate was purified by silica gel chromatography using 30% hexanes in CHCl$_3$ to recover 18.38 g (65%) of a white solid. This was recrystallized from EtOAc to give 11.16 g of a white solid.

$^1$NMR

F. 2-[4-(N,N-Dimethylamino)-2-[(1-tert-butoxycarbonylpiperidin-4-yloxy)-1-benzoylamino]-N-(4-chlorophenyl)benzamide The 2-(1-tert-butoxycarbonylpiperidin-4-yloxy)-4-(N,N-dimethylamino)benzoic acid (950 mg, 2.61 mmol) was dissolved in methylene chloride (15 mL). Pyridine (0.27 mL, 3.39 mmol) and DMF (1 drop) were added, followed by oxalyl chloride (0.27 mL, 3.13 mmol). Vigorous bubbling occurred. After 45 minutes, more pyridine (0.27 mL, 3.39 mmol) was added, followed by the N-(4-chlorophenyl)-2-amino-benzamide (645 mg, 2.61 mmol). The reaction was stirred for 2 hours and then diluted with methylene chloride and washed with 50% saturated aqueous sodium bicarbonate.

The organic layer was concentrated and purified by flash column chromatography (about 120 g silica, 100% CH$_2$Cl$_2$ to 10% EtOAc/CH$_2$Cl$_2$) to give the desired product (207 mg, 0.35 mmol, 13%).

$^1$NMR (300 MHz, CDCl$_3$): δ 8.48 (br s, 1H), 8.27 (d, J=8.4 Hz, 1H), 8.07 (d, J=9.0 Hz, 1H), 7.57 (m, 4H), 7.42 (m, 1H), 7.33 (m, 2H), 7.11 (m, 1H), 6.56 (m, 2H), 4.66 (m, 1H), 3.75 (m, 1H), 3.20 (m, 1H), 3.05 (m, 6H), 2.1 (m, 2H), 1.60 (m, 4H), 1.43 (s, 9H). IS-MS, m/e: 593 (m+1).

G. N-(4-Chlorophenyl)-2-[4-(N,N-dimethylamino)-2-(piperidin-4-yloxy)-benzoylamino]benzamide The 2-[4-(N,N-dimethylamino)-2-(1-tert-butoxycarbonylpiperidin-4-yloxy)-benzoylamino]-N-(4-chlorophenyl)benzamide (178 mg, 0.30 mmol) was dissolved in methylene chloride (2 mL) and TFA (1 mL). After 1 hour, the reaction was concentrated, diluted with methylene chloride, and washed with saturated aqueous sodium carbonate.

The organic layer was dried over sodium sulfate, filtered, and concentrated. The crude residue was purified by flash column chromatography (about 10 g silica, 10% EtOAc/CH$_2$Cl$_2$ to 3:2:20:75 MeOH/Et$_3$N/EtOAc/CH$_2$Cl$_2$) to give the desired product (122 mg, 0.25 mmol, 82%) as a white solid.

$^1$NMR (300 MHz, DMSO-d$_6$): 10.80 (br s, 1H), 10.60 (br s, 1H), 8.40 (d, J=8.3 Hz, 1H), 7.80-7.67 (m, 4H), 7.50 (t, J=4.9 Hz, 1H), 7.40 (d, J=9.0 Hz, 2H), 7.20 (t, J=7.1 Hz, 1H), 6.40 (dd, J=2.3, 9.0 Hz, 1H), 6.30 (m, 1H), 4.63 (m, 1H), 3.00 (s, 6H), 2.77 (m, 2H), 2.52 (m, 2H), 1.85 (m, 2H), 1.65 (m, 2H). IS-MS, m/e: 493.3 (m+1). Analysis for C$_{27}$H$_{29}$ClN$_4$O$_3$.0.5H$_2$O: Calcd: C, 64.60; H, 6.02; N, 11.16; Found: C, 64.57; H, 5.91; N, 11.17.

EXAMPLE 2

Preparation of N-(5-Chloropyridin-2-yl)-2-[4-(N,N-dimethylamino)-2-(piperidin-4-yloxy)benzoylamino]benzamide Hydrochloride

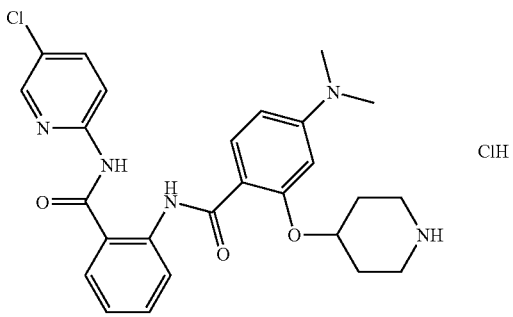

A. N-(5-Chloropyridin-2-yl)-2-nitrobenzamide

To a stirring solution of 2-amino-5-chloropyridine (3.7 g, 29 mmol) and pyridine (7.3 mL, 90 mmol) in dichloromethane (200 mL) was added 2-nitrobenzoyl chloride (5.7 g, 30 mmol). After stirring for 4 h, the solvents were removed in vacuo and the residue was partitioned between ethyl acetate and water. The layers were separated and the organic phase was washed again with water and once with brine, then dried with $MgSO_4$, filtered and partially concentrated in vacuo. The precipitate was filtered, washed with diethyl ether and dried in vacuo to give 6.4 g (79%) of an off-white solid.

$^1$NMR FD-MS, m/e 276.9 (m) Analysis for $C_{12}H_8ClN_3O_3$: Calcd: C, 51.91; H, 2.90; N, 15.13; Found: C, 52.61; H, 2.89; N, 15.29.

B. N-(5-Chloropyridin-2-yl)-2-aminobenzamide

To a solution of N-(5-chloropyridin-2-yl)-2-nitrobenzamide (2 g, 7.2 mmol) in THF (50 mL) and ethyl acetate (50 mL) was added Raney Ni (0.2 g) and the mixture was placed under hydrogen (4.1 bar) in a high pressure apparatus. After shaking overnight, the mixture was filtered and concentrated in vacuo and purified by flash chromatography to give 1.5 g (83%) of an off-white solid.

$^1$NMR

C. 2-[4-(N,N-Dimethylamino)-2-(1-tert-butoxycarbonylpiperidin-4-yloxy)-benzoylamino]-N-(5-chloropyridin-2-yl)benzamide To a mixture of 2-(1-tert-butoxycarbonylpiperidin-4-yloxy)-4-(N,N-dimethyl-amino)benzoic acid (950 mg, 2.61 mmol), pyridine (0.23 mL, 2.86 mmol), DMF (1 drop) and methylene chloride (15 mL) was added oxalyl chloride (0.24 mL, 2.73 mmol) dropwise. After 15 minutes, more pyridine (0.23 mL, 2.86 mmol) was added, followed by the N-(4-chlorophenyl)-2-aminobenzamide (645 mg, 2.61 mmol). The reaction was stirred for 1 hour, diluted with methylene chloride, washed with 50% saturated aqueous sodium bicarbonate, and dried over $Na_2SO_4$. The organic solution was concentrated, chromatographed (2000 g silica, 5% EtOAc/$CH_2Cl_2$ to 15% EtOAc/$CH_2Cl_2$), and triturated with ether to give the desired product (1.32 g, 83%).

$^1$NMR (300 MHz, $CDCl_3$): δ 8.57 (s, 1H), 8.51 (d, J=8.7 Hz, 1H), 8.24 (m, 2H), 8.04 (d, J=8.7 Hz, 1H), 7.76 (dd, J=2.4, 8.7 Hz, 1H), 7.64 (d, J=8.7 Hz, 1H), 7.55 (m, 1H), 7.20 (m, 1H), 6.47 (d, 8.7 Hz, 1H), 6.43 (br s, 1H), 4.65 (m, 1H), 3.86 (m, 1H), 3.17 (m, 1H), 3.05 (s, 6H), 2.06 (m, 2H), 1.60 (m, 4H), 1.45 (s, 9H). IS-MS, m/e: 594.5 (m+1). Analysis for $C_{31}H_{36}ClN_5O_5$. $0.5H_2O$: Calcd: C, 61.74; H, 6.18; N, 11.61; Found: C, 61.68; H, 6.15; N, 11.47.

D. 2-[4-(N,N-Dimethylamino)-2-(piperidin-4-yloxy)benzoylamino]-N-(5-chloro-pyridin-2-yl)benzamide Using a procedure similar to Example 1-G, 2-[4-(N,N-dimethylamino)-2-(1-tert-butoxycarbonylpiperidin-4-yloxy)benzoylamino]-N-(5-chloropyridin-2-yl)benzamide gave the desired product (638 mg, 60%) as a white solid after chromatography and $CH_2Cl_2$/ether trituration.

$^1$NMR IS-MS, m/e: 494.2 (m+1).

E. N-(5-Chloropyridin-2-yl)-2-[4-(N,N-dimethylamino)-2-(piperidin-4-yloxy)-benzoylamino]benzamide hydrochloride Purification by HPLC (Vydac, 5% $CH_3$ CN in 0.1% TFA/$H_2O$ to 70% $CH_3$ CN in 0.1% TFA/$H_2O$, t=31.2 m) of N-(5-chloropyridin-2-yl)-2-[4-(N,N-dimethylamino)-2-(piperidin-4-yloxy)benzoylamino]benzamide followed by treatment with HCl gave the desired salt as a white solid (118 mg, 44%).

$^1$NMR IS-MS, m/e: 494.0 (m+1).

EXAMPLE 3

Preparation of N-(5-Chloropyridin-2-yl)-2-[4-(N,N-dimethylamino)-2-(1-isopropyl-piperidin-4-yloxy)benzoylamino]benzamide Hydrochloride

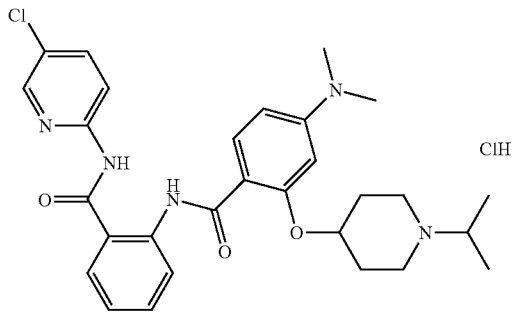

To a mixture of N-(5-chloropyridin-2-yl)-2-[4-(N,N-dimethylamino)-2-(piperidin-4-yloxy)benzoylamino]benzamide (250 mg, 0.51 mmol), acetone (0.07 mL, 1.0 mmol) and 20% AcOH/MeOH (2 mL) was added a solution of 0.25 M $NaCNBH_3$/MeOH (2 mL, 0.5 mmol). The reaction was stirred for 24 hours and then it was diluted with water and $CH_2Cl_2$. After partitioning, the organic layer was washed with 50% satd $Na_2CO_3$, dried over $Na_2SO_4$, and concentrated. The residue was HPLC chromatographed (Vydac, 5% $CH_3$ CN in 0.1% TFA/$H_2O$ to 70% $CH_3$ CN in 0.1% TFA/

H$_2$O, t=28.8 m) and then treated with HCl to give the desired product as a white solid (66 mg, 23%).

$^1$NMR IS-MS, m/e: 536.1 (m+1).

EXAMPLE 4

Preparation of N-(5-Chloropyridin-2-yl)-2-[4-(morpholin-4-yl)-2-(piperidin-4-yl-oxy)benzoylamino]benzamide

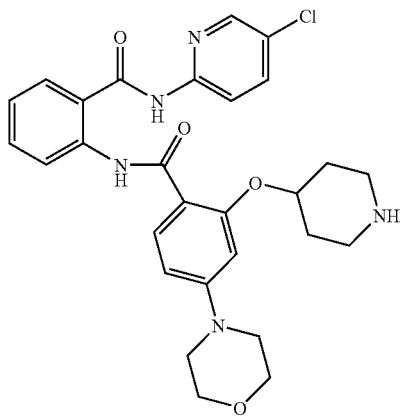

A. 4-Fluoro-2-hydroxybenzoic acid

Potassium carbonate (51.6 g, 373 mmol) was dried by heating at 200° C. for 12 hours. This was treated with 3-fluorophenol (16.5 g, 147 mmol) in a sealed container which was then pressurized with carbon monoxide at 61.2 bar. The reaction was heated to 175° C. for 5 hours. Subsequently, the reaction mixture was dissolved in water, acidified with concentrated hydrochloric acid, and filtered. The solid was washed with water, then hexanes. The solid was then dissolved in EtOAc, dried over magnesium sulfate, and concentrated to give 12 g of solid. This crude solid was purified by flash chromatography using CHCl$_3$/MeOH/HOAc 98:1:1 to give 11 g of a white solid which was recrystallized from toluene to give 9.5 g of the product as needles.

$^1$NMR FD-MS, m/e 155 (m−1) Analysis for C$_7$H$_5$FO$_3$.0.1C$_7$H$_8$.0.3H$_2$O: Calcd: C, 54.17; H, 3.78; Found: C, 54.12; H, 3.39.

B. Methyl 4-fluoro-2-hydroxybenzoate

A solution of 4-fluoro-2-hydroxybenzoic acid (9.8 g, 62.3 mmol) in benzene (100 mL) and MeOH (20 mL) was cooled in an ice bath and a 2 M hexane solution of trimethylsilyldiazomethane (50 mL) was added dropwise. The reaction was stirred overnight at ambient temperature, diluted with benzene (348 mL) and MeOH (39 mL), and treated with more of the trimethylsilyldiazomethane solution (15 mL). The mixture was concentrated in vacuo to dryness to give 10.4 g of an oil which crystallized.

$^1$NMR FD-MS, m/e 170 (m+) Analysis for C$_8$H$_7$FO$_3$: Calcd: C, 56.48; H, 4.15; Found: C, 56.17; H, 4.28.

C. Methyl 2-(1-tert-butoxycarbonylpiperidin-4-yloxy)-4-fluorobenzoate

Using a procedure analogous to Example 1-C, methyl 2-hydroxy-4-fluorobenzoate gave the desired product as a white solid (17.8 g, 67%).

$^1$NMR (300 MHz, CDCl$_3$) δ ppm: 7.85 (dd, J=6.9, 8.7 Hz, 1H), 6.68 (m, 2H), 4.58 (m, 1H), 3.87 (s, 3H), 3.57 (m, 4H), 1.86 (m, 4H), 1.47 (s, 9H). IS-MS, m/e: 354.3 (m+1). Analysis for C$_{18}$H$_{24}$FNO$_5$: Calcd: C, 61.18; H, 6.85; N, 3.96; Found: C, 61.14; H, 6.74; N, 4.01.

D. 2-(1-tert-Butoxycarbonylpiperidin-4-yloxy)-4-fluorobenzoic acid

A mixture of methyl-2-(1-tert-butoxycarbonylpiperidin-4-yloxy)-4-fluorobenzoate (3.05 g, 8.64 mmol), 1 M aq LiOH (15 mL, 15 mmol), MeOH (15 mL), and THF (45 mL) was stirred overnight. The reaction was diluted with EtOAc, washed with satd citric acid, dried over MgSO$_4$, concentrated, and triturated with ether to give the desired product as a white solid (2.23 g, 76%).

$^1$NMR (300 MHz, CDCl$_3$): δ 7.68 (m, 1H), 7.10 (d, J=8.7 Hz, 1H), 6.79 (m, 1H), 4.72 (m, 1H), 3.48 (m, 4H), 1.65 (m, 2H), 1.60 (m, 2H), 1.37 (s, 9H). IS-MS, m/e: 340 (m+1).

E. 2-[4-Fluoro-2-(1-tert-butoxycarbonylpiperidin-4-yloxy)benzoylamino]-N-(5-chloropyridin-2-yl)benzamide The 2-(1-tert-butoxycarbonylpiperidin-4-yloxy)-4-fluorobenzoic acid (507 mg, 2.05 mmol) was diluted with methylene chloride (20 mL). DMF (4 drops) and pyridine (0.2 mL, 2.47 mmol) were added, followed by oxalyl chloride (0.2 mL, 2.29 mmol). Vigorous bubbling occurred. After 1.5 hours, the reaction was concentrated in vacuo. The residue was diluted with methylene chloride (20 mL). N-(5-Chloropyridin-2-yl)-2-aminobenzamide (507 mg, 2.05 mmol) was added, followed by pyridine (0.2 mL, 2.47 mmol). After stirring overnight, the reaction was diluted with methylene chloride (100 mL) and washed with water (2×10 mL). The organic layer was dried over magnesium sulfate, filtered, and concentrated. The crude residue was purified by flash column chromatography (100% CH$_2$Cl$_2$ to 10% EtOAc/CH$_2$Cl$_2$) to give the desired product (992 mg, 1.74 mmol, 85%) as a white solid.

IR(CHCl$_3$): 1675, 1503, 1375, 1296 cm$^{-1}$. $^1$NMR (400 MHz, DMSO-d$_6$): δ 11.23 (s, 1H); 11.04 (s, 1H); 8.40 (d, J=2.8 Hz, 1H); 8.35 (d, J=8.4 Hz, 1H); 8.12 (d, J=9.2 Hz, 1H); 7.93-7.89 (m, 2H); 7.79 (d, J=8.0 Hz, 1H); 7.23 (m, 2H); 6.89 (t, J=8.4 Hz, 1H); 4.79 (m, 1H); 3.70 (m, 2H); 3.01 (m, 2H); 1.84 (m, 4H); 1.32 (s, 9H). IS-MS, m/e 569.4 (m+1).

F. 2-[4-(Morpholin-4-yl)-2-(1-tert-butoxycarbonylpiperidin-4-yloxy)benzoylamino]-N-(5-chloropyridin-2-yl)benzamide The 2-[4-fluoro-2-(1-tert-butoxycarbonylpiperidin-4-yloxy)benzoylamino]-N-(5-chloropyridin-2-yl)benzamide (203 mg, 0.35 mmol) was diluted with morpholine (4 mL, 45.9 mmol). The mixture was heated to 129° C. for 2 days. The reaction was diluted with methylene chloride (100 mL) and washed with water (2×10 mL). The aqueous layers were combined and extracted with ethyl acetate (100 mL). The organic layers were combined, dried over sodium sulfate, filtered, and concentrated. The crude residue was purified by flash column chromatography (about 25 g silica, 10% EtOAc/

$CH_2Cl_2$ to 20% $EtOAc/CH_2Cl_2$) to give the desired product (125 mg, 0.20 mmol, 56%) as a white solid.

$^1$NMR (300 MHz, DMSO-$d_6$): δ 11.19 (s, 1H); 10.89 (s, 1H); 8.39 (s, 1H); 8.32 (d, J=8.1 Hz, 1H); 8.13 (d, J=8.7 Hz, 1H); 7.90 (d, J=9.0 Hz, 1H); 7.74 (t, J=8.3 Hz, 1H); 7.50 (t, J=7.7 Hz, 1H); 7.15 (t, J=7.5 Hz, 1H); 6.59 (s, 2H); 4.80 (m, 1H); 3.70 (m, 4H); 3.29 (m, 4H); 3.22 (m, 2H); 3.00 (m, 2H); 1.91-1.75 (m, 4H); 1.31 (s, 9H). IS-MS, m/e 636.2 (m+1).

G. N-(5-Chloropyridin-2-yl)-2-[4-(morpholin-4-yl)-2-(piperidin-4-yloxy)-benzoylamino]benzamide The 2-[4-(morpholin-4-yl)-2-(1-tert-butoxycarbonylpiperidin-4-yloxy)-benzoylamino]-N-(5-chloropyridin-2-yl)benzamide (164 mg, 0.26 mmol) was dissolved in TFA (3 mL). After 5 minutes, the reaction was concentrated in vacuo. The residue was diluted with methylene chloride (100 mL) and washed with saturated aqueous sodium carbonate. The organic layer was dried over sodium sulfate, filtered, and concentrated to give the desired product (138 mg, 0.26 mmol, 100%).

$^1$NMR (300 MHz, DMSO-$d_6$): δ 11.16 (s, 1H); 10.89 (s, 1H); 8.41 (d, J=2.4 Hz, 1H); 8.29 (d, J=8.4 Hz, 1H); 8.11 (d, J=9.0 Hz, 1H); 7.93 (dd, J=9.0, 2.7 Hz, 1H); 7.77 (d, J=8.1 Hz, 1H); 7.71 (d, J=8.7 Hz, 1H); 7.53 (t, J=7.8 Hz, 1H); 7.17 (t, J=7.5 Hz, 1H); 6.63 (d, J=11.7, 1H); 6.61 (s, 1H); 4.90 (m, 1H); 3.70 (m, 4H); 3.24-2.99 (m, 8H); 2.02 (m, 4H). IS-MS, m/e 536.3 (m+1). Analysis for $C_{28}H_{30}ClN_5O_4 \cdot H_2O$: Calcd: C, 60.70; H, 5.82; N, 12.64; Found: C, 60.83; H, 5.83; N, 12.25.

EXAMPLE 5

Preparation of N-(5-Chloropyridin-2-yl)-2-[2-(piperidin-4-yloxy)-4-(pyrrolidin-1-yl)-benzoylamino]benzamide

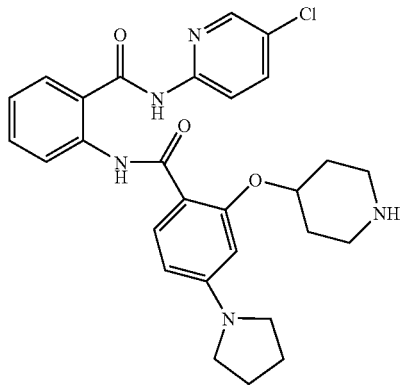

A. 2-[4-(Pyrrolidin-1-yl)-2-(1-tert-butoxycarbonylpiperidin-4-yloxy)benzoylamino]-N-(5-chloropyridin-2-yl)benzamide Using methods substantially equivalent to those described in example 4-F except that the reaction was heated to 80° C., 2-[4-(pyrrolidin-1-yl)-2-(1-tert-butoxycarbonyl-piperidin-4-yloxy)benzoylamino]-N-(5-chloropyridin-2-yl)benzamide (101 mg, 0.16 mmol, 90%) was prepared from 2-[4-fluoro-2-(1-tert-butoxycarbonylpiperidin-4-yloxy)-benzoylamino]-N-(5-chloropyridin-2-yl)benzamide and pyrrolidine.

$^1$NMR (400 MHz, DMSO-$d_6$): δ 11.18 (s, 1H); 10.83 (s, 1H); 8.39 (d, J=2.8 Hz, 1H); 8.31 (d, J=8.4 Hz, 1H); 8.15 (d, J=8.8 Hz, 1H); 7.90 (dd, J=8.8, 2.8 Hz, 1H); 7.73 (m, 2H); 7.49 (t, J=7.6 Hz, 1H); 7.13 (t, J=7.4 Hz, 1H); 6.22 (d, J=8.8, 1H); 6.15 (s, 1H); 4.78 (m, 1H); 3.69 (m, 2H); 3.27 (m, 4H); 3.00 (m, 2H); 1.93-1.82 (m, 8H); 1.32 (s, 9H). IS-MS, m/e 620.1 (m+1).

B. N-(5-Chloropyridin-2-yl)-2-[2-(piperidin-4-yloxy)-4-(pyrrolidin-1-yl)benzoylamino]benzamide Using methods substantially equivalent to those described in example 4-G, N-(5-chloropyridin-2-yl)-2-[2-(piperidin-4-yloxy)-4-(pyrrolidin-1-yl)benzoylamino]-benzamide (39 mg, 0.07 mmol, 76%) was prepared from 2-[4-(pyrrolidin-1-yl)-2-(1-tert-butoxycarbonylpiperidin-4-yloxy)benzoylamino]-N-(5-chloropyridin-2-yl)benzamide.

IR(KBr): 1603, 1502, 1375, 1292 $cm^{-1}$. $^1$NMR (400 MHz, DMSO-$d_6$): δ 10.77 (s, 1H); 8.40 (d, J=2.0 Hz, 1H); 8.36 (d, J=8.4 Hz, 1H); 8.19 (d, J=9.2 Hz, 1H); 7.93 (dd, J=8.8, 2.8 Hz, 1H); 7.72 (m, 2H); 7.49 (t, J=8.0 Hz, 1H); 7.13 (t, J=7.6 Hz, 1H); 6.21 (d, J=9.2 Hz, 1H); 6.12 (s, 1H); 4.60 (m, 1H); 2.79 (m, 2H); 2.50 (m, 6H); 1.86 (m, 6H); 1.65 (m, 2H). IS-MS, m/e 520.2 (m+1). Analysis for $C_{28}H_{30}ClN_5O_3 \cdot 1.1H_2O$: Calcd: C, 62.30; H, 6.01; N, 12.97; Found: C, 62.14; H, 5.52; N, 12.59.

EXAMPLE 6

Preparation of 2-[2-(1-tert-Butoxycarbonylpiperidin-4-yloxy)-4-(piperidin-1-yl)-benzoylamino]-N-(5-chloropyridin-2-yl)benzamide

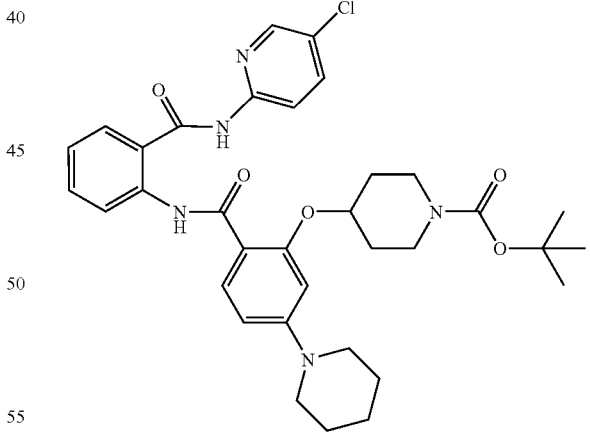

Using methods substantially equivalent to those described in example 4-F except that the reaction was heated to 106° C., 2-[4-(piperidin-1-yl)-2-(1-tert-butoxycarbonyl-piperidin-4-yloxy)benzoylamino]-N-(5-chloropyridin-2-yl)benzamide (200 mg, 0.32 mmol, 44%) was prepared from 2-[4-fluoro-2-(1-tert-butoxycarbonylpiperidin-4-yloxy)-benzoylamino]-N-(5-chloropyridin-2-yl)benzamide and piperidine.

$^1$NMR (300 MHz, DMSO-d$_6$): δ 11.18 (s, 1H); 10.85 (s, 1H); 8.39 (d, J=2.4 Hz, 1H); 8.31 (d, J=8.4 Hz, 1H); 8.14 (d, J=9.0 Hz, 1H); 7.90 (dd, J=9.2, 2.6 Hz, 1H); 7.72 (d, J=8.7 Hz, 2H); 7.49 (t, J=7.7 Hz, 1H); 7.14 (t, J=7.8 Hz, 1H); 6.57 (d, J=9.9, 1H); 6.54 (s, 1H); 4.81 (m, 1H); 3.67 (m, 2H); 3.29 (m, 4H); 3.00 (m, 2H); 1.85 (m, 4H); 1.54 (m, 6H); 1.31 (s, 9H). IS-MS, m/e 634.3 (m+1). Analysis for C$_{34}$H$_{40}$ClN$_5$O$_5$: Calcd: C, 64.39; H, 6.36; N, 11.0; Found: C, 64.66; H, 6.37; N, 10.95.

EXAMPLE 7

Preparation of N-(5-Chloropyridin-2-yl)-2-[4-(piperidin-1-yl)-2-(piperidin-4-yloxy)-benzoylamino] benzamide Dihydrochloride (Hydrate)

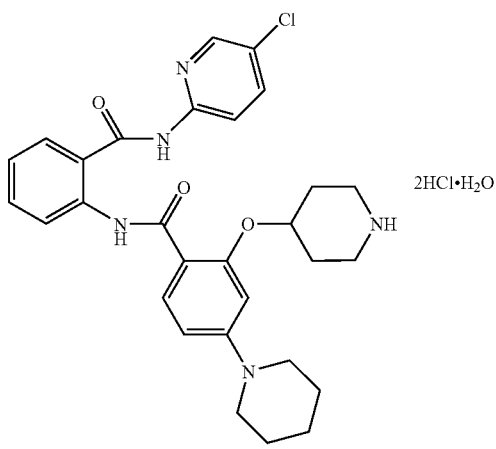

Using methods substantially equivalent to those described in example 4-G, N-(5-chloropyridin-2-yl)-2-[4-(piperidin-1-yl)-2-(piperidin-4-yloxy)benzoylamino]-benzamide (144 mg, 0.27 mmol, 100%) was prepared from 2-[4-(piperidin-1-yl)-2-(1-tert-butoxycarbonylpiperidin-4-yloxy)benzoylamino]-N-(5-chloropyridin-2-yl)-benzamide. The hydrochloride salt was prepared by treating the free base with 1 N HCl in MeOH.

$^1$NMR (300 MHz, DMSO-d$_6$): δ 11.15 (s, 1H); 10.88 (s, 1H); 8.40 (d, J=2.4 Hz, 1H); 8.27 (d, J=8.1 Hz, 1H); 8.12 (d, J=9.0 Hz, 1H); 7.94 (dd, J=8.9, 2.3 Hz, 1H); 7.76 (m, 3H); 7.53 (d, J=7.5 Hz, 1H); 7.18 (t, J=7.5 Hz, 1H); 6.85 (m, 3H); 4.90 (m, 1H); 3.13 (m, 2H); 3.02 (m, 2H); 2.10-1.98 (m, 4H); 1.59 (m, 6H). IS-MS, m/e 534.2 (m+1). Analysis for C$_{29}$H$_{32}$ClN$_5$O$_3$.2HCl.H$_2$O: Calcd: C, 56.55; H, 5.73; N, 11.37; Found: C, 56.67; H, 5.52; N, 11.20.

EXAMPLE 8

Preparation of 2-[4-(tert-Butyl)-2-(3,3-dimethylpiperidin-4-yloxy)benzoylamino]-N-(5-chloropyridin-2-yl)benzamide Trifluoracetate

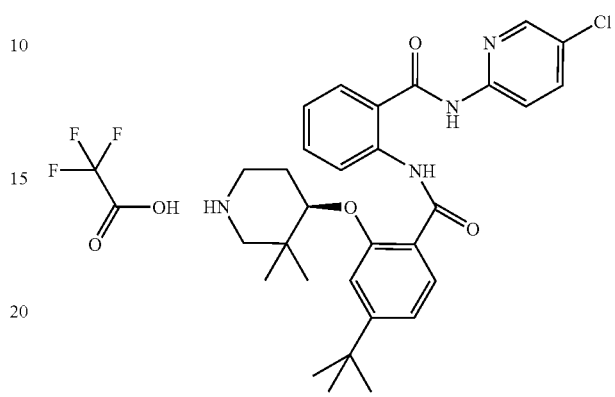

A. 3-(tert-Butyl)methoxymethylphenyl ether

A dry reaction flask equipped with a magnetic stirring bar and a rubber septum was charged with 3-tert-butylphenol (15.02 g, 100 mmol), N,N-diisopropylethylamine (34.83 mL, 200 mmol) and CH$_2$Cl$_2$. The reaction mixture was cooled to 0° C. Methyl chloromethyl ether (8.96 mL, 118 mmol) was added under N$_2$ to the reaction mixture over a period of 20 min. The reaction was stirred at 0° C. for 1 h and at room temperature for 2 h. The reaction was then quenched with H$_2$O (1000 mL) and the organic layer was separated and washed with H$_2$O (200 mL). The organic solution was dried (Na$_2$SO$_4$) and concentrated. The residue was dissolved in CH$_2$Cl$_2$ (500 mL) and extracted with 2 N NaOH (500 mL). The organic layer was dried (Na$_2$SO$_4$) and the solvent was removed under reduced pressure to obtain the desired product (10.44 g, 54%), TLC Rf: 0.75 (20% EtOAc/n-hexanes).

$^1$NMR (400 MHz, CDCl$_3$): δ 7.23 (m, 1H); 7.04 (bm, 2H); 6.87 (m, 1H); 5.17 (s, 2H); 3.48 (s, 3H); 1.30 (s, 9H).

B. 4-tert-Butyl-2-(methoxymethoxy)benzoic acid

A dry reaction flask equipped with a magnetic stirring bar and a addition funnel was charged with 3-(tert-butyl)methoxymethylphenyl ether (10.40 g, 53.60 mmol) and ethyl ether (200 mL) under N$_2$. The reaction flask was cooled to 0° C. Then tert-BuLi (1.7 M, pentane, 34.68 mL, 58.96 mmol) was added over a period of 20 min using an addition funnel. The reaction was stirred at 0° C. for 2 h. Carbon dioxide (gas) was bubbled into this turbid solution until it became clear. The reaction was stirred for an additional 2 h at room temperature. The reaction was quenched with H$_2$O (100 mL), stirred for 30 minutes, acidified with conc HCl (to pH 4-5), and extracted with ethyl ether (3×300 mL). The organic solution was dried (Na$_2$SO$_4$) and the solvent was removed. The resulting residue containing the desired acid was dissolved in ethyl ether (300 mL) and extracted with 2 N NaOH (3×75 mL). The aqueous alkaline solution was acidified with conc HCl (to pH 6). The resulting colorless solid was filtered and dried to obtain 8.24 g (65%) of the requisite acid; mp: 72° C., TLC Rf: 0.08 (40% EtOAc/n-hexanes).

¹NMR (400 MHz, CDCl₃) δ 10.7 (bs, 1H); 7.86 (dd, 1H, J=4 and 8.4 Hz); 7.07 (bd, 1H); 6.99 (dd, 1H, J=2 and 6.4 Hz); 5.22 (s, 2H); 3.37 (s, 3H); 1.13 (s, 9H).

C. Methyl 4-tert-butyl-2-hydroxybenzoate

A dry reaction flask equipped with a stirring bar and a rubber septum was charged with 4-tert-butyl-2-(methoxymethoxy)benzoic acid (11.9 g, 50 mmol) and MeOH (166 mL). The solution was cooled to 0° C. and dry HCl gas was bubbled into the reaction. The reaction color changed from faint yellow to peach and again back to faint yellow. The reaction mixture was refluxed for 18 h, cooled to room temperature, and the solvent was removed. The resulting thick oil was diluted with CH₂Cl₂ (100 mL) and washed with H₂O (100 mL) and 5% aqueous NaHCO₃ solution (2×50 mL). The organic solution was dried (Na₂SO₄) and the solvent was removed to obtain the requisite compound (9.10 g, 87%) as a colorless liquid, TLC Rf: 0.77 (10% EtOAc/n-hexanes).

¹H NMR (400 MHz, CDCl₃) δ 10.66 (s, 1H); 7.72 (d, 1H, J=8.4 Hz); 6.97 (d, 1H, J=2 Hz); 6.90 (dd, 1H, J=2 and 8.4 Hz); 3.91 (s, 3H); 1.29 (s, 9H).

D. 1-Boc-3,3-Dimethylpiperidin-4-one

To a stirring solution of 1-Boc-piperidin-4-one (10.28 g, 51.6 mmol) in THF (170 mL) at −78° C. was added via syringe a solution of lithium hexamethyldisilazide (1 M in hexanes, 54.2 mL, 54.2 mmol), followed 20 min later by methyl iodide (3.53 mL, 56.7 mmol). After an additional 2 h, the cooling bath was removed and the solution was allowed to warm to room temperature. After an additional 10 h, the solvent was removed in vacuo and the residue was flushed through a pad of silica gel with ethyl acetate and then concentrated in vacuo. The residue was then chromatographed, eluting with a gradient from 5% ethyl acetate in hexanes through 25% ethyl acetate in hexanes. The product containing fractions (clean only) were combined and concentrated in vacuo to give 0.54 g (5%) of the title compound.

¹NMR

E. 1-Boc-3,3-dimethylpiperidin-4-ol

To a stirring solution of 1-Boc-3,3-dimethylpiperidin-4-one (0.48 g, 2.1 mmol) in methanol (20 mL) at 0° C., was added sodium borohydride (0.096 g, 2.5 mmol). After 1 h, satd aq ammonium chloride (1 mL) was added and the solution was concentrated in vacuo. The residue was flushed through a pad of silica gel, eluting with ethyl acetate and the filtrate was concentrated in vacuo to give 0.46 g (96%) of a clear colorless oil.

¹NMR IS-MS, m/e 230.1 (m+1)

F. Methyl 4-tert-butyl-2-(1-Boc-3,3-dimethylpiperidin-4-yloxy)benzoate

By methods substantially equivalent to those described in Example 1-C, methyl 4-tert-butyl-2-(1-Boc-3,3-dimethylpiperidin-4-yloxy)benzoate (0.058 g, 6%) was prepared from methyl 4-tert-butyl-2-hydroxybenzoate and 1-Boc-3,3-dimethylpiperidin-4-ol.

¹NMR IS-MS, m/e 420.1 (m+1)

G. 4-tert-Butyl-2-(1-Boc-3,3-dimethylpiperidin-4-yloxy)benzoic acid

By methods substantially equivalent to those described in Example 1-D, 4-tert-butyl-2-(1-Boc-3,3-dimethylpiperidin-4-yloxy)benzoic acid (0.045 g, 85%) was prepared from methyl 4-tert-butyl-2-(1-Boc-3,3-dimethylpiperidin-4-yloxy)benzoate.

¹NMR IS-MS, m/e 406.1 (m+1)

H. 2-[4-(tert-Butyl)-2-(3,3-dimethylpiperidin-4-yloxy)benzoylamino]-N-(5-chloropyridin-2-yl)benzamide trifluoroacetate By methods substantially equivalent to those described in Example 1-F and 1-G, 2-[4-(tert-butyl)-2-(3,3-dimethylpiperidin-4-yloxy)benzoylamino]-N-(5-chloropyridin-2-yl) benzamide trifluoroacetate (3.5 mg, 5%) was prepared from 4-tert-butyl-2-(1-Boc-3,3-dimethylpiperidin-4-yloxy)benzoic acid and N-(5-chloropyridin-2-yl)-2-aminobenzamide.

¹NMR IS-MS, m/e 535.1 (m+1)

EXAMPLE 9

Preparation of 2-[2-(1-tert-Butoxycarbonylpiperidin-4-yloxy)-4-(3-hydroxy-pyrrolidin-1-yl)benzoylamino]-N-(5-chloropyridin-2-yl)benzamide

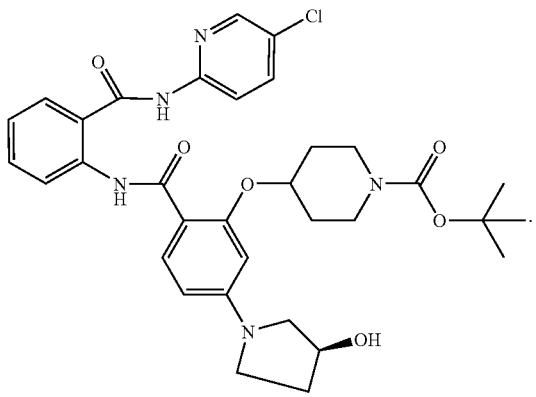

Using methods substantially equivalent to those described in example 4-F except that the workup used saturated aqueous citric acid instead of water, 2-[2-(1-tert-butoxy-carbonylpiperidin-4-yloxy)-4-(3-hydroxypyrrolidin-1-yl)benzoylamino]-N-(5-chhloro-pyridin-2-yl)benzamide (160 mg, 0.25 mmol, 47%) was prepared from 2-[4-fluoro-2-(1-tert-butoxycarbonylpiperidin-4-yloxy)benzoylamino]-N-(5-chloropyridin-2-yl)-benzamide and 3-hydroxypyrrolidine.

¹NMR (300 MHz, DMSO-d₆): δ 11.17 (s, 1H); 10.83 (s, 1H); 8.39 (d, J=2.1 Hz, 1H); 8.31 (d, J=8.7 Hz, 1H); 8.14 (d, J=9.0 Hz, 1H); 7.90 (dd, J=9.0, 2.4 Hz, 1H); 7.73 (m, 2H); 7.48 (t, J=7.7 Hz, 1H); 7.13 (t, J=7.4 Hz, 1H); 6.19 (d, J=9.0, 1H); 6.13 (s, 1H); 4.98 (d, J=3.6 Hz, 1H); 4.78 (m, 1H); 4.37 (br s, 1H); 3.69 (m, 2H); 3.45-3.11 (m, 4H); 3.00 (m, 2H); 1.89 (m, 6H); 1.32 (s, 9H). IS-MS, m/e 636.2 (m+1). Analysis for C₃₃H₃₈ClN₅O₆: Calcd: C, 62.31; H, 6.02; N, 11.01; Found: C, 62.07; H, 5.84; N, 11.02.

EXAMPLE 10

Preparation of N-(5-Chloropyridin-2-yl)-2-[4-(3-hydroxypyrrolidin-1-yl)-2-(piperidin-4-yloxy)benzoylamino]benzamide

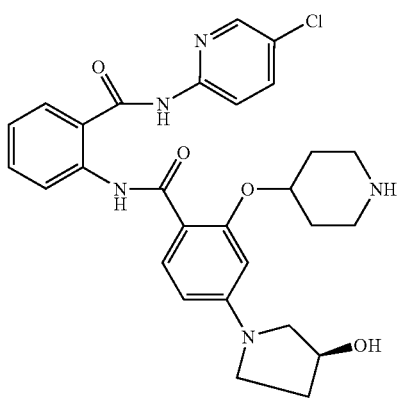

Using methods substantially equivalent to those described in example 4-G, N-(5-chloropyridin-2-yl)-2-[4-(3-hydroxypyrrolidin-1-yl)-2-(piperidin-4-yloxy)benzoylamino]-benzamide (72 mg, 0.13 mmol, 67%) was prepared from 2-[2-(1-tert-butoxycarbonyl-piperidin-4-yloxy)-4-(3-hydroxypyrrolidin-1-yl)benzoylamino]-N-(5-chloropyridin-2-yl)-benzamide.
$^1$NMR (300 MHz, DMSO-$d_6$): δ 11.15 (s, 1H); 10.84 (s, 1H); 8.41 (d, J=1.8 Hz, 1H); 8.28 (d, J=8.1 Hz, 1H); 8.11 (d, J=9.0 Hz, 1H); 7.93 (dd, J=8.7, 2.4 Hz, 1H); 7.75 (d, J=7.8 Hz, 1H); 7.70 (d, J=9.0 Hz, 1H); 7.51 (t, J=7.5 Hz, 1H); 7.15 (t, J=7.5 Hz, 1H); 6.23 (d, J=9.0, 1H); 6.15 (s, 1H); 4.89 (m, 1H); 4.38 (m, 1H); 3.58-3.01 (m, 8H); 2.06-1.90 (m, 6H). IS-MS, m/e 536.2 (m+1). Analysis for $C_{28}H_{30}ClN_5O_4$.TFA.1.5$H_2O$: Calcd: C, 53.22; H, 5.06; N, 10.34; Found: C, 53.43; H, 4.74; N, 10.08.

EXAMPLE 11

Preparation of N-(5-Chloropyridin-2-yl)-2-[4-(4-methylpiperazin-1-yl)-2-(piperidin-4-yloxy)benzoylamino]benzamide Dihydrochloride

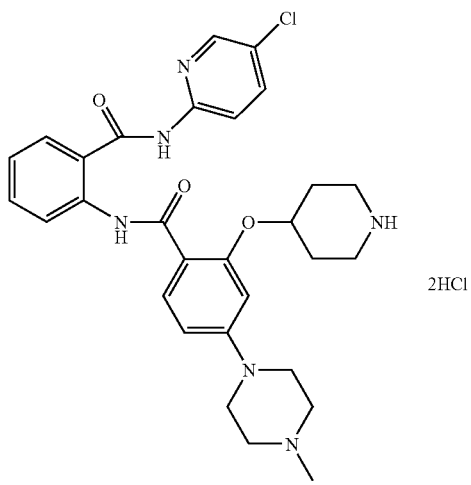

A. 2-[4-(4-Methylpiperazin-1-yl)-2-(1-tert-butoxycarbonylpiperidin-4-yloxy)-benzoylamino]-N-(5-chloropyridin-2-yl)benzamide Using methods substantially equivalent to those described in Example 4-F, 2-[4-(4-methylpiperazin-1-yl)-2-(1-tert-butoxycarbonylpiperidin-4-yloxy)benzoylamino]-N-(5-chloropyridin-2-yl)benzamide (132 mg, 0.20 mmol, 60%) was prepared from 2-[4-fluoro-2-(1-tert-butoxycarbonylpiperidin-4-yloxy)benzoylamino]-N-(5-chloro-pyridin-2-yl)benzamide and 1-methylpiperazine.
$^1$NMR (400 MHz, DMSO-$d_6$): δ 11.19 (s, 1H); 10.88 (s, 1H); 8.39 (d, J=3.2 Hz, 1H); 8.32 (d, J=8.4 Hz, 1H); 8.14 (d, J=8.8 Hz, 1H); 7.90 (dd, J=9.0, 3.0 Hz, 1H); 7.74 (m, 2H); 7.50 (t, J=8.0 Hz, 1H); 7.15 (t, J=7.4 Hz, 1H); 6.59 (m, 2H); 4.81 (m, 1H); 3.67 (m, 2H); 3.27 (m, 2H); 3.00 (m, 4H); 2.47 (s, 3H); 2.22 (m, 4H); 1.86 (m, 4H); 1.32 (s, 9H). IS-MS, m/e 649.5 (m+1). Analysis for $C_{34}H_{41}ClN_6O_5$: Calcd: C, 62.91; H, 6.37; N, 12.95; Found: C, 62.62; H, 6.43; N, 12.93.

B. N-(5-Chloropyridin-2-yl)-2-[4-(4-methylpiperazin-1-yl)-2-(piperidin-4-yloxy)-benzoylamino]benzamide dihydrochloride Using methods substantially equivalent to those described in example 4-G, N-(5-chloropyridin-2-yl)-2-[4-(4-methylpiperazin-1-yl)-2-(piperidin-4-yloxy)-benzoylamino]benzamide was prepared from 2-[4-(4-methylpiperazin-1-yl)-2-(1-tert-butoxycarbonylpiperidin-4-yloxy)benzoylamino]-N-(5-chloropyridin-2-yl)benzamide.

The impure product was purified by RPHPLC to give the dihydrochloride salt (66 mg, 0.11 mmol, 26%).
$^1$NMR (300 MHz, DMSO-$d_6$): δ 11.17 (s, 1H); 10.91 (s, 1H); 8.41 (d, J=2.4 Hz, 1H); 8.30 (d, J=8.4 Hz, 1H); 8.10 (d, J=9.0 Hz, 1H); 7.94 (dd, J=8.9, 2.6 Hz, 1H); 7.79 (d, J=7.5 Hz, 1H); 7.72 (d, J=8.7 Hz, 1H); 7.54 (t, J=8.0 Hz, 1H); 7.18 (t, J=7.8 Hz, 1H); 6.68 (m, 2H); 4.93 (m, 2H); 4.03 (m, 2H); 3.53-2.98 (m, 10H); 2.79 (d, J=3.6 Hz, 1H); 2.46 (s, 3H); 2.04 (m, 4H). IS-MS, m/e 549.3 (m+1). Analysis for $C_{29}H_{33}ClN_6O_3$.2HCl.0.5$H_2O$: Calcd: C, 55.20; H, 5.75; N, 13.32; Found: C, 55.65; H, 5.34; N, 13.13.

EXAMPLE 12

Preparation of 2-[2-(1-tert-Butoxycarbonylpiperidin-4-yloxy)-4-(3-hydroxy-piperidin-1-yl)benzoylamino]-N-(5-chloropyridin-2-yl)benzamide

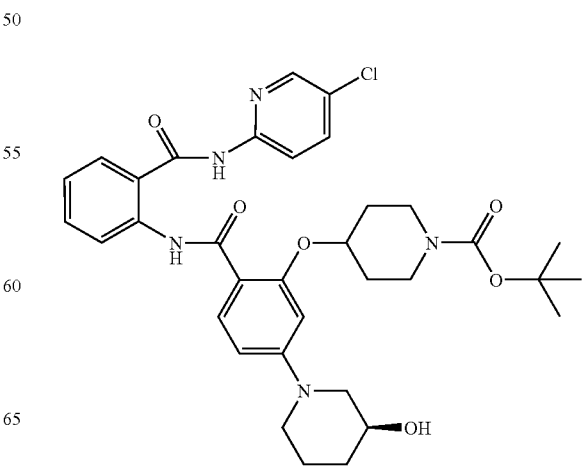

Using methods substantially equivalent to those described in Example 4-F, except that the reaction was quenched with water and the resulting precipitate was collected, 2-[2-(1-tert-butoxycarbonylpiperidin-4-yloxy)-4-(3-hydroxypiperidin-1-yl)-benzoylamino]-N-(5-chloropyridin-2-yl)-benzamide (166 mg, 0.26 mmol, 34%) was prepared from 2-[4-fluoro-2-(1-tert-butoxycarbonylpiperidin-4-yloxy)benzoylamino]-N-(5-chloropyridin-2-yl)benzamide and 3-hydroxypiperidine.

$^1$NMR (300 MHz, DMSO-$d_6$): δ 11.18 (s, 1H); 10.85 (s, 1H); 8.39 (d, J=1.5 Hz, 1H); 8.31 (d, J=8.4 Hz, 1H); 8.14 (d, J=9.0 Hz, 1H); 7.90 (dd, J=9.2, 1.7 Hz, 1H); 7.72 (d, J=8.4 Hz, 2H); 7.49 (t, J=7.5 Hz, 1H); 7.17 (t, J=7.5 Hz, 1H); 6.53 (m, 2H); 4.81 (m, 2H); 3.72-2.68 (m, 8H); 1.90-1.69 (m, 8H); 1.31 (s, 9H). IS-MS, m/e 650.4 (m+1). Analysis for $C_{34}H_{40}ClN_5O_6$: Calcd: C, 62.81; H, 6.20; N, 10.77; Found: C, 62.58; H, 5.92; N, 11.07.

EXAMPLE 13

Preparation of N-(5-Chloropyridin-2-yl)-2-[4-(3-hydroxypiperidin-1-yl)-2-(piperidin-4-yloxy)benzoylamino]benzamide

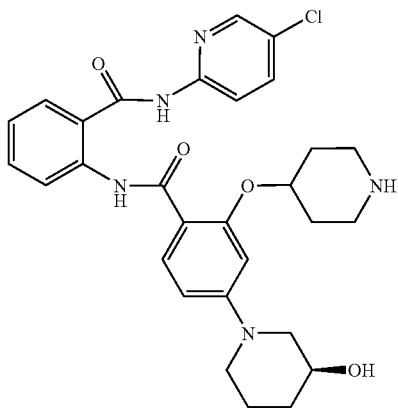

Using methods substantially equivalent to those described in example 4-G, N-(5-chloropyridin-2-yl)-2-[4-(3-hydroxypiperidin-1-yl)-2-(piperidin-4-yloxy)-benzoylamino]benzamide (67 mg, 0.12 mmol, 53%) was prepared from 2-[2-(1-tert-butoxycarbonylpiperidin-4-yloxy)-4-(3-hydroxypiperidin-1-yl)benzoylamino]-N-(5-chloropyridin-2-yl)-benzamide.

$^1$NMR (300 MHz, DMSO-$d_6$): δ 11.16 (s, 1H); 10.87 (s, 1H); 8.42 (d, J=2.1 Hz, 1H); 8.29 (d, J=8.1 Hz, 1H); 8.11 (d, J=9.0 Hz, 1H); 7.93 (dd, J=11.49, 2.4 Hz, 1H); 7.77 (d, J=7.2 Hz, 1H); 7.68 (d, J=9.0 Hz, 1H); 7.52 (t, J=8.1 Hz, 1H); 7.17 (t, J=8.1 Hz, 1H); 6.59 (d, J=9.0 Hz, 1H); 6.55 (s, 1H); 4.90 (m, 1H); 3.87 (m, 1H); 3.20-1.69 (m, 16H). IS-MS, m/e 550.4 (m+1).

EXAMPLE 14

Preparation of 2-[2-(1-tert-Butoxycarbonylpiperidin-4-yloxy)-4-(4-hydroxy-piperidin-1-yl)benzoylamino]-N-(5-chloropyridin-2-yl)benzamide

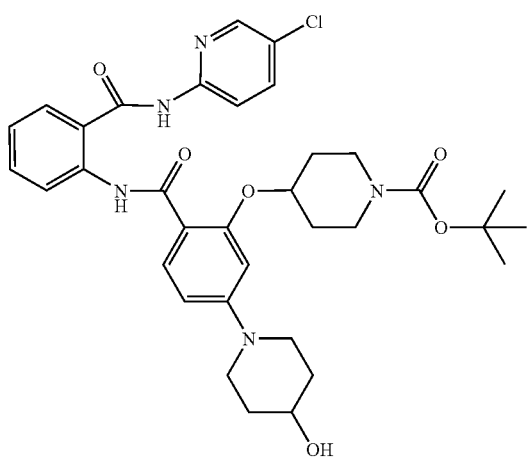

Using methods substantially equivalent to those described in Example 4-F except that the workup used saturated aqueous citric acid instead of water, 2-[2-(1-tert-butoxy-carbonylpiperidin-4-yloxy)-4-(4-hydroxypiperidin-1-yl)benzoylamino]-N-(5-chloro-pyridin-2-yl)benzamide (196 mg, 0.30 mmol, 39%) was prepared from 2-[4-fluoro-2-(1-tert-butoxycarbonylpiperidin-4-yloxy)benzoylamino]-N-(5-chloropyridin-2-yl)-benzamide and 4-hydroxypiperidine.

$^1$NMR (300 MHz, DMSO-$d_6$): δ 11.18 (s, 1H); 10.86 (s, 1H); 8.39 (d, J=2.4 Hz, 1H); 8.31 (d, J=8.4 Hz, 1H); 8.14 (d, J=9.0 Hz, 1H); 7.90 (dd, J=8.7, 2.4 Hz, 1H); 7.72 (d, J=8.4 Hz, 1H); 7.72 (d, J=8.4 Hz, 2H); 7.49 (t, J=8.3 Hz, 1H); 7.14 (t, J=7.7 Hz, 1H); 6.55 (m, 2H); 4.81 (m, 1H); 4.67 (m, 1H); 3.67 (m, 1H); 2.99 (m, 4H); 1.80 (m, 8H). IS-MS, m/e 650.4 (m+1). Analysis for $C_{34}H_{40}ClN_5O_6$: Calcd: C, 62.81; H, 6.20; N, 10.7; Found: C, 63.09; H, 6.18; N, 10.74.

EXAMPLE 15

Preparation of N-(5-Chloropyridin-2-yl)-2-[4-(4-hydroxypiperidin-1-yl)-2-(piperidin-4-yloxy)benzoylamino]benzamide

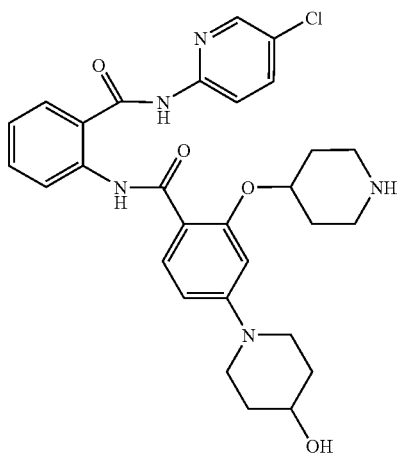

Using methods substantially equivalent to those described in example 4-G, N-(5-chloropyridin-2-yl)-2-[4-(4-hydroxypiperidin-1-yl)-2-(piperidin-4-yloxy)-benzoylamino]benzamide (62 mg, 0.11 mmol, 45%) was prepared from 2-[2-(1-tert-butoxycarbonylpiperidin-4-yloxy)-4-(4-hydroxypiperidin-1-yl)benzoylamino]-N-(5-chloropyridin-2-yl)benzamide.

[1]NMR (300 MHz, DMSO-$d_6$): δ 11.51 (s, 1H); 10.87 (s, 1H); 8.41 (s, 1H); 8.29 (d, J=8.4 Hz, 1H); 8.11 (d, J=9.0 Hz, 1H); 7.94 (d, J=8.7 Hz, 1H); 7.77 (d, J=7.5 Hz, 1H); 7.68 (d, J=8.4 Hz, 1H); 7.52 (t, J=7.5 Hz, 1H); 7.17 (t, J=7.5 Hz, 1H); 6.61 (d, J=9.0 Hz, 1H); 6.57 (s, 1H); 4.89 (m, 1H); 4.30 (m, 4H); 3.68 (m, 2H); 3.15 (m, 1H); 2.99 (m, 2H); 2.02 (m, 4H); 1.76 (m, 2H); 1.38 (m, 2H). IS-MS, m/e 550.4 (m+1).

EXAMPLE 16

Preparation of 2-[4-(tert-Butyl)-2-(piperidin-4-yloxy)benzoylamino]-4-chloro-N-(5-chloropyridin-2-yl)benzamide Hydrochloride

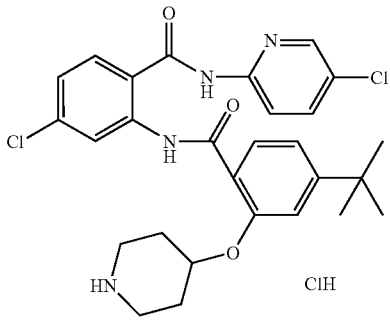

A.
N-(5-Chloropyridin-2-yl)-2-nitro-4-chlorobenzamide

To a stirring suspension of 2-nitro-4-chlorobenzoic acid (20 g, 99 mmol) in dichloromethane (500 mL) was added a few drops of DMF, followed by oxalyl chloride (15.1 g, 119 mmol). After 1 h, the solvent was removed in vacuo and the residue was dissolved in dichloromethane (500 mL). To this stirring solution was added pyridine (24 mL, 297 mmol) followed by 2-amino-5-chloropyridine (12.7 g, 99 mmol). After stirring overnight, the solvents were removed in vacuo and the residue was stirred vigorously with ethyl acetate and water for several hours. The mixture was filtered to give a white solid, which was washed with ethyl acetate and dried in vacuo to give 23 g (74%) of the title compound. The combined ethyl acetate washings and extract were then washed twice with 1 M citric acid, once with brine, twice with saturated aq sodium bicarbonate, and again with brine. The organic phase was then dried with MgSO$_4$, filtered and concentrated in vacuo. The solid was suspended in diethyl ether, sonicated and filtered to give a second crop of the title compound as a white solid (5.79 g, 19%).
[1]NMR IS-MS, m/e 312.0 (m+1) Analysis for $C_{12}H_7Cl_2N_3O_3$: Calcd: C, 46.18; H, 2.26; N, 13.46; Found: C, 46.24; H, 2.37; N, 13.43.

B.
N-(5-Chloropyridin-2-yl)-2-amino-4-chlorobenzamide

Using methods substantially equivalent to those described in example 2-B, N-(5-chloropyridin-2-yl)-2-amino-4-chlorobenzamide (7.85 g, 87%) was prepared from N-(5-chloropyridin-2-yl)-2-nitro-4-chlorobenzamide.
[1]NMR IS-MS, m/e 280.2 (m−1) Analysis for $C_{12}H_9Cl_2N_3O$: Calcd: C, 51.09; H, 3.22; N, 14.89; Found: C, 51.52; H, 3.56; N, 14.68.

C. Methyl 4-(tert-Butyl)-2-(1-Boc-piperidin-4-yloxy)benzoate

To a stirring solution of methyl 4-tert-butyl-2-hydroxybenzoate (9.45 g, 45.4 mmol), 1-Boc-piperidine-4-ol (9.6 g, 47.7 mmol) and triphenylphosphine (12.5 g, 47.7 mmol) in THF (125 mL) was added, dropwise via an addition funnel, a solution of diisopropyl azodicarboxylate (9.4 mL, 47.7 mmol) in THF (25 mL). After 72 h, the solvent was removed in vacuo and the residue was dissolved in a minimal amount of chloroform and vacuum filtered through a pad of silica gel, eluting with a solution of 20% ethyl acetate in hexanes. The filtrate was then concentrated in vacuo and the residue was chromatographed over silica gel, eluting with a gradient of 5% ethyl acetate in hexanes through 20% ethyl acetate in hexanes. The product containing fractions were combined and concentrated in vacuo to give 12.9 g (73% of a thick colorless oil).
[1]NMR ES-MS, m/e 392.3 (MH+)

D. 4-(tert-Butyl)-2-(1-Boc-piperidin-4-yloxy)benzoic acid

To a stirring solution of methyl 4-(tert-Butyl)-2-(1-Boc-piperidin-4-yloxy)-benzoate (12.9 g, 33 mmol) in p-dioxane (150 mL) was added a solution of LiOH hydrate (2.8 g, 66 mmol) in water (75 mL). The next morning, the solvent was removed in vacuo and the residue was diluted with water (200 mL) and washed with diethyl ether. The aqueous phase was then adjusted to pH 3 with citric acid and extracted twice with diethyl ether. The combined ether extracts were then washed twice with brine, dried with MgSO$_4$, filtered and concentrated in vacuo to give 11.3 g (91%) of a white foam.
[1]NMR IS-MS, m/e 378.5 (m+1) Analysis for $C_{21}H_{31}NO_5$: Calcd: C, 66.82; H, 8.28; N, 3.71; Found: C, 67.06; H, 8.39; N, 3.71.

E. 4-(tert-Butyl)-2-(1-Boc-piperidin-4-yloxy)benzoyl chloride

To a stirring solution of 4-(tert-butyl)-2-(1-Boc-piperidin-4-yloxy)benzoic acid (4.0 g, 10.6 mmol) in dichloromethane (20 mL) at 0° C., was added oxalyl chloride (13 mmol), followed by a small amount of DMF. After 30 min, the solvents were removed in vacuo and the residue was dissolved in dichloromethane to make a solution of the title compound, approximately 0.1 g/mL.

F. 2-[4-(tert-Butyl)-2-(1-Boc-piperidin-4-yloxy)benzoylamino]-N-(5-chloropyridin-2-yl)-4-chlorobenzamide To a stirring solution of N-(5-chloropyridin-2-yl)-2-amino-4-chlorobenzamide (0.74 g, 26.5 mmol) in pyridine (1 mL) and dichloromethane (20 mL) at 0° C. was added a solution of 4-(tert-butyl)-2-(1-Boc-piperidin-4-yloxy)benzoyl chloride (1.05 g, 26.5 mmol) in dichloromethane (10.5 mL). The cold bath was then removed and after 72 h, the solvent was removed in vacuo and the residue was dissolved in ethyl acetate and washed with water, followed by satd aq NaHCO$_3$ and then brine. The organic phase was then dried with MgSO$_4$, filtered and concentrated in vacuo. The residue was chromatographed over silica gel, eluting with a solution of 20% ethyl acetate in hexanes.

The product containing fractions were combined and concentrated in vacuo to give 0.89 g (52%) of a white solid.

$^1$NMR IS-MS, m/e 641.2 (m+1) Analysis for C$_{33}$H$_{38}$Cl$_2$N$_4$O$_5$: Calcd: C, 61.78; H, 5.97; N, 8.73; Found: C, 62.15; H, 6.20; N, 8.43.

G. 2-[4-(tert-Butyl)-2-(piperidin-4-yloxy)benzoylamino]-4-chloro-N-(5-chloro-pyridin-2-yl)benzamide hydrochloride 2-[4-(tert-Butyl)-2-(1-Boc-piperidin-4-yloxy)benzoylamino]-N-(5-chloropyridin-2-yl)-4-chlorobenzamide (0.4 g, 0.64 mmol) was dissolved in 4 N HCl/p-dioxane (15 mL). After stirring for 30 min, the solution was concentrated in vacuo and the residue was purified by RPHPLC, eluting with a gradient of 20% through 60% acetonitrile in 0.05% aq HCl over 320 min. The clean product containing fractions were combined, partially concentrated and lypholyzed to give 0.0864 g (23%) of white solid.

$^1$NMR IS-MS, m/e 541.1 (m+1) Analysis for C$_{28}$H$_{30}$Cl$_2$N$_4$O$_3$·1.3HCl·1.1H$_2$O: Calcd: C, 55.25; H, 5.55; N, 9.20; Cl, 19.22; Found: C, 55.28; H, 5.32; N, 9.40; Cl, 19.16.

EXAMPLE 17

Preparation of 2-[4-(tert-Butyl)-2-(piperidin-4-yloxy)benzoylamino]-5-chloro-N-(5-chloropyridin-2-yl)benzamide Hydrochloride

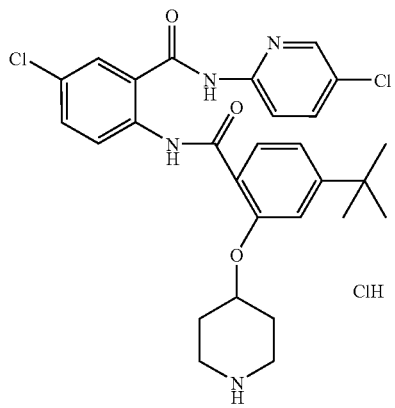

A.
N-(5-Chloropyridin-2-yl)-2-nitro-5-chlorobenzamide

Using methods substantially equivalent to those described in Example 16-A, N-(5-chloropyridin-2-yl)-2-nitro-5-chlorobenzamide (26.4 g, 85%) was prepared from 2-amino-5-chloropyridine and 2-nitro-5-chlorobenzoic acid.

$^1$NMR IS-MS, m/e 312.0 (m+1) Analysis for C$_{12}$H$_7$Cl$_2$N$_3$O$_3$: Calcd: C, 46.18; H, 2.26; N, 13.46; Found: C, 46.37; H, 2.41; N, 13.43.

B.
N-(5-Chloropyridin-2-yl)-2-amino-5-chlorobenzamide

Using methods substantially equivalent to those described in example 2-B, N-(5-chloropyridin-2-yl)-2-amino-5-chlorobenzamide (7.79 g, 72%) was prepared from N-(5-chloropyridin-2-yl)-2-nitro-5-chlorobenzamide.

$^1$NMR IS-MS, m/e 282.1 (m+1) Analysis for C$_{12}$H$_9$Cl$_2$N$_3$O: Calcd: C, 51.09; H, 3.22; N, 14.89; Cl, 25.13; Found: C, 51.29; H, 3.36; N, 14.89; Cl, 25.41.

C. 2-[4-(tert-Butyl)-2-(1-Boc-piperidin-4-yloxy)benzoylamino]-5-chloro-N-(5-chloropyridin-2-yl)benzamide By methods substantially equivalent to those described in Example 16-F, 2-[4-(tert-butyl)-2-(1-Boc-piperidin-4-yloxy)benzoylamino]-5-chloro-N-(5-chloropyridin-2-yl)benzamide (0.81 g, 48%) was prepared from 4-(tert-butyl)-2-(1-Boc-piperidin-4-yloxy)benzoyl chloride and N-(5-chloropyridin-2-yl)-2-amino-5-chlorobenzamide.

$^1$NMR IS-MS, m/e 641.0 (m+1) Analysis for C$_{33}$H$_{38}$Cl$_2$N$_4$O$_5$: Calcd: C, 61.78; H, 5.97; N, 8.73; Found: C, 62.27; H, 6.18; N, 8.41.

D. 2-[4-(tert-Butyl)-2-(1-Boc-piperidin-4-yloxy)benzoylamino]-5-chloro-N-(5-chloropyridin-2-yl)benzamide hydrochloride By methods substantially equivalent to those described in Example 16-G, 2-[4-(tert-butyl)-2-(piperidin-4-yloxy)benzoylamino]-N-(5-chloropyridin-2-yl)-5-chloro-benzamide hydrochloride (0.326 g, 88%) was prepared from 2-[4-(tert-butyl)-2-(1-Boc-piperidin-4-yloxy)benzoylamino]-5-chloro-N-(5-chloropyridin-2-yl)benzamide.

$^1$NMR IS-MS, m/e 541.0 (m+1)

EXAMPLE 18

Preparation of 2-[4-(tert-Butyl)-2-(piperidin-4-yloxy)benzoylamino]-N-(5-chloropyridin-2-yl)-5-fluorobenzamide Hydrochloride

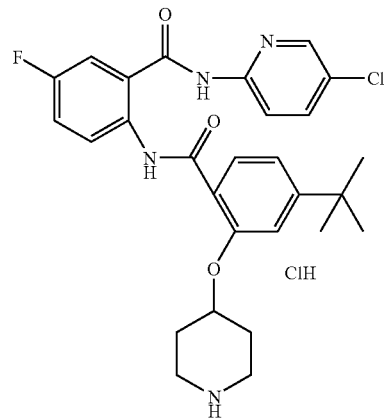

A.
N-(5-Chloropyridin-2-yl)-2-nitro-5-fluorobenzamide

Using methods substantially equivalent to those described in example 16-A, N-(5-chloropyridin-2-yl)-2-nitro-5-fluorobenzamide (8.7 g, 70%) was prepared from 2-nitro-5-fluorobenzoic acid and 2-amino-5-chloropyridine.

$^1$NMR IS-MS, m/e 296.2 (m+1) Analysis for C$_{12}$H$_7$ClFN$_3$O$_3$: Calcd: C, 48.75; H, 2.39; N, 14.21; Found: C, 48.96; H, 2.59; N, 14.02.

B. N-(5-chloropyridin-2-yl)-2-amino-5-fluorobenzamide

Using methods substantially equivalent to those described in example 2-B, N-(5-chloropyridin-2-yl)-2-amino-5-fluorobenzamide (11.6 g, 86%) was prepared from N-(5-chloropyridin-2-yl)-2-nitro-5-fluorobenzamide.

$^1$NMR IS-MS, m/e 264.1 (m−1) Analysis for $C_{12}H_9CFN_3O$: Calcd: C, 54.25; H, 3.42; N, 15.82; Found: C, 54.46; H, 3.58; N, 15.84.

C. 2-[4-(tert-Butyl)-2-(1-Boc-piperidin-4-yloxy) benzoylamino]-N-(5-chloropyridin-2-yl)-5-fluorobenzamide By methods substantially equivalent to those described in Example 16-F, 2-[4-(tert-butyl)-2-(1-Boc-piperidin-4-yloxy)benzoylamino]-N-(5-chloropyridin-2-yl)-5-fluorobenzamide (1.17 g, 70%) was prepared from 4-(tert-butyl)-2-(1-Boc-piperidin-4-yloxy)benzoyl chloride and N-(5-chloropyridin-2-yl)-2-amino-5-fluorobenzamide.

$^1$NMR IS-MS, m/e 625.0 (m+1) Analysis for $C_{33}H_{38}ClFN_4O_5$: Calcd: C, 63.40; H, 6.13; N, 8.96; Found: C, 64.25; H, 6.57; N, 8.63.

D. 2-[4-(tert-Butyl)-2-(piperidin-4-yloxy)benzoylamino]-N-(5-chloropyridin-2-yl)-5-fluorobenzamide hydrochloride By methods substantially equivalent to those described in Example 16-G, 2-[4-(tert-butyl)-2-(piperidin-4-yloxy)benzoylamino]-N-(5-chloropyridin-2-yl)-5-fluorobenzamide hydrochloride (0.36 g, 99%) was prepared from 2-[4-(tert-butyl)-2-(1-Boc-piperidin-4-yloxy)benzoylamino]-N-(5-chloropyridin-2-yl)-5-fluorobenzamide.

$^1$NMR IS-MS, m/e 525.0 (m+1) Analysis for $C_{28}H_{30}ClFN_4O_3F\cdot2.0HCl\cdot0.4H_2O$: Calcd: C, 55.57; H, 5.46; N, 9.26; Cl, 17.58; Found: C, 55.92; H, 5.36; N, 9.35; Cl, 17.54.

EXAMPLE 19

Preparation of 2-[4-[3-(tert-Butoxycarbonylamino)pyrrolidin-1-yl]-2-(1-tert-butoxy-carbonylpiperidin-4-yloxy)benzoylamino]-N-(5-chloropyridin-2-yl)benzamide

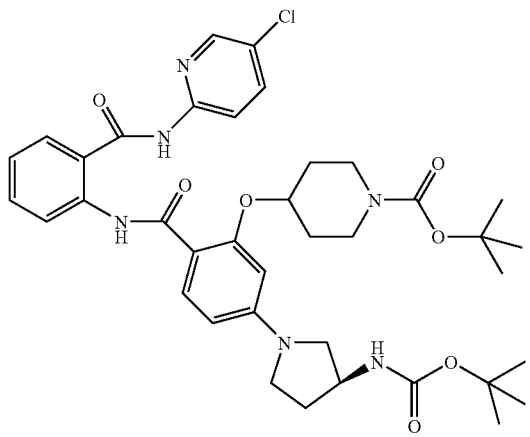

Using methods substantially equivalent to those described in Example 4-F except that saturated aqueous citric acid was used instead of water in the workup, 2-[4-[3-(tert-butoxycarbonylamino)pyrrolidin-1-yl]-2-(1-tert-butoxycarbonylpiperidin-4-yloxy)-benzoylamino]-N-(5-chloropyridin-2-yl) benzamide (234 mg, 0.32 mmol, 44%) was prepared from 2-[4-fluoro-2-(1-tert-butoxycarbonylpiperidin-4-yloxy)benzoylamino]-N-(5-chloropyridin-2-yl)benzamide and 3-tert-butoxycarbonylaminopyrrolidine.

$^1$NMR (300 MHz, DMSO-$d_6$): δ 11.17 (s, 1H); 10.83 (s, 1H); 8.39 (d, J=2.4 Hz, 1H); 8.30 (d, J=8.1 Hz, 1H); 8.14 (d, J=9.0 Hz, 1H); 7.90 (dd, J=2.6, 8.9 Hz, 1H); 7.72 (m, 2H); 7.48 (t, J=7.8 Hz, 1H); 7.15 (m, 2H); 6.19 (d, J=9.0 Hz, 1H); 6.13 (s, 1H); 4.79 (m, 1H); 4.06 (m, 1H); 3.68 (m, 2H); 3.54-3.37 (m, 2H); 3.03 (m, 4H); 2.05 (m, 1H); 1.87 (m, 5H); 1.36 (s, 9H); 1.32 (s, 9H). IS-MS, m/e 735.5 (m+1). Analysis for $C_{38}H_{47}ClN_6O_7$: Calcd: C, 62.07; H, 6.44; N, 11.43; Found: C, 62.73; H, 6.53; N, 11.53.

EXAMPLE 20

Preparation of 2-[4-(3-Aminopyrrolidin-1-yl)-2-(piperidin-4-yloxy)benzoylamino]-N-(5-chloropyridin-2-yl)benzamide

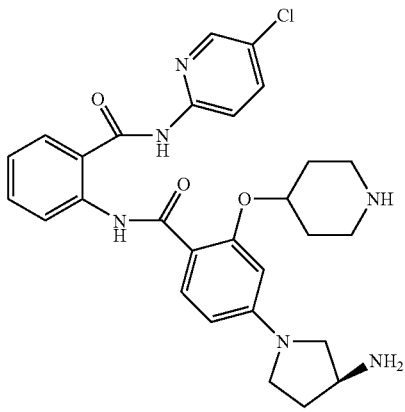

Using methods substantially equivalent to those described in Example 4-G, 2-[4-(3-aminopyrrolidin-1-yl)-2-(piperidin-4-yloxy)benzoylamino]-N-(5-chloropyridin-2-yl)benzamide (98 mg, 0.18 mmol, 67%) was prepared from 2-[4-[3-(tert-butoxycarbonyl-amino)pyrrolidin-1-yl]-2-(1-tert-butoxycarbonylpiperidin-4-yloxy)benzoylamino]-N-(5-chloropyridin-2-yl)benzamide.

$^1$NMR (300 MHz, DMSO-$d_6$): δ 10.77 (s, 1H); 8.40 (d, J=2.1 Hz, 1H); 8.35 (d, J=8.4 Hz, 1H); 8.18 (d, J=9.3 Hz, 1H); 7.93 (dd, J=2.1, 9.0 Hz, 1H); 7.72 (m, 2H); 7.48 (t, J=7.8 Hz, 1H); 7.13 (t, J=7.5 Hz, 1H); 6.18 (d, J=8.7 Hz, 1H); 6.08 (s, 1H); 4.61 (m, 1H); 3.59-1.65 (m, 18H). IS-MS, m/e 535.2 (m+1).

EXAMPLE 21

Preparation of 2-[2-(1-tert-Butoxycarbonylpiperidin-4-yloxy)-4-(methylthio)-benzoylamino]-N-(5-chloropyridin-2-yl)benzamide

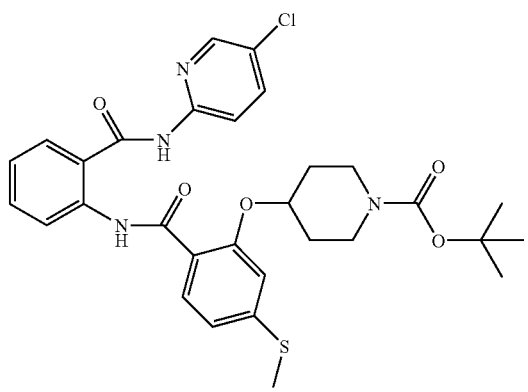

A. 2-hydroxy-4-(methylthio)benzoic acid

2-Methoxy-4-(methylthio)benzoic acid (1.002 g, 5.05 mmol) was dissolved in dichloromethane (18 mL). The solution was cooled to −65° C. in a dry ice/chloroform bath. A dichloromethane solution of boron tribromide (5.4 mL, 5.4 mmol) was then added slowly. After 3 hours, the reaction was quenched with water (5 mL) and 1 N HCl (10 mL). After stirring for 10 minutes, the reaction was extracted with dichloromethane (100 mL). The organic layer was washed with 1 N HCl (10 mL) and then dried over magnesium sulfate, filtered, and concentrated to give the pure product as a pale yellow solid (866 mg, 4.70 mmol, 93%).

IR(CHCl$_3$): 1657, 1616, 1451, 1287, 1225, 918 cm$^{-1}$.
$^1$NMR (400 MHz, DMSO-d$_6$): δ 7.63 (d, J=8.0 Hz, 1H); 6.75 (m, 2H); 2.46 (s, 3H). IS-MS, m/e 185.2 (m+1). Analysis for C$_8$H$_8$SO$_3$: Calcd: C, 52.16; H, 4.38; Found: C, 52.26; H, 4.40.

B. Methyl 2-hydroxy-4-(methylthio)benzoate

The 2-hydroxy-4-(methyltho)benzoic acid (836 mg, 4.54 mmol) was dissolved in MeOH (45 mL). Thionyl chloride (0.35 mL, 4.80 mmol) was added and the solution was heated to 65° C. and left overnight. TLC indicated that there was still starting material present so more thionyl chloride (1.0 mL, 13.7 mmol) was added. After about 1.5 hour, TLC indicated formation of baseline material; so the reaction was concentrated in vacuo.

The crude residue was purified using flash column chromatography (CH$_2$Cl$_2$) to give the desired compound as an off-white solid (567 mg, 2.86 mmol, 63%).

IR(CHCl$_3$): 1670, 1441, 1340, 1291, 1110, 910 cm$^{-1}$.
$^1$NMR (300 MHz, DMSO-d$_6$): δ 10.62 (s, 1H); 7.63 (d, J=9.0 Hz, 1H); 6.77 (m, 2H); 3.83 (s, 3H); 2.46 (s, 3H). IS-MS, m/e 199.1 (m+1). Analysis for C$_9$H$_{10}$O$_3$S: Calcd: C, 54.53; H, 5.08; Found: C, 54.47; H, 4.95.

C. Methyl 2-(1-tert-butoxycarbonylpiperidin-4-yloxy)-4-(methylthio)benzoate

The methyl 2-hydroxy-4-(methylthio)benzoate (4.00 g, 20.2 mmol) was dissolved in THF (300 mL). The solution was cooled to 0° C. and the N-Boc-4-hydroxypiperidine (4.07 g, 20.2 mmol) and triphenylphosphine (6.35 g, 24.2 mmol) were added, followed by diethyl azodicarboxylate (4.0 mL, 25.4 mmol). After 5 minutes, the reaction was allowed to warm to room temperature and left overnight. The reaction was concentrated in vacuo and the crude material was purified by flash column chromatography (about 500 g silica, 15% EtOAc/hexanes tthrough 20% EtOAc/hexanes) to give the desired product (7.185 g, 18.83 mmol, 93%).

IR(CHCl$_3$): 1683, 1593, 1435, 1235 cm$^{-1}$.
$^1$NMR (400 MHz, DMSO-d$_6$): δ 7.60 (d, J=8.0 Hz, 1H); 6.97 (s, 1H); 6.85 (d, J=8.0 Hz, 1H); 4.76 (m, 1H); 3.72 (s, 3H); 3.38 (m, 4H); 2.48 (s, 3H); 1.75 (m, 2H); 1.60 (m, 2H); 1.37 (s, 9H). IS-MS, m/e 382.4 (m+1). Analysis for C$_{19}$H$_{27}$NO$_5$S: Calcd: C, 59.82; H, 7.13; N, 3.67; Found: C, 59.58; H, 7.00; N, 3.73.

D. 2-(1-tert-Butoxycarbonylpiperidin-4-yloxy)-4-(methylthio)benzoic acid

The methyl 2-(1-tert-butoxycarbonylpiperidin-4-yloxy)-4-(methylthio)benzoate (504 mg, 1.32 mmol) was dissolved in a mixture of 1 M LiOH (2 mL), MeOH (2 mL), and THF (6 mL) and left to stir overnight. The mixture was concentrated in vacuo to remove MeOH and THF. The residue was diluted with dichloromethane (50 mL), washed with saturated aqueous citric acid (2×5 mL) and water (2×5 mL), dried over sodium sulfate, filtered, and concentrated to give the desired product as a yellow solid (417 mg, 1.13 mmol, 86%).

$^1$NMR (300 MHz, DMSO-d$_6$): δ 7.58 (d, J=8.1 Hz, 1H); 6.95 (s, 1H); 6.83 (d, J=8.1 Hz, 1H); 4.73 (m, 1H); 3.48-3.32 (m, 4H); 1.87 (s, 3H); 1.74 (m, 2H); 1.58 (m, 2H); 1.36 (s, 9H). IS-MS, m/e 368.1 (m+1). Analysis for C$_{18}$H$_{25}$NO$_5$S: Calcd: C, 58.84; H, 6.86; N, 3.81; Found: C, 58.80; H, 6.64; N, 4.00.

E. 2-[2-(1-tert-Butoxycarbonylpiperidin-4-yloxy)-4-(methylthio)benzoylamino]-N-(5-chloropyridin-2-yl)benzamide Using methods substantially equivalent to those described in Example 4-E, 2-[2-(1-tert-butoxycarbonylpiperidin-4-yloxy)-4-(methylthio)benzoylamino]-N-(5-chloro-pyridin-2-yl)benzamide (432 mg, 0.72 mmol, 75%) was prepared from N-(5-chloro-pyridin-2-yl)-2-aminobenzamide and 2-(1-tert-butoxycarbonylpiperidin-4-yloxy)-4-(methylthio)benzoic acid.

IR(CHCl$_3$): 1676, 1593, 1502, 1375, 1295 cm$^{-1}$. $^1$NMR (300 MHz, DMSO-d$_6$): δ 11.21 (s, 1H); 11.00 (s, 1H); 8.39 (d, J=2.1 Hz, 1H); 8.35 (d, J=8.1 Hz, 1H); 7.90 (dd, J=2.1, 9.0 Hz, 1H); 7.77 (m, 2H); 7.53 (t, J=7.8 Hz, 1H); 7.18 (t, J=7.6 Hz, 1H); 7.04 (s, 1H); 6.91 (d, J=8.4 Hz, 1H); 4.83 (m, 1H); 3.65 (m, 2H); 3.01 (m, 2H); 2.50 (s, 3H); 1.82 (m, 4H); 1.31 (s, 9H). IS-MS, m/e 597.4 (m+1). Analysis for C$_{30}$H$_{33}$ClN$_4$O$_5$S: Calcd: C, 60.34; H, 5.57; N, 9.38; Found: C, 60.34; H, 5.52; N, 9.19.

EXAMPLE 22

Preparation of N-(5-Chloropyridin-2-yl)-2-[4-(methylthio)-2-(piperidin-4-yloxy)-benzoylamino]benzamide

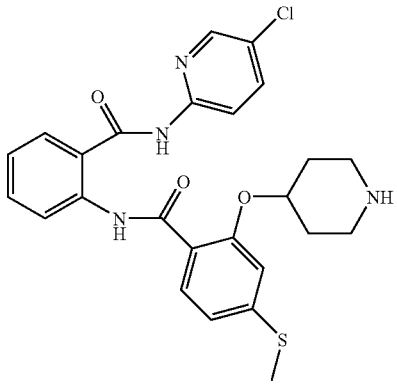

Using methods substantially equivalent to those described in Example 4-G, N-(5-chloropyridin-2-yl)-2-[4-(methylthio)-2-(piperidin-4-yloxy)benzoylamino]-benzamide (83 mg, 0.17 mmol, 100%) was prepared from 2-[2-(1-tert-butoxycarbonyl-piperidin-4-yloxy)-4-(methylthio)benzoylamino]-N-(5-chloropyridin-2-yl)benzamide.

IR(CHCl$_3$): 1662, 1593, 1502, 1375, 1296 cm$^{-1}$. $^1$NMR (400 MHz, DMSO-d$_6$): δ 8.42 (d, J=2.8 Hz, 1H); 8.32 (d, J=8.0 Hz, 1H); 8.11 (d, J=8.8 Hz, 1H); 7.93 (dd, J=2.4, 8.8 Hz, 1H); 7.80 (d, J=6.0 Hz, 1H); 7.73 (d, J=8.4 Hz, 1H); 7.55 (t, J=8.8 Hz, 1H); 7.21 (t, J=8.4 Hz, 1H); 7.05 (s, 1H); 6.95 (d, J=8.0 Hz, 1H); 4.88 (m, 1H); 3.19 (m, 2H); 2.94 (m, 2H); 2.50 (s, 3H); 1.96 (m, 4H). IS-MS, m/e 497.2 (m+1). Analysis for C$_{25}$H$_{25}$ClN$_4$O$_3$S: Calcd: C, 60.42; H, 5.07; N, 11.27; Found: C, 60.30; H, 5.11; N, 11.35.

EXAMPLE 23

Preparation of 2-[2-(1-tert-Butoxycarbonylpiperidin-4-yloxy)-4-(methylsulfinyl)-benzoylamino]-N-(5-chloropyridin-2-yl)benzamide

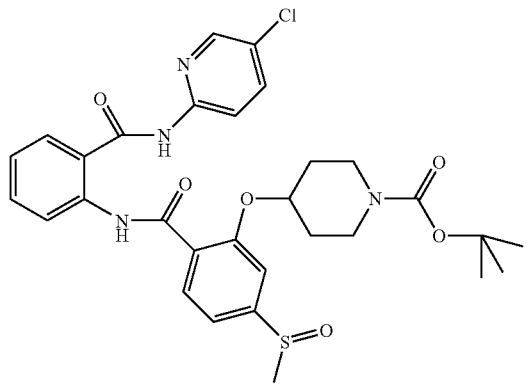

The 2-[2-(1-tert-butoxycarbonylpiperidin-4-yloxy)-4-(methylthio)benzoylamino]-N-(5-chloropyridin-2-yl)benzamide (291 mg, 0.49 mmol) was dissolved in chloroform (2.5 mL). Camphorsulfonic acid (20 mg, 0.09 mmol) was added, followed by t-butyl hydroperoxide solution (0.1 mL, 1.00 mmol). The reaction was stirred overnight and then loaded directly onto a column for flash column chromatographic purification (about 30 g silica, 10% EtOAc/CH$_2$Cl$_2$ through 100% EtOAc). The pure material (75 mg, 0.12 mmol, 25%) was obtained as a white solid.

$^1$NMR (300 MHz, DMSO-d$_6$): δ 11.22 (s, 1H); 11.09 (s, 1H); 8.40 (d, J=2.4 Hz, 1H); 8.36 (d, J=8.4 Hz, 1H); 8.10 (d, J=8.7 Hz, 1H); 7.96 (d, J=8.1 Hz, 1H); 7.90 (dd, J=2.6, 8.9 Hz, 1H); 7.80 (d, J=7.5 Hz, 1H); 7.56 (t, J=8.0 Hz, 1H); 7.48 (s, 1H); 7.34 (d, J=8.1 Hz, 1H); 7.22 (t, J=7.4 Hz, 1H); 4.84 (m, 1H); 3.49 (m, 2H); 3.06 (m, 2H); 2.77 (s, 3H); 1.86 (m, 2H); 1.77 (m, 2H); 1.31 (s, 9H). IS-MS, m/e 613.2 (m+1).

EXAMPLE 24

Preparation of N-(5-Chloropyridin-2-yl)-2-[4-(methylsulfinyl)-2-(piperidin-4-yloxy)-benzoylamino] benzamide

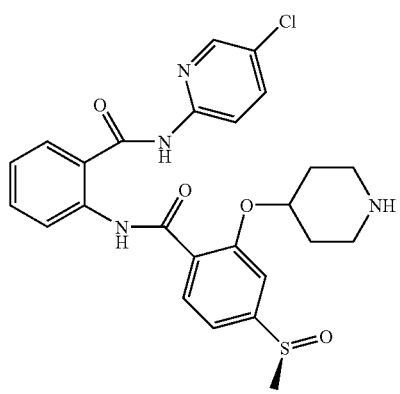

Using methods substantially equivalent to those described in example 4-G, N-(5-chloropyridin-2-yl)-2-[4-(methylsulfinyl)-2-(piperidin-4-yloxy)benzoylamino]-benzamide (55 mg, 0.11 mmol, 100%) was prepared from 2-[2-(1-tert-butoxycarbonyl-piperidin-4-yloxy)-4-(methylsulfinyl)-benzoylamino]-N-(5-chloropyridin-2-yl)-benzamide.

$^1$NMR (300 MHz, DMSO-d$_6$): δ 11.02 (br s, 1H); 8.41 (d, J=2.1 Hz, 1H); 8.29 (d, J=8.4 Hz, 1H); 8.10 (d, J=9.0 Hz, 1H); 7.89 (m, 2H); 7.81 (d, J=7.5 Hz, 1H); 7.57 (t, J=7.8 Hz, 1H); 7.47 (s, 1H); 7.35 (d, J=8.1 Hz, 1H); 7.23 (t, J=7.7 Hz, 1H); 4.86 (m, 1H); 3.04 (m, 2H); 2.90 (m, 2H); 2.77 (s, 9H); 2.00 (m, 2H); 1.86 (m, 2H). IS-MS, m/e 513.4 (m+1).

EXAMPLE 25

Preparation of 2-[2-(1-tert-Butoxycarbonylpiperidin-4-yloxy)-4-(methylsulfonyl)-benzoylamino]-N-(5-chloropyridin-2-yl)benzamide

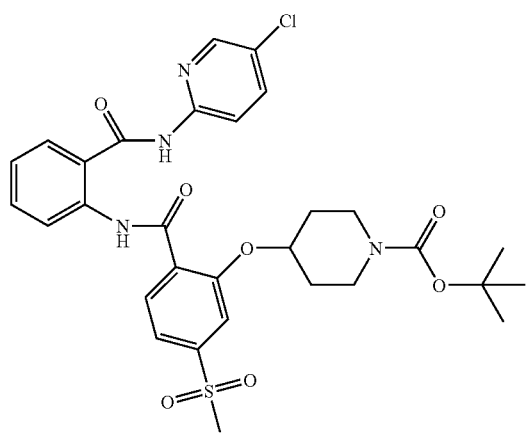

The 2-[2-(1-tert-butoxycarbonylpiperidin-4-yloxy)-4-(methylthio)benzoylamino]-N-(5-chloropyridin-2-yl)benzamide (193 mg, 0.32 mmol) was dissolved in chloroform (5 mL). After the solution had been cooled to 0° C., 3-chloroperoxybenzoic acid (mCPBA) (259 mg, 0.87 mmol, 58% purity) was added in portions. After 30 minutes, the reaction was warmed to room temperature and calcium hydroxide (80 mg, 1.1 mmol) was added. After 5 minutes, the reaction was filtered and the filtrate was concentrated in vacuo. The crude material was purified by flash column chromatography (~20 g silica, 10% EtOAc/CH$_2$Cl$_2$ through 100% EtOAc) to give the desired product (146 mg, 0.23 mmol, 73%) as a white solid.

$^1$NMR (300 MHz, DMSO-d$_6$): δ 11.21 (s, 1H); 11.10 (s, 1H); 8.40 (s, 1H); 8.33 (d, J=8.1 Hz, 1H); 8.09 (d, J=9.0 Hz, 1H); 7.96 (d, J=8.1 Hz, 1H); 7.90 (dd, J=2.4, 9.0 Hz, 1H); 7.81 (d, J=7.2 Hz, 1H); 7.66 (s, 1H); 7.57 (d, J=7.8 Hz, 1H); 7.24 (t, J=7.8 Hz, 1H); 4.91 (m, 1H); 3.61-3.55 (m, 2H); 3.26 (s, 3H); 3.20-3.07 (m, 2H); 1.94-1.70 (m, 4H); 1.31 (s, 9H). IS-MS, m/e 629.3 (m+1).

EXAMPLE 26

Preparation of N-(5-Chloropyridin-2-yl)-2-[4-(methylsulfonyl)-2-(piperidin-4-yloxy)-benzoylamino]benzamide

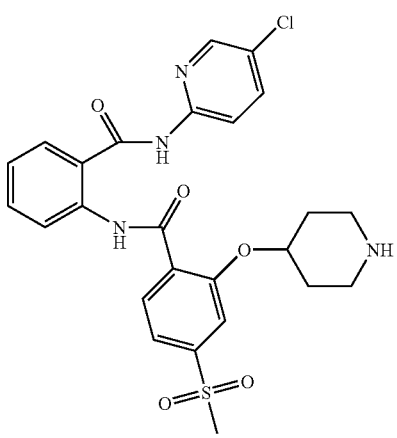

Using methods substantially equivalent to those described in Example 4-G, N-(5-chloropyridin-2-yl)-2-[4-(methylsulfonyl)-2-(piperidin-4-yloxy)benzoylamino]-benzamide (81 mg, 0.15 mmol, 85%) was prepared from 2-[2-(1-tert-butoxycarbonyl-piperidin-4-yloxy)-4-(methylsulfonyl)benzoylamino]-N-(5-chloropyridin-2-yl)-benzamide.

$^1$NMR (300 MHz, DMSO-d$_6$): δ 8.41 (d, J=2.4 Hz, 1H); 8.37 (d, J=8.1 Hz, 1H); 8.13 (d, J=9.0 Hz, 1H); 7.96 (s, 1H); 7.92 (dd, J=2.9, 8.6 Hz, 1H); 7.81 (d, J=7.8 Hz, 1H); 7.62-7.54 (m, 3H); 7.23 (t, J=7.7 Hz, 1H); 4.74 (m, 1H); 3.29 (s, 2H); 2.77 (m, 2H); 2.51-2.46 (m, 2H); 1.85-1.82 (m, 2H); 1.61-1.55 (m, 2H). IS-MS, m/e 529.1 (m+1). Analysis for C$_{25}$H$_{25}$ClN$_4$O$_5$S: Calcd: C, 56.76; H, 4.76; N, 10.59; Found: C, 56.51; H, 4.83; N, 10.30.

EXAMPLE 27

Preparation of 2-[2-(3-tert-Butoxycarbonylamino-2,2-dimethylpropoxy)-4-(pyrrolidin-1-yl)benzoylamino]-N-(5-chloropyridin-2-yl)benzamide

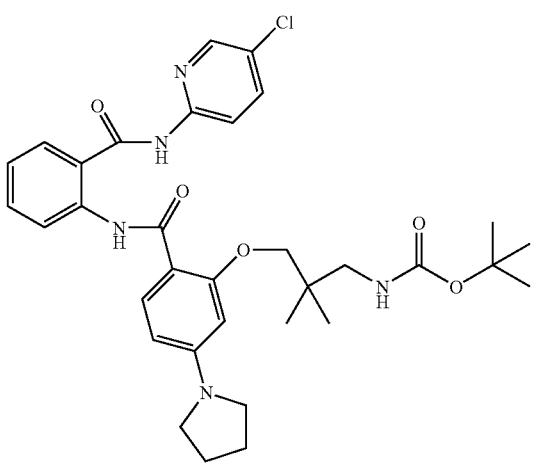

A. 3-tert-Butoxycarbonylamino-2,2-dimethylpropanol

To a solution of neopentanolamine (75 g, 728 mmol) and sodium carbonate (77.2 g, 728 mmol) in p-dioxane (1 L) and water (1 L) at 0° C. was added di-tert-butyl dicarbonate (175 g, 801 mmol). After stirring overnight, the solution was concentrated in vacuo and the residue was partitioned between ethyl acetate and water. The organic phase was washed again with brine and then dried with MgSO$_4$, filtered, and concentrated in vacuo to give 139 g (94%) of a thick, colorless syrup.
$^1$NMR

B. Methyl 2-(3-tert-butoxycarbonylamino-2,2-dimethylpropoxy)-4-fluorobenzoate Using methods substantially equivalent to those described in Example 21-C, methyl 2-(3-tert-butoxycarbonylamino-2,2-dimethylpropoxy)-4-fluorobenzoate (8.52 g, 24.0 mmol, 81%) was prepared from methyl 4-fluoro-2-hydroxybenzoate and 3-tert-butoxycarbonylamino-2,2-dimethylpropanol.

IR(CHCl$_3$): 1716, 1501, 1251, 1165 cm$^{-1}$. $^1$NMR (400 MHz, DMSO-d$_6$): δ 7.75 (t, J=8.0 Hz, 1H); 6.94 (d, J=11.6 Hz, 1H); 6.80 (t, J=8.4 Hz, 2H); 3.77 (s, 3H); 3.69 (s, 2H); 2.95 (d, J=6.4 Hz, 2H); 1.33 (s, 9H); 0.90 (s, 6H). IS-MS, m/e 356.3 (m+1). Analysis for C$_{18}$H$_{26}$FNO$_5$.0.25CH$_2$Cl$_2$: Calcd: C, 58.20; H, 7.09; N, 3.72; Found: C, 58.42; H, 7.12; N, 3.81.

C. 2-(3-tert-Butoxycarbonylamino-2,2-dimethylpropoxy)-4-fluorobenzoic acid

Using methods substantially equivalent to those described in Example 21-D, 2-(3-tert-butoxycarbonylamino-2,2-dimethylpropoxy)-4-fluorobenzoic acid (8.01 g, 23.5 mmol, 99%) was prepared from methyl 2-(3-tert-butoxycarbonylamino-2,2-dimethylpropoxy)-4-fluorobenzoate.

IR(CHCl$_3$): 2979, 1698, 1611, 1515, 1164 cm$^{-1}$. $^1$NMR (300 MHz, DMSO-d$_6$): δ 7.71 (t, J=7.8 Hz, 1H); 6.90 (d, J=11.4 Hz, 1H); 6.81-6.74 (m, 1H); 3.66 (s, 2H); 2.93 (d,

J=6.3 Hz, 2H); 1.32 (s, 9H); 0.89 (s, 6H). IS-MS, m/e 342.1 (m+1). Analysis for $C_{17}H_{24}FNO_5$: Calcd: C, 59.81; H, 7.09; N, 4.10; Found: C, 59.83; H, 7.01; N, 4.27.

D. 2-[2-(3-tert-Butoxycarbonylamino-2,2-dimethyl-propoxy)-4-fluorobenzoylamino]-N-(5-chloropyridin-2-yl)benzamide Using methods substantially equivalent to those described in Example 4-E, 2-[2-(3-tert-butoxycarbonylamino-2,2-dimethylpropoxy)-4-fluorobenzoylamino]-N-(5-chloropyridin-2-yl)benzamide (10 g, 17.5 mmol, 82%) was prepared from 2-(3-tert-butoxycarbonylamino-2,2-dimethylpropoxy)-4-fluorobenzoic acid and N-(5-chloro-pyridin-2-yl)-2-aminobenzamide.

IR(KBr): 1711, 1665, 1504, 1375 cm$^{-1}$. $^1$NMR (400 MHz, DMSO-d$_6$): δ 11.03 (s, 1H); 10.66 (s, 1H); 8.38 (s, 1H); 8.11 (d, J=8.0 Hz, 1H); 8.07 (d, J=8.8 Hz, 1H); 7.88 (dd, J=2.4, 8.8 Hz, 1H); 7.79 (d, J=7.6 Hz, 1H); 7.66 (t, J=8.0 Hz, 1H); 7.55 (t, J=7.8 Hz, 1H); 7.22 (t, J=7.6 Hz, 1H); 7.05 (d, J=11.2 Hz, 1H); 6.87-6.82 (m, 1H); 3.79 (s, 2H); 2.84 (d, J=6.0 Hz, 2H); 1.28 (s, 9H); 0.80 (s, 6H). IS-MS, m/e 571.3 (m+1). Analysis for $C_{29}H_{32}FClN_4O_5$: Calcd: C, 61.00; H, 5.65; N, 9.81; Found: C, 61.08; H, 5.74; N, 9.51.

E. 2-[2-(3-tert-Butoxycarbonylamino-2,2-dimethyl-propoxy)-4-(pyrrolidin-1-yl)-benzoylamino]-N-(5-chloropyridin-2-yl)benzamide Using methods substantially equivalent to those described in Example 4-F, except that the reaction was heated to 80° C., 2-[2-(3-tert-butoxycarbonylamino-2,2-dimethyl-propoxy)-4-(pyrrolidin-1-yl)benzoylamino]-N-(5-chloropyridin-2-yl)benzamide (453 mg, 0.73 mmol, 43%) was prepared from 2-[2-(3-tert-butoxycarbonylamino-2,2-dimethyl-propoxy)-4-fluorobenzoylamino]-N-(5-chloropyridin-2-yl)benzamide and pyrrolidine.

IR(CHCl$_3$): 1710, 1603, 1504, 1375 cm$^{-1}$. $^1$NMR (400 MHz, DMSO-d$_6$): δ 11.01 (s, 1H); 10.49 (s, 1H); 8.37 (d, J=2.4 Hz, 1H); 8.14 (d, J=8.4 Hz, 1H); 8.08 (d, J=8.8 Hz, 1H); 7.89 (dd, J=2.8, 8.8 Hz, 1H); 7.75 (d, J=8.0 Hz, 1H); 7.59 (t, J=8.4 Hz, 1H); 7.50 (t, J=7.8 Hz, 1H); 7.16 (t, J=7.6 Hz, 1H); 6.83 (m, 1H); 6.18 (d, J=8.8 Hz, 1H); 6.12 (s, 1H); 3.85 (s, 2H); 3.30-3.27 (m, 4H); 2.85 (d, J=6.4 Hz, 2H); 1.95-1.92 (m, 4H); 1.30 (s, 9H); 0.81 (s, 6H). IS-MS, m/e 622.5 (m+1). Analysis for $C_{33}H_{40}ClN_5O_5$: Calcd: C, 63.71; H, 6.48; N, 11.26; Found: C, 63.53; H, 6.58; N, 11.07.

EXAMPLE 28

Preparation of 2-[2-(3-tert-Butoxycarbonylamino-2,2-dimethylpropoxy)-4-(morpholin-4-yl)benzoylamino]-N-(5-chloropyridin-2-yl)benzamide

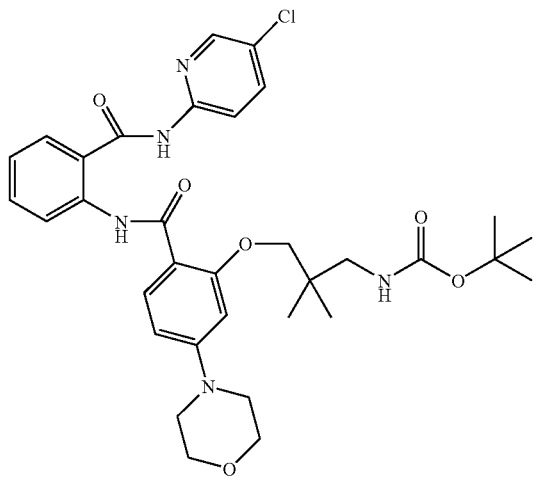

Using methods substantially equivalent to those described in Example 4-F except that saturated aqueous citric acid was used in the workup instead of water, 2-[2-(3-tert-butoxycarbonylamino-2,2-dimethylpropoxy)-4-(morpholin-4-yl)benzoylamino]-N-(5-chloropyridin-2-yl)benzamide (150 mg, 0.24 mmol, 36%) was prepared from 2-[2-(3-tert-butoxycarbonylamino-2,2-dimethylpropoxy)-4-fluorobenzoylamino]-N-(5-chloropyridin-2-yl)benzamide and morpholine.

$^1$NMR (400 MHz, DMSO-d$_6$): δ 11.02 (s, 1H); 10.53 (s, 1H); 8.37 (d, J=2.4 Hz, 1H); 8.14 (d, J=8.0 Hz, 1H); 8.07 (d, J=9.2 Hz, 1H); 7.88 (dd, J=2.6, 9.0 Hz, 1H); 7.77 (d, J=7.6 Hz, 1H); 7.58 (d, J=8.4 Hz, 1H); 7.52 (t, J=7.8 Hz, 1H); 7.18 (t, J=7.6 Hz, 1H); 6.80 (m, 1H); 6.57 (d, J=8.0 Hz, 1H); 6.56 (s, 1H); 3.83 (s, 2H); 3.71 (m, 4H); 3.21 (m, 4H); 2.85 (d, J=6.0 Hz, 2H); 1.29 (s, 9H); 0.80 (s, 6H). IS-MS, m/e 638.2 (m+1). Analysis for $C_{33}H_{40}ClN_5O_6$: Calc: C, 62.11; H, 6.32; N, 10.97; Found: C, 62.11; H, 6.30; N, 10.76.

EXAMPLE 29

Preparation of 2-[2-(2-tert-Butoxycarbonylaminoethoxy)-4-(morpholin-4-yl)-benzoylamino]-N-(5-chloropyridin-2-yl)-4-fluorobenzamide

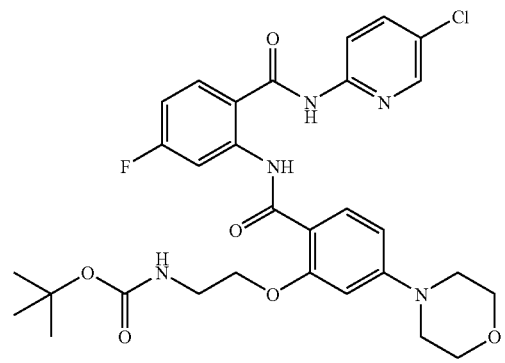

A. Ethyl 2-(2-tert-butoxycarbonylaminoethoxy)-4-fluorobenzoate

To a solution of 2-tert-butoxycarbonylaminoethanol (4.34 g, 26.9 mmol) in THF (16 mL) at 0° C. under $N_2$, was added $K^+$-OtBu (26.9 mL, 26.9 mmol, 1.0 M in THF).

The reaction was stirred for 20 min at 0° C. during which time a thick slurry formed. The anion solution was then poured into a solution of ethyl 2,4-difluorobenzoate (5.00 g, 26.9 mmol) in THF (16 mL) which had been cooled to −65° C. The reaction was allowed to slowly warm to room temperature and was stirred for 18 hr. The reaction was diluted with dichloromethane and washed with water. The water layer was extracted with additional dichloromethane and the dichloromethane layers combined and washed with brine, dried, and concentrated in vacuo to give a yellow oil. Purification on silica gel, eluting with a gradient of 4:1 to 3:1, hexane:EtOAc, yielded 3.82 g (43.5%) of the desired product as a colorless oil.

B. Ethyl 2-[2-(2-tert-butoxycarbonylaminoethoxy)-4-(morpholin-4-yl)benzoate

Ethyl 2-(2-tert-butoxycarbonylaminoethoxy)-4-fluorobenzoate (1.75 g, 5.35 mmol) and morpholine (1 mL) were heated at 90° C. in a sealed vial for 7 days. The reaction was diluted with dichloromethane (25 mL), washed with water, dried, and the solvent was removed in vacuo. Purification via silica gel chromatography, eluting with a gradient of hexane and ethyl acetate, yielded 0.791 g (37.5%) of the desired product as a colorless oil.

C. 2-[2-(2-tert-butoxycarbonylaminoethoxy)-4-(morpholin-4-yl)benzoic acid

In a manner substantially equivalent to Example 21-D, ethyl 2-(2-tert-butoxycarbonylaminoethoxy)-4-(1-morpholino)benzoate (0.790 g, 2.00 mmol) yielded 0.617 g (84.1%) of the desired product as a white solid.

IS-MS, m/z 367.1 (m+1), 365.2 (m−1)

D. 4-Fluoro-2-nitrobenzoic acid

To a stirring solution of $KMnO_4$ (76 g, 483 mmol) in water (1 L) was added 4-fluoro-2-nitrotoluene and the solution was heated to reflux. After 4 h, the hot mixture was filtered and the filtrate was cooled with ice, washed with diethyl ether, acidified with conc HCl, and then extracted twice with diethyl ether. The combined ether extracts were washed with brine, dried with $MgSO_4$, filtered and concentrated in vacuo to give 12.07 g (34%) of a white solid.

$^1$NMR IS-MS, m/e 184.0 (m−1)- Analysis for $C_7H_4FNO_4$: Calcd: C, 45.42; H, 2.18; N, 7.57; Found: C, 45.63; H, 2.30; N, 7.61.

E. N-(5-Chloropyridin-2-yl)-4-fluoro-2-nitrobenzamide

Using methods substantially equivalent to those described in Example 16-A, N-(5-chloropyridin-2-yl)-4-fluoro-2-nitrobenzamide (16.06 g, 88%) was prepared from 4-fluoro-2-nitrobenzoic acid and 2-amino-5-chloropyridine.

$^1$NMR IS-MS, m/e 296.2 (m+1) Analysis for $C_{12}H_7ClFN_3O_3$: Calcd: C, 48.75; H, 2.38; N, 14.21; Found: C, 48.96; H, 2.66; N, 14.40.

F. N-(5-Chloropyridin-2-yl)-2-amino-4-fluorobenzamide

Using methods substantially equivalent to those described in Example 2-B, N-(5-chloropyridin-2-yl)-2-amino-4-fluorobenzamide (7.98 g, 88%) was prepared from N-(5-chloropyridin-2-yl)-4-fluoro-2-nitrobenzamide.

$^1$NMR IS-MS, m/e 264.2 (m−1)- Analysis for $C_{12}H_9ClFN_3O$: Calcd: C, 54.25; H, 3.42; N, 15.82; Found: C, 54.45; H, 3.65; N, 15.76.

G. 2-[2-(2-tert-Butoxycarbonylaminoethoxy)-4-(morpholin-4-yl)benzoylamino]-N-(5-chloropyridin-2-yl)-4-fluorobenzamide The 2-[2-(2-tert-butoxycarbonylaminoethoxy)-4-(morpholin-4-yl)benzoic acid (825 mg, 2.25 mmol) was mixed with $CH_2Cl_2$ (20 mL), cooled to 0° C. under $N_2$, and treated with a 2 M $CH_2Cl_2$ solution of oxalyl chloride (1.2 mL) and 1 drop of DMF. The reaction was stirred at 0° C. for 1 hour, concentrated to dryness, mixed with $CH_2Cl_2$ (5 mL), and added to a cold solution of the N-(5-chloropyridin-2-yl)-2-amino-4-fluoro-benzamide in pyridine (20 mL). The reaction was stirred at 0° C. for 3 hours, then overnight at ambient temperature. The reaction was concentrated to dryness, mixed with toluene, and reconcentrated to dryness. The residue was partitioned between saturated aqueous $NaHCO_3$ (50 mL) and EtOAc (75 mL). The aqueous layer was extracted with EtOAc (50 mL). The combined organic layers were dried over $MgSO_4$ and concentrated to 1 g of an oil which was purified by flash chromatography using Hex/EtOAc to give 0.67 g (1.1 mmol, 48%) of a white solid.

$^1$NMR IS-MS m/e 612 (m−2) Analysis for $C_{30}H_{33}ClFN_5O_6$: Calcd: C, 58.68; H, 5.42; N, 11.40; Found: C, 58.83; H, 5.43; N, 11.23.

EXAMPLE 30

Preparation of 2-[2-(3-amino-2,2-dimethylpropoxy)-4-(morpholin-4-yl)-benzoylamino]-N-(5-chloropyridin-2-yl)benzamide

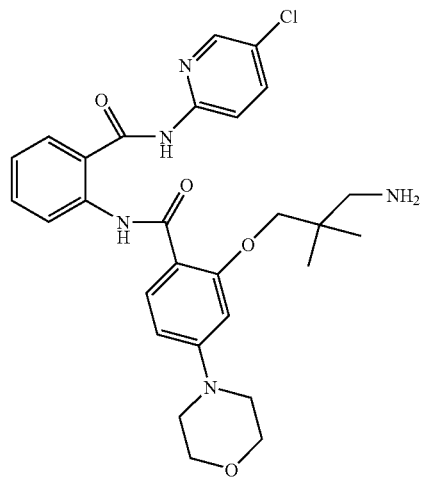

Using methods substantially equivalent to those described in Example 4-G, 2-[2-(3-amino-2,2-dimethylpropoxy)-4-(morpholin-4-yl)benzoylamino]-N-(5-chloro-pyridin-2-yl)

benzamide (106 mg, 0.12 mmol, 100%) was prepared from 2-[2-(3-tert-butoxycarbonylamino-2,2-dimethylpropoxy)-4-(morpholin-4-yl)benzoylamino]-N-(5-chloropyridin-2-yl)benzamide.

$^1$NMR (400 MHz, DMSO-d$_6$): δ 8.41 (d, J=2.4 Hz, 1H); 8.16 (d, J=8.0 Hz, 1H); 8.07 (d, J=9.2 Hz, 1H); 7.91 (dd, J=2.6, 9.2 Hz, 1H); 7.83 (d, J=8.0 Hz, 1H); 7.75 (br s, 1H); 7.59-7.54 (m, 2H); 7.21 (t, J=8.0 Hz, 1H); 6.60 (d, J=8.8 Hz, 1H); 6.57 (s, 1H); 3.94 (s, 2H); 3.72-3.70 (m, 4H); 3.27-3.22 (m, 4H); 2.84 (s, 2H); 0.97 (s, 6H). IS-MS, m/e 538.4 (m+1). Analysis for C$_{28}$H$_{32}$ClN$_5$O$_4$.CH$_2$Cl$_2$: Calc: C, 56.75; H, 5.40; N, 11.03; Found: C, 56.46; H, 5.24; N, 10.70.

EXAMPLE 31

Preparation of 2-[2-(3-Amino-2,2-dimethylpropoxy)-4-(pyrrolidin-1-yl)benzoyl-amino]-N-(5-chloropyridin-2-yl)benzamide

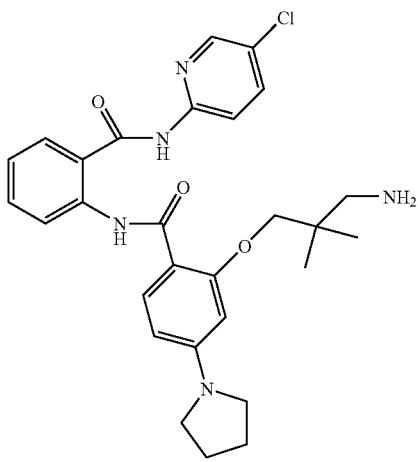

Using methods substantially equivalent to those described in Example 4-G, 2-[2-(3-amino-2,2-dimethylpropoxy)-4-(pyrrolidin-1-yl)benzoylamino]-N-(5-chloro-pyridin-2-yl)benzamide (386 mg, 0.74 mmol, 100%) was prepared from 2-[2-(3-tert-butoxycarbonylamino-2,2-dimethylpropoxy)-4-(pyrrolidin-1-yl)benzoylamino]-N-(5-chloropyridin-2-yl)benzamide.

$^1$NMR (400 MHz, DMSO-d$_6$): δ 8.40 (s, 1H); 8.17 (d, J=8.4 Hz, 1H); 8.08 (d, J=8.4 Hz, 1H); 7.91 (d, J=9.2 Hz, 1H); 7.79 (d, J=7.6 Hz, 1H); 7.58 (d, J=9.2 Hz, 1H); 7.51 (t, J=8.0 Hz, 1H); 7.17 (t, J=8.0 Hz, 1H); 6.19 (d, J=7.6 Hz, 1H); 6.15 (s, 1H); 3.94 (s, 2H); 3.28 (br s, 4H); 2.63 (m, 2H); 1.93 (br s, 4H); 0.89 (s, 6H). IS-MS, m/e 522.2 (m+1). Analysis for C$_{28}$H$_{32}$ClN$_5$O$_3$: Calc: C, 60.75; H, 5.80; N, 12.17; Found: C, 60.79; H, 5.61; N, 11.92.

EXAMPLE 32

Preparation of 2-[2-(1-tert-Butoxycarbonylpiperidin-4-yloxy)-4-(morpholin-4-yl)-benzoylamino]-5-chloro-N-(5-chloropyridin-2-yl)benzamide

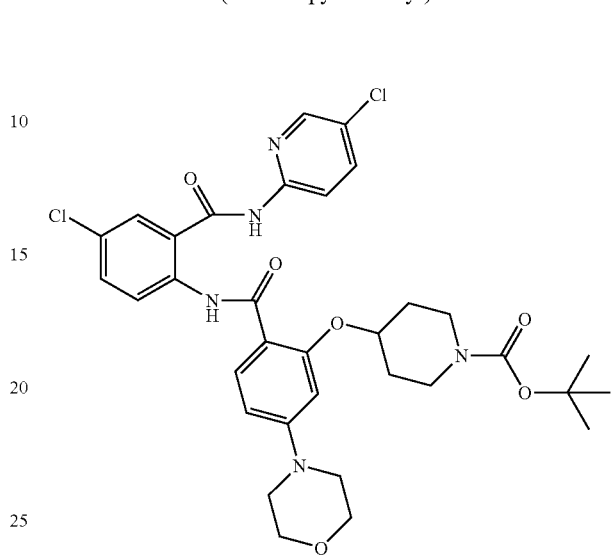

A. 2-[2-(1-tert-Butoxycarbonylpiperidin-4-yloxy)-4-fluorobenzoylamino]-5-chloro-N-(5-chloropyridin-2-yl)benzamide Using methods substantially equivalent to those described in Example 4-E, 2-[2-(1-tert-butoxycarbonylpiperidin-4-yloxy)-4-fluorobenzoylamino]-N-(5-chloro-pyridin-2-yl)-5-chlorobenzamide (2.28 g, 3.78 mmol, 44%) was prepared from N-(5-chloropyridin-2-yl)-2-amino-5-chlorobenzamide and 2-(1-tert-butoxycarbonyl-piperidin-4-yloxy)-4-fluorobenzoic acid.

IR(CHCl$_3$): 1678, 1496, 1375, 1275 cm$^{-1}$. $^1$NMR (400 MHz, DMSO-d$_6$): δ 11.36 (s, 1H); 10.98 (s, 1H); 8.41 (d, J=2.8 Hz, 1H); 8.36 (d, J=8.8 Hz, 1H); 8.10 (d, J=8.8 Hz, 1H); 7.92-7.89 (m, 2H); 7.85 (s, 1H); 7.61 (dd, J=2.6, 9.0 Hz, 1H); 7.25 (d, J=11.6 Hz, 1H); 6.89 (t, J=8.2 Hz, 1H); 4.79 (m, 1H); 3.68 (d, J=15.2 Hz, 2H); 3.01 (m, 2H); 1.89-1.78 (m, 4H); 1.33 (s, 9H) IS-MS, m/e 603.48 (m+1) Analysis for C$_{29}$H$_{29}$Cl$_2$ FN$_4$O$_5$: Calc: C, 57.72; H, 4.84; N, 9.28; Found: C, 57.89; H, 4.85; N, 9.47.

B. 2-[2-(1-tert-Butoxycarbonylpiperidin-4-yloxy)-4-(morpholin-4-yl)benzoylamino]-5-chloro-N-(5-chloropyridin-2-yl)benzamide Using methods substantially equivalent to those described in example 4-F, 2-[2-(1-tert-butoxycarbonylpiperidin-4-yloxy)-4-(morpholin-4-yl)benzoylamino]-5-chloro-N-(5-chloropyridin-2-yl)benzamide (1.3611 g, 2.03 mmol, 55%) was prepared from 2-[2-(1-tert-butoxycarbonylpiperidin-4-yloxy)-4-fluorobenzoylamino]-N-(5-chloropyridin-2-yl)-5-chlorobenzamide and morpholine.

$^1$NMR (400 MHz, DMSO-d$_6$): δ 11.33 (s, 1H); 10.84 (s, 1H); 8.41 (s, 1H); 8.35 (d, J=9.2 Hz, 1H); 8.12 (d, J=8.8 Hz, 1H); 7.91 (d, J=8.8 Hz, 1H); 7.79-7.75 (m, 2H); 7.57 (d, J=9.2 Hz, 1H); 6.61-6.59 (m, 2H); 4.80 (br s, 1H); 3.70 (m, 4H); 3.23 (m, 6H); 2.99 (m, 2H); 1.86-1.78 (m, 4H); 1.32 (s, 9H).

IS-MS, m/e 670.4 (m+1) Analysis for $C_{33}H_{37}Cl_2N_5O_6$: Calc: C, 59.11; H, 5.56; N, 10.44; Found: C, 59.81; H, 5.58; N, 10.59.

EXAMPLE 33

Preparation of 5-Chloro-N-(5-chloropyridin-2-yl)-2-[4-(morpholip-4-yl)-2-(piperidin-4-yloxy)benzoylamino]benzamide

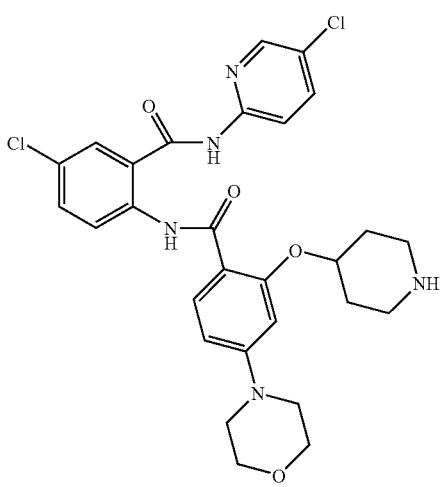

Using methods substantially equivalent to those described in Example 4-G, 5-chloro-N-(5-chloropyridin-2-yl)-2-[4-(morpholin-4-yl)-2-(piperidin-4-yloxy)-benzoylamino]benzamide (1.17 g, 2.05 mmol, 100%) was prepared from 2-[2-(1-tert-butoxycarbonylpiperidin-4-yloxy)-4-(morpholin-4-yl)benzoylamino]-5-chloro-N-(5-chloropyridin-2-yl) benzamide.

$^1$NMR (400 MHz, DMSO-$d_6$): δ 10.83 (s, 1H); 8.43 (d, J=2.0 Hz, 1H); 8.33 (dd, J=1.8, 9.0 Hz, 1H); 8.11 (d, J=8.8 Hz, 1H); 7.94 (d, J=9.2 Hz, 1H); 7.83 (s, 1H); 7.72 (dd, J=1.8, 8.6 Hz, 1H); 7.59 (dd, J=2.2. 11.0 Hz, 1H); 6.63 (d, J=8.8 Hz, 1H); 6.60 (s, 1H); 4.86 (br s, 1H); 4.07 (m, 2H); 3.70 (m, 2H); 3.27-2.93 (m, 8H); 2.00 (m, 2H); 1.93 (m, 2H). IS-MS, m/e 570.3 (m+1). Analysis for $C_{28}H_{29}Cl_2N_5O_4$. $1.05CH_2Cl_2$: Calc: C, 53.78; H, 4.66; N, 10.42; Found: C, 53.48; H, 4.41; N, 10.26.

EXAMPLE 34

Preparation of 2-[2-(2-Aminoethoxy)-4-(morpholin-4-yl)benzoylamino]-N-(5-chloropyridin-2-yl)-4-fluorobenzamide Trifluoroacetate

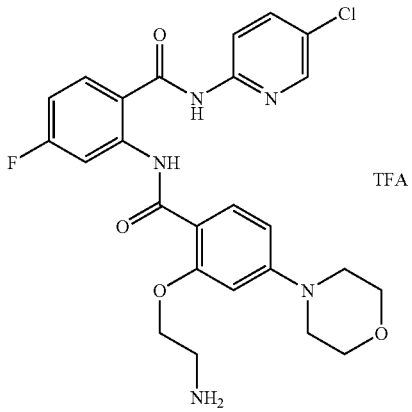

The 2-[2-(2-tert-butoxycarbonylaminoethoxy)-4-(morpholin-4-yl)benzoylamino]-N-(5-chloropyridin-2-yl)-4-fluorobenzamide (570 mg, 0.93 mmol) was mixed with $CH_2Cl_2$ (5 mL), anisole (1 mL), and trifluoroacetic acid (2 mL). The mixture was stirred at ambient temperature for 2 hours, concentrated to dryness, mixed with diethyl ether, and sonicated for 5 minutes to give a white fluffy solid which was filtered to give 490 mg (62%) of the desired product as the trifluoroacetate salt.

$^1$NMR FD-MS, m/e 512 (m–1) Analysis for $C_{25}H_{25}$ $ClFN_5O_4.1.5C_2 HF_3O_2$: Calcd: C, 49.10; H, 3.90; N, 10.22; Found: C, 49.27; H, 3.95; N, 10.16.

EXAMPLE 35

Preparation of 2-[2-(2-tert-Butoxycarbonylaminoethoxy)-4-(morpholin-4-yl)-benzoylamino]-5-chloro-N-(5-chloropyridin-2-yl)benzamide

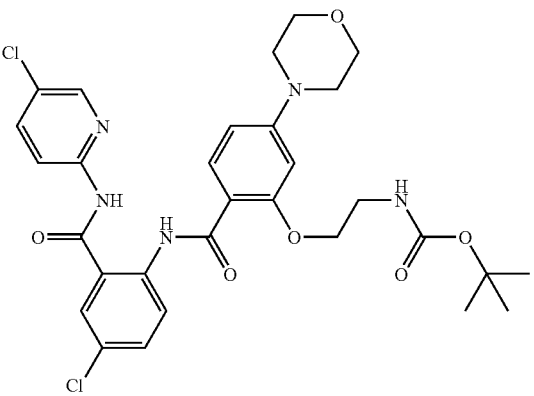

A. 2-(2-tert-Butoxycarbonylaminoethoxy)-4-fluorobenzoic acid

A mixture of methyl 2-(2-tert-butoxycarbonylaminoethoxy)-4-fluorobenzoate (4.2 g, 13.4 mmol), THF (100 mL), and MeOH (50 mL) was treated with 1 M lithium hydroxide (16 mL) and stirred for 48 hours at ambient temperature. The reaction was acidified with 10% aqueous citric acid (50 mL), diluted with brine (100 mL), and extracted with EtOAc (3×100 mL). The combined organic layers were dried over $MgSO_4$ and concentrated to give 3.93 g (13.1 mmol, 98%) of a white solid.

B. 2-[2-(2-tert-Butoxycarbonylaminoethoxy)-4-fluorobenzoylamino]-5-chloro-N-(5-chloropyridin-2-yl)benzamide Using methods substantially equivalent to those described in Example 29-G, the compound was prepared in a 75% yield from N-(5-chloropyridin-2-yl)-2-amino-5-chloro-benzamide and 2-(2-tert-butoxycarbonylaminoethoxy)-4-fluorobenzoic acid.

$^1$NMR IS-MS, m/e 563 (m+) Analysis for $C_{26}H_{25}Cl_2$ $FN_4O_5$: Calcd: C, 55.43; H, 4.47; N, 9.94; Found: C, 55.35; H, 4.42; N, 9.81.

C. 2-[2-(2-tert-Butoxycarbonylaminoethoxy)-4-(morpholin-4-yl)benzoylamino]-5-chloro-N-(5-chloropyridin-2-yl)benzamide A mixture of 2-[2-(2-tert-butoxycarbonylaminoethoxy)-4-fluoroberzoylamino]-5-chloro-N-(5-chloropyridin-2-yl)benzamide (1.4 g, 2.5 mmol), morpholine (10.1 g, 116 mmol), and $K_2CO_3$ (0.5 g) was heated in a sealed tube at 120° C. for 16 hours. The reaction was filtered, then concentrated to dryness under vacuum. The residue was dissolved in $CH_2Cl_2$ and purified by chromatography using 30% EtOAc in hexanes to give 810 mg (51%) of product.

$^1$NMR IS-MS, m/e 630 (m+) Analysis for $C_{30}H_{33}Cl_2N_5O_6$: Calcd: C, 57.15; H, 5.28; N, 11.11; Found: C, 57.14; H, 5.46; N, 11.05.

EXAMPLE 36

Preparation of N-(5-Chloropyridin-2-yl)-2-[2-[1-(2-hydroxypropyl)piperidin-4-yl-oxy]-4-(pyrrolidin-1-yl)benzoylamino]benzamide

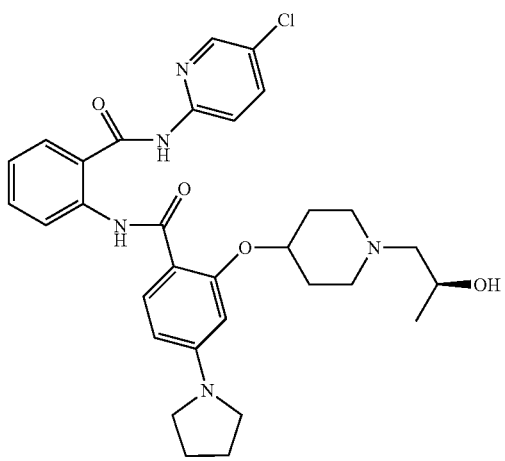

The N-(5-chloropyridin-2-yl)-2-[2-(piperidin-4-yloxy)-4-(pyrrolidin-1-yl)-benzoylamino]benzamide (304 mg, 0.58 mmol) was diluted with methanol (1 mL).

Propylene oxide (81 μL, 1.16 mmol) was added and the reaction was heated at 60° C. for minutes. The reaction was concentrated and the crude residue was purified by flash column chromatography (about 35 g silica, 5% MeOH/$CH_2Cl_2$ through 10% MeOH/$CH_2Cl_2$) to give the desired product (133 mg, 0.23 mmol, 40%) as a white solid.

$^1$NMR (400 MHz, DMSO-$d_6$): δ 11.14 (s, 1H); 10.78 (s, 1H); 8.39 (d, J=2.4 Hz, 1H); 8.34 (d, J=8.4 Hz, 1H); 8.19 (d, J=9.6 Hz, 1H); 7.92 (d, J=9.2 Hz, 1H); 7.74-7.70 (m, 2H); 7.49 (t, J=7.8 Hz, 1H); 7.13 (t, J=7.2 Hz, 1H); 6.21 (d, J=8.8 Hz, 1H); 4.18 (s, 1H); 3.27 (m, 1H); 2.59 (m, 2H); 2.12-1.85 (m, 12H); 0.96 (d, J=6.4 Hz, 3H). IS-MS, m/e 578.4 (m+1). Analysis for $C_{31}H_{36}ClN_5O_4 \cdot 0.50H_2O$: Calc: C, 63.42; H, 6.35; N, 11.93; Found: C, 63.76; H, 6.28; N, 11.74.

EXAMPLE 37

Preparation of 5-Chloro-N-(5-chloropyridin-2-yl)-2-[2-[1-(2-hydroxypropyl)-piperidin-4-yloxy]-4-(morpholin-4-yl)benzoylamino]benzamide

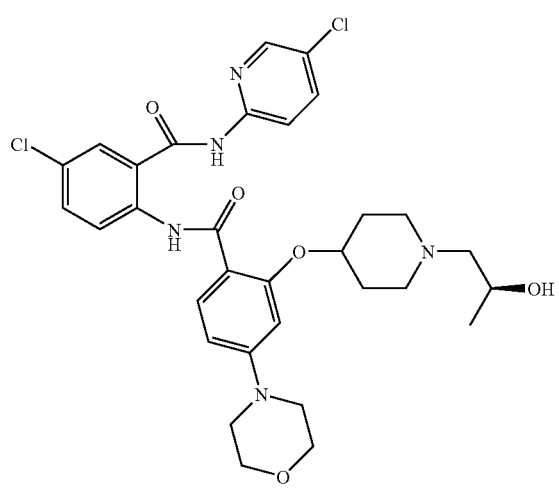

Using methods substantially equivalent to those described in Example 36, 5-chloro-N-(5-chloropyridin-2-yl)-2-[2-[1-(2-hydroxypropyl)piperidin-4-yloxy]-4-(morpholin-4-yl)benzoylamino]benzamide (54 mg, 0.09 mmol, 11%) was prepared from 5-chloro-N-(5-chloropyridin-2-yl)-2-[4-(morpholin-4-yl)-2-(piperidin-4-yloxy)-benzoylamino]benzamide.

$^1$NMR (400 MHz, DMSO-$d_6$): δ 11.30 (s, 1H); 10.80 (s, 1H); 8.40 (s, 1H); 8.38 (d, J=9.3 Hz, 1H); 8.16 (d, J=8.7 Hz, 1H); 7.93 (dd, J=2.1, 8.7 Hz, 1H); 7.78 (s, 1H); 7.74 (d, J=8.7 Hz, 1H); 7.56 (dd, J=2.1, 9.3 Hz, 1H); 6.59 (d, J=9.3 Hz, 1H); 6.56 (s, 1H); 4.62 (br s, 1H); 4.17 (s, 1H); 3.69 (s, 4H); 3.21 (s, 8H); 2.56 (m, 2H); 2.12-1.81 (m, 4H); 0.95 (d, J=6.0 Hz, 3H). IS-MS, m/e 629.2 (m+2). Analysis for $C_{31}H_{35}Cl_2N_5O_5$: Calc: C, 59.24; H, 5.61; N, 11.14; Found: C, 59.29; H, 5.87; N, 11.04.

EXAMPLE 38

Preparation of 2-[2-(2-Aminoethoxy)-4-(morpholin-4-yl)benzoylamino]-5-chloro-N-(5-chloropyridin-2-yl)benzamide Trifluoroacetate

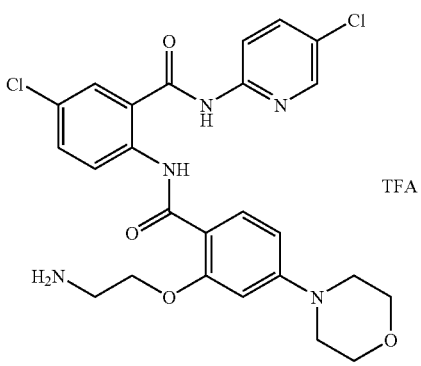

Using methods substantially equivalent to those described in Example 34, 2-[2-(2-aminoethoxy)-4-(morpholin-4-yl)benzoylamino]-5-chloro-N-(5-chloropyridin-2-yl)benzamide trifluoroacetate was prepared in a 74% yield from 2-[2-(2-tert-butoxy-carbonylaminoethoxy)-4-(morpholin-4-yl)benzoylamino]-5-chloro-N-(5-chloropyridin-2-yl)benzamide.

¹NMR IS-MS, m/e 530 (m+) Analysis for $C_{25}H_{25}Cl_2N_5O_4/1.1C_2HF_3O_2$: Calcd: C, 49.81; H, 4.01; N, 10.81; Found: C, 49.76; H, 3.82; N, 10.88.

EXAMPLE 39

Preparation of 2-[2-(2-tert-Butoxycarbonylaminoethoxy)-4-(morpholin-4-yl)-benzoylamino]-4-chloro-N-(5-chloropyridin-2-yl)benzamide

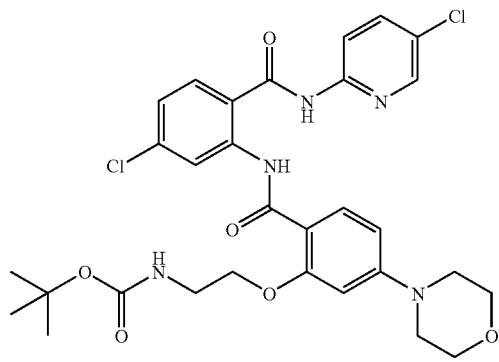

Using methods substantially equivalent to those described in Example 29-G, 2-[2-(2-tert-butoxycarbonylaminoethoxy)-4-(morpholin-4-yl)benzoylamin]-4-chloro-N-(5-chloropyridin-2-yl)benzamide was prepared in a 74% yield from 2-amino-4-chloro-N-(5-chloropyridin-2-yl)benzamide and 2-(2-tert-butoxycarbonylaminoethoxy)-4-(morpholin-4-yl)benzoic acid.

¹NMR IS-MS, m/e 630 (m+) Analysis for $C_{30}H_{33}Cl_2N_5O_6.0.1H_2O$: Calcd: C, 56.98; H, 5.29; N, 11.08; Found: C, 57.10; H, 5.63; N, 10.89.

EXAMPLE 40

Preparation of 2-[2-(2-tert-Butoxycarbonylaminoethoxy)-4-(morpholin-4-yl)-benzoylamino]-N-(5-chloropyridin-2-yl)-5-fluorobenzamide

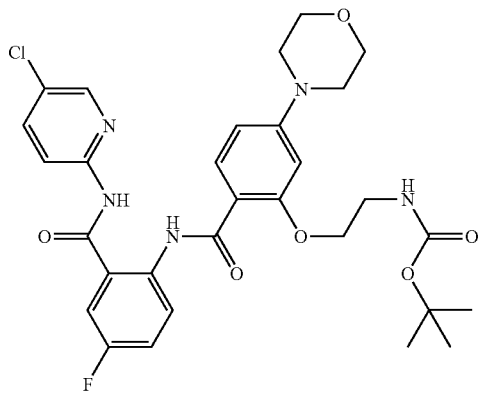

A. 2-[2-(2-tert-butoxycarbonylaminoethoxy)-4-fluorobenzoylamino]-N-(5-chloro-pyridin-2-yl)-5-fluorobenzamide Using methods substantially equivalent to those described in Example 29-G, 2-[2-(2-tert-butoxycarbonylaminoethoxy)-4-fluorobenzoylamino]-N-(5-chloropyridin-2-yl)-5-fluorobenzamide was prepared in a 69% yield from 2-(2-tert-butoxycarbonyl-aminoethoxy)-4-fluorobenzoic acid and 2-amino-N-(5-chloropyridin-2-yl)-5-fluoro-benzamide.

¹NMR IS-MS, m/e 545 (m−1) Analysis for $C_{26}H_{25}ClF_2N_4O_5.0.5H_2O$: Calcd: C, 56.17; H, 4.71; N, 10.08; Found: C, 55.81; H, 4.59; N, 9.76.

B. 2-[2-(2-tert-Butoxycarbonylaminoethoxy)-4-(morpholin-4-yl)benzoylamino]-N-(5-chloropyridin-2-yl)-5-fluorobenzamide A mixture of 2-[2-(2-tert-butoxycarbonylaminoethoxy)-4-fluorobenzoylamino]-N-(5-chloropyridin-2-yl)-5-fluorobenzamide (0.8 g, 1.5 mmol), morpholine (10 mL), and $K_2CO_3$ (0.2 g) was heated in a sealed tube at 100° C. for 12 hours and then 120° C. for 4 h.

The reaction was filtered, and concentrated to dryness. The residue was dissolved in $CH_2Cl_2$ and purified by chromatography to give 260 mg (28%) of product.

¹NMR FD-MS, m/e 614 (m+) Analysis for $C_{30}H_{33}ClFN_5O_6.H_2O$: Calcd: C, 56.84; H, 5.60; N, 11.05; Found: C, 57.00; H, 5.49; N, 10.93.

EXAMPLE 41

Preparation of 2-[2-(2-Aminoethoxy)-4-(morpholin-4-yl)benzoylamino]-N-(5-chloro-pyridin-2-yl)-5-fluorobenzamide Trifluoroacetate

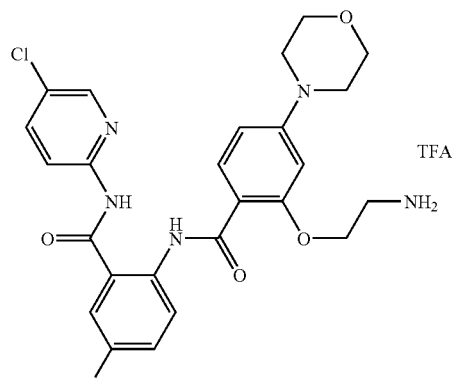

Using methods substantially equivalent to those described in Example 34, 2-2-(2-aminoethoxy)-4-(morpholin-4-yl)benzoylamino]-N-(5-chloropyridin-2-yl)-5-fluorobenzamide trifluoroacetate was prepared in a 74% yield from 2-[2-(2-tert-butoxy-carbonylaminoethoxy)-4-(morpholin-4-yl)benzoylamino]-N-(5-chloropyridin-2-yl)-5-fluorobenzamide.

¹NMR FD-MS, m/e 514 (m+1) Analysis for $C_{25}H_{25}ClFN_5O_4.1.1C_2HF_3O_2$: Calcd: C, 51.09; H, 4.11; N, 10.95; Found: C, 51.04; H, 4.31; N, 10.71.

EXAMPLE 42

Preparation of 2-[4-Chloro-2-(piperidin-4-yloxy)benzoylamino]-N-(5-chloropyridin-2-yl)benzamide Trifluoroacetate

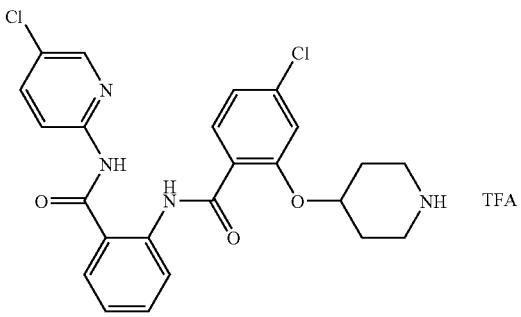

A. Methyl 4-chloro-2-hydroxybenzoate

Using methods substantially equivalent to those described in Example 4-B, methyl 4-chloro-2-hydroxybenzoate was prepared in a 84% yield from 4-chloro-2-hydroxy-benzoic acid.

[1]NMR IS-MS, m/e 187 (m+1) Analysis for $C_8H_7ClO_3 \cdot 0.4H_2O$: Calcd: C, 49.58; H, 4.06; Found: C, 49.82; H, 3.87.

B. Methyl 2-(1-tert-butoxycarbonylpiperidin-4-yloxy)-4-chlorobenzoate

Using methods substantially equivalent to those described in Example 29-A, methyl 2-(1-tert-butoxycarbonylpiperidin-4-yloxy)-4-chlorobenzoate was prepared in a 76% yield from methyl 4-chloro-2-hydroxybenzoate and 4-hydroxy-1-tert-butoxycarbonylpiperidine.

[1]NMR IS-MS, m/e 370 (m+1)

C. 2-(1-tert-Butoxycarbonylpiperidin-4-yloxy)-4-chlorobenzoic acid

Using methods substantially equivalent to those described in Example 35-A, 2-(1-tert-butoxycarbonylpiperidin-4-yloxy)-4-chlorobenzoic acid was prepared in a 97% yield from methyl 2-(1-tert-butoxycarbonylpiperidin-4-yloxy)-4-chlorobenzoate.

[1]NMR IS-MS, m/e 354 (m−1)

D. 2-[2-(1-tert-Butoxycarbonylpiperidin-4-yloxy)-4-chlorobenzoylamino]-N-(5-chloropyridin-2-yl)benzamide Using methods substantially equivalent to those described in Example 29-G, 2-[2-(1-tert-butoxycarbonylpiperidin-4-yloxy)-4-chlorobenzoylamino]-N-(5-chloro-pyridin-2-yl)benzamide was prepared in a 97% yield from 2-amino-N-(5-chloropyridin-2-yl)benzamide and 2-(1-tert-butoxycarbonylpiperidin-4-yloxy)-4-chlorobenzoic acid.

[1]NMR IS-MS M/e 585 (m+)

E. 2-[4-Chloro-2-(piperidin-4-yloxy)benzoylamino]-N-(5-chloropyridin-2-yl)-benzamide Trifluoroacetate Using methods substantially equivalent to those described in Example 34, 2-[4-chloro-2-(piperidin-4-yloxy)benzoylamino]-N-(5-chloropyridin-2-yl)benzamide trifluoroacetate was prepared in a quantitative yield from 2-[2-(1-tert-butoxycarbonyl-piperidin-4-yloxy)-4-chlorobenzoylamino]-N-(5-chloropyridin-2-yl)benzamide.

[1]NMR IS-MS 485 (m+)

EXAMPLE 43

Preparation of 2-[2-(1-tert-Butoxycarbonylpiperidin-4-yloxy)-4-(morpholin-4-yl)-benzoylamino]-4-chloro-N-(5-chloropyridin-2-yl)benzamide.

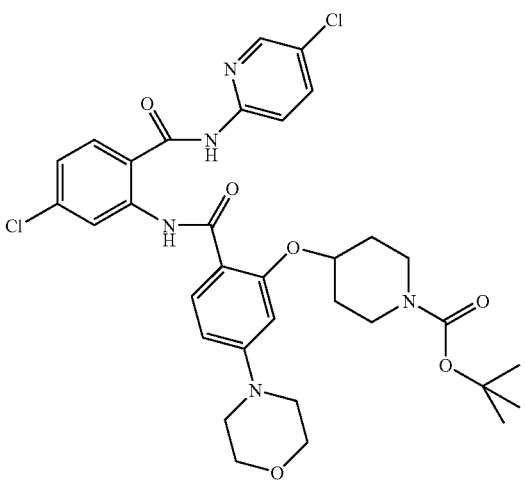

A. 2-[2-(1-tert-Butoxycarbonylpiperidin-4-yloxy)-4-fluorobenzoylamino]-4-chloro-N-(5-chloropyridin-2-yl)benzamide Using methods substantially equivalent to those described in Example 4-E, 2-[2-(1-tert-butoxycarbonylpiperidin-4-yloxy)-4-fluorobenzoylamino]-4-chloro-N-(5-chloropyridin-2-yl)benzamide (3.89 g, 6.44 mmol, 86%) was prepared from 2-amino-4-chloro-N-(5-chloropyridin-2-yl)benzamide and 2-(1-tert-butoxycarbonylpiperidin-4-yloxy)-4-fluorobenzoic acid.

[1]NMR (400 MHz, DMSO-$d_6$): δ 11.34 (s, 1H); 11.18 (s, 1H); 8.52 (s, 1H); 8.41 (d, J=2.0 Hz, 1H); 8.10 (d, J=8.8 Hz, 1H); 7.92-7.85 (m, 2H); 7.83 (d, J=8.8 Hz, 1H); 7.30-7.24 (m, 2H); 6.91 (t, J=8.2 Hz, 1H); 4.78 (s, 1H); 3.67 (d, J=12.0 Hz, 2H); 3.00 (m, 2H); 1.88 (m, 2H); 1.77 (m, 2H); 1.32 (s, 9H). IS-MS, m/e 603.2 (m+1). Analysis for $C_{29}H_{29}Cl_2FN_4O_5$: Calc: C, 57.72; H, 4.84; N, 9.28; Found: C, 57.80; H, 4.72; N, 9.48.

B. 2-[2-(1-tert-Butoxycarbonylpiperidin-4-yloxy)-4-(morpholin-4-yl)benzoylamino]-4-chloro-N-(5-chloropyridin-2-yl)benzamide Using methods substantially equivalent to those described in Example 4-F, 2-[2-(1-tert-butoxycarbonylpiperidin-4-yloxy)-4-(morpholin-4-yl)benzoylamino]-4-chloro-N-(5-chloropyridin-2-yl)benzamide (1.32 g, 1.97 mmol, 42%) was prepared from 2-[2-(1-tert-butoxycarbonylpiperidin-4-yloxy)-4-fluorobenzoylamino]-4-chloro-N-(5-chloropyridin-2-yl)benzamide and morpholine.

[1]NMR (400 MHz, DMSO-d6): δ 11.30 (s, 1H); 11.03 (s, 1H); 8.51 (s, 1H); 8.41 (s, 1H); 8.12 (d, J=8.4 Hz, 1H); 7.92 (d, J=8.8 Hz, 1H); 7.79-7.74 (m, 2H); 7.23 (d, J=8.0 Hz, 1H); 6.61 (d, J=14.8 Hz, 1H); 6.60 (s, 1H); 4.81 (m, 1H); 3.70 (m, 6H); 3.24 (m, 4H); 2.98 (m, 2H); 1.85-1.78 (m, 4H); 1.32 (s, 9H). IS-MS, m/e 670.4 (m+1). Analysis for $C_{33}H_{37}Cl_2N_5O_6$: Calc: C, 59.11; H, 5.56; N, 10.44; Found: C, 59.39; H, 5.58; N, 10.50.

EXAMPLE 44

Preparation of 2-[2-(2-Aminoethoxy)-4-(morpholin-4-yl)benzoylamino]-4-chloro-N-(5-chloropyridin-2-yl)benzamide Trifluoroacetate.

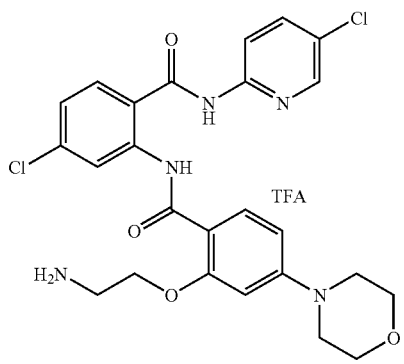

Using methods substantially equivalent to those described in Example 34, 2-[2-(2-aminoethoxy)-4-(morpholin-4-yl) benzoylamino]-4-chloro-N-(5-chloropyridin-2-yl)benzamide trifluoroacetate was prepared in a 78% yield from 2-[2-(2-tert-butoxy-carbonylaminoethoxy)-4-(morpholin-4-yl) benzoylamino]-N-(5-chloropyridin-2-yl)-4-chlorobenzamide.

[1]NMR IS-MS, m/e 529 (m−1)

EXAMPLE 45

Preparation of 4-Chloro-N-(5-chloropyridin-2-yl)-2-[4-(morpholin-4-yl)-2-(piperidin-4-yloxy)benzoylamino]benzamide.

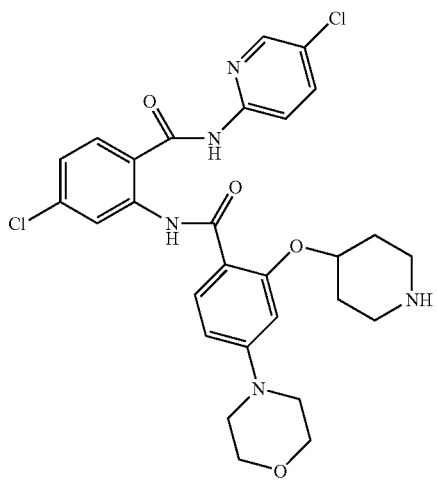

Using methods substantially equivalent to those described in example 4-G, 4-chloro-N-(5-chloropyridin-2-yl)-2-[4-(morpholin-4-yl)-2-(piperidin-4-yloxy)-benzoylamino]benzamide (1.06 g, 1.86 mmol, 89%) was prepared from 2-[2-(1-tert-butoxycarbonylpiperidin-4-yloxy)-4-(morpholin-4-yl)benzoylamino]-N-(5-chloropyridin-2-yl)-4-chlorobenzamide.

[1]NMR (400 MHz, DMSO-d6): δ 8.54 (d, J=2.0 Hz, 1H); 8.42 (d, J=2.0 Hz, 1H); 8.15 (d, J=9.2 Hz, 1H); 7.95 (dd, J=2.6, 9.0 Hz, 1H); 7.78 (d, J=8.8 Hz, 1H); 7.73 (d, J=8.8 Hz, 1H); 7.23 (dd, J=2.2, 8.2 Hz, 1H); 6.62 (d, J=8.8 Hz, 1H); 6.58 (s, 1H); 4.71 (m, 1H); 3.70 (m, 4H); 3.23 (m, 4H); 2.84 (m, 2H); 2.62 (m, 2H); 1.86 (m, 2H); 1.71 (m, 2H). IS-MS, m/e 570.3 (m+1). Analysis for $C_{28}H_{29}Cl_2N_5O_4 \cdot 0.75H_2O$: Calc: C, 57.59; H, 5.26; N, 11.99; Found: C, 57.20; H, 4.90; N, 11.68.

EXAMPLE 46

Preparation of 4-Chloro-N-(5-chloropyridin-2-yl)-2-[4-(morpholin-4-yl)-2-[1-(2-hydroxypropyl)piperidin-4-yloxy]benzoylamino]benzamide.

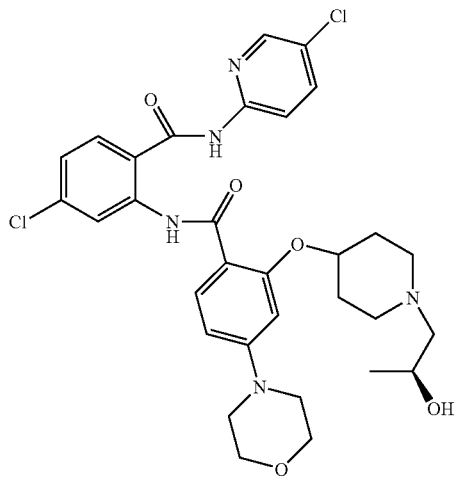

Using methods substantially equivalent to those described in Example 36, 4-chloro-N-(5-chloropyridin-2-yl)-2-[4-(morpholin-4-yl)-2-[1-(2-hydroxypropyl)-piperidin-4-yloxy]benzoylamino]benzamide (132 mg, 0.21 mmol, 34%) was prepared from 4-chloro-N-(5-chloropyridin-2-yl)-2-[4-(morpholin-4-yl)-2-(piperidin-4-yloxy)-benzoylamino]benzamide and propylene oxide.

[1]NMR (400 MHz, DMSO-d6): δ 11.28 (s, 1H); 10.99 (s, 1H); 8.56 (s, 1H); 8.41 (d, J=2.8 Hz, 1H); 8.16 (d, J=8.8 Hz, 1H); 7.94 (dd, J=2.6, 9.0 Hz, 1H); 7.76 (m, 2H); 7.23 (dd, J=2.0, 8.4 Hz, 1H); 6.61 (d, J=9.2 Hz, 1H); 6.57 (s, 1H); 4.59 (m, 1H); 4.16 (m, 1H); 3.70 (m, 4H); 3.23 (m, 4H); 2.54 (m, 2H); 2.13-1.81 (m, 8H); 0.95 (d, J=6.4 Hz, 3H). IS-MS, m/e 628.3 (m+1). Analysis for $C_{31}H_{35}Cl_2N_5O_5$: Calc: C, 59.24; H, 5.61; N, 11.14; Found: C, 59.35; H, 5.51; N, 11.15.

EXAMPLE 47

Preparation of 2-[2-(3-tert-Butoxycarbonylamino-2-methylpropoxy)-4-(pyrrolidin-1-yl)benzoylamino]-N-(5-chloropyridin-2-yl)benzamide.

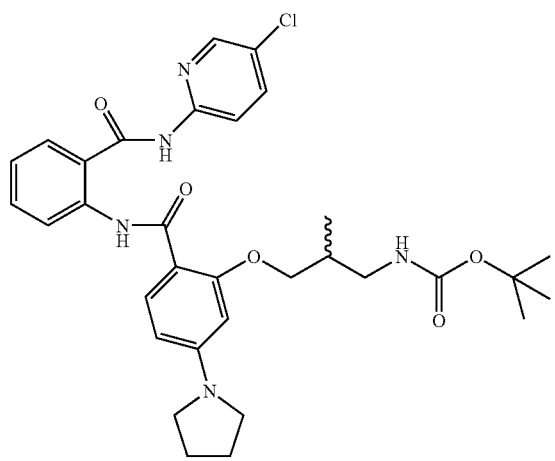

A. tert-Butyl N-(2-methylallyl)carbamate

Potassium carbonate (14.17 g, 102.5 mmol) was added to a mixture of 2-methyl-allylamine hydrochloride in acetone (500 mL), followed by di-tert-butyl dicarbonate (12.18 g, 55.8 mmol). Water (200 mL) was added to get all of the solids to go into solution. After stirring overnight, the reaction was concentrated to less than 200 mL. The residue was extracted with ethyl acetate (2×). The organic layers were combined, dried over sodium sulfate, and concentrated. The crude residue was purified by flash column chromatography (5% EtOAc/hexanes) to give the desired product (7.11 g, 41.6 mmol, 89%) as a colorless oil.

IR(CHCl$_3$): 1711, 1506, 1368, 1167 cm$^{-1}$. $^1$NMR (300 MHz, DMSO-d$_6$): δ 6.98 (br s, 1H); 4.69 (s, 2H); 3.40 (d, J=6.0 Hz, 2H); 1.59 (s, 3H); 1.34 (s, 9H).

B. 2-Methyl-3-(tert-butoxycarbonylamino)propanol

The tert-butyl N-(2-methylallyl)carbamate (213 mg, 1.24 mmol) was diluted with THF (12 mL) and the mixture was cooled to 0° C. Borane-dimethylsulfide complex (0.9 mL, 1.8 mmol) was added. After 1.5 hours, the reaction was cooled to −40° C. and 1 N NaOH (5 mL) and 30% hydrogen peroxide (5 mL) were carefully added. After 15 minutes, the reaction was warmed slowly until the frozen mixture melted. Ethyl acetate (100 mL) was then added, and the mixture was washed with brine (3×10 mL). The combined aqueous layers were extracted with ethyl acetate (100 mL). The organic layers were combined, dried over sodium sulfate, filtered, and concentrated. The crude residue was purified by flash column chromatography (about 20 g silica, 10% EtOAc/CH$_2$Cl$_2$ through 15% EtOAc/CH$_2$Cl$_2$) to give the desired product (209 mg, 1.10 mmol, 89%).

IR(CHCl$_3$): 1693, 1512, 1368, 1134 cm$^{-1}$. $^1$NMR (300 MHz, DMSO-d$_6$): δ 6.70 (br s, 1H); 3.17 (m, 2H); 2.87 (m, 1H); 2.70 (m, 1H); 1.56 (m, 1H); 1.33 (s, 9H); 0.74 (d, J=6.6 Hz, 3H). FD-MS, m/e 189 (m)

C. 2-(3-tert-Butoxycarbonylamino-2-methylpropoxy)-4-fluorobenzoic acid

Using methods substantially equivalent to those described in Example 21-C, ethyl-2-(3-tert-butoxycarbonylamino-2-methylpropoxy)-4-fluorobenzoate was prepared from ethyl-2,4-difluorobenzoate and 2-methyl-3-tert-butoxycarbonylaminopropanol. The impure material was saponified using methods substantially equivalent to those described in Example 21-D to give 2-(3-tert-butoxycarbonylamino-2-methylpropoxy)-4-fluoro-benzoic acid (554 mg, 1.69 mmol, 7% for 2 steps after RPHPLC purification).

$^1$NMR (400 MHz, DMSO-d$_6$): δ 7.71 (d, J=7.6 Hz, 1H); 6.95-6.78 (m, 2H); 3.88 (m, 2H); 1.97 (m, 1H); 1.33 (s, 9H); 0.92 (d, J=6.8 Hz, 3H); IS-MS, m/e 228.2 (m-BOC+1) Analysis for C$_{16}$H$_{22}$FNO$_5$: Calc: C, 58.71; H, 6.77; N, 4.28; Found: C, 58.96; H, 6.90; N, 4.37.

D. 2-[2-(3-tert-Butoxycarbonylamino-2-methylpropoxy)-4-fluorobenzoylamino]-N-(5-chloropyridin-2-yl)benzamide Using methods substantially equivalent to those described in Example 4-E, 2-[2-(3-tert-butoxycarbonylamino-2-methylpropoxy)-4-fluorobenzoylamino]-N-(5-chloropyridin-2-yl)benzamide (527 mg, 0.95 mmol, 68%) was prepared from N-(5-chloropyridin-2-yl)-2-aminobenzamide and 2-(3-tert-butoxycarbonylamino-2-methylpropoxy)-4-fluorobenzoic acid.

$^1$NMR (400 MHz, DMSO-d$_6$): δ 11.13 (s, 1H); 11.03 (s, 1H); 8.40 (d, J=2.0 Hz, 1H); 8.32 (d, J=8.0 Hz, 1H); 8.11 (d, J=8.8 Hz, 1H); 7.94-7.87 (m, 2H); 7.78 (d, J=8.8 Hz, 1H); 7.54 (t, J=8.0 Hz, 1H); 7.21 (t, J=7.4 Hz, 1H); 7.05 (d, J=10.4 Hz, 1H); 6.89 (t, J=7.2 Hz, 1H); 6.80 (m, 1H); 4.10 (m, 1H); 3.98 (m, 1H); 2.86 (m, 2H); 2.13 (m, 1H); 1.29 (s, 9H); 0.76 (d, J=6.8 Hz, 3H). IS-MS, m/e 557.1 (m+1) Analysis for C$_{28}$H$_{30}$ClFN$_4$O$_5$: Calc: C, 60.38; H, 5.43; N, 10.06; Found: C, 60.59; H, 5.55; N, 9.98.

E. 2-[2-(3-tert-Butoxycarbonylamino-2-methylpropoxy)-4-(pyrrolidin-1-yl)-benzoylamino]-N-(5-chloropyridin-2-yl)benzamide Using methods substantially equivalent to those described in example 4-F, except that the reaction was heated to 80° C., 2-[2-(3-tert-butoxycarbonylamino-2-methyl-propoxy)-4-(pyrrolidin-1-yl)benzoylamino]-N-(5-chloropyridin-2-yl)benzamide (427 mg, 0.70 mmol, 83%) was prepared from 2-[2-(3-tert-butoxycarbonylamino-2-methyl-propoxy)-4-fluorobenzoylamino]-N-(5-chloropyridin-2-yl)benzamide and pyrrolidine.

$^1$NMR (300 MHz, DMSO-d$_6$): δ 11.11 (s, 1H); 10.94 (s, 1H); 8.39 (m, 1H); 8.14 (d, J=8.7 Hz, 1H); 7.93 (dd, J=1.8, 8.7 Hz, 1H); 7.77 (d, J=8.7 Hz, 1H); 7.70 (d, J=7.8 Hz, 1H); 7.48 (t, J=7.8 Hz, 1H); 7.12 (t, J=7.4 Hz, 1H); 6.83 (m, 1H); 6.20 (d, J=8.7 Hz, 1H); 6.05 (s, 1H); 4.15 (m, 1H); 3.92 (m, 1H); 3.29 (d, J=12.9 Hz, 4H); 2.83 (m, 2H); 2.17 (m, 1H); 1.94 (d, J=6.0 Hz, 4H); 1.31 (s, 9H); 0.74 (d, J=6.6 Hz, 1H). IS-MS, m/e 608.2 (m+1). Analysis for C$_{32}$H$_{38}$ClN$_5$O$_5$: Calc: C, 63.20; H, 6.30; N, 11.52; Found: C, 63.43; H, 6.10; N, 11.62.

EXAMPLE 48

Preparation of 2-[2-(3-Amino-2-methylpropoxy)-4-(pyrrolidin-1-yl)benzoylamino]-N-(5-chloropyridin-2-yl)benzamide.

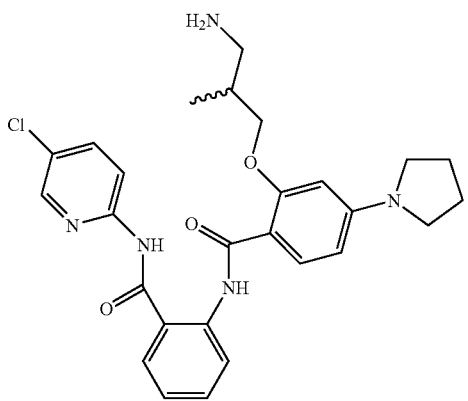

Using methods substantially equivalent to those described in Example 4-G, 2-[2-(3-amino-2-methylpropoxy)-4-(pyrrolidin-1-yl)benzoylamino]-N-(5-chloropyridin-2-yl)benzamide (342 mg, 0.67 mmol, 100%) was prepared from 2-[2-(3-tert-butoxy-carbonylamino-2-methylpropoxy)-4-(pyrrolidin-1-yl)benzoylamino]-N-(5-chloropyridin-2-yl)benzamide.
$^1$NMR (400 MHz, DMSO-d$_6$): δ 8.42 (d, J=2.0 Hz, 1H); 8.37 (dd, J=0.8, 8.4 Hz, 1H); 8.11 (d, J=9.2 Hz, 1H); 7.95 (dd, J=2.8, 8.8 Hz, 1H); 7.78-7.72 (m, 1H); 7.50 (t, J=7.2 Hz, 1H); 7.14 (t, J=7.4 Hz, 1H); 6.22 (d, J=8.8 Hz, 1H); 6.12 (s, 1H); 4.17 (m, 1H); 4.05 (m, 1H); 2.73 (dd, J=6.0, 12.8 Hz, 1H); 2.57 (dd, J=6.4, 12.8 Hz, 1H); 2.22 (m, 1H); 1.94 (m, 4H); 0.85 (d, J=6.8 Hz, 1H). IS-MS, m/e 508.2 (m+1). Analysis for C$_{27}$H$_{30}$ClN$_5$O$_{3.0.65}$CH$_2$Cl$_2$: Calc: C, 59.53; H, 5.53; N, 12.26; Found: C, 59.34; H, 5.46; N, 12.09.

EXAMPLE 49

Preparation of 2-[2-(1-tert-Butoxycarbonylpiperidin-4-yloxy)-4-(morpholiin-4-yl)-benzoylamino]-N-(5-chloropyridin-2-yl)-5-fluorobenzamide.

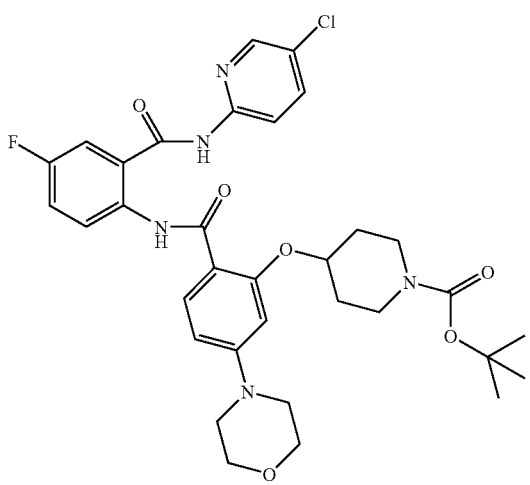

A. Methyl 2-(1-tert-butoxycarbonylpiperidin-4-yloxy)-4-(morpholin-4-yl)benzoate

Using methods substantially equivalent to those described in Example 29-B, methyl 2-(1-tert-butoxycarbonylpiperidin-4-yloxy)-4-fluoro benzoate (7.76 g, 22.0 mmol) and morpholine (40 mL) afforded, after purification by chromatography (SiO2: 25 to 40% EtOAc in hexanes), 2.43 g (26%) of the title compound.
$^1$NMR IS-MS, m/e=420 (m)

B. 2-(1-tert-Butoxycarbonylpiperidin-4-yloxy)-4-(morpholin-4-yl)benzoic acid

Using methods substantially equivalent to those described in Example 21-D, methyl 2-(1-tert-butoxycarbonylpiperidin-4-yloxy)-4-(morpholin-4-yl)benzoate (2.40 g, 5.71 mmol), lithium hydroxide monohydrate (605 mg, 15.1 mmol), and 2:1 (10% water in tetrahydrofuran):methanol (75 mL) afforded 2.16 g (93%) of the title compound; which was used without further purification.
$^1$NMR IS-MS, m/e=406 (m)

C. 2-[2-(1-tert-butoxycarbonylpiperidin-4-yloxy)-4-(morpholin-4-yl)-benzoylamino]-N-(5-chloropyridin-2-yl)-5-fluorobenzamide Using methods substantially equivalent to those described in Example 4-E, 2-[2-(1-tert-butoxycarbonylpiperidin-4-yloxy)-4-(morpholin-4-yl)benzoylamino]-N-(5-chloropyridin-2-yl)-5-fluorobenzamide (1.33 g, 2.03 mmol, 90%) was prepared from N-(5-chloropyridin-2-yl)-2-amino-5-fluorobenzamide and 2-(1-tert-butoxycarbonyl-piperidin-4-yloxy)-4-(morpholin-4-yl)benzoic acid.
$^1$NMR (400 MHz, DMSO-d$_6$): δ 11.27 (s, 1H); 10.76 (s, 1H); 8.40 (d, J=2.8 Hz, 1H); 8.28 (dd, J=5.2, 9.2 Hz, 1H); 8.13 (d, J=8.8 Hz, 1H); 7.91 (dd, J=2.2, 9.0 Hz, 1H); 7.77 (d, J=9.6 Hz, 1H); 7.59 (dd, J=3.0, 9.4 Hz, 1H); 7.39 (m, 1H); 6.60 (d, J=5.2 Hz, 1H); 6.60 (s, 1H); 4.85 (m, 1H); 3.70 (m, 4H); 3.23 (m, 4H); 3.00 (m, 2H); 2.47 (m, 2H); 1.87-1.79 (m, 4H); 1.33 (s, 9H); IS-MS, m/e 654.2 (m+1) Analysis for C$_{33}$H$_{37}$ClFN$_5$O$_6$: Calc: C, 60.59; H, 5.70; N, 10.71; Found: C, 60.50; H, 5.86; N, 10.54.

EXAMPLE 50

Preparation of N-(5-Chloropyridin-2-yl)-5-fluoro-2-[4-(morpholin-4-yl)-2-(piperidin-4-yloxy)benzoylamino]benzamide and Hydrochloride.

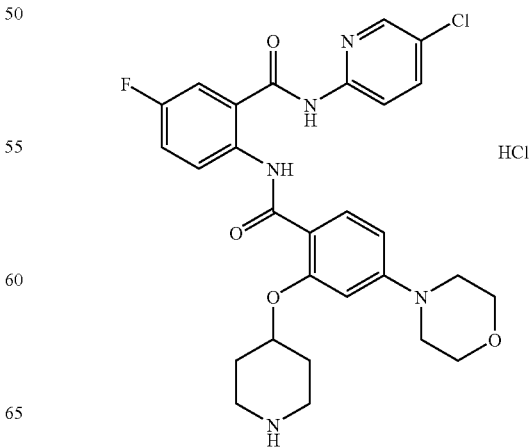

Using methods substantially equivalent to those described in Example 4-G, N-(5-chloropyridin-2-yl)-5-fluoro-2-[4-(morpholin-4-yl)-2-(piperidin-4-yloxy)-benzoylamino]benzamide (1.123 g, 2.03 mmol, 100%) was prepared from 2-[2-(1-tert-butoxycarbonylpiperidin-4-yloxy)-4-(morpholin-4-yl)benzoylamino]-N-(5-chloropyridin-2-yl)-5-fluorobenzamide. The salt was prepared by treatment of the free base with HCl.

$^1$NMR (400 MHz, DMSO-$d_6$): δ 8.41 (d, J=2.8 Hz, 1H); 8.32 (m, 1H); 8.18 (d, J=8.8 Hz, 1H); 7.94 (dd, J=2.8, 8.8 Hz, 1H); 7.76 (d, J=8.8 Hz, 1H); 7.58 (dd, J=2.8, 9.2 Hz, 1H); 7.38 (m, 1H); 6.59 (d, J=8.8 Hz, 1H); 6.57 (s, 1H); 4.64 (m, 1H); 3.69 (m, 4H); 3.21 (m, 4H); 2.77 (m, 2H); 2.46 (m, 2H); 1.81 (m, 2H); 1.60 (m, 2H). IS-MS, m/e 554.2 (m+1). Analysis for (free base) $C_{28}H_{29}ClFN_5O_{4.0.30}H_2O$: Calc: C, 60.12; H, 5.33; N, 12.52; Found: C, 60.17; H, 5.25; N, 12.13.

EXAMPLE 51

Preparation of 2-[2-(1-tert-Butoxycarbonylpiperidin-4-yloxy)-4-(morpholin-4-yl)-benzoylamino]-N-(5-chloropyridin-2-yl)-4-fluorobenzamide.

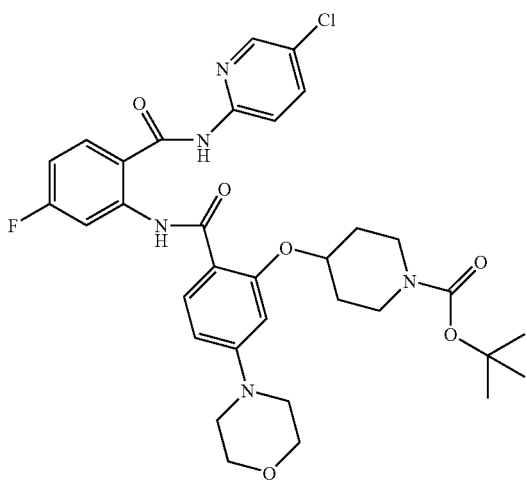

Using methods substantially equivalent to those described in Example 4-E, 2-[2-(1-tert-butoxycarbonylpiperidin-4-yloxy)-4-(morpholin-4-yl)benzoylamino]-N-(5-chloropyridin-2-yl)-4-fluorobenzamide (1.29 g, 1.97 mmol, 91%) was prepared from N-(5-chloropyridin-2-yl)-2-amino-4-fluorobenzamide and 2-(1-tert-butoxycarbonyl-piperidin-4-yloxy)-4-(morpholin-4-yl)benzoic acid.

$^1$NMR (400 MHz, DMSO-$d_6$): δ 11.24 (s, 1H); 11.17 (s, 1H); 8.40 (d, J=2.8 Hz, 1H); 8.31 (dd, J=2.8, 12.4 Hz, 1H); 8.11 (d, J=8.8 Hz, 1H); 7.92-7.83 (m, 1H); 7.75 (d, J=9.2 Hz, 1H); 7.01 (m, 1H); 6.61 (d, J=10.8 Hz, 1H); 6.60 (s, 1H); 4.79 (m, 1H); 3.70 (m, 4H); 3.24 (m, 4H); 2.99 (m, 2H); 2.47 (m, 2H); 1.86 (m, 2H); 1.77 (m, 2H); 1.31 (s, 9H). IS-MS, m/e 654.2 (m+1).

EXAMPLE 52

Preparation of N-(5-Chloropyridin-2-yl)-4-fluoro-2-[4-(morpholin-4-yl)-2-(piperidin-4-yloxy)benzoylamino]benzamide.

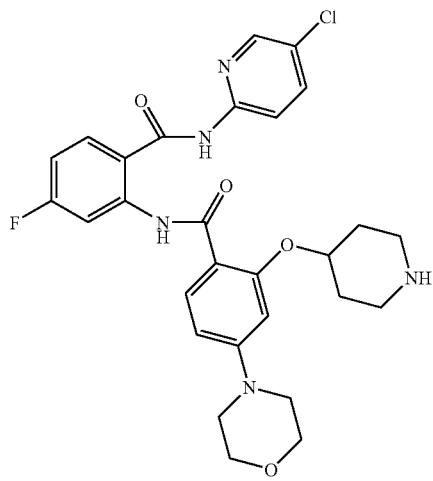

Using methods substantially equivalent to those described in Example 4-G, N-(5-chloropyridin-2-yl)-4-fluoro-2-[4-(morpholin-4-yl)-2-(piperidin-4-yloxy)-benzoylamino]benzamide (1.05 g, 1.90 mmol, 99%) was prepared from 2-[2-(1-tert-butoxycarbonylpiperidin-4-yloxy)-4-(morpholin-4-yl)benzoylamino]-N-(5-chloropyridin-2-yl)-4-fluorobenzamide.

$^1$NMR (400 MHz, DMSO-$d_6$): δ 8.42 (d, J=2.4 Hz, 1H); 8.34 (dd, J=2.8, 12.4 Hz, 1H); 8.14 (d, J=8.8 Hz, 1H); 7.94 (dd, J=2.8, 8.8 Hz, 1H); 7.85 (m, 1H); 7.73 (d, J=8.8 Hz, 1H); 7.02 (m, 1H); 6.62 (d, J=10.8 Hz, 1H); 6.58 (s, 1H); 4.71 (m, 1H); 3.70 (m, 4H); 3.29 (m, 2H); 2.84 (m, 2H); 2.61 (m, 2H); 1.85 (m, 2H); 1.80 (m, 2H). IS-MS, m/e 554.2 (m+1). Analysis for $C_{28}H_{29}ClFN_5O_{4.0.15}CH_2Cl_2$: Calc: C, 59.78; H, 5.19; N, 12.32; Found: C, 59.76; H, 5.04; N, 11.98.

EXAMPLE 53

Preparation of 2-[4-(tert-Butyl)-2-(piperidin-4-yloxy)benzoylamino]-N-(5-chloro-pyridin-2-yl)-4-fluorobenzamide Hydrochloride.

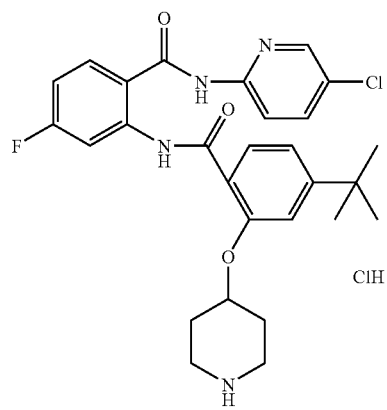

By methods substantially equivalent to those described in Examples 16-F and 16-G, 2-[4-(tert-butyl)-2-(piperidin-4-yloxy)benzoylamino]-N-(5-chloropyridin-2-yl)-4-fluorobenzamide hydrochloride (0.35 g, 11%) was prepared from N-(5-chloropyridin-2-yl)-2-amino-4-fluorobenzamide and 4-(tert-butyl)-2-(piperidin-4-yloxy)benzoyl chloride.

$^1$NMR IS-MS, m/e 525.3 (m+1) Analysis for $C_{28}H_{30}ClFN_4O_3 \cdot 1.7 HCl \cdot 1.2H_2O$: Calcd: C, 55.26; H, 5.65; N, 9.21; Cl, 15.73; Found: C, 55.51; H, 5.54; N, 8.85; Cl, 15.81.

EXAMPLE 54

Preparation of N-(5-Chloropyridin-2-yl)-5-fluoro-2-[2-[1-(2-hydroxypropyl)-piperidin-4-yloxy]-4-(morpholin-4-yl)benzoylamino]benzamide.

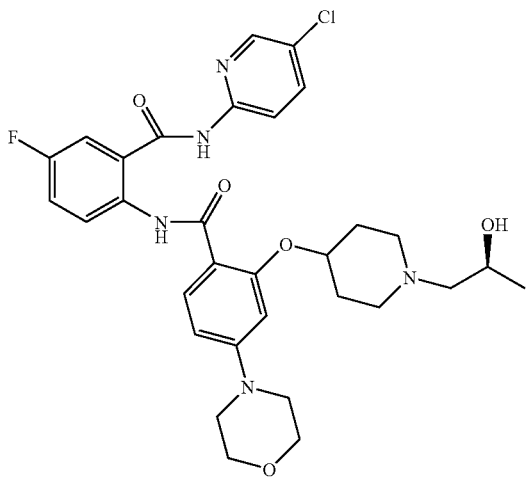

By methods substantially equivalent to those described in Example 36, N-(5-chloropyridin-2-yl)-5-fluoro-2-[2-[1-(2-hydroxypropyl)piperidin-4-yloxy]-4-(morpholin-4-yl)benzoylamino]benzamide (379 mg, 0.62 mmol, 73%) was prepared from N-(5-chloropyridin-2-yl)-5-fluoro-2-[4-(morpholin-4-yl)-2-(piperidin-4-yloxy)-benzoylamino]benzamide.

$^1$NMR (400 MHz, DMSO-$d_6$): δ 11.24 (s, 1H); 10.72 (s, 1H); 8.40 (d, J=2.0 Hz, 1H); 8.33-8.29 (m, 1H); 8.17 (d, J=8.4 Hz, 1H); 7.93 (dd, J=2.4, 9.2 Hz, 1H); 7.75 (d, J=8.8 Hz, 1H); 7.58 (dd, J=3.0, 9.0 Hz, 1H); 7.39 (t, J=8.8 Hz, 1H); 6.59 (d, J=9.6 Hz, 1H); 6.57 (s, 1H); 4.60 (m, 1H); 4.17 (m, 1H); 3.69 (m, 4H); 3.22-3.12 (m, 4H); 2.59 (m, 2H); 2.13-2.02 (m, 4H); 1.84 (m, 4H); 0.96 (d, J=6.0 Hz, 3H). IS-MS, m/e 612.2 (m+1).

EXAMPLE 55

Preparation of N-(5-Chloropyridin-2-yl)-4-fluoro-2-[2-[1-(2-hydroxypropyl)-piperidin-4-yloxy]-4-(morpholin-4-yl)benzoylamino]benzamide.

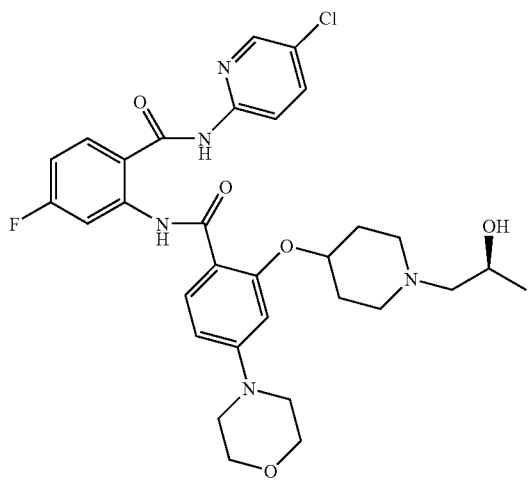

By methods substantially equivalent to those described in Example 36, N-(5-chloropyridin-2-yl)-4-fluoro-2-[2-[1-(2-hydroxypropyl)piperidin-4-yloxy]-4-(morpholin-4-yl)benzoylamino]benzamide (253 mg, 0.41 mmol, 49%) was prepared from N-(5-chloropyridin-2-yl)-5-fluoro-2-[4-(morpholin-4-yl)-2-(piperidin-4-yloxy)-benzoylamino]benzamide.

$^1$NMR (300 MHz, DMSO-$d_6$): δ 11.21 (s, 1H); 11.12 (s, 1H); 8.40 (d, J=2.4 Hz, 1H); 8.35 (dd, J=2.3, 12.5 Hz, 1H); 8.15 (d, J=9.0 Hz, 1H); 7.93 (dd, J=2.4, 8.7 Hz, 1H); 7.84 (t, J=7.5 Hz, 1H); 7.73 (d, J=8.7 Hz, 1H); 6.99 (t, J=6.8 Hz, 1H); 6.60 (d, J=9.0 Hz, 1H); 6.56 (s, 1H); 4.58 (br s, 1H); 4.16 (s, 2H); 4.06 (d, J=5.1 Hz, 1H); 3.73-3.59 (m, 4H); 3.27-3.12 (m, 4H); 2.52 (m, 2H); 2.16-1.99 (m, 4H); 1.85-1.74 (m, 4H); 0.94 (d, J=6.0 Hz, 3H). IS-MS, m/e 612.2 (m+1). Analysis for $C_{31}H_{35}ClFN_5O_5$: Calc: C, 60.83; H, 5.76; N, 11.44; Found: C, 61.11; H, 5.56; N, 11.71.

EXAMPLE 56

Preparation of 2-[4-(tert-Butyl)-2-(piperidin-4-yloxy)benzylamino]-5-chloro-N-(5-chloropyridin-2-yl)benzamide.

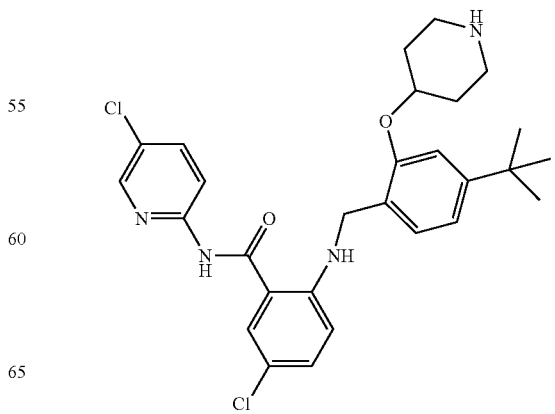

A. 4-(tert-Butyl)-2-(1-Boc-piperidin-4-yloxy)benzyl alcohol

To a solution of borane-trimethylamine complex (1.35 mL of a 1 M solution in tetrahydrofuran) in tetrahydrofuran (3 mL) stirring at 0° C., a solution of 4-(tert-butyl)-2-(1-Boc-piperidine-4-yloxy)benzoic acid (0.51 g, 1.35 mmol) in tetrahydrofuran (7 mL) was added slowly via cannula. After the addition was complete the reaction mixture was stirred at room temperature for 4 h, then an additional amount of borane-trimethylamine complex was added (1.35 mL of a 1 M solution in tetrahydrofuran). The reaction mixture was stirred at room temperature for another 2 h. After quenching with ice, the mixture was partitioned between brine and dichloromethane. The organic layer was separated and the aqueous layer was extracted with dichloromethane (3×). The combined organic layers were dried with magnesium sulfate, filtered, and concentrated in vacuo to a residue (0.42 g, 86%) which was identified as the title compound and used directly in the next step without further purification.

$^1$NMR FD-MS, m/e 364.1 (m+1).

B. 4-(tert-Butyl)-2-(1-Boc-piperidin-4-yloxy)benzaldehyde

To a solution of oxalyl chloride (0.30 mL, 3.46 mmol) in dichloromethane (5 mL) stirring at −78° C. under nitrogen atmosphere, dimethylsulfoxide was added dropwise (0.49 mL, 6.93 mmol). After 10 min, a solution of the crude 4-(tert-butyl)-2-(1-Boc-piperidine-4-yloxy)benzyl alcohol (0.42 g, 1.15 mmol) in dichloromethane (6 mL) was added slowly via cannula. After the addition was complete, the reaction mixture was stirred at −78° C. for 1 h. The reaction was then treated with triethylamine (1.6 mL, 11.5 mmol) and allowed to warm up to room temperature overnight. The reaction mixture was partitioned between brine and dichloromethane. The organic layer was separated and the aqueous layer was extracted with dichloromethane. The combined organic layers were dried with magnesium sulfate, filtered, and concentrated in vacuo to a brown residue which was purified on a silica gel chromatotron plate. Elution with ethyl acetate-hexanes (1:5) afforded the title compound (0.42 g, 100%) as a clear oil which foamed up under vacuum.

$^1$NMR FD-MS, m/e 362.1 (m+1).

C. 2-[4-(tert-Butyl)-2-(1-Boc-piperidin-4-yloxy) benzylamino]-5-chloro-N-(5-chloropyridin-2-yl) benzamide A solution of the 4-(tert-butyl)-2-(1-Boc-piperidine-4-yloxy)benzaldehyde (0.15 g, 0.42 mmol), N-(5-chloropyridin-2-yl)-2-amino-5-chlorobenzamide (0.12 g, 0.42 mmol) and catalytic pyridinium p-toluenesulfonate in toluene (8 mL) was treated with excess magnesium sulfate (0.5 g). The reaction mixture was then heated at 75° C. overnight. The reaction was cooled down to room temperature, filtered, and concentrated in vacuo to an oily residue which was redissolved in acetic acid (1.4 mL). The resulting solution was treated with borane-trimethylamine complex (0.2 g, 2.74 mmol) and stirred at room temperature for 3 h. The reaction mixture was then partition between 5 N aqueous sodium hydroxide and dichloromethane. The organic layer was separated and the aqueous layer was extracted with dichloromethane. The combined organic extracts were dried with magnesium sulfate, filtered, and concentrated in vacuo to a residue which was purified on a silica gel chromatotron plate. Elution with ethyl acetate-hexanes (95:5) then (9:1) provided the title compound (0.23 g, 87%) as a yellow oil which foamed up under vacuum. Recrystallization of the oil from ethyl acetate-hexanes provided analytically pure product (0.17 mg) as a pale-yellow crystalline solid.

$^1$NMR mp 161.3-162.9° C. FD-MS, m/e 627.1 (m). Analysis for $C_{33}H_{40}Cl_2N_4O_4$: Calcd: C, 63.15; H, 6.42; N, 8.93; Found: C, 63.03; H, 6.58; N, 8.86.

D. 2-[4-(tert-Butyl)-2-(piperidin-4-yloxy)benzylamino]-5-chloro-N-(5-chloropyridin-2-yl)benzamide A solution of the 2-[4-(tert-butyl)-2-(1-Boc-piperidin-4-yloxy)benzylamino]-5-chloro-N-(5-chloropyridin-2-yl)benzamide (0.2 g, 0.32 mmol) in trifluoroacetic acid (5 mL) was stirred at room temperature for 2 h. The mixture was poured into ice, then taken to basic pH with 5 N aqueous sodium hydroxide, and extracted with dichloromethane. The organic layer was separated, and the aqueous layer was thoroughly extracted with dichloromethane. The combined organic layers were dried with magnesium sulfate, filtered, and concentrated in vacuo to a yellow oily residue which was purified on a silica gel chromatotron plate. Elution with 9:1 dichloromethane-2 N ammonia in methanol provided the title compound as a clear oil which foamed up under vacuum (0.15 mg, 87%). Recrystallization of the oil from ethyl acetate-hexanes provided analytically pure product (0.09 mg) as a yellow-white crystalline solid.

$^1$NMR mp 153.6-154.5° C. FD-MS, m/e 527.0 (m). Analysis for $C_{28}H_{32}Cl_2N_4O_2$: Calcd: C, 63.76; H, 6.11; N, 10.62; Found: C, 63.87; H, 6.21; N, 10.65.

EXAMPLE 57

Preparation of 2-[4-(Benzyloxy)-2-(piperidin-4-yloxy)benzoylamino]-N-(5-chloro-pyridin-2-yl)benzamide Dihydrochloride.

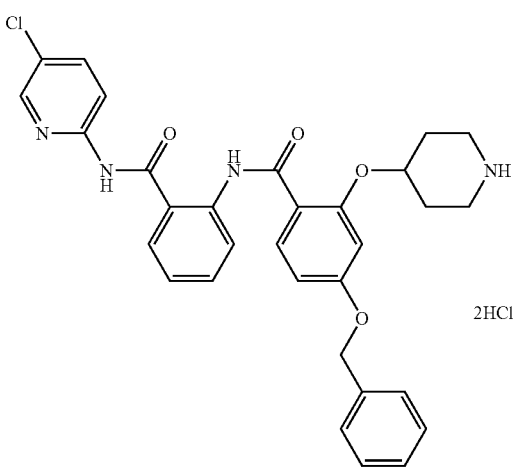

A. Methyl 4-benzyloxy-2-(piperidin-4-yloxy)benzoate

Using methods substantially equivalent to those described in Example 1-C, methyl 4-benzyloxy-2-hydroxybenzoate (2.0 g, 8.1 mmol), N-tert-butoxycarbonyl-4-hydroxy-piperidine (1.6 g, 8.1 mmol), triphenylphosphine (2.1 g, 8.1 mmol), and diethyl azodicarboxyalte (1.3 mL, 8.1 mmol) afforded, after purification by chromatography (SiO$_2$: 5 to 15% EtOAc in hexanes), 2.57 g (74%) of the title compound.
$^1$NMR IS-MS, m/e=429 (m)

B. 4-Benzyloxy-2-(1-tert-butoxycarbonylpiperidin-4-yloxy)benzoic acid

Using methods substantially equivalent to those described in Example 1-D, methyl 4-benzyloxy-2-(piperidin-4-yloxy)benzoate (2.20 g, 5.13 mmol) afforded 2.01 g (94%) of the title compound.
$^1$NMR IS-MS, m/e=429 (m)

C. 2-[4-(B enzyloxy)-2-(1-tert-butoxycarbonylpiperidin-4-yloxy)benzoylamino]-N-(5-chloropyridin-2-yl)benzamide Using methods substantially equivalent to those described in Example 1-F, 4-benzyloxy-2-(1-tert-butoxycarbonylpiperidin-4-yloxy)benzoic acid (529 mg, 1.27 mmol) and N-(5-chloropyridin-2-yl)-2-aminobenzamide (297 mg, 1.20 mmol) afforded, after purification by chromatography (SiO2: EtOAc in hexanes), 493 mg (63%) of the title compound.
$^1$NMR IS-MS, m/e=656 (m)

D. 2-[4-(B enzyloxy)-2-(piperidin-4-yloxy)benzoylamino]-N-(5-chloropyridin-2-yl)-benzamide hydrochloride To a solution of 2-[4-(benzyloxy)-2-(1-tert-butoxycarbonylpiperidin-4-yloxy)-benzoylamino]-N-(5-chloropyridin-2-yl)benzamide (130 mg, 0.2 mmol) in methylene chloride (20 mL) was added trifluoroacetic acid (2 mL). The reaction was stirred for 2 h at room temperature, then it was diluted with methanol and purified by SCX column to give 112 mg (100%) of the product. The product was dissolved in methanol, and 2 M HCl in methanol (1 mL) was added. The solution was stirred for 15 minutes and then concentrated in vacuo to give 120 mg of a tan solid.
$^1$NMR FD-MS, m/e 648 Analysis for C$_{31}$H$_{29}$ClN$_4$O$_4$.2HCl.H$_2$0: Calcd: C, 57.46; H, 5.13; N, 8.65; Found: C, 57.88; H, 5.05; N, 8.70.

EXAMPLE 58

Preparation of N-(5-Chloropyridin-2-yl)-2-[4-(pyrrolidin-1-yl)-2-(1-trifluoroacetyl-piperidin-4-yloxy)benzoylamino]benzamide.

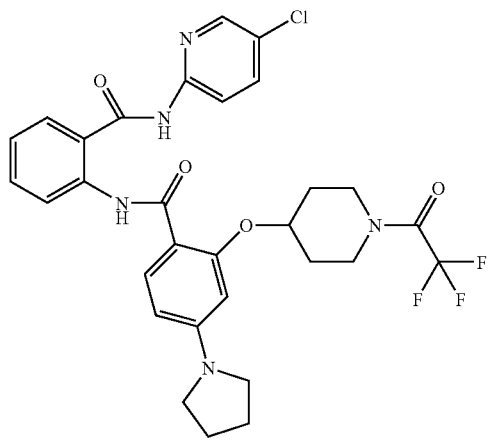

The N-(5-chloropyridin-2-yl)-2-[2-(piperidin-4-yloxy)-4-(pyrrolidin-1-yl)-benzoylamino]benzamide (287 mg, 0.55 mmol) was diluted with methylene chloride (6 mL) and pyridine (49 µL, 0.61 mmol). Excess trifluoroacetic anhydride (TFAA) was added. After 5 minutes, the reaction was diluted with methylene chloride (100 mL) and extracted with saturated aqueous sodium bicarbonate (3×10 mL). The organic layer was dried over sodium sulfate, filtered, and concentrated. The crude residue was purified by flash column chromatography (about 35 g silica, 10% EtOAc/CH$_2$Cl$_2$) to give the desired product (240 mg, 0.39 mmol, 71%) as a yellow solid.
$^1$NMR (400 MHz, DMSO-d$_6$): δ 8.42 (d, J=2.8 Hz, 1H); 8.13 (d, J=8.0 Hz, 1H); 7.87 (dd, J=3.0, 8.6 Hz, 1H); 7.71 (d, J=7.2 Hz, 1H); 7.55-7.32 (m, 3H); 6.14 (m, 2H); 4.84 (s, 1H); 3.98 (m, 2H); 3.76 (m, 2H); 3.27 (m, 4H); 1.95-1.69 (m, 8H).

EXAMPLE 59

Preparation of 2-[4-(tert-Butyl)-2-(piperidin-4-yloxy)benzylamino]-N-(5-chloro-pyridin-2-yl)benzamide.

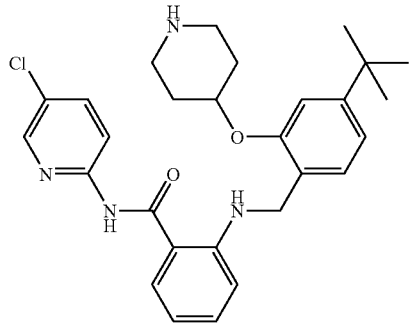

A. 2-[4-(tert-Butyl)-2-(1-Boc-piperidin-4-yloxy)benzylamino]-N-(5-chloropyridin-2-yl)benzamide N-(5-Chloropyridin-2-yl)-2-aminobenzamide (0.09 g, 0.39 mmol) was converted into the title compound (0.24 g, 100%) using the procedure described in Example 56-C. The product was obtained as a yellow oil, which was further purified by recrystallization from ethyl acetate-hexanes, giving rise to a yellow-white solid (0.14 g).
$^1$NMR mp 182.6-183.1° C. FD-MS, m/e 593.6 (m) Analysis for C$_{33}$H$_{41}$ClN$_4$O$_4$: Calcd: C, 66.82; H, 6.97; N, 9.45; Found: C, 67.06; H, 7.14; N, 9.56.

B. 2-[4-(tert-Butyl)-2-(piperidin-4-yloxy)benzylamino]-N-(5-chloropyridin-2-yl)-benzamide 2-[4-(tert-butyl)-2-(1-Boc-piperidin-4-yloxy)benzylamino]-N-(5-chloropyridin-2-yl)benzamide (0.19 g, 0.32 mmol) was converted to the title compound (0.14 g, 88%) using the procedure described in Example 56-D. The product was obtained as a foam which was further purified by recrystallization from ethyl acetate-hexanes, giving rise to a white, powdery solid (0.09 g).
$^1$NMR mp 169.0-170.0° C. FD-MS, m/e 493.3 (m) Analysis for C$_{28}$H$_{33}$ClN$_4$O$_2$: Calcd: C, 68.21; H, 6.75; N, 11.36; Found: C, 68.29; H, 6.95; N, 11.47.

EXAMPLE 60

Preparation of 2-[4-(1-Amino-1-methyl)ethyl-2-(piperidin-4-yloxy)benzoylamino]-N-(5-chloropyridin-2-yl)benzamide Bis(trifluoroacetate).

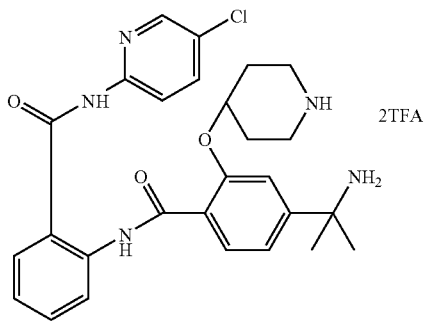

A. 3-Isopropyl-1-methoxymethoxybenzene

Into methylene chloride (300 mL) was dissolved 3-isopropylphenol (27.24 g, 200 mmol). After cooling the solution in an ice bath, diisopropylethyl amine (69.7 mL, 400 mmol) was added in one portion, followed by the dropwise addition of chloromethyl methyl ether (18.9 mL, 236 mmol) in methylene chloride (50 mL). The reaction mixture was gradually allowed to warm to room temperature. After 16 h, the reaction mixture was diluted with cold water (500 mL) and methylene chloride. The mixture was shaken in a separatory funnel and the layers were separated. The organic layer was extracted with cold water (2×500 mL), dried (MgSO$_4$), and concentrated under vacuum. The product was dissolved in ether (200 mL) and stirred with 5 N NaOH (200 mL) at room temperature for 5 min. The ether layer was separated and extracted with cold 1 N HCl (200 mL), dried (MgSO$_4$), and concentrated under vacuum. The product was chromatographed over silica (0 to 30% EtOAc in hexane gradient), giving 20.0 g (56%) of the title compound.

[1]NMR FD-MS, m/e: 180 (m)

B. 4-Isopropyl-2-methoxymethoxybenzoic acid

Into ether (450 mL) was dissolved 3-isopropyl-1-methoxymethoxybenzene (20.0 g, 111 mmol), and the resulting solution was cooled to −15° C. via an ice-salt-acetone-bath. Under nitrogen, 1.7 M tert-butyl lithium (78.4 mL, 133.2 mmol) was added dropwise over 10 min. and the reaction mixture was stirred for an additional 10 min. Excess carbon dioxide was bubbled in over 5 min; then the reaction mixture was poured into cold water (400 mL) and shaken in a separatory funnel. The aqueous layer was acidified with cold 1 N HCl and shaken with ether (300 mL). The ether layer was washed with water (300 mL), dried (MgSO$_4$), and concentrated under vacuum. The product was dissolved in a minimum amount of hexanes, giving 19.5 g (78%) of the title compound as a solid on standing at room temperature.

[1]NMR IS-MS, m/e: 225 (m+1), 223 (m−1)

C. Methyl 4-isopropyl-2-methoxymethoxybenzoate

Into methylene chloride (40 mL) was dissolved 4-isopropyl-2-methoxymethoxy-benzoic acid (6.0 g, 26.8 mmol). Methanol (10 mL) was added, followed by the dropwise addition of 2 M hexane solution of trimethylsilyldiazomethane (14.7 mL). After 2 h, HOAc (0.5 mL) was added and the solvent was removed under vacuum, giving the title compound as an oil, which was used in next step without further purification.

[1]NMR

D. Methyl 4-(1-bromo-1-methyl)ethyl-2-methoxymethoxybenzoate

Into CCl$_4$ (50 mL) was dissolved methyl 4-isopropyl-2-methoxymethoxybenzoate (3.36 g, 14.1 mmol). To this solution was added N-bromosuccinimide (3.02 g, 16.92 mmol), followed by azobis(isobutyronitrile) (AIBN) (about 30 mg). Under nitrogen, the reaction mixture was heated and stirred at gentle reflux for 4 h. The reaction mixture was cooled to room temperature and filtered, giving the title compound as as a crude oil.

[1]NMR

E. Methyl 4-(1-azido-1-methyl)ethyl-2-hydroxybenzoate

The crude methyl 4-(1-bromo-1-methyl)ethyl-2-methoxymethoxybenzoate was dissolved in dry DMF (30 mL). To this solution was added NaN$_3$ (1.1 g, 16.9 mmol) in one portion at room temperature. The reaction mixture was stirred for 4 h and then shaken between EtOAc (200 mL) and cold dilute HCl (200 mL). The layers were separated and the organic layer was washed with cold dilute HCl (200 mL), dried (MgSO$_4$), and concentrated under vacuum.

The crude azide product was combined with another preparation (approx. 22.5 mmol total) and dissolved in chloroform (80 mL). To this solution was added NaN$_3$ (4.39 g, 67.5 mmol). The mixture was cooled in an ice bath and a mixture of 80 mL CHCl$_3$ and TFA was added dropwise over 30 min. The reaction was allowed to warm gradually to room temperature. After 48 h, the reaction mixture was washed with cold water (2×300 mL) and then with satd NaHCO$_3$. The organic layer was dried (MgSO$_4$) and concentrated under vacuum, giving 4.47 g (85% yield) of the title compound as an oil.

[1]NMR

F. Methyl 4-(1-amino-1-methy)ethyl-2-hydroxybenzoate

The methyl 4-(1-azido-1-methyl)ethyl-2-hydroxybenzoate (1.05 g) was dissolved in EtOH (30 mL), then 5% BaSO$_4$ on palladium (0.5 g) was added. At atmospheric pressure, excess hydrogen was applied for 16 h. The reaction mixture was filterd and concentrated under vacuum, giving 0.93 g (100%) of the title compound as a solid after trituration with hexanes.

[1]NMR

G. Methyl 4-(1-tert-butoxycarbonylamino-1-methyl)ethyl-2-hydroxybenzoate

The methyl 4-(1-amino-1-methy)ethyl-2-hydroxybenzoate (0.93 g, 4.4 mmol) was dissolved in methylene chloride (30 mL), then di-tert-butyl dicarbonate (1.92 g, 8.8 mmol) and diisopropylethyl amine (1.53 mL, 8.8 mmol) were added. After 4 h, the reaction mixture was diluted with methylene chloride (100 mL) and extracted with water (2×150 mL). The product was dried (MgSO$_4$), concentrated under vacuum, and chromatographed over silica (0 to 30% EtOAc in hexane gradient), giving 0.576 g (42% yield) of the title compound as an oil.
[1]NMR Analysis for $C_{16}H_{23}NO_5$: Calcd: C, 62.12; H, 7.49; N, 4.53; Found: C, 62.34; H, 7.27; N, 4.49.

H. Methyl 4-(1-tert-butyloxycarbonylamino-1-methyl)ethyl-2-(1-tert-butyloxy-carbonylpiperidin-4-yloxy)benzoate The methyl 4-(1-tert-butoxycarbonylamino-1-methyl)ethyl-2-hydroxybenzoate (0.5 g, 1.84 mmol), 4-hydroxy-1-tert-butoxycarbonylpiperidine (0.371 g, 1.84 mmol), and triphenylphosphine (0.482 g, 0.84 mmol) were diluted with THF (20 mL). The reaction mixture was cooled in an ice bath and diisopropyl azodicarboxylate (0.372 g, 1.84 mmol) was added dropwise over 10 min. The reaction mixture was allowed to gradually warm to room temperature. After 16 h, the reaction was diluted with methylene chloride (100 mL), extracted with water (150 mL), dried ($MgSO_4$), and concentrated under vacuum. The product was chromatographed over silica (0 to 30% EtOAc in hexane gradient), giving 321 mg (35% yield) of the title compound as an oil.
[1]NMR

I. 2-[4-(1-tert-Butoxycarbonylamino-1-methyl)ethyl-2-(1-tert-butoxylcarbonyl-piperidin-4-yloxy)benzoylamino]-N-(5-chloropyridin-2-yl)benzamide The methyl 4-(1-tert-butyloxycarbonylamino-1-methyl)ethyl-2-(1-tert-butoxy-carbonylpiperid-4-oxy)benzoate (0.321 g, 0.65 mmol) was dissolved in THF (15 mL).

A 5 mL aqueous solution of $LiOH·H_2O$ (60 mg, 1.43 mmol) was added, and the mixture stirred at 65° C. in an oil bath for 24 h. Solvent was removed under vacuum. The product was diluted with toluene (2×35 mL) and concentrated to give the crude lithium salt of the benzoate.

The lithium benzoate was dispersed in methylene chloride (20 mL) and a catalytic amount of DMF was added. The solution was cooled in an ice bath, and oxalyl chloride (0.1 mL, 0.78 mmol) was added. After stirring for 1 h, the ice bath was removed. The reaction mixture was stirred for an additional hour, and then solvent was removed under vacuum. The benzoyl chloride product was concentrated under vacuum from toluene (2×35 mL) and was used subsequently without further purification.

The crude benzoyl chloride product in methylene chloride (10 mL) was added dropwise to a 0° C. solution of N-(5-chloropyridin-2-yl)-2-aminobenzamide (0.161 g, 0.65 mmol) and pyridine (0.11 mL, 1.3 mmol) in methylene chloride (20 mL). The reaction mixture was allowed to gradually warm to room temperature. After 16 h, the reaction mixture was diluted with methylene chloride (100 mL) and extracted with cold water (2×150 mL). The organic layer was dried ($MgSO_4$) and concentrated. The product was chromatographed over silica (0 to 30% EtOAc in hexane gradient), giving 164 mg of the desired product.
[1]NMR

J. 2-[4-(1-Amino-1-methyl)ethyl-2-(1-piperidin-4-yloxy)benzoylamino]-N-(5-chloropyridin-2-yl)benzamide trifluoroacetate The 2-[4-(1-tert-butoxycarbonylamino-1-methyl)ethyl-2-(1-tert-butoxycarbonyl-piperidin-4-yloxy)benzoylamino-N-(5-chloropyridin-2-yl)benzamide was dissolved in methylene chloride (2 mL) and TFA (2 mL). After 4 h at room temperature, the solvent was removed under vacuum and the residue was triturated with hexane and then with ether, to give 1-50 mg of the title compound as a solid.
[1]NMR MS-FD, m/e: 508 (m−2TFA) Analysis for $C_{27}H_{30}ClN_5O_2·2CF_3COOH$: Calcd: C, 50.59; H, 4.38; N, 9.51; Found: C, 49.91; H, 4.21; N, 9.43.

EXAMPLE 61

Preparation of N-(5-Chloropyridin-2-yl)-2-[2-[1-(2-hydroxypropyl)piperidin-4-yloxy]-4-(methylthio)benzoylamino]benzamide.

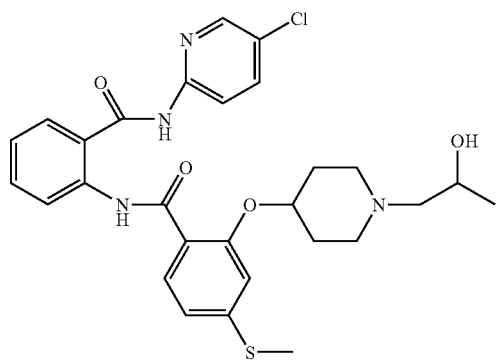

Using methods substantially equivalent to those described in Example 36, N-(5-chloropyridin-2-yl)-2-[2-[1-(2-hydroxypropyl)piperidin-4-yloxy]-4-(methylthio)-benzoylamino]benzamide (197 mg, 0.35 mmol, 89%) was prepared from N-(5-chloro-pyridin-2-yl)-2-[4-(methylthio)-2-(piperidin-4-yloxy)benzoylamino]benzamide.
[1]NMR (400 MHz, DMSO-$d_6$): δ 11.18 (s, 1H); 10.96 (s, 1H); 8.40 (s, 1H); 8.38 (d, J=9.6 Hz, 1H); 8.15 (d, J=8.4 Hz, 1H); 7.92 (dd, J=2.4, 8.8 Hz, 1H); 7.77 (d, J=7.6 Hz, 2H); 7.54 (t, J=7.8 Hz, 1H); 7.19 (t, J=7.6 Hz, 1H); 7.00 (s, 1H); 6.91 (d, J=7.6 Hz, 1H); 4.64 (m, 1H); 3.64 (m, 1H); 2.49 (s, 3H); 2.29-1.83 (m, 7H); 0.95 (d, J=6.4 Hz, 3H). IS-MS, m/e 555.2 (m+1). Analysis for $C_{28}H_{31}ClN_4O_4S$: Calc: C, 60.59; H, 5.63; N, 10.09; Found: C, 60.75; H, 5.60; N, 10.19.

EXAMPLE 62

Preparation of N-(5-Chloropyridin-2-yl)-2-[4-(methylthio)-2-(1-trifluoroacetyl-piperidin-4-yloxy)benzoylamino]benzamide.

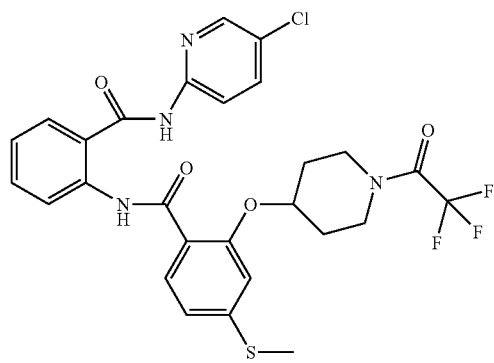

Using methods substantially equivalent to those described in Example 58, N-(5-chloropyridin-2-yl)-2-[4-(methylthio)-2-(1-trifluoracetylpiperidin-4-yloxy)-benzoylamino]benzamide (321 mg, 0.54 mmol, 77%) was prepared from N-(5-chloro-pyridin-2-yl)-2-[4-(methylthio)-2-(piperidin-4-yloxy)benzoylamino]benzamide.

$^1$NMR (300 MHz, DMSO-$d_6$): δ 11.21 (s, 1H); 10.98 (s, 1H); 8.37 (m, 2H); 8.01 (d, J=9.0 Hz, 1H); 7.79 (m, 3H); 7.53 (t, J=7.7 Hz, 1H); 7.18 (t, J=7.5 Hz, 1H); 7.07 (s, 1H); 6.93 (d, J=8.4 Hz, 1H); 4.95 (m, 1H); 3.96 (m, 2H); 3.71 (m, 2H); 2.51 (s, 3H); 2.08-1.78 (m, 4H). IS-MS, m/e 593.03 (m+1). Analysis for $C_{27}H_{24}ClF_3N_4O_4S$: Calc: C, 54.69; H, 4.08; N, 9.45; Found: C, 55.64; H, 4.75; N, 9.48.

EXAMPLE 63

Preparation of N-(5-Chloropyridin-2-yl)-5-fluoro-2-[4-(methylthio)-2-(piperidin-4-yloxy)benzoylamino]benzamide.

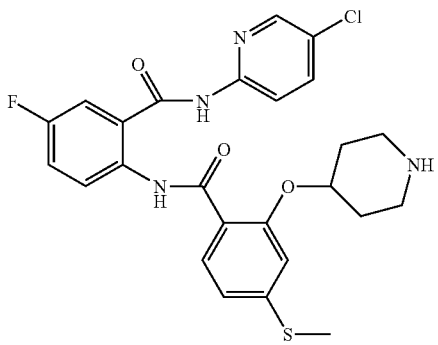

A. 2-[2-(1-tert-Butoxycarbonylpiperidin-4-yloxy)-4-(methylthio)benzoylamino]-N-(5-chloropyridin-2-yl)-5-fluorobenzamide Using methods substantially equivalent to those described in Example 4-E, 2-[2-(1-tert-butoxycarbonylpiperidin-4-yloxy)-4-(methylthio)benzoylamino]-N-(5-chloropyridin-2-yl)-5-fluorobenzamide (837 mg, 1.36 mmol, 78%) was prepared from N-(5-chloropyridin-2-yl)-2-amino-5-fluorobenzamide and 2-(1-tert-butoxycarbonyl-piperidin-4-yloxy)-4-(methylthio)benzoic acid.

$^1$NMR (400 MHz, DMSO-$d_6$): δ 11.29 (s, 1H); 10.86 (s, 1H); 8.41 (d, J=2.8 Hz, 1H); 8.31 (dd, J=5.4, 9.4 Hz, 1H); 8.11 (d, J=9.2 Hz, 1H); 7.91 (dd, J=2.6, 9.4 Hz, 1H); 7.80 (d, J=8.0 Hz, 1H); 7.63 (dd, J=2.6, 9.4 Hz, 1H); 7.44-7.39 (m, 1H); 7.05 (s, 1H); 6.92 (dd, J=1.2, 8.4 Hz, 1H); 4.84 (m, 1H); 3.68 (d, J=13.6 Hz, 1H); 3.02 (m, 2H); 2.47 (s, 3H); 1.87 (m, 2H); 1.78 (m, 2H); 1.33 (s, 9H). IS-MS, m/e 615.2 (m+1). Analysis for $C_{30}H_{32}ClFN_4O_5S$: Calc: C, 58.28; H, 5.24; N, 9.11; Found: C, 58.64; H, 5.44; N, 8.90.

B. N-(5-Chloropyridin-2-yl)-5-fluoro-2-[4-(methylthio)-2-(piperidin-4-yloxy)-benzoylamino]benzamide Using methods substantially equivalent to those described in Example 4-G, N-(5-chloropyridin-2-yl)-5-fluoro-2-[4-(methylthio)-2-(piperidin-4-yloxy)benzoylamino]-benzamide (684 mg, 1.11 mmol, 84%) was prepared from 2-[2-(1-tert-butoxycarbonyl-piperidin-4-yloxy)-4-(methylthio)benzoylamino]-N-(5-chloropyridin-2-yl)-5-fluoro-benzamide.

$^1$NMR (300 MHz, DMSO-$d_6$): δ 8.41 (d, J=1.8 Hz, 1H); 8.28 (m, 1H); 8.12 (d, J=8.7 Hz, 1H); 7.93 (dd, J=2.3, 8.9 Hz, 1H); 7.74 (d, J=8.4 Hz, 1H); 7.64 (d, J=9.0 Hz, 1H); 7.42 (t, J=8.6 Hz, 1H); 7.02 (s, 1H); 6.92 (d, J=8.4 Hz, 2H); 4.79 (m, 1H); 2.96 (m, 2H); 2.76 (m, 2H); 2.46 (s, 3H); 1.95 (m, 2H); 1.79 (m, 2H). IS-MS m/e: 515.3 (m+1). Analysis for $C_{25}H_{24}ClFN_4O_3S$: Calc: C, 54.98; H, 4.53; N, 9.86; Found: C, 54.79; H, 4.58; N, 9.79.

EXAMPLE 64A

Preparation of N-(5-Chloropyridin-2-yl)-2-[4-isopropyl-2-(4-oxocyclohexyloxy)-benzoylamino]benzamide.

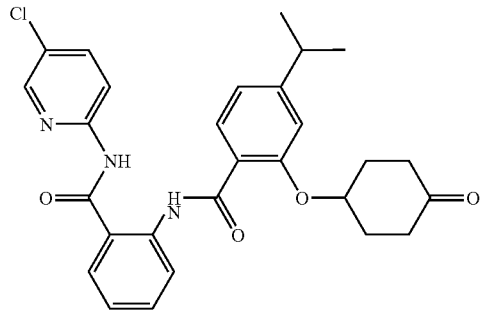

A. 2-[2-Methoxymethyloxy-4-isopropylbenzoylamino]-N-(5-chloropyridin-2-yl)-benzamide To a stirring solution of 2-methoxymethyloxy-4-isopropylbenzoic acid (3.0 g, 13.4 mmol) in THF (50 mL) was added sodium ethoxide (0.91 g, 13.4 mmol). After 15 min, the solvent was removed in vacuo and the residue was suspended in dichloromethane (50 mL). To this mixture was added a couple drops of DMF followed by oxalyl chloride (1.7 g, 13.4 mmol). After another 30 min, the solvent was removed in vacuo and the residue was again suspended in dichloromethane (150 mL). To this mixture was added pyridine (2.9 g, 36.5 mmol), followed by N-(5-chloropyridin-2-yl)-2-aminobenzamide (3.02 g, 12.2 mmol). After stirring for 2 h, the solvent was removed in vacuo and the residue was partitioned between ethyl acetate (400 mL) and water (200 mL). The organic phase was washed twice with 1 M citric acid, once with brine, twice with saturated aq sodium bicarbonate and once with brine. The organic phase was then dried with MgSO$_4$ and filtered. To this solution was added silica gel (about 10 g) and the solvent was removed in vacuo. The resulting dry pack was loaded onto the top of a silica gel column loaded with 10% ethyl acetate in hexanes and eluted with a gradient of 10% ethyl acetate in hexanes through 30% ethyl acetate in hexanes. The clean product containing fractions were combined and concentrated in vacuo to give 2.18 g (39%) of off white solid. Another set of fractions which contained a small amount of impurity were combined and concentrated in vacuo to give 2.09 g (about 38%) of an off white solid.

$^1$NMR ES_MS, m/e 454.1 (m+1)

B. 2-[2-Hydroxy-4-isopropylbenzoylamino]-N-(5-chloropyridin-2-yl)benzamide

To a stirring solution of 2-[2-methoxymethyloxy-4-isopropylbenzoylamino]-N-(5-chloropyridin-2-yl)benzamide (5.74 g, 12.6 mmol) in dichloromethane (20 mL) was added TFA (100 mL) followed by water (100 mL). After stirring for 15 min, the solvents were removed in vacuo and the residue was partitioned between ethyl acetate (500 mL) and water (200 mL). At this point, the mixture was filtered to give 1.13 g (22%) of white solid. The filtrate was returned to a separatory funnel and the layers were separated. The organic phase was then washed with 1 M citric acid, once with brine, twice with saturated aq sodium bicarbonate, and once again with brine. The organic phase was then dried with $MgSO_4$, filtered and concentrated to a volume of about 50 mL in vacuo. At this point, a significant amount of precipitate had formed; so the mixture was sonicated and filtered to give another 2.76 g (53%) of the title compound.

$^1$NMR ES-MS, m/e 410.3 (m+1) Analysis for $C_{22}H_{20}N_3O_3Cl$: Calcd: C, 64.47; H, 4.92; N, 10.25; Found: C, 64.36; H, 4.92; N, 10.16.

C. N-(5-Chloropyridin-2-yl)-2-[2-(1,4-dioxaspiro[4.5]dec-8-yloxy)-4-isopropyl-benzoylamino]benzamide 4-Hydroxycyclohexanone-1,1-ethylene ketal (0.63 g, 4 mmol), 2-[4-isopropyl-2-hydroxybenzoylamino]-N-(5-chloropyridin-2-yl)benzamide (1.64 g, 4 mmol), triphenyl-phosphine (1.05 g, 4 mmol), and dry DMF (2 mL) were sonicated for 5 min at room temperature. DIAD (0.8 mL, 4 mmol) was added and sonication was continued for 1 h. Ether (40 mL) was added and the solution was chilled overnight in the freezer to crystallize triphenylphosphine oxide. The crystals were filtered, washed with a little ether, and the combined filtrates were evaporated to dryness to give a yellow oil.

Chromatographic purification (Merck silica gel 60, elution with hexane (100-60%) and ethyl acetate (0-40%)) gave 960 mg (44%) of the desired ketal.

$^1$NMR IS-MS: [m+1]$^+$=550.3, [m−1]$^-$=548.3 Calcd for $C_{30}H_{32}N_3O_5Cl$: [m+1]$^+$=550.0, [m−1]$^-$=548.0

D. N-(5-Chloropyridin-2-yl)-2-[2-(1,4-dioxaspiro[4.5]dec-8-yloxy)-4-isopropyl-benzoylamino]benzamide (960 mg, 1.75 mmol) was dissolved in THF (30 mL). The solution was cooled to ice-water bath temperature and 5 M HCl (5.6 mL, 28 mmol) was added dropwise. The reaction was allowed to warm to room temperature and stir for 6 h. Water (100 mL) was added, and the pH was adjusted to 8 with 5 M NaOH. THF was removed on the rotary evaporator and the precipitated white solid was filtered, washed with water, and dried under vacuum to give 790 mg (90%) of the desired ketone as a white solid.

$^1$NMR Analysis for $C_{28}H_{28}ClN_3O_4$: Calcd: C, 66.46; H, 5.58; N, 8.30; Found: C, 66.65; H, 5.46; N, 8.32.

EXAMPLE 64B

Preparation of 2-[2-[4-(Benzylamino)cyclohexyloxy]-4-isopropylbenzoylamino]-N-(5-chloropyridin-2-yl)benzamide.

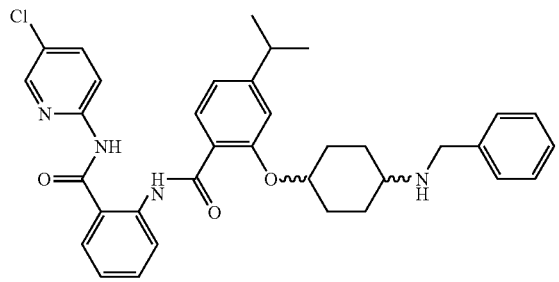

N-(5-Chloropyridin-2-yl)-2-[4-isopropyl-2-(4-oxocyclohexyloxy)benzoylamino]-benzamide (51 mg, 0.10 mmol) and benzylamine (16 mg, 0.15 mmol) were suspended in 7:1:1 dry MeOH-DMF-methylene chloride. Sodium borohydride (50 mg) was added and the reaction was agitated overnight at room temperature. Aldehyde resin (150 mg, 1 mmol aldehyde/gram, 0.15 mmol) was added to the resulting homogeneous solution, and the mixture was agitated overnight at room temperature. The mixture was filtered, the resin was washed with methylene chloride, and the filtrate was evaporated under vacuum.

The crude product was dissolved in MeOH and added to an SCX column. The column was washed thoroughly with MeOH; then the product was eluted with 2 M ammonia in MeOH. Evaporation of the methanolic ammonia eluates gave 2-[2-[4-(benzylamino)-cyclohexyloxy]-4-isopropylbenzoylamino]-N-(5-chloropyridin-2-yl)benzamide (48 mg, 81%).

$^1$NMR IS-MS: [m+1]$^+$=597.1, [m−1]$^-$=595.1 Calcd for $C_{35}H_{37}N_4O_3Cl$: [m+1]$^+$=597.0, [m−1]$^-$=595.0

EXAMPLE 65

Preparation of N-(5-Chloropyridin-2-yl)-5-fluoro-2-[2-[1-(2-hydroxypropyl)-piperidin-4-yloxy]-4-(methylthio)benzoylamino]benzamide.

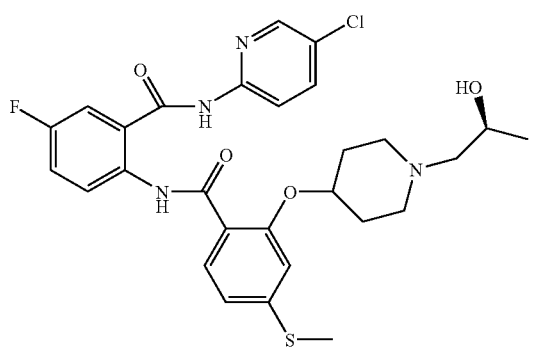

Using methods substantially equivalent to those described in Example 36, N-(5-chloropyridin-2-yl)-5-fluoro-2-[2-[1-(2-hydroxypropyl)piperidin-4-yloxy]-4-(methylthio)benzoylamino]benzamide (122 mg, 0.21 mmol, 55%) was prepared from N-(5-chloropyridin-2-yl)-5-fluoro-2-[4-(methylthio)-2-(piperidin-4-yloxy)benzoylamino]-benzamide.

¹NMR (300 MHz, DMSO-d₆): δ 11.26 (s, 1H); 10.82 (s, 1H); 8.40 (d, J=1.2 Hz, 1H); 8.33 (m, 1H); 8.15 (d, J=9.0 Hz, 1H); 7.93 (dd, J=2.1, 9.0 Hz, 1H); 7.77 (d, J=8.4 Hz, 1H); 7.62 (dd, J=2.0, 9.5 Hz, 1H); 7.41 (t, J=8.4 Hz, 1H); 7.00 (s, 1H); 6.90 (d, J=8.1 Hz, 1H); 4.63 (m, 1H); 4.17 (s, 1H); 3.64 (m, 1H); 2.56 (m, 2H); 2.49 (s, 3H); 2.19-1.77 (m, 7H); 0.95 (d, J=6.3 Hz, 3H). IS-MS, m/e 573.2 (m+1)

EXAMPLE 66

Preparation of N-(5-Chloropyridin-2-yl)-4-fluoro-2-[4-(methylthio)-2-(piperidin-4-yloxy)benzoylamino]benzamide.

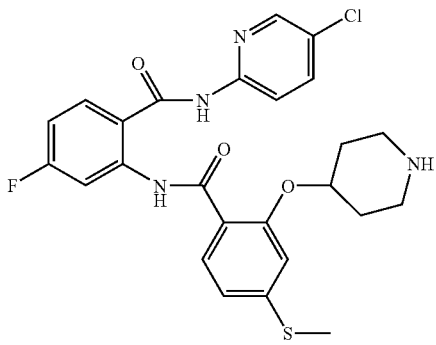

A. 2-[2-(1-tert-Butoxycarbonylpiperidin-4-yloxy)-4-(methylthio)benzoylamino]-N-(5-chloropyridin-2-yl)-4-fluorobenzamide Using methods substantially equivalent to those described in Example 4-E, 2-[2-(1-tert-butoxycarbonylpiperidin-4-yloxy)-4-(methylthio)benzoylamino]-N-(5-chloro-pyridin-2-yl)-4-fluorobenzamide (708 mg, 1.15 mmol, 87%) was prepared from 2-(1-tert-butoxycarbonylpiperidin-4-yloxy)-(4-methylthio)benzoic acid and N-(5-chloropyridin-2-yl)-2-amino-4-fluorobenzamide.

¹NMR (300 MHz, DMSO-d₆): δ 11.29 (s, 1H); 11.26 (s, 1H); 8.41 (s, 1H); 8.33 (dd, J=1.5, 11.1 Hz, 1H); 8.09 (d, J=9.0 Hz, 1H); 7.89 (m, 2H); 7.78 (d, J=8.1 Hz, 1H); 7.05 (m, 2H); 6.92 (d, J=8.4 Hz, 1H); 4.82 (m, 1H); 3.63 (d, J=12.9 Hz, 2H); 3.00 (t, J=10.4 Hz, 2H); 2.50 (s, 3H); 1.88-1.73 (m, 4H); 1.31 (s, 9H). IS-MS, m/e 615.2 (m+1). Analysis for $C_{30}H_{32}ClFN_4O_5S$: Calc: C, 58.58; H, 5.24; N, 9.11; Found: C, 58.89; H, 5.14; N, 9.15.

B. N-(5-Chloropyridin-2-yl)-4-fluoro-2-[4-(methylthio)-2-(piperidin-4-yloxy)-benzoylamino]benzamide Using methods substantially equivalent to those described in Example 4-G, N-(5-chloropyridin-2-yl)-4-fluoro-2-[4-(methylthio)-2-(piperidin-4-yloxy)benzoylamino]-benzamide (554 mg, 1.08 mmol, 100%) was prepared from 2-[2-(1-tert-butoxycarbonyl-piperidin-4-yloxy)-4-(methylthio)benzoylamino]-N-(5-chloropyridin-2-yl)-4-fluoro-benzamide.

IS-MS m/e: 515.3 (m+1) Analysis for $C_{25}H_{24}ClFN_4O_3S$: Calc: C, 58.31; H, 4.70; N, 10.88; Found: C, 58.02; H, 4.68; N, 10.59.

EXAMPLE 67

Preparation of N-(5-Chloropyridin-2-yl)-5-fluoro-2-[4-(methylthio)-2-(1-trifluoroacetylpiperidin-4-yloxy)benzoylamino]benzamide.

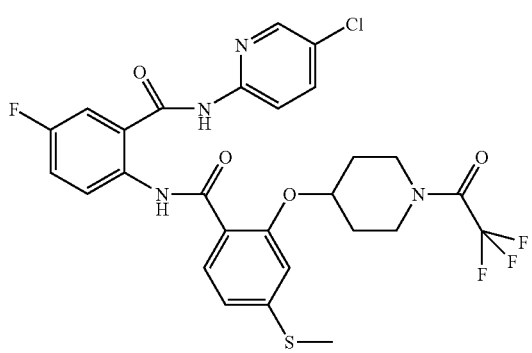

Using methods substantially equivalent to those described in Example 58, N-(5-chloropyridin-2-yl)-5-fluoro-2-[4-(methylthio)-2-(1-trifluoroacetylpiperidin-4-yloxy)benzoylamino]benzamide (179 mg, 0.29 mmol, 55%) was prepared from N-(5-chloropyridin-2-yl)-5-fluoro-2-[4-(methylthio)-2-(piperidin-4-yloxy)benzoylamino]-benzamide.

¹NMR (400 MHz, DMSO-d₆): δ 11.29 (s, 1H); 10.84 (s, 1H); 8.41 (d, J=2.0 Hz, 1H); 8.32 (dd, J=5.2, 9.2 Hz, 1H); 8.01 (d, J=8.8 Hz, 1H); 7.82 (m, 2H); 7.63 (dd, J=2.8, 9.2 Hz, 1H); 7.42 (dt, J=2.8, 8.2 Hz, 1H); 7.08 (s, 1H); 6.94 (d, J=8.0 Hz, 1H); 4.97 (m, 1H); 3.73 (d, J=14.8 Hz, 2H); 3.41 (t, J=11.4 Hz, 2H); 2.47 (s, 3H); 2.05-1.79 (m, 4H). IS-MS, m/e 611.0 (m+1). Analysis for $C_{27}H_{23}ClF_4N_4O_4S$: Calc: C, 53.08; H, 3.79; N, 9.17; Found: C, 52.94; H, 3.82; N, 8.92.

EXAMPLE 68

Preparation of N-(5-Chloropyridin-2-yl)-4-fluoro-2-[2-[1-(2-hydroxypropyl)-piperidin-4-yloxy]-4-(methylthio)benzoylamino]benzamide.

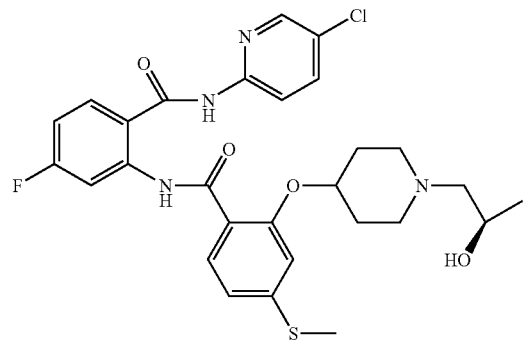

Using methods substantially equivalent to those described in Example 36, N-(5-chloropyridin-2-yl)-4-fluoro-2-[2-[1-(2-hydroxypropyl)piperidin-4-yloxy]-4-(methylthio)benzoylamino]benzamide (111 mg; 0.19 mmol, 50%) was prepared from N-(5-chloropyridin-2-yl)-4-fluoro-2-[4-(methylthio)-2-(piperidin-4-yloxy)benzoylamino]-benzamide.

¹NMR (400 MHz, DMSO-d₆): δ 11.25 (s, 2H); 8.41 (d, J=2.4 Hz, 1H); 8.37 (dd, J=2.8, 12.8 Hz, 1H); 8.14 (d, J=8.8 Hz, 1H); 7.95-7.87 (m, 2H); 7.77 (d, J=8.4 Hz, 1H); 7.05 (dt, J=2.4, 8.0 Hz, 1H); 7.00 (s, 1H); 6.92 (d, J=8.4 Hz, 1H); 4.62 (m, 1H); 4.16 (d, J=3.6 Hz, 1H); 3.62 (m, 1H); 2.53 (m, 2H); 2.47 (s, 3H); 2.12-1.77 (m, 6H); 0.94 (d, J=6.0 Hz, 3H). IS-MS, m/e 573.2 (m+1).

EXAMPLE 69

Preparation of N-(5-Chloropyridin-2-yl)-4-fluoro-2-[4-(methylthio)-2-(1-trifluoroacetylpiperidin-4-yloxy)benzoylamino]benzamide.

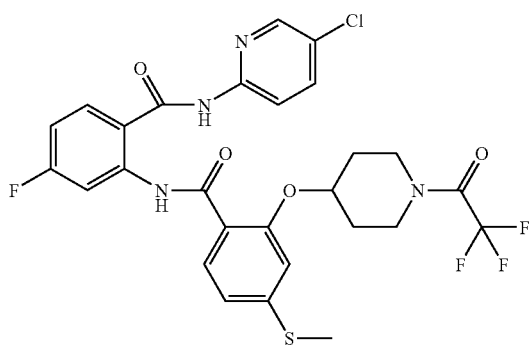

Using methods substantially equivalent to those described in Example 58, N-(5-chloropyridin-2-yl)-4-fluoro-2-[4-(methylthio)-2-(1-trifluoroacetylpiperidin-4-yloxy)benzoylamino]benzamide (135 mg, 0.22 mmol, 76%) was prepared from N-(5-Chloropyridin-2-yl)-4-fluoro-2-[4-(methylthio)-2-(piperidin-4-yloxy)benzoyl-amino]benzamide.

¹NMR (300 MHz, DMSO-d₆): δ 11.27 (s, 2H); 8.40 (d, J=2.4 Hz, 1H); 8.34 (dd, J=2.3, 12.5 Hz, 1H); 7.98 (d, J=8.7 Hz, 1H); 7.85 (m, 3H); 7.05 (m, 2H); 6.94 (d, J=8.1 Hz, 1H); 4.94 (m, 1H); 3.94 (m, 2H); 3.66 (m, 2H); 2.51 (s, 3H); 2.09-1.81 (m, 4H). IS-MS, m/e 611.0 (m+1). Analysis for $C_{27}H_{23}ClF_4N_4O_4S$: Calc: C, 53.08; H, 3.79; N, 9.17; Found: C, 53.14; H, 4.06; N, 8.95.

EXAMPLE 70

Preparation of 2-[2-(4-Aminocyclohexyl)-4-isopropylbenzoylamino]-N-(5-chloro-pyridin-2-yl)benzamide.

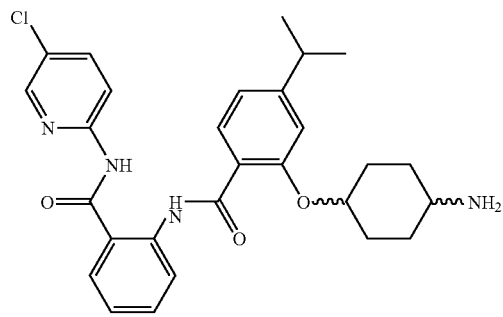

N-(5-Chloropyridin-2-yl)-2-[4-isopropyl-2-(4-oxocyclohexyloxy)benzoylamino]-benzamide (51 mg, 0.10 mmol), ammonium acetate (77 mg, 1 mmol), and sodium cyanoborohydride (6 mg, 0.1 mmol) were dissolved in 0.5 mL of dry. 1:1 MeOH-methylene chloride by brief sonication. The solution was agitated for 24 h at room temperature. The resulting mixture was filtered and the filtrate was washed with MeOH and methylene chloride. The combined filtrates were evaporated to dryness under vacuum. The residue was taken up in methylene chloride-water and the pH was adjusted to 3 with 5 M HCl.

The methylene chloride layer was washed with brine, dried over sodium sulfate, and evaporated in vacuo to give 44 mg of crude product. Chromatography (1 g silica gel column, chloroform (100-80%) and MeOH (0-20%)) gave 16 mg of 2-[2-(4-amino-cyclohexyl)-4-isopropylbenzoylamino]-N-(5-chloropyridin-2-yl)benzamide as a colorless glassy solid.

IS-MS: $[m+1]^+$=507.1, $[m-1]^-$=505.2 Calcd for $C_{28}H_{31}ClN_4O_3$: $[m+1]^+$=507.0, $[m-1]^-$=505.0

EXAMPLE 71

Preparation of 2-[2-(Piperidin-4-yloxy)-4-(pyrrolidin-1-yl)benzoylamino]-N-(thiazol-2-yl)benzamide.

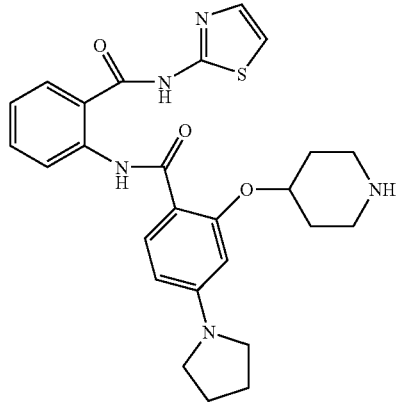

A. Methyl 2-(1-tert-butoxycarbonylpiperidin-4-yloxy)-4-(pyrrolidin-1-yl)benzoate The methyl 2-(1-tert-butoxycarbonylpiperidin-4-yloxy)-4-fluorobenzoate (7.99 mmol, 22.6 mmol) was diluted with pyrrolidine (18 mL, 215.6 mmol). The resulting mixture was heated to 80° C. After 3 hours, the reaction was cooled to room temperature and quenched with water (50 mL). The mixture was extracted with dichloromethane (200 mL). The organic layer was washed with saturated aqueous citric acid (3×50 mL), dried over sodium sulfate, filtered, and concentrated to a colorless oil (9.14 g, 22.6 mmol, 100%).

¹NMR (400 MHz, DMSO-d₆): δ 7.59 (d, J=9.2 Hz, 1H); 6.14 (dd, J=2.2, 8.6 Hz, 1H); 6.09 (s, 1H); 4.67 (m, 1H); 3.65 (s, 3H); 3.44-3.23 (m, 8H); 1.91 (s, 4H); 1.74 (m, 2H); 1.64 (m, 2H); 1.37 (s, 9H). FIA-MS, m/e 405.5 (m+1). Analysis for $C_{22}H_{32}N_2O_5$: Calc: C, 65.32; H, 7.97; N, 6.93; Found: C, 65.62; H, 8.00; N, 7.14.

B. 2-(1-tert-Butoxycarbonylpiperidin-4-yloxy)-4-(pyrrolidin-1-yl)benzoic acid

Using methods substantially equivalent to those described in Example 21-D, except that the reaction was heated to 60°

C., 2-(1-tert-butoxycarbonylpiperidin-4-yloxy)-4-(pyrrolidin-1-yl)benzoic acid (6.90 g, 17.7 mmol, 78%) was prepared from methyl-2-(1-tert-butoxycarbonylpiperidin-4-yloxy)-4-(pyrrolidin-1-yl)benzoate.

$^1$NMR (400 MHz, DMSO-$d_6$): δ 11.47 (br s, 1H); 7.56 (d, J=8.8 Hz, 1H); 6.11 (d, J=8.4 Hz, 1H); 6.05 (s, 1H); 4.64 (m, 1H); 3.44-3.11 (m, 8H); 1.88 (m, 4H); 1.72 (m, 2H); 1.60 (m, 2H); 1.33 (s, 9H). FIA-MS, m/e 391.3 (m+1). Analysis for $C_{21}H_{30}N_2O_5$: Calc: C, 64.60; H, 7.74; N, 7.17; Found: C, 67.23; H, 8.13; N, 7.65.

C. Methyl 2-[2-(1-tert-butoxycarbonylpiperidin-4-yloxy)-4-(pyrrolidin-1-yl)-benzoylamino]benzoate Using methods substantially equivalent to those described in Example 4-E, methyl 2-[2-(1-tert-butoxycarbonylpiperidin-4-yloxy)-4-(pyrrolidin-1-yl)benzoylamino]benzoate (5.88 g, 11.23 mmol, 81%) was prepared from 2-(1-tert-butoxycarbonylpiperidin-4-yloxy)-4-(pyrrolidin-1-yl)benzoic acid and methyl 2-aminobenzoate.

IR(CHCl$_3$): 1604, 1515, 1448, 1266 cm$^{-1}$.

$^1$NMR (300 MHz, DMSO-$d_6$): δ 11.37 (s, 1H); 8.56 (d, J=8.4 Hz, 1H); 7.92 (d, J=7.8 Hz, 1H); 7.72 (d, J=8.7 Hz, 1H); 7.56 (t, J=7.7 Hz, 1H); 7.11 (t, J=7.5 Hz, 1H); 6.23 (d, J=9.0 Hz, 1H); 6.17 (s, 1H); 4.77 (m, 1H); 3.79 (s, 3H); 3.67 (d, J=13.5 Hz, 2H); 3.29 (m, 4H); 3.03 (m, 2H); 1.94 (m, 4H); 1.69 (m, 2H); 1.33 (m, 2H); 1.32 (s, 9H). IS-MS, m/e 524.5 (m+1). Analysis for $C_{29}H_{37}N_3O_3$: Calc: C, 66.52; H, 7.12; N, 8.02; Found: C, 67.11; H, 7.07; N, 8.19.

D. 2-[2-(1-tert-Butoxycarbonylpiperidin-4-yloxy)-4-(pyrrolidin-1-yl)benzoylamino]-benzoic acid Using methods substantially equivalent to those described in Example 21-D, 2-[2-(1-tert-butoxycarbonylpiperidin-4-yloxy)-4-(pyrrolidin-1-yl)benzoylamino]benzoic acid (6.34 g, 12.4 mmol, 100%) was prepared from methyl 2-[2-(1-tert-butoxycarbonyl-piperidin-4-yloxy)-4-(pyrrolidin-1-yl)benzoylamino]benzoate.

IR(CHCl$_3$): 1668, 1605, 1514, 1389, 1286 cm$^{-1}$.

$^1$NMR (300 MHz, DMSO-$d_6$): δ 8.50 (d, J=8.4 Hz, 1H); 7.90 (d, J=7.8 Hz, 1H); 7.57 (d, J=8.4 Hz, 1H); 7.34 (t, J=7.4 Hz, 1H); 6.95 (t, J=7.4 Hz, 1H); 6.18 (d, J=8.7 Hz, 1H); 6.11 (s, 1H); 4.66 (m, 1H); 3.51 (m, 2H); 3.26 (m, 4H); 3.13 (m, 2H); 1.93 (m, 4H); 1.89-1.71 (m, 4H); 1.32 (s, 9H). IS-MS m/e: 510.4 (m+1). Analysis for $C_{28}H_{35}N_3O_6$: Calc: C, 65.99; H, 6.92; N, 8.25; Found: C, 65.76; H, 6.80; N, 8.50.

E. 2-[2-(1-tert-Butoxycarbonylpiperidin-4-yloxy)-4-(pyrrolidin-1-yl)phenyl]-4H-3,1-benzoxazin-4-one The 2-[2-(1-tert-butoxycarbonylpiperidin-4-yloxy)-4-(pyrrolidin-1-yl)-benzoylamino]benzoic acid (about 11.23 mmol) was diluted with methylene chloride (115 mL). DMF (4 drops) and pyridine (1.1 mL, 13.6 mmol) were added, followed by oxalyl chloride (1.1 mL, 12.6 mmol). A precipitate formed immediately. After 2 hours, the reaction was filtered and the filtrate was concentrated in vacuo. The crude residue from the filtrate concentration was purified by flash column chromatography (5% EtOAc/CH$_2$Cl$_2$) to give the desired product (4.83 g, 9.82 mmol, 87%) as a yellow solid.

$^1$NMR (400 MHz, DMSO-$d_6$): δ 8.04 (dd, J=1.6, 7.6 Hz, 1H); 7.84 (t, J=8.6 Hz, 1H); 7.79 (d, J=9.2 Hz, 1H); 7.48 (m, 2H); 6.27 (dd, J=2.0, 8.8 Hz, 1H); 6.19 (s, 1H); 4.82 (m, 1H); 3.45-3.32 (m, 4H); 3.29 (m, 4H); 1.95 (m, 6H); 1.76 (m, 2H); 1.37 (s, 9H). IS-MS m/e: 492.3 (m+1). Analysis for $C_{28}H_{33}N_3O_5$: Calc: C, 68.42; H, 6.77; N, 8.55; Found: C, 68.51; H, 6.57; N, 8.66.

F. 2-[2-(1-tert-Butoxycarbonylpiperidin-4-yloxy)-4-(pyrrolidin-1-yl)benzoylamino]-N-(thiazol-2-yl)benzamide The 2-aminothiazole (245 mg, 2.45 mmol) was diluted with THF (3 mL) and the mixture was cooled to 0° C. A 3.0 M ether solution of methylmagnesium bromide (0.8 mL, 2.4 mmol) was then added. After 20 minutes, this mixture was added via syringe to a solution of 2-[2-(1-tert-butoxycarbonylpiperidin-4-yloxy)-4-(pyrrolidin-1-yl)phenyl]-4H-3,1-benzoxazin-4-one (299 mg, 0.61 mmol) in THF (3 mL) at 0° C. The flask containing the magnesium salt of 2-aminothiazole was rinsed with THF (1 mL) and the washings were added to the reaction. The reaction was allowed to slowly warm to room temperature overnight. The reaction was quenched with saturated aqueous ammonium chloride (1 mL), diluted with EtOAc (100 mL), and washed with water (2×10 mL). The organic layer was dried over sodium sulfate, filtered, and concentrated. The crude residue was purified by flash column chromatography (about 35 g silica, 20% EtOAc/CH$_2$Cl$_2$).

The mixed fractions were combined, concentrated, and purified again using flash column chromatography (10% EtOAc/CH$_2$Cl$_2$). The product containing fractions from both purifications were combined, concentrated, and triturated with toluene (3×) to give the desired product (232 mg, 0.39 mmol, 64%) as a white solid.

$^1$NMR (300 MHz, DMSO-$d_6$): δ 8.30 (d, J=8.1 Hz, 1H); 7.81-7.74 (m, 3H); 7.51 (m, 1H); 7.15 (m, 2H); 6.22 (d, J=9.0 Hz, 1H); 6.17 (s, 1H); 4.80 (m, 1H); 3.76 (d, J=12.3 Hz, 2H); 3.29 (m, 4H); 3.02 (m, 2H); 1.94 (m, 8H). MS-FIA m/e: 592.6 (m+1). Analysis for $C_{31}H_{37}N_5O_5S$: Calc: C, 62.92; H, 6.30; N, 11.84; Found: C, 63.22; H, 6.22; N, 11.77.

G. 2-[2-(Piperidin-4-yloxy)-4-(pyrrolidin-1-yl)benzoylamino]-N-(thiazol-2-yl)-benzamide Using methods substantially equivalent to those described in example 4-G, 2-[2-(piperidin-4-yloxy)-4-(pyrrolidin-1-yl)benzoylamino]-N-(thiazol-2-yl)benzamide (174 mg, 0.35 mmol, 100%) was prepared from 2-[2-(1-tert-Butoxycarbonylpiperidin-4-yloxy)-4-(pyrrolidin-1-yl)benzoylamino]-N-(thiazol-2-yl)benzamide.

$^1$NMR (400 MHz, DMSO-$d_6$): δ 8.37 (d, J=8.0 Hz, 1H); 7.88 (d, J=7.2 Hz, 1H); 7.72 (t, J=8.8 Hz, 1H); 7.47 (m, 2H); 7.15 (m, 2H); 6.22 (d, J=8.0 Hz, 1H); 6.15 (s, 1H); 4.72 (m, 1H); 3.28 (m, 4H); 2.96 (m, 2H); 2.68 (m, 2H); 1.90 (m, 8H). MS-FIA m/e: 492.3 (m+1).

EXAMPLE 72

Preparation of N-(4-Methylthiazol-2-yl)-2-[2-(piperidin-4-yloxy)-4-(pyrrolidin-1-yl)-benzoylamino] Benzamide.

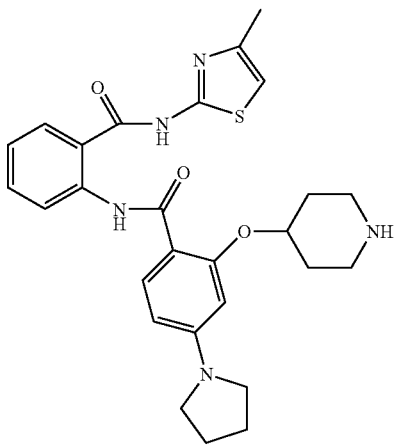

A. 2-[2-(1-tert-Butoxycarbonylpiperidin-4-yloxy)-4-(pyrrolidin-1-yl)benzoylamino]-N-(4-methylthiazol-2-yl)benzamide Using methods substantially equivalent to those described in example 71-F, 2-[2-(1-tert-butoxycarbonylpiperidin-4-yloxy)-4-(pyrrolidin-1-yl)benzoylamino]-N-(4-methylthiazol-2-yl)benzamide (198 mg, 0.33 mmol, 53%) was prepared from 2-[2-(1-tert-butoxycarbonyl-piperidin-4-yloxy)-4-(pyrrolidin-1-yl)phenyl]-4H-3,1-benzoxazin-4-one and the magnesium salt of 2-amino-4-methylthiazole.

$^1$NMR (400 MHz, DMSO-d$_6$): δ 8.31 (m, 1H); 7.76 (d, J=8.4 Hz, 2H); 7.51 (t, J=7.6 Hz, 1H); 7.14 (t, J=7.2 Hz, 1H); 6.73 (s, 1H); 6.22 (d, J=10.0 Hz, 1H); 6.17 (s, 1H); 4.80 (m, 1H); 3.74 (m, 2H); 3.29 (m, 4H); 3.00 (m, 2H); 2.26 (s, 3H); 1.95 (m, 8H); 1.31 (s, 9H) IS-MS m/e: 606.4 (m+1). Analysis for C$_{32}$H$_{39}$N$_5$O$_5$S 0.25H$_2$O: Calc: C, 62.98; H, 6.52; N, 11.48; Found: C, 62.64; H, 6.31; N, 11.86.

B. N-(4-Methylthiazol-2-yl)-2-[2-(piperidin-4-yloxy)-4-(pyrrolidin-1-yl)-benzoylamino]benzamide Using methods substantially equivalent to those described in example 4-G, N-(4-methylthiazol-2-yl)-2-[2-(piperidin-4-yloxy)-4-(pyrrolidin-1-yl)benzoylamino]-benzamide (149 mg, 0.29 mmol, 98%) was prepared from 2-[2-(1-tert-butoxycarbonyl-piperidin-4-yloxy)-4-(pyrrolidin-1-yl)benzoylamino]-N-(4-methylthiazol-2-yl)benzamide.

$^1$NMR (400 MHz, DMSO-d$_6$): δ 8.36 (d, J=7.6 Hz, 1H); 7.88 (d, J=8.8 Hz, 1H); 7.72 (d, J=8.8 Hz, 1H); 7.52 (t, J=8.0 Hz, 1H); 7.15 (t, J=7.6 Hz, 1H); 6.78 (s, 1H); 6.25 (d, J=9.2 Hz, 1H); 6.18 (s, 1H); 4.86 (m, 1H); 3.29 (m, 4H); 3.08 (m, 2H); 2.89 (m, 2H); 2.26 (s, 3H); 2.07-1.94 (m, 8H). IS-MS m/e: 506.2 (m+1).

EXAMPLE 73

Preparation of 5-Chloro-N-(5-chloropyridin-2-yl)-2-[4-(methylthio)-2-(piperidin-4-yloxy)benzoylamino] benzamide.

A. 2-[2-(1-tert-Butoxycarbonylpiperidin-4-yloxy)-4-(methylthio)benzoylamino]-5-chloro-N-(5-chloropyridin-2-yl)benzamide Using methods substantially equivalent to those described in Example 4-E, 2-[2-(1-tert-butoxycarbonylpiperidin-4-yloxy)-4-(methylthio)benzoylamino]-5-chloro-N-(5-chloropyridin-2-yl)benzamide (1.48 g, 2.35 mmol, 79%) was prepared from N-(5-chloropyridin-2-yl)-2-amino-5-chlorobenzamide and 2-(1-tert-butoxycarbonyl-piperidin-4-yloxy)-4-(methylthio)benzoic acid.

$^1$NMR (400 MHz, DMSO-d$_6$): δ 11.35 (s, 1H); 10.95 (s, 1H); 8.41 (d, J=2.8 Hz, 1H); 8.37 (d, J=8.8 Hz, 1H); 8.10 (d, J=9.2 Hz, 1H); 7.91 (d, J=9.2 Hz, 1H); 7.83 (d, J=2.4 Hz, 1H); 7.79 (d, J=8.0 Hz, 1H); 7.60 (d, J=6.6 Hz, 1H); 7.05 (s, 1H); 6.92 (d, J=8.4 Hz, 1H); 4.68 (m, 1H); 3.66 (d, J=13.2 Hz, 2H); 3.02 (m, 2H); 2.47 (s, 3H); 1.95 (m, 2H); 1.86 (m, 2H); 1.32 (s, 9H). IS-MS m/e: 631.2 (m+1). Analysis for C$_{30}$H$_{32}$Cl$_2$N$_4$O$_5$S: Calc: C, 57.05; H, 5.11; N, 8.87; Found: C, 57.33; H, 5.15; N, 8.61.

B. 5-Chloro-N-(5-chloropyridin-2-yl)-2-[4-(methylthio)-2-(piperidin-4-yloxy)-benzoylamino]benzamide Using methods substantially equivalent to those described in Example 4-G, 5-chloro-N-(5-chloropyridin-2-yl)-2-[4-(methylthio)-2-(piperidin-4-yloxy)benzoyl-amino]benzamide (171 mg, 0.32 mmol, 100%) was prepared from 2-[2-(1-tert-butoxycarbonylpiperidin-4-yloxy)-4-(methylthio) benzoylamino]-5-chloro-N-(5-chloropyridin-2-yl) benzamide.

$^1$NMR (300 MHz, DMSO-d$_6$): δ 8.42 (s, 1H); 8.40 (d, J=5.4 Hz, 1H); 8.14 (d, J=9.0 Hz, 1H); 7.94 (dd, J=2.6, 8.9 Hz, 1H); 7.83 (d, J=2.4 Hz, 1H); 7.77 (dd, J=2.4, 9.0 Hz, 1H); 7.00 (s, 1H); 6.91 (d, J=8.4 Hz, 1H); 4.68 (m, 1H); 2.81-2.74 (m, 2H); 2.54-2.46 (m, 2H); 2.49 (s, 3H); 1.95-1.81 (m, 2H);

1.65-1.58 (m, 2H). MS-FIA m/e: 531.1 (m+1). Analysis for $C_{25}H_{24}Cl_2 N_4O_3S$: Calc: C, 56.50; H, 4.55; N, 10.54; Found: C, 56.78; H, 4.53; N, 10.28.

EXAMPLE 74

Preparation of 5-Chloro-N-(5-chloropyridin-2-yl)-2-[4-(methylsulfinyl)-2-(piperidin-4-yloxy)benzoylamino]benzamide Hydrochloride.

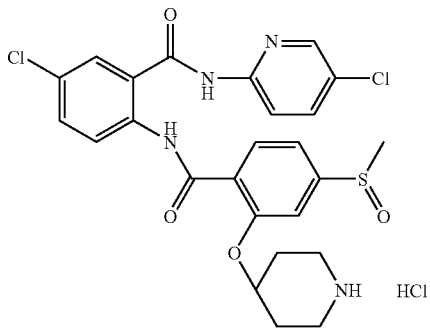

A. 2-[2-(1-tert-Butoxycarbonylpiperidin-4-yloxy)-4-(methylsulfinyl)benzoylamino]-5-chloro-N-(5-chloropyridin-2-yl)benzamide Using methods substantially equivalent to those described in Example 23, 2-[2-(1-tert-butoxycarbonylpiperidin-4-yloxy)-4-(methylsulfinyl)benzoylamino]-5-chloro-N-(5-chloropyridin-2-yl)benzamide (273 mg, 0.42 mmol, 34%) was prepared from 2-[2-(1-tert-butoxycarbonylpiperidin-4-yloxy)-4-(methylthio)benzoylamino]-5-chloro-N-(5-chloropyridin-2-yl)benzamide.

$^1$NMR (300 MHz, DMSO-$d_6$): δ 11.35 (s, 1H); 11.02 (s, 1H); 8.41 (d, J=2.4 Hz, 1H); 8.37 (d, J=9.0 Hz, 1H); 8.09 (d, J=8.7 Hz, 1H); 7.91 (m, 3H); 7.63 (dd, J=2.3, 8.9 Hz, 1H); 7.49 (s, 1H); 7.34 (d, J=8.1 Hz, 1H); 4.84 (m, 1H); 3.69 (m, 2H); 3.07 (m, 2H); 2.77 (s, 3H); 1.84 (m, 4H); 1.32 (s, 9H). IS-MS m/e: 647.4 (m+1). Analysis for $C_{30}H_{32}Cl_2 N_4O_6S$: Calc: C, 55.64; H, 4.98; N, 8.65; Found: C, 56.03; H, 5.07; N, 8.21.

B. 5-Chloro-N-(5-chloropyridin-2-yl)-2-[4-(methylsulfinyl)-2-(piperidin-4-yloxy)-benzoylamino]benzamide hydrochloride Using methods substantially equivalent to those described in Example 4-G, 5-chloro-N-(5-chloropyridin-2-yl)-2-[4-(methylsulfinyl)-2-(piperidin-4-yloxy)-benzoylamino]-benzamide (214 mg, 0.39 mmol, 100%) was prepared from 2-[2-(1-tert-butoxycarbonylpiperidin-4-yloxy)-4-(methylsulfinyl)benzoylamino]-N-(5-chloropyridin-2-yl)-5-chlorobenzamide.

$^1$NMR (300 MHz, DMSO-$d_6$): δ 8.42 (s, 1H); 8.36 (d, J=8.7 Hz, 1H); 8.11 (d, J=9.0 Hz, 1H); 7.94 (m, 2H); 7.86 (s, 1H); 7.63 (d, J=8.7 Hz, 1H); 7.46 (s, 1H); 7.33 (d, J=8.1 Hz, 1H); 4.75 (m, 1H); 2.88 (m, 2H); 2.76 (s, 3H); 2.64 (m, 2H); 1.89 (m, 2H); 1.70 (m, 2H). MS-FIA m/e: 547.2 (m+1). Analysis for $C_{25}H_{24}Cl_2 N_4O_4S.0.25H_2O$: Calc: C, 54.40; H, 4.47; N, 10.15; Found: C, 54.34; H, 4.35; N, 9.87.

To the free amine starting material, prepared in a manner similar to that described above, (1.5 g, 2.74 mmol) dissolved in 10% MeOH/$CH_2Cl_2$ (15 mL) was added 5 N HCl (0.55 mL, 2.7 mmol). After stirring for 1 h, the mixture was concentrated and vacuum dried to give the title compound as a white solid (1.60 g, quantitative).

IS-MS, m/e: 547 (m+1). Analysis for $C_{25}H_{24}Cl_2 N_4O_4S.HCl.0.25H_2O$: Calcd: C, 51.03; H, 4.37; N, 9.52; Found: C, 50.80; H, 4.09; N, 9.40.

EXAMPLE 75

Preparation of 5-Chloro-N-(5-chloropyridin-2-yl)-2-[4-(methylsulfonyl)-2-(piperidin-4-yloxy)benzoylamino]benzamide.

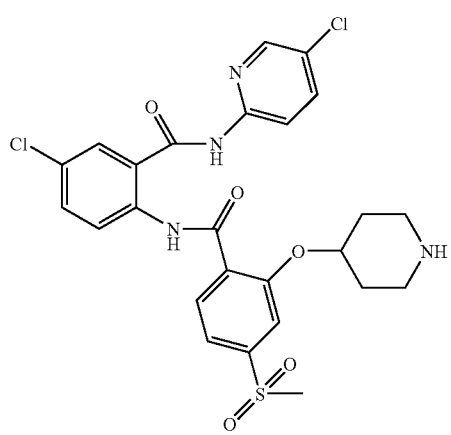

A. 2-[4-(Methylsulfonyl)-2-(1-tert-butoxycarbonylpiperidin-4-yloxy)benzoylamino]-N-(5-chloropyridin-2-yl)-5-chlorobenzamide Using methods substantially equivalent to those described in example 25, 2-[2-(1-tert-butoxycarbonylpiperidin-4-yloxy)-4-(methylsulfonyl)benzoylamino]-5-chloro-N-(5-chloropyridin-2-yl)benzamide (402 mg, 0.61 mmol, 87%) was prepared from 2-[2-(1-tert-butoxycarbonylpiperidin-4-yloxy)-4-(methylthio)benzoylamino]-5-chloro-N-(5-chloropyridin-2-yl)benzamide.

$^1$NMR (400 MHz, DMSO-$d_6$): δ 11.34 (s, 1H); 11.03 (s, 1H); 8.41 (s, 1H); 8.32 (d, J=8.8 Hz, 1H); 8.08 (d, J=8.8 Hz, 1H); 7.97-7.87 (m, 3H); 7.67-7.56 (m, 3H); 4.92 (m, 1H); 3.56 (m, 2H); 3.29 (s, 3H); 3.11 (m, 2H); 1.96-1.87 (m, 4H); 1.32 (s, 9H). IS-MS m/e: 663.1 (m+1). Analysis for $C_{30}H_{32}Cl_2 N_4O_7S$: Calc: C, 54.30; H, 4.86; N, 8.44; Found: C, 54.45; H, 5.11; N, 8.15.

B. 5-Chloro-N-(5-chloropyridin-2-yl)-2-[4-(methylsulfonyl)-2-(piperidin-4-yloxy)-benzoylamino]benzamide Using methods substantially equivalent to those described in Example 4-G, 5-chloro-N-(5-chloropyridin-2-yl)-2-[4-(methylsulfonyl)-2-(piperidin-4-yloxy)-benzoylamino]benzamide (291 mg, 0.52 mmol, 92%) was prepared from 2-[2-(1-tert-butoxycarbonylpiperidin-4-yloxy)-4-(methylsulfonyl)benzoylamino]-5-chloro-N-(5-chloropyridin-2-yl)benzamide.

$^1$NMR (300 MHz, DMSO-$d_6$): δ 8.42 (d, J=1.8 Hz, 1H); 8.23 (d, J=9.0 Hz, 1H); 8.09 (d, J=8.7 Hz, 1H); 7.90 (m, 3H); 7.61 (m, 3H); 4.92 (m, 1H); 3.04 (m, 2H); 2.89 (m, 2H); 1.95

(m, 2H); 1.82 (m, 2H). MS-FIA m/e: 563.2 (m+11). Analysis for $C_{25}H_{24}Cl_2N_4O_5S$—$CH_2Cl_2$: Calc: C, 49.11; H, 3.97; N, 8.48; Found: C, 49.50; H, 4.06; N, 8.47.

EXAMPLE 76

Preparation of 2-[4-(1-Amino-1-methyl)ethyl-2-(piperidin-4-yloxy)benzoylamino]-5-chloro-N-(5-chloro-pyridin-2-yl)benzamide Trihydrochloride.

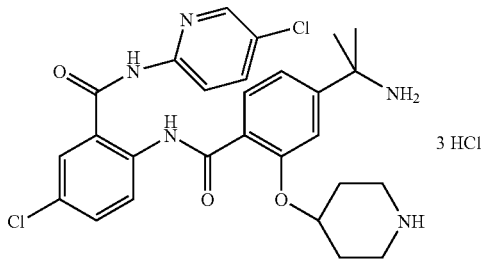

Using methods substantially equivalent to those described in Example 60-I & J, 2-[4-(1-amino-1-methyl)ethyl-2-(piperidin-4-yloxy)benzoylamino]-5-chloro-N-(5-chloro-pyridin-2-yl)benzamide trifluoroacetate (300 mg, 0.34 mmol, 85%) was prepared from methyl 4-[1-(tert-butoxycarbonylamino)-1-methyl]ethyl-2-[1-(tert-butoxycarbonyl)-piperidin-4-yloxy]benzoate and N-(5-chloropyridin-2-yl)-2-amino-5-chlorobenzamide.

[1]NMR

The product was further purified by RPHPLC, giving 127 mg of the title compound as the hydrochloride salt.
[1]NMR

EXAMPLE 77

Preparation of 2-[4-(4-Chlorophenyl)-2-(piperidin-4-yloxy)benzoylamino]-N-(5-chloropyridin-2-yl)benzamide Trifluoroacetate.

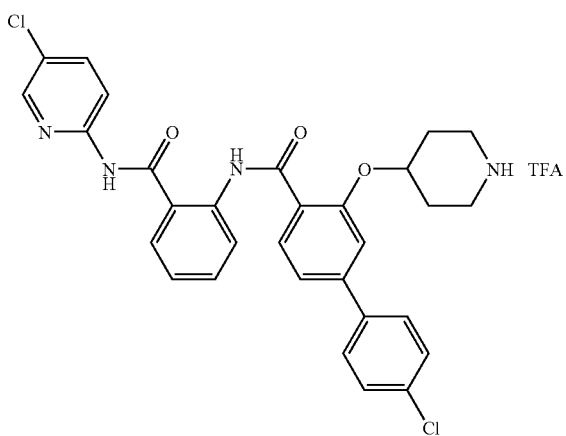

A. Methyl 4-bromo-2-(1-tert-butoxycarbonylpiperidin-4-yloxy)benzoate

Using a procedure analagous to that described in Example 21-C, methyl 4-bromo-2-(1-tert-butoxycarbonylpiperidin-4-yloxy)benzoate (1.7 g, 91%) was prepared from methyl 4-bromo-2-hydroxybenzoate.
[1]NMR FD-MS, m/e 416.19

B. Methyl 2-(1-tert-butoxycarbonylpiperidin-4-yloxy)-4-(4-chlorophenyl)benzoate

To a solution of methyl 4-bromo-2-(1-tert-butoxycarbonylpiperidin-4-yloxy)-benzoate (0.207 g, 0.5 mmol) in 1,2-dimethoxyethane (3 mL) was added 4-chlorophenyl-boronic acid (0.094 g, 0.6 mmol), tetrakis(triphenylphospine)palladium(0) (0.010 g), and 1 M aq potassium phosphate (0.8 mL). The reaction mixture was heated at 80° C. overnight under a nitrogen atmosphere. The reaction was then cooled to room temperature and water (10 mL) and ethyl acetate (50 mL) were added. The layers were separated and the aqueous layer was extracted with ethyl acetate (2×25 mL). The organic layer was dried over magnesium sulfate, filtered, and concentrated in vacuo. The crude material was purified by RPHPLC (ethyl acetate/hexane 1:4) to give 0.190 g (85%) of product.
[1]NMR FD-MS, m/e (m+1) 446

C. 2-(1-tert-Butoxycarbonylpiperidin-4-yloxy)-4-(4-chlorophenyl)benzoic acid

A solution of methyl 2-(1-tert-butoxycarbonylpiperidin-4-yloxy)-4-(4-chloro-phenyl)benzoate (0.3 g 0.67 mmol) in dioxane (10 mL) and aqueous NaOH (2 g in 10 mL $H_2O$) was heated at reflux for 4 h. The reaction was then cooled to room temperature, acidified to pH 3 with 1 N HCl, and extracted with ethyl acetate (3×50 mL). The organic layers were combined, dried over magnesium sulfate, filtered, and concentrated in vacuo to give 0.293 g of product (100%).

D. 2-(1-tert-Butoxycarbonylpiperidin-4-yloxy)-4-(4-chlorophenyl)benzoylamino]-N-(5-chloropyridin-2-yl)benzamide Using a procedure analogous to Example 4-E, 2-(1-tert-butoxycarbonylpiperidin-4-yloxy)-4-(4-chlorophenyl)benzoylamino]-N-(5-chloropyridin-2-yl)benzamide (0.15 g, 34%) was prepared from 2-(1-tert-butoxycarbonylpiperidin-4-yloxy)-4-(4-chlorophenyl)-benzoic acid and N-(5-chloro-pyridin-2-yl)-2-aminobenzamide.

E. 2-[4-(4-Chlorophenyl)-2-(piperidin-4-yloxy)benzoylamino]-N-(5-chloropyridin-2-yl)benzamide trifluoroacetate Using a procedure analogous to Example 57-D, 2-[4-(4-chlorophenyl)-2-(piperidin-4-yloxy)benzoylamino]-N-(5-chloropyridin-2-yl)benzamide trifluoroacetate (0.087 g, 69%) was prepared from 2-(1-tert-butoxycarbonylpiperidin-4-yloxy)-4-(4-chlorophenyl)benzoylamino]-N-(5-chloropyridin-2-yl)benzamide.
[1]NMR FD-MS, m/e 563.33

EXAMPLE 78

Preparation of 1-[2-[4-(Methylthio)-2-(piperidin-4-yloxy)benzoylamino]benzoyl]-piperazine.

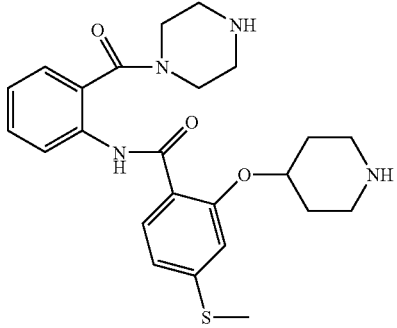

A. 1-(tert-Butoxycarbonyl)-4-(2-nitrobenzoyl)piperazine

To a mixture of 1-(tert-butoxycarbonyl)piperazine (11.18 g, 60 mmol) in $CH_2Cl_2$ (120 mL) at 0° C. was added 2-nitrobenzoyl chloride (8.0 mL, 60.6 mmol). The reaction was warmed to room temperature and stirred for 2 hours. A solution of 50% satd $Na_2CO_3$ was added and the mixture was extracted with $CH_2Cl_2$. The organic layer was washed with satd citric acid and water, dried over $MgSO_4$, and concentrated to a slurry. Ether was added to the mixture and it was filtered to give the desired product as a white solid (16.0 g, 79%).

$^1$NMR (300 MHz, $CDCl_3$): δ 8.21 (d, J=8.4 Hz, 1H), 7.74 (m, 1H), 7.60 (m, 1H), 7.40 (d, 1H), 3.90 (m, 1 h), 3.70 (m, 1H), 3.60 (m, 2H), 3.40 (m, 2H), 3.20 (m, 2H), 1.47 (s, 9H). IS-MS, m/e: 336 (m+1).

B. 1-(2-Aminobenzoyl)-4-(tert-butoxycarbonyl)piperazine

Using a procedure analogous to Example 2-B, 1-(tert-butoxycarbonyl)-4-(2-nitro-benzoyl)piperazine gave 1-(2-aminobenzoyl)-4-(tert-butoxycarbonyl)piperazine as a white solid (12.07 g, 83%).

$^1$NMR IS-MS, m/e: 306 (m+1).

C. 1-(tert-Butoxycarbonyl)-4-[2-[2-(1-tert-butoxycarbonylpiperidin-4-yloxy)-4-(methylthio)benzoylamino]benzoyl]piperazine Using methods substantially equivalent to those described in Example 4-E, 1-(tert-butoxycarbonyl)-4-[2-[2-(1-tert-butoxycarbonylpiperidin-4-yloxy)-4-(methylthio)-benzoylamino]benzoyl]piperazine (1.32 g, 2.02 mmol, 81%) was prepared from 1-(2-aminobenzoyl)-4-(tert-butoxycarbonyl) piperazine and 2-(1-tert-butoxycarbonyl-piperidin-4-yloxy)-(4-methylthio)benzoic acid.

$^1$NMR (300 MHz, DMSO-$d_6$): δ 9.98 (s, 1H); 8.03 (d, J=8.1 Hz, 1H); 7.83 (d, J=8.4 Hz, 1H); 7.43 (t, J=7.8 Hz, 1H); 7.33 (t, J=7.8 Hz, 1H); 7.18 (t, J=7.5 Hz, 1H); 7.08 (s, 1H); 6.93 (d, J=8.7 Hz, 1H); 4.83 (m, 1H); 3.78 (d, J=13.2 Hz, 2H); 3.54 (m, 2H); 3.27 (m, 6H); 3.00 (m, 2H); 2.46 (s, 3H); 1.90-1.73 (m, 4H); 1.35 (s, 18H). IS-MS m/e: 655.5 (m+1).

Analysis for $C_{34}H_{46}N_4O_7S$: Calc: C, 62.36; H, 7.08; N, 8.56; Found: C, 62.41; H, 6.92; N, 8.31.

D. 1-[2-[4-(Methylthio)-2-(piperidin-4-yloxy)benzoylamino]benzoyl]piperazine Using methods substantially equivalent to those described in Example 4-G, 1-[2-[4-(methylthio)-2-(piperidin-4-yloxy) benzoylamino]benzoyl]piperazine (103 mg, 0.23 mmol, 73%) was prepared from 1-(tert-butoxycarbonyl)-4-[2-[2-(1-tert-butoxycarbonyl-piperidin-4-yloxy)-4-(methylthio)benzoylamino]benzoyl]piperazine.

$^1$NMR (300 MHz, DMSO-$d_6$): δ 8.12 (d, J=7.8 Hz, 1H); 7.92 (t, J=8.3 Hz, 1H); 7.83 (d, J=8.4 Hz, 1H); 7.69 (d, J=8.1 Hz, 1H); 7.60 (t, J=7.4 Hz, 1H); 7.07 (s, 1H); 6.99 (d, J=8.4 Hz, 1H); 5.00 (m, 1H); 3.36-3.12 (m, 12H); 2.46 (s, 3H); 2.05 (m, 4H). IS-MS m/e: 453.9 (m).

EXAMPLE 79

Preparation of 5-Chloro-N-(5-chloropyridin-2-yl)-2-[2-(piperidin-4-yloxy)-4-(thiophen-3-yl)benzoylamino]benzamide Hydrochloride.

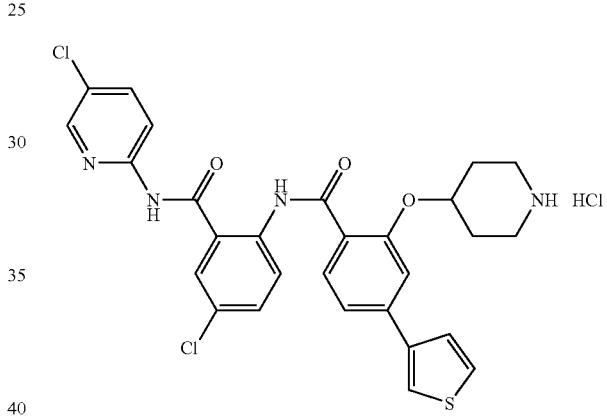

A. Methyl 2-(1-tert-Butoxycarbonylpiperidin-4-yloxy)-4-(thiophen-3-yl)benzoate Using a procedure analogous to Example 77-B, methyl 2-(1-tert-butoxycarbonyl-piperidin-4-yloxy)-4-(thiophen-3-yl)benzoate (0.22 g, 88%) was prepared from methyl 4-bromo-2-(1-tert-butoxycarbonylpiperidine-4-yloxy)benzoate.

$^1$NMR FD-MS, m/e (+1) 418

B. 2-(1-tert-Butoxycarbonylpiperidin-4-yloxy)-4-(thiophen-3-yl)benzoic acid

Using a procedure analogous to Example 77-C, 2-(1-tert-butoxycarbonylpiperidin-4-yloxy)-4-(thiophen-3-yl)benzoic acid (0.202 g, 95%) was prepared from methyl 2-(1-tert-butoxycarbonylpiperidin-4-yloxy)-4-(thiophen-3-yl) benzoate.

C. 2-[2-(1-tert-Butoxycarbonylpiperidin-4-yloxy)-4-(thiophen-3-yl)benzoylamino]-N-(5-chloropyridin-2-yl)-5-chlorobenzamide Using a procedure analogous to Example 4-E, 2-[2-(1-tert-butoxycarbonyl-piperidin-4-yloxy)-4-(thiophen-3-yl)benzoylamino]-N-(5-chloropyridin-2-yl)-5-chloro-benzamide (0.220 g, 65%) was prepared from 2-(1-tert-butoxycarbonylpiperidin-4-yloxy)-4-(thiophen-3-yl)benzoic acid and N-(5-chloropyridin-2-yl)-2-amino-5-chloro-benzamide.

[1]NMR FD-MS, m/e (m+1) 667

D. 5-Chloro-N-(5-chloropyridin-2-yl)-2-[2-(piperidin-4-yloxy)-4-(thiophen-3-yl)-benzoylamino]benzamide Hydrochloride Using a procedure analogous to Example 57-D, 5-chloro-N-(5-chloropyridin-2-yl)-2-[2-(piperidin-4-yloxy)-4-(thiophen-3-yl)benzoylamino]benzamide trifluoroacetate (0.096 g, 51%) was prepared from 2-[2-(1-tert-butoxycarbonylpiperidin-4-yloxy)-4-(thiophen-3-yl)benzoylamino]-N-(5-chloropyridin-2-yl)-5-chlorobenzamide. The compound was purified by RPHPLC to give the hydrochloride salt.

[1]NMR FD-MS, m/e 569.31

EXAMPLE 80

Preparation of 5-Chloro-N-(5-chloropyridin-2-yl)-2-[4-(4-methoxyphenyl)-2-(piperidin-4-yloxy)benzoylamino]benzamide Hydrochloride.

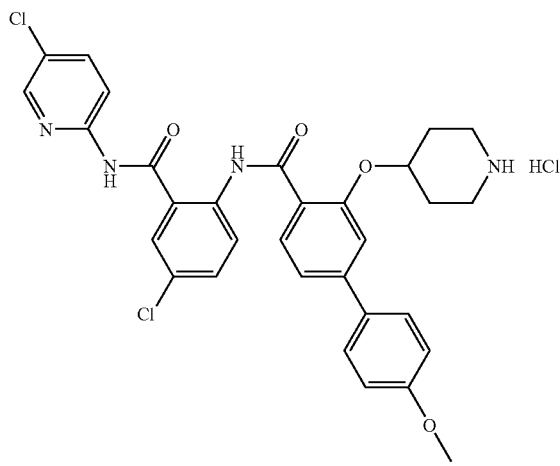

A. Methyl 2-(1-tert-Butoxycarbonylpiperidin-4-yloxy)-4-(4-methoxyphenyl)benzoate Using a procedure analogous to Example 77-B, methyl 2-(1-tert-butoxycarbonyl-piperidin-4-yloxy)-4-(4-methoxyphenyl)benzoate (0.208 g, 100%) was prepared from methyl 4-bromo-2-(1-tert-butoxycarbonylpiperidin-4-yloxy)benzoate.

[1]NMR FD-MS, m/e (+1) 442.1

B. 2-(1-tert-Butoxycarbonylpiperidin-4-yloxy)-4-(4-methoxyphenyl)benzoic acid Using a procedure analogous to Example 77-C, 2-(1-tert-butoxycarbonylpiperidin-4-yloxy)-4-(4-methoxyphenyl)benzoic acid (0.175 g, 87%) was prepared from methyl 2-(1-tert-butoxycarbonylpiperidin-4-yloxy)-4-(4-methoxyphenyl)benzoate.

C. 2-[2-(1-tert-Butoxycarbonylpiperidin-4-yloxy)-4-(4-methoxyphenyl)-benzoylamino]-5-chloro-N-(5-chloropyridin-2-yl)benzamide Using a procedure analogous to Example 4-E, 2-[2-(1-tert-butoxycarbonyl-piperidin-4-yloxy)-4-(4-methoxyphenyl) benzoylamino]-5-chloro-N-(5-chloropyridin-2-yl)benzamide (0.180 g, 65%) was prepared from 2-(1-tert-butoxycarbonylpiperidin-4-yloxy)-4-(4-methoxyphenyl) benzoic acid and N-(5-chloropyridin-2-yl)-2-amino-5-chlorobenzamide.

[1]NMR FD-MS, m/e (m+1) 691

D. 5-Chloro-N-(5-chloropyridin-2-yl)-2-[4-(4-methoxyphenyl)-2-(piperidin-4-yloxy)benzoylamino]benzamide hydrochloride Using a procedure analogous to Example 57-D followed by treatment with HCl, 5-chloro-N-(5-chloropyridin-2-yl)-2-[4-(4-methoxyphenyl)-2-(piperidin-4-yloxy)-benzoylamino]benzamide hydrochloride (0.112 g, 72%) was prepared from 2-[2-(1-tert-butoxycarbonylpiperidin-4-yloxy)-4-(4-methoxyphenyl)benzoylamino]-5-chloro-N-(5-chloropyridin-2-yl)benzamide.

[1]NMR FD-MS, m/e 591.43

EXAMPLE 81

Preparation of 2-[4-(1-Amino-1-methyl)ethyl-2-(piperidin-4-yloxy)benzoylamino]-N-(5-chloropyridin-2-yl)-5-fluorobenzamide Trihydrochloride.

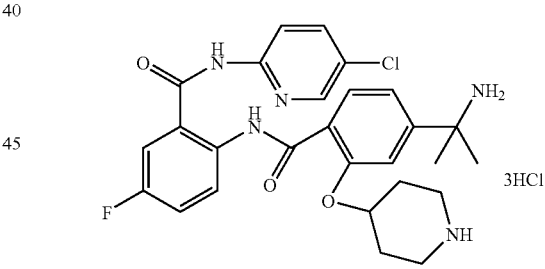

Using methods substantially equivalent to those described in Example 60-I-&-J, 2-[4-(1-amino-1-methyl)ethyl-2-(piperidin-4-yloxy)benzoylamino]-N-(5-chloropyridin-2-yl)-5-fluorobenzamide trifluoroacetate (250 mg, 0.29 mmol, 72%) was prepared from methyl 4-[1-(tert-butoxycarbonylamino)-1-methylethyl]-2-(1-tert-butoxycarbonyl-piperidin-4-yloxy) benzoate and N-(5-chloropyridin-2-yl)-2-amino-5-fluorobenzamide.

[1]NMR

This product was subjected to reverse phase HPLC to obtain 165 mg of the title compound as the hydrochloride salt.

[1]NMR

EXAMPLE 82

Preparation of N-(5-Chloropyridin-2-yl)-5-fluoro-2-[4-(methylsulfinyl)-2-(piperidin-4-yloxy)benzoylamino]benzamide.

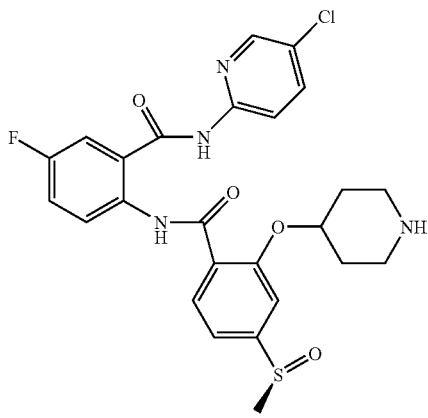

A. 2-[2-(1-tert-Butoxycarbonylpiperidin-4-yloxy)-4-(methylsulfinyl)benzoylamino]-N-(5-chloropyridin-2-yl)-5-fluorobenzamide Using methods substantially equivalent to those described in Example 23, 2-[2-(1-tert-butoxycarbonylpiperidin-4-yloxy)-4-(methylsulfinyl)benzoylamino]-N-(5-chloropyridin-2-yl)-5-fluorobenzamide (134 mg, 0.21 mmol, 21%) was prepared from 2-[2-(1-tert-butoxycarbonyl-4-(methylthio)piperidin-4-yloxy)benzoylamino]-N-(5-chloro-pyridin-2-yl)-5-fluorobenzamide.

$^1$NMR (300 MHz, DMSO-$d_6$): δ 11.29 (s, 1H); 10.93 (s, 1H); 8.40 (d, J=2.7 Hz, 1H); 8.30 (m, 1H); 8.10 (d, J=9.0 Hz, 1H); 7.93 (m, 3H); 7.65 (dd, J=2.9, 9.2 Hz, 1H); 7.48 (s, 1H); 7.34 (d, J=8.1 Hz, 1H); 4.84 (m, 1H); 3.63 (d, J=12.9 Hz, 2H); 3.13 (m, 2H); 2.76 (s, 3H); 1.95-1.74 (m, 4H); 1.32 (s, 9H). IS-MS m/e: 631.3 (m+1).

B. N-(5-Chloropyridin-2-yl)-5-fluoro-2-[4-(methylsulfinyl)-2-(piperidin-4-yloxy)-benzoylamino]benzamide Using methods substantially equivalent to those described in Example 4-G, N-(5-chloropyridin-2-yl)-5-fluoro-2-[4-(methylsulfinyl)-2-(piperidin-4-yloxy)-benzoylamino]benzamide (102 mg, 0.19 mmol, 100%) was prepared from 2-[2-(1-tert-butoxycarbonylpiperidin-4-yloxy)-4-(methylsulfinyl)benzoylamino]-N-(5-chloropyridin-2-yl)-5-fluorobenzamide.

$^1$NMR (300 MHz, DMSO-$d_6$): δ 8.42 (d, J=2.1 Hz, 1H); 8.30 (m, 1H); 8.13 (d, J=8.7 Hz, 1H); 7.93 (m, 3H); 7.65 (dd, J=2.7, 9.0 Hz, 1H); 7.45 (s, 1H); 7.32 (d, J=8.1 Hz, 1H); 4.72 (m, 1H); 2.85 (m, 3H); 2.76 (s, 3H); 2.57 (m, 2H); 1.88 (m, 2H); 1.65 (m, 2H). IS-MS m/e: 531.1 (m+1). Analysis for $C_{25}H_{24}ClFN_4O_4S \cdot 0.2CH_2Cl_2 \cdot 0.1H_2O$: Calc: C, 55.25; H, 4.49; N, 10.15; Found: C, 55.42; H, 4.81; N, 9.85.

EXAMPLE 83

Preparation of 2-[2-(3-Aminopropoxy)-4-(pyrrolidinyl)benzoylamino]-N-(5-chloro-pyridin-2-yl)-5-fluorobenzamide.

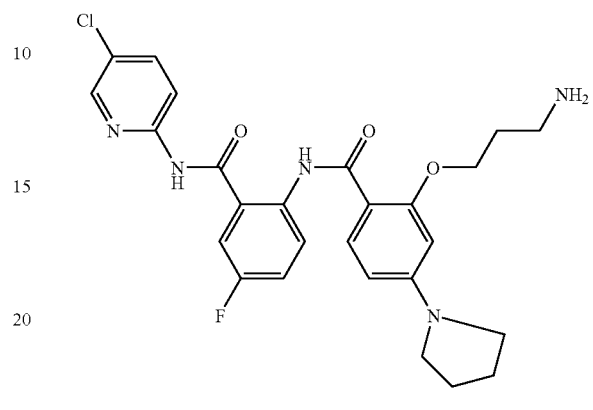

A. Methyl 4-fluoro-2-(3-tert-butoxycarbonylaminopropoxy)benzoate

Using a procedure analogous to Example 1-C, methyl 2-hydroxy-4-fluorobenzoate and 3-(tert-butoxycarbonylamino)propanol gave the desired product as a white solid (20.6 g, 84%). $^1$NMR IS-MS, m/e: 328 (m+1).

B. 4-Fluoro-2-(3-tert-butoxycarbonylaminopropoxy)benzoic acid

Using a procedure analogous to Example 21-D, 4-fluoro-2-(3-tert-butoxy-carbonylaminopropoxy)benzoic acid was prepared from methyl 4-fluoro-2-(3-tert-butoxycarbonylaminopropoxy)benzoate.

C. N-(5-Chloropyridin-2-yl)-5-fluoro-2-[4-fluoro-2-(3-tert-butoxycarbonyl-aminopropoxy)benzoylamino]benzamide Using a procedure similar to Example 4-E, 2-[4-fluoro-2-(3-tert-butoxycarbonyl-aminopropoxy)benzoylamino]-N-(5-chloropyridin-2-yl)-5-fluorobenzamide (5.1 g, 77%) was prepared from 4-fluoro-2-(3-tert-butoxycarbonylaminopropoxy)benzoic acid and N-(5-chloropyridin-2-yl)-5-fluorobenzamide.

$^1$NMR FD-MS, m/e 561.19 Analysis for $C_{27}H_{27}ClF_2N_4O_5$: Calcd: C, 57.81; H, 4.85; N, 9.99; Found: C, 58.25; H, 5.32; N, 9.71.

D. 2-[2-(3-tert-Butoxycarbonylaminopropoxy)-4-(pyrrolidin-1-yl)benzoylamino]-N-(5-chloropyridin-2-yl)-5-fluorobenzamide A solution of N-(5-chloropyridin-2-yl)-5-fluoro-2-[4-fluoro-2-(3-tert-butoxycarbonylaminopropoxy)benzoylamino]benzamide (0.4 g, 0.71 mmol) in pyrrolidine (10 mL) was heated at 80° C. for 6 hr. The reaction was concentrated in vacuo and the residue was purified by RPLC (ethyl acetate/hexane 1:4) to give pure product (0.345 g, 79%).

$^1$NMR FD-MS, m/e 612.23

E. 2-[2-(3-Aminopropoxy)-4-(pyrrolidinyl)benzoylamino]-N-(5-chloropyridin-2-yl)-5-fluorobenzamide Using a procedure analogous to Example 57-D, 2-[2-(3-aminopropoxy)-4-(pyrrolidinyl)benzoylamino]-N-(5-chloropyridin-2-yl)-5-fluorobenzamide (0.240 g, 86%) was prepared from 2-[2-(3-tert-butoxycarbonylaminopropoxy)-4-(pyrrolidin-1-yl)-benzoylamino]-N-(5-chloropyridin-2-yl)-5-fluorobenzamide.

$^1$NMR FD-MS, m/e 512.49

EXAMPLE 84

Preparation of 2-[4-tert-Butyl-2-[1-(2-hydroypropyl)-piperidin-4-yloxy]-benzoylamino]-N-(5-chloropyridin-2-yl)-5-fluorobenzamide.

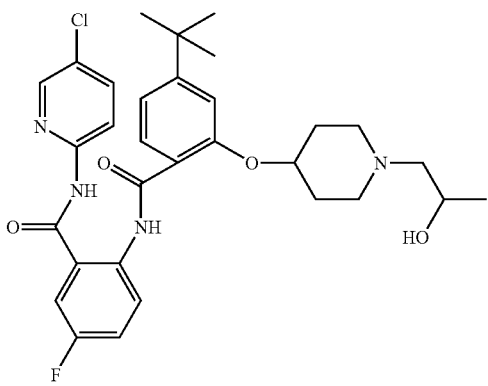

The 2-[4-tert-butyl-2-(piperidin-4-yloxy)benzoylamino]-N-(5-chloropyridin-2-yl)-5-fluorobenzamide (400 mg, 0.76 mmol) was placed in a screw-top vial and diluted with dry MeOH (15 mL). The vial was purged with nitrogen. Propylene oxide (0.133 mL, 1.91 mmol) was added and the vial was sealed. The reaction was heated at 65° C. for 1.5 h. More propylene oxide (0.133 mL) was added to the reaction and it was heated (sealed) at 80° C. for 2 hours longer. After cooling, the solvents were evaporated in vacuo and the residue was triturated in MeOH (15 mL), filtered, rinsed with diethyl ether, and dried to give desired product as a white solid (396.5 mg, 0.68 mmol, 89%).

$^1$NMR (300 Hz, DMSO-d$_6$): δ 11.25 (s, 1H); 10.83 (s, 1H); 8.4 (s, 1H); 8.35 (m, 1H), 8.13 (d, J=8.9 Hz, 1H); 7.93 (m, 1H); 7.75 (d, J=8.1 Hz, 1H); 7.63 (d, J=11.7 Hz, 1H); 7.41 (t, J=1.9 Hz, 1H), 7.1 (s, 1H); 7.04 (d, J=8.2 Hz, 1H); 4.62 (m, 1H); 4.16 (s, 1H); 3.63 (m, 1H); 2.55 (m, 2H); 2.13 (m, 2H); 2.05 (m, 2H); 1.74-1.87 (m, 4H); 1.25 (s, 9H); 0.94 (d, J=6.0 Hz, 3H) ppm. IS-MS, 583.2 m/e Analysis for C$_{31}$H$_{36}$ClFN$_4$O$_4$: Calcd: C, 63.86; H, 6.22; N, 9.61; Found: C, 63.56; H, 6.03; N, 9.56.

EXAMPLE 85

Preparation of 2-[4-(tert-Butyl)-2-(piperidin-4-yloxy)benzoylamino]-5-chloro-N-(5-fluoropyridin-2-yl)benzamide Trifluoroacetate.

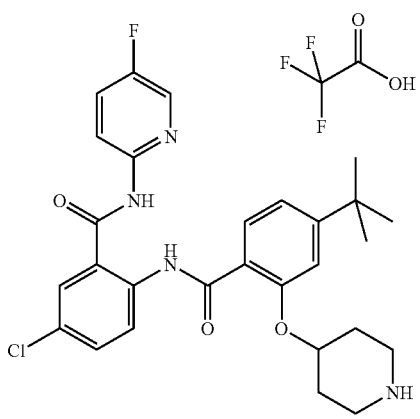

A. 5-Chloro-N-(5-fluoropyridin-2-yl)-2-nitrobenzamide

By methods substantially equivalent to those described in Example 16-A, 5-chloro-N-(5-fluoropyridin-2-yl)-2-nitrobenzamide (4.27 g, 80%) was prepared from 5-chloro-2-nitrobenzoic acid and 2-amino-5-fluoropyridine.

$^1$NMR IS-MS, m/e 296.2 (m+1) Analysis for C$_{12}$H$_7$ClFN$_3$O$_3$: Calcd: C, 48.75; H, 2.39; N, 14.21; Found: C, 48.97; H, 2.61; N, 14.13.

B. 2-Amino-5-chloro-N-(5-fluoropyridin-2-yl)benzamide

By methods substantially equivalent to those described in Example 2-B, 2-amino-5-chloro-N-(5-fluoropyridin-2-yl)benzamide (1.87 g, 88%) was prepared from 5-chloro-N-(5-fluoropyridin-2-yl)-2-nitrobenzamide.

$^1$NMR IS-MS, m/e 266.0 (m+1)

C. 2-[4-(tert-Butyl)-2-(1-Boc-piperidin-4-yloxy)benzoylamino]-5-chloro-N-(5-fluoropyridin-2-yl)benzamide By methods substantially equivalent to those described in Example 16-F, 2-[4-(tert-butyl)-2-(1-Boc-piperidin-4-yloxy)benzoylamino]-5-chloro-N-(5-fluoropyridin-2-yl)benzamide (0.36 g, 41%) was prepared from 4-(tert-butyl)-2-(1-Boc-piperidin-4-yloxy)benzoyl chloride and 2-amino-5-chloro-N-(5-fluoropyridin-2-yl)benzamide.

$^1$NMR IS-MS, m/e 625.4 (m+1) Analysis for C$_{33}$H$_{38}$ClFN$_4$O$_5$: Calcd: C, 63.40; H, 6.13; N, 8.96; Found: C, 63.63; H, 6.26; N, 8.69.

D. 2-[4-(tert-Butyl)-2-(piperidin-4-yloxy)benzoylamino]-5-chloro-N-(5-fluoro-pyridin-2-yl)benzamide trifluoroacetate To a stirring solution of 2-[4-(tert-butyl)-2-(1-Boc-piperidin-4-yloxy)benzoyl-amino]-5-chloro-N-(5-fluoropyridin-2-yl)benzamide (0.3 g, 0.48 mmol) and anisole (0.26 mL) in dichloromethane (10 mL) was added TFA (1 mL). After 2 h, the solvent was removed in vacuo and the residue was suspended in diethyl ether and concentrated in vacuo twice and then again suspended in diethyl ether with vigorous stirring. The solid was washed with diethyl ether, filtered and dried in vacuo to give 0.28 g (90%) of off-white solid,
$^1$NMR IS-MS, m/e 525.1 (m+1) Analysis for $C_{28}H_{30}ClFN_4O_3$-TFA: Calcd: C, 56.39; H, 4.89; N, 8.77; F, 11.89; Found: C, 56.23; H, 4.90; N, 8.64; F, 12.05.

EXAMPLE 86

Preparation of N-(5-Chloropyridin-2-yl)-5-fluoro-2-[4-(isopropoxy)-2-(piperidin-4-yloxy)benzoylamino]benzamide.

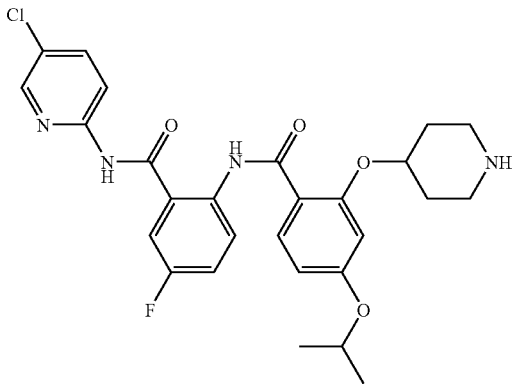

A. Methyl 2-(1-tert-butoxycarbonylpiperidin-4-yloxy)-4-hydroxybenzoate

To a solution of methyl 4-benzyloxy-2-(piperidin-4-yloxy)benzoate (2 g) in methanol (50 mL) was added Pd/C (200 mg). The mixture was stirred under balloon pressure of hydrogen overnight. The catalyst was filtered off and the filtrate was concentrated to provide clean product (1.55 g, 97%).
$^1$NMR FD-MS, m/e (m−1) 350.1

B. Methyl 2-(1-tert-butoxycarbonylpiperidin-4-yloxy)-4-isopropoxybenzoate

To a solution of methyl 2-(1-tert-butoxycarbonylpiperidin-4-yloxy)-4-hydroxy-benzoate (0.735 g, 2.1 mmol), triphenylphosphine (0.551 g, 2.1 mmol), and isopropanol (0.158 mL, 2 mmol) in tetrahydrofuran was added diisopropyl azodicarboxylate (0.433 mL, 2.2 mmol) dropwise. The solution was sonicated for 30 minutes. The reaction mixture was purified without workup by RPLC (EtOAc/Hexane 3:7) to give 0.675 g (86%) of pure product.
$^1$NMR FD-MS, m/e (m+1) 394.1

C. 2-(1-tert-Butoxycarbonylpiperidin-4-yloxy)-4-isopropoxybenzoic acid

Using a procedure analogous to Example 77-C, 2-(1-tert-butoxycarbonylpiperidin-4-yloxy)-4-isopropoxybenzoic acid (0.490 g, 100%) was prepared from methyl 2-(1-tert-butoxycarbonylpiperidin-4-yloxy)-4-isopropoxybenzoate.

D. 2-[2-(1-tert-Butoxycarbonylpiperidin-4-yloxy)-4-isopropoxybenzoylamino]-N-(5-chloropyridin-2-yl)-5-fluorobenzamide Using a procedure analogous to Example 4-E, 2-[2-(1-tert-butoxycarbonyl-piperidin-4-yloxy)-4-isopropoxybenzoylamino]-N-(5-chloropyridin-2-yl)-5-fluoro-benzamide (0.326 g, 80%) was prepared from 2-(1-tert-butoxycarbonylpiperidin-4-yloxy)-4-isopropoxybenzoic acid and N-(5-chloropyridin-2-yl)-2-amino-5-fluoro-benzamide.
$^1$NMR FD-MS, m/e 627.34 Analysis for $C_{32}H_{36}ClFN_4O_6$: Calcd: C, 61.29; H, 5.79; N, 8.93; Found: C, 61.57; H, 5.88; N, 8.96.

E. N-(5-Chloropyridin-2-yl)-5-fluoro-2-[4-isopropoxy-2-(piperidin-4-yloxy)benzoylamino]benzamide Using a procedure analogous to Example 57-D, N-(5-chloropyridin-2-yl)-5-fluoro-2-[4-isopropoxy-2-(piperidin-4-yloxy)benzoylamino]benzamide (0.246 g, 95%) was prepared from 2-[2-(1-tert-butoxycarbonylpiperidin-4-yloxy)-4-isoproxy-benzoylamino]-N-(5-chloropyridin-2-yl)-5-fluorobenzamide.
$^1$NMR FD-MS, m/e 527.2

EXAMPLE 87

Preparation of 5-Chloro-N-(5-chloropyridin-2-yl)-2-[4-(isopropoxy)-2-(piperidin-4-yloxy)benzoylamino]benzamide.

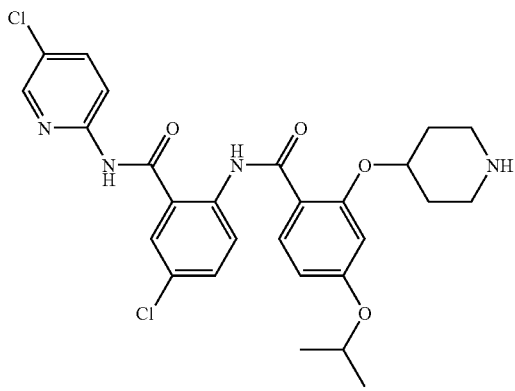

A. 2-[2-(1-tert-Butoxycarbonylpiperidin-4-yloxy)-4-(isopropoxy)benzoylamino]-5-chloro-N-(5-chloropyridin-2-yl)benzamide Using a procedure analogous to Example 4-E, 2-[2-(1-tert-butoxycarbonyl-piperidin-4-yloxy)-4-(isopropoxy)benzoylamino]-5-chloro-N-(5-chloropyridin-2-yl)-benzamide (0.372 g, 91%) was prepared from 2-(1-tert-butoxycarbonylpiperidin-4-yloxy)-4-isopropoxybenzoic acid and 5-chloro-N-(5-chloropyridin-2-yl)benzamide.
$^1$NMR FD-MS, m/e 643.33

B. 5-Chloro-N-(5-chloropyridin-2-yl)-2-[4-(isopropoxy)-2-(piperidin-4-yloxy)benzoylamino]benzamide Using a procedure analogous to Example 57-D, 5-chloro-N-(5-chloropyridin-2-yl)-2-[4-(isopropoxy)-2-(piperidin-4-yloxy)benzoylamino]benzamide (0.295 g, 99%) was prepared from 2-[4-(isopropoxy)-2-(1-tert-butoxycarbonylpiperidin-4-yloxy)-benzoylamino]-N-(5-chloropyridin-2-yl)-5-chlorobenzamide.

$^1$NMR FD-MS, m/e 643.28 Analysis for $C_{27}H_{28}Cl_2N_4O_4$: Calcd: C, 59.67; H, 5.19; N, 10.31; Found: C, 59.93; H, 4.97; N, 10.23.

EXAMPLE 88

Preparation of N-(5-Chloropyridin-2-yl)-5-fluoro-2-[4-(methylsulfonyl)-2-(piperidin-4-yloxy)benzoylamino]benzamide.

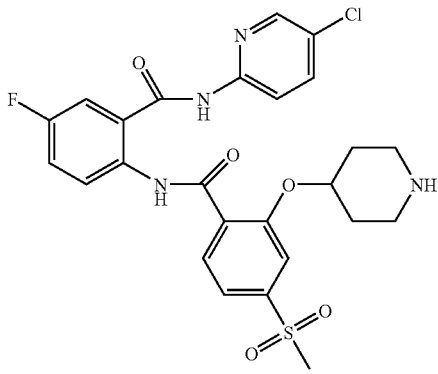

A. Methyl 2-(1-tert-butoxycarbonylpiperidin-4-yloxy)-4-(methylsulfonyl)benzoate The methyl-2-(1-tert-butoxycarbonylpiperidin-4-yloxy)-4-(methylthio)benzoate (3.65 g, 9.56 mmol) was dissolved in chloroform (100 mL). After the solution had been cooled to 0° C., mCPBA (7.68 g, 25.81 mmol, 58% purity) was added in portions. After minutes, the reaction was extracted with saturated aqueous sodium bicarbonate (2×50 mL). The organic layer was dried over sodium sulfate, filtered, and concentrated. The crude material was purified by flash column chromatography (5% EtOAc/CH$_2$Cl$_2$ through 10% EtOAc/CH$_2$Cl$_2$) to give the desired product (2.996 g, 7.25 mmol, 76%).

$^1$NMR (300 MHz, DMSO-d$_6$): δ 7.81 (d, J=8.1 Hz, 1H); 7.63 (s, 1H); 7.52 (d, J=8.1 Hz, 1H); 4.88 (m, 1H); 3.80 (s, 3H); 3.33 (m, 5H); 1.79 (m, 2H); 1.62 (m, 2H). FIA-MS, m/e 414.2 (m+1).

B. 2-(1-tert-Butoxycarbonylpiperidin-4-yloxy)-4-(methylsulfonyl)benzoic acid Using methods substantially equivalent to those described in Example 21-D, 2-(1-tert-butoxycarbonylpiperidin-4-yloxy)-4-(methylsulfonyl)benzoic acid (2.79 g, 6.98 mmol, 96%) was prepared from methyl 2-(1-tert-butoxycarbonylpiperidin-4-yloxy)-4-(methylsulfonyl)benzoate.

$^1$NMR (300 MHz, DMSO-d$_6$): δ 7.16 (d, J=7.8 Hz, 1H); 7.60 (s, 1H); 7.49 (d, J=7.8 Hz, 1H); 5.72 (m, 1H); 3.39-3.30 (m, 4H); 1.80 (m, 2H); 1.62 (s, 2H). FIA-MS, m/e 400.1 (m+1). Analysis for $C_{18}H_{25}NO_7S$: Calc: C, 54.12; H, 6.31; N, 3.51; Found: C, 54.13; H, 6.29; N, 3.26.

C. 2-[2-(1-tert-Butoxycarbonylpiperidin-4-yloxy)-4-(methylsulfonyl)benzoylamino]-N-(5-chloropyridin-2-yl)-5-fluorobenzamide Using methods substantially equivalent to those described in Example 4-E, 2-[2-(1-tert-butoxycarbonylpiperidin-4-yloxy)-4-(methylsulfonyl)benzoylamino]-N-(5-chloropyridin-2-yl)-5-fluorobenzamide (120 mg, 0.19 mmol, 26%) was prepared from 2-(1-tert-butoxycarbonylpiperidin-4-yloxy)-4-(methylsulfonyl)benzoic acid and N-(5-chloropyridin-2-yl)-2-amino-5-fluorobenzamide.

$^1$NMR (400 MHz, DMSO-d$_6$): δ 11.28 (s, 1H); 10.94 (s, 1H); 8.41 (d, J=2.0 Hz, 1H); 8.26 (m, 1H); 8.09 (d, J=8.8 Hz, 1H); 7.96 (d, J=8.0 Hz, 1H); 7.91 (m, 1H); 7.67 (s, 1H); 7.57 (d, J=8.4 Hz, 1H); 7.45 (m, 1H); 4.91 (m, 1H); 3.57 (m, 2H); 3.26 (s, 3H); 3.12 (m, 2H); 1.95 (m, 2H); 1.75 (m, 2H); 1.33 (s, 9H). IS-MS m/e: 647.5 (m+1). Analysis for $C_{30}H_{32}ClFN_4O_7S \cdot 0.5H_2O$: Calc: C, 54.92; H, 5.07; N, 8.54; Found: C, 54.81; H, 5.19; N, 8.32.

D. N-(5-Chloropyridin-2-yl)-5-fluoro-2-[4-(methylsulfonyl)-2-(piperidin-4-yloxy)-benzoylamino]benzamide Using methods substantially equivalent to those described in Example 4-G, N-(5-chloropyridin-2-yl)-5-fluoro-2-[4-(methylsulfonyl)-2-(piperidin-4-yloxy)-benzoylamino]benzamide (75 mg, 0.14 mmol, 81%) was prepared from 2-[2-(1-tert-butoxycarbonylpiperidin-4-yloxy)-4-(methylsulfonyl)benzoylamino]-N-(5-chloropyridin-2-yl)-5-fluorobenzamide.

$^1$NMR (400 MHz, DMSO-d$_6$): δ 8.42 (d, J=1.8 Hz, 1H); 8.28 (dd, J=5.1, 8.7 Hz, 1H); 8.12 (d, J=9.0 Hz, 1H); 7.93 (d, J=7.8 Hz, 1H); 7.65 (m, 3H); 7.55 (d, J=8.1 Hz, 1H); 7.45 (t, J=6.3 Hz, 1H); 4.76 (m, 1H); 3.29 (s, 3H); 2.82 (m, 2H); 2.54 (m, 2H); 1.89 (m, 2H); 1.62 (m, 2H). IS-MS m/e: 547.2 (m+1).

EXAMPLE 89

Preparation of N-(5-Chloropyridin-2-yl)-5-fluoro-2-[2-(piperidin-4-yloxy)-4-(pyrrolidin-1-yl)benzoylamino]benzamide Hydrochloride.

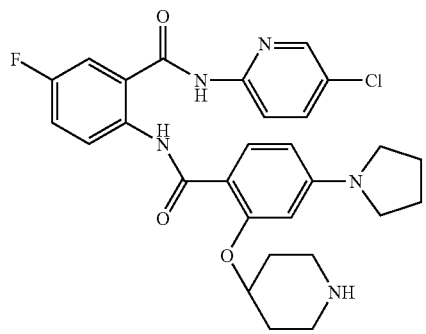

ClH

A. 2-[2-(1-tert-Butoxycarbonylpiperidin-4-yloxy)-4-(pyrrolidin-1-yl)benzoylamino]-N-(5-chloropyridin-2-yl)-5-fluorobenzamide By methods substantially analogous to those described in Example 4-E, 2-[2-(1-tert-butoxycarbonylpiperidin-4-yloxy)-4-(pyrrolidin-1-yl)benzoylamino]-N-(5-chloropyridin-2-yl)-5-fluorobenzamide (6.11 g, 90%) was prepared from 2-(1-tert-butoxycarbonylpiperidin-4-yloxy)-4-(pyrrolidin-1-yl)benzoic acid and N-(5-chloro-pyridin-2-yl)-2-amino-5-fluorobenzamide.

IR(CHCl$_3$): 1680, 1602, 1504, 1375, 1285 cm$^{-1}$.

$^1$NMR (300 MHz, DMSO-d$_6$) δ ppm: 11.27 (s, 1H), 10.72 (s, 1H), 8.43 (d, J=2.6 Hz, 1H), 8.30 (dd, J=5.0, 9.4 Hz, 1H), 8.17 (d, J=9.0 Hz, 1H), 7.94 (dd, J=2.6, 9.0 Hz, 1H), 7.78 (d, J=9.0 Hz, 1H), 7.60 (dd, J=2.6, 9.0 Hz, 1H), 7.34 (m, 1H), 6.24 (dd, J=1.8, 9.0 Hz, 1H), 6.18 (d, J=1.8 Hz, 1H), 4.81 (m, 1H), 3.75 (m, 2H), 3.27 (m, 2H), 3.03 (m, 2H) 1.90 (m, 10H), 1.40 (s, 9H). IS-MS, m/e: 638.2 (m+1). Analysis for C$_{33}$H$_{37}$ClFN$_5$O$_5$: Calcd: C, 62.11; H, 5.84; N, 10.97; Found: C, 61.81; H, 5.70; N, 10.67.

B. N-(5-Chloropyridin-2-yl)-5-fluoro-2-[4-(pyrrolidin-1-yl)-2-(piperidin-4-yloxy)-benzoylamino]benzamide Using procedures described in Example 4-G, N-(5-chloropyridin-2-yl)-5-fluoro-2-[4-(pyrrolidin-1-yl)-2-(piperidin-4-yloxy)benzoylamino]benzamide (3.38 g, 66%) was prepared from 2-[2-(1-tert-butoxycarbonylpiperidin-4-yloxy)-4-(pyrrolidin-1-yl)-benzoylamino]-N-(5-chloropyridin-2-yl)-5-fluorobenzamide.

IR (CHCl$_3$): 1602, 1504, 1374, 1286 cm$^{-1}$. $^1$NMR (300 MHz, DMSO-d$_6$) δ ppm: 10.7 (br s, 1H), 8.43 (d, J=2.6 Hz, 1H), 8.35 (dd, J=5.3, 9.0 Hz, 1H), 8.22 (d, J=8.7 Hz, 1H), 7.97 (dd, J=3.0, 8.7 Hz, 1H), 7.77 (d, J=9.0 Hz, 1H), 7.58 (dd, J=3.0, 9.4 Hz, 1H), 7.39 (m, 1H), 6.24 (dd, J=1.9, 8.7 Hz, 1H), 6.14 (d, J=1.9 Hz, 1H), 4.60 (m, 1H), 3.3 (m, 4H), 2.80 (m, 2H), 2.47 (m, 2H), 1.94 (m, 4H), 1.87 (m, 2H), 1.67 (m, 2H). IS-MS, m/e: 538 (m+1).

C. N-(5-Chloropyridin-2-yl)-5-fluoro-2-[2-(piperidin-4-yloxy)-4-(pyrrolidin-1-yl)-benzoylamino]benzamide hydrochloride To a solution of N-(5-chloropyridin-2-yl)-5-fluoro-2-[4-(pyrrolidin-1-yl)-2-(piperidin-4-yloxy)benzoylamino]benzamide (1.5 g, 2.74 mmol) and 10%
MeOH:CH$_2$Cl$_2$ (15 mL) was added 5 N HCl (0.55 mL, 2.74 mmol). The reaction was stirred for one hour. It was then concentrated to dryness to yield N-(5-chloropyridin-2-yl)-5-fluoro-2-[2-(piperidin-4-yloxy)-4-(pyrrolidin-1-yl)benzoylamino]benzamide hydrochloride as a solid (1.6 g, 100%).

IS-MS, m/e: 538.4 (m+1). Analysis for C$_{28}$H$_{30}$Cl$_2$FN$_5$O$_3$: Calcd: C, 58.54; H, 5.26; N, 12.19; Found: C, 58.53; H, 5.35; N, 12.34.

EXAMPLE 90

Preparation of 5-Chloro-N-(5-chloropyridin-2-yl)-2-[2-(piperidin-4-yloxy)-4-(pyrrolidin-1-yl)benzoylamino]benzamide.

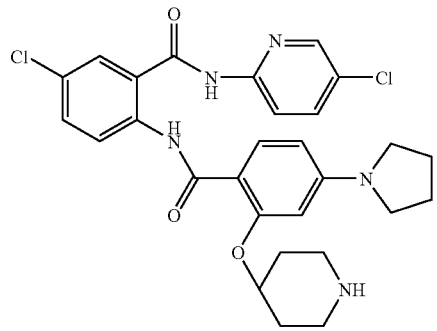

A. 2-[2-(1-tert-Butoxycarbonylpiperidin-4-yloxy)-4-(pyrrolidin-1-yl)benzoylamino]-5-chloro-N-(5-chloropyridin-2-yl)benzamide.

By methods substantially analogous to those described in example 4-E, 2-[2-(1-tert-butoxycarbonylpiperidin-4-yloxy)-4-(pyrrolidin-1-yl)benzoylamino]-5-chloro-N-(5-chloropyridin-2-yl)benzamide (260 mg, 35%) was prepared from 2-(1-tert-butoxycarbonylpiperidin-4-yloxy)-4-(pyrrolidin-1-yl)benzoic acid and N-(5-chloro-pyridin-2-yl)-2-amino-5-chlorobenzamide.

$^1$NMR (300 MHz, DMSO-d$_6$) δ ppm: 11.32 (s, 1H), 10.8 (s, 1H), 8.40 (d, J=2.4 Hz, 1H), 8.34 (d, J=8.9 Hz, 1H), 8.12 (d, J=8.9 Hz, 1H), 7.92 (dd, J=2.4, 8.90 Hz, 1H), 7.75 (m, 2H), 7.54 (dd, J=2.30, 8.9 Hz, 1H), 6.21 (d, J=8.9 Hz, 1H), 6.14 (s, 1H), 4.77 (m, 1H), 3.68 (m, 2H), 3.3 (m, 2H), 3.00 (m, 2H), 1.90 (m, 10H), 1.32 (s, 9H). IS-MS, m/e: 654.3 (m+1). Analysis for C$_{33}$H$_{37}$Cl$_2$N$_5$O$_5$: Calcd: C, 60.55; H, 5.70; N, 10.70; Found: C, 60.66; H, 5.79; N, 10.40.

B. 5-Chloro-N-(5-chloropyridin-2-yl)-2-[2-(piperidin-4-yloxy)-4-(pyrrolidin-1-yl)-benzoylamino]benzamide Using the procedure described in Example 4-G, 2-[2-(1-tert-butoxycarbonyl-piperidin-4-yloxy)-4-(pyrrolidin-1-yl)benzoylamino]-5-chloro-N-(5-chloropyridin-2-yl)benzamide gave 5-chloro-N-(5-chloropyridin-2-yl)-2-[2-(piperidin-4-yloxy)-4-(pyrrolidin-1-yl)benzoylamino]benzamide (200 mg, 98%).

$^1$NMR (300 MHz, DMSO-d$_6$) δ ppm: 8.40 (m, 2H), 8.18 (d, J=8.9 Hz, 1H), 7.94 (dd, J=2.4, 8.9 Hz, 1H), 7.74 (m, 2H), 7.54 (dd, J=2.4, 8.9 Hz, 1H), 6.21 (d, J=8.9 Hz, 1H), 6.11 (s, 1H), 4.59 (m, 1H), 3.26 (m, 2H), 2.75 (m, 2H), 2.46 (m, 2H), 1.95 (m, 4H), 1.84 (m, 4H), 1.60 (m, 2H). IS-MS, m/e: 554.21 (m+1). Analysis for C$_{28}$H$_{29}$Cl$_2$N$_5$O$_3$.0.5H$_2$O: Calcd: C, 59.69; H, 5.27; N, 12.43; Found: C, 59.52; H, 5.33; N, 12.07.

EXAMPLE 91

Preparation of 5-Fluoro-N-(2-fluorophenyl)-2-[2-(1-methylpiperidin-4-yloxy)-4-(pyrrolidin-1-yl)benzoylamino]benzamide.

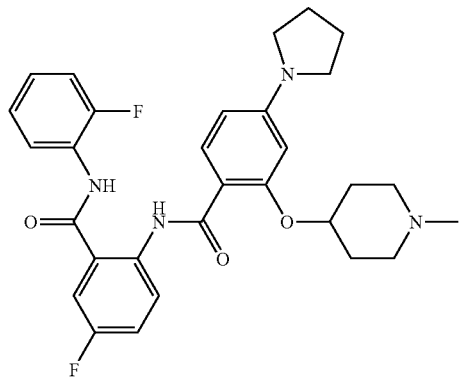

A. Methyl 4-fluoro-2-(1-methylpiperidin-4-yloxy)benzoate

A mixture of methyl 4-fluoro-2-hydroxybenzoate (12 g, 70.5 mmol), triphenyl-phosphine (22.2 g, 84.6 mmol), N-methyl-4-hydroxypiperidine (8.1 g, 70.3 mmol) and benzene (25 mL) was heated until all the solids dissolved. The solution was cooled to 0° C., then sonicated while adding diethyl azodicarboxylate (14.7 g, 84.6 mmol) dropwise. After the addition was complete, the reaction was sonicated for an additional 60 minutes, and then purified by flash chromatography, eluting sequentially with 50% EtOAc in hexanes followed by 1%, 2%, 5% then 10% MeOH in $CHCl_3$, to yield 10.8 g (40.4 mmol, 57%) of an oil.

[1]NMR

B. Methyl 2-(1-methylpiperidin-4-yloxy)-4-(pyrrolidin-1-yl)benzoate

The methyl 4-fluoro-2-(1-methylpiperidin-4-yloxy)benzoate (10.6 g, 40 mmol) was mixed with pyrrolidine (14 g, 200 mmol) and heated at 70° C. for 3 hours, then heated at 100° C. for 1 hour before concentrating under vacuum. The residue was partitioned between EtOAc (100 mL) and saturated aqueous $NaHCO_3$ (100 mL). The aqueous layer was saturated with NaCl and extracted with EtOAc (100 mL). The combined organic layer was dried over $MgSO_4$ and concentrated to 12.5 g of an oil which was purified by flash chromatography, using THF/Hex/$Et_3$ N 20/75/5 then 40/55/5 and finally 60/35/5, to give 11.9 g (37 mmol, 93%) of the desired product as an oil.

[1]NMR

C. 2-(1-Methylpiperidin-4-yloxy)-4-(pyrrolidin-1-yl)benzoic acid

A mixture of the methyl 2-(1-methylpiperidin-4-yloxy)-4-(pyrrolidin-1-yl)-benzoate (11.9 g, 37.4 mmol) and EtOH (100 mL) was treated with a solution of KOH (10.5 g, 187 mmol) in $H_2O$ (100 mL). The resulting mixture was heated to reflux for 3 h.

The reaction mixture was neutralized with 5 N HCl (37.4 mL) and concentrated under vacuum. It was mixed with 1 liter 50/50 THF/MeOH and filtered. The filtrate was concentrated to 9.46 g solid (83%).

[1]NMR

D. Methyl 5-fluoro-2-[2-(1-methylpiperidin-4-yloxy)-4-(pyrrolidin-1-yl)-benzoylamino]benzoate The 2-(1-methylpiperidin-4-yloxy)-4-(pyrrolidin-1-yl) benzoic acid (9.3 mg, 30.6 mmol) was mixed with $CH_2Cl_2$ (100 mL) then treated with 2 M $CH_2Cl_2$ solution of oxalyl chloride (30 mL) at ambient temperature overnight. Subsequently, 3 drops of DMF were added and the reaction was stirred an additional 2 hours. The reaction was concentrated to dryness, mixed with $CH_2Cl_2$ (75 mL), then added to a cold solution of methyl 2-amino-5-fluorobenzoate in pyridine (100 mL) and $CH_2Cl_2$ (25 mL). The reaction was stirred at 0° C. for 3 hours, concentrated to dryness, then partitioned between water (400 mL) and EtOAc (400 mL). The aqueous layer was extracted with EtOAc (200 mL). The combined organic layer was dried over $MgSO_4$ and concentrated to an oil which was purified by flash chromatography, using THF/Hex/$Et_3$ N 20/75/5 then 40/55/5, to give 7.9 g (17.3 mmol, 57%) of a solid.

[1]NMR IS-MS, m/e 456 (m+1)

E. 5-Fluoro-2-[2-(1-methylpiperidin-4-yloxy)-4-(pyrrolidin-1-yl)benzoylamino]-benzoic acid A solution of methyl 5-fluoro-2-[2-(1-methylpiperidin-4-yloxy)-4-(pyrrolidin-1-yl)benzoylamino]benzoate (7.8 g, 17 mmol) in EtOH (100 mL) and water (100 mL) was treated with KOH (4.8 g, 85 mmol) and stirred at 70° C. for 1 hour. The reaction was concentrated under vacuum, quenched with glacial acetic acid (5.1 g), and allowed to stand at ambient temperature for crystallization. The solid was filtered to recover 7.4 g (98%).

[1]NMR IS-MS, m/e 442 (m+1)

F. 6-Fluoro-2-[2-(1-methylpiperidin-4-yloxy)-4-(pyrrolidin-1-yl)phenyl]-4H-3,1-benzoxazin-4-one

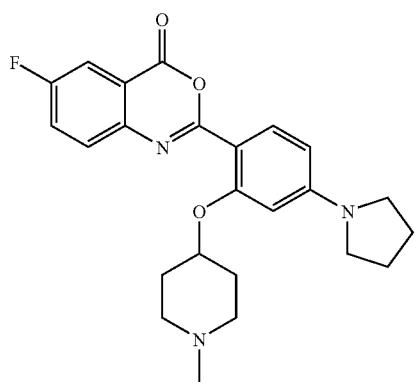

A solution of 5-fluoro-2-[2-(1-methylpiperidin-4-yloxy)-4-(pyrrolidin-1-yl)-benzoylamino]benzoic acid (7.4 g, 16.8 mmol) in dry DMF (120 mL) was treated with S1-(3-dimethylaminopropyl)-3-ethylcarbodiimide hydrochloride (6.42 g, 33.5 mmol). The reaction was stirred at ambient temperature overnight. The mixture was poured into brine (300 mL)

and extracted with 10% MeOH in EtOAc (3×100 mL). The combined extracts were washed with water (2×400 mL), then brine (2×400 mL), dried over MgSO$_4$, and concentrated to a solid which was purified by chromatography on silica, using 40/55/5 THF/Hex/Et$_3$N in hexanes, to give 3.4 g (48%) of a yellow solid.

$^1$NMR IS-MS 424 (m+) Analysis for C$_{24}$H$_{26}$ FN$_3$O$_3$: Calcd: C, 66.65; H, 6.29; N, 9.72; Found: C, 66.73; H, 6.10; N, 9.82.

G. 5-Fluoro-N-(2-fluorophenyl)-2-[2-(1-methylpiperidin-4-yloxy)-4-(pyrrolidin-1-yl)benzoylamino]benzamide A solution of 2-fluoroaniline (22.1 mg, 0.18 mmol) in dry THF (1 mL) was treated with a 1 M diethyl ether solution of allyl magnesium bromide (0.2 mL). The reaction was stirred for 5 minutes before adding 6-fluoro-2-[4-(pyrrolidin-1-yl)-2-(1-methylpiperidin-4-yloxy)phenyl]-4H-3,1-benzoxazin-4-one (25 mg, 0.06 mmol) in THF (1 mL). The reaction was stirred overnight at ambient temperature, concentrated to dryness and mixed with saturated aqueous NaHCO$_3$ (1 mL) and CH$_2$Cl$_2$ (2 mL). The mixture was filtered through a plug of diatomaceous earth and treated with an isocyanate resin (methylisocyanate polystyrene HL, 0.360 mmol) overnight. Purification consisted of applying this mixture directly onto a column of silica and eluting with 1% MeOH in CHCl$_3$.

$^1$NMR IS-MS, m/e 535 (m+1)

EXAMPLE 92

Preparation of 2-[4-tert-Butyl-2-(1-methylpiperidin-4-yloxy)benzoylamino]-N-(5-chloropyridin-2-yl)-5-fluoro-benzamide.

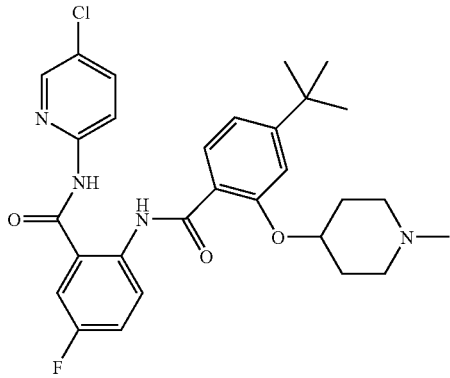

The 2-[4-tert-butyl-2-(piperidin-4-yloxy)-benzoylamino]-N-(5-chloropyridin-2-yl)-5-fluorobenzamide (450 mg, 0.86 mmol) was placed in a dry flask and diluted with dry MeOH (0.95 mL). Paraformaldehyde (54.0 mg, 1.8 mmol) and NaCNBH$_4$ (167.0 mg, 2.7 mmol) were added, followed by acetic acid (0.5 mL). The reaction was allowed to stir for 18 h. More paraformaldehyde (54.0 mg), NaCNBH$_4$ (107.0 mg) and acetic acid (1.0 mL) were added, and the reaction was stirred another 18 hrs under N$_2$ at room temperature. The solvents were removed in vacuo, and the residue was diluted with H$_2$O (5.0 mL). The flask was cooled in an ice bath while the pH was adjusted to 8 using saturated sodium bicarbonate. This solution was extracted with EtOAc (5×90 mL). The organics were combined and washed with a saturated solution of sodium bicarbonate and then brine. The organic layer was dried over MgSO$_4$ and the solvents were removed in vacuo to obtain the desired product as a white solid (338.2 mg, 0.63 mmol, 73%).

$^1$NMR (300 Hz, DMSO-d$_6$): δ 11.26 (s, 1H); 10.81 (s, 1H); 8.41 (s, 1H); 8.37 (m, 1H); 8.13 (d, J=9.0 Hz, 1H); 7.92 (d, J=8.8 Hz, 1H); 7.73 (d, J=8.1 Hz, 1H); 7.61 (d, J=9.1 Hz, 1H); 7.43 (t, J=8.3 Hz, 1H); 7.09 (s, 1H); 7.05 (d, J=8.2 Hz, 1H); 4.60 (m, 1H); 2.39 (m, 2H); 1.84-2.01 (m, 5H); 1.73-1.80 (m, 4H); 1.25 (s, 9H) ppm. IS-MS, 539.3 m/e Analysis for C$_{29}$H$_{32}$ClFN$_4$O$_3$: Calcd: C, 64.62; H, 5.98; N, 10.39; Found: C, 64.39; H, 5.94; N, 10.34.

EXAMPLE 93

Preparation of 5-Chloro-N-(5-chloropyridin-2-yl)-2-[4-(dimethylamino)-2-(piperidin-4-yloxy)benzoylamino]benzamide.

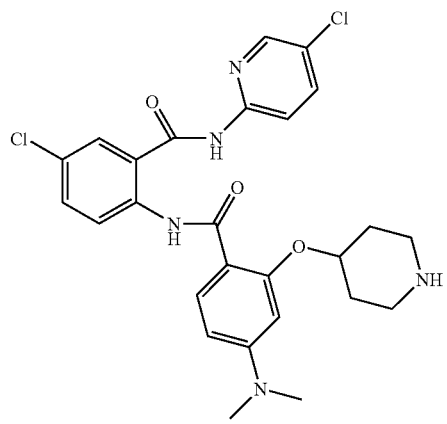

A. 2-[2-(1-tert-Butoxycarbonylpiperidin-4-yloxy)-4-(dimethylamino)benzoylamino]-N-(5-chloropyridin-2-yl)-5-chlorobenzamide Using methods substantially equivalent to those described in Example 4-E, 2-[2-(1-tert-butoxycarbonylpiperidin-4-yloxy)-4-(dimethylamino)benzoylamino]-N-(5-chloropyridin-2-yl)-5-chlorobenzamide (229 mg, 0.36 mmol, 48%) was prepared from 4-(dimethylamino)-2-(1-tert-butoxycarbonylpiperidin-4-yloxy)benzoic acid and N-(5-chloropyridin-2-yl)-2-amino-5-chlorobenzamide.

$^1$NMR (400 MHz, DMSO-d$_6$): δ 11.32 (s, 1H); 10.79 (s, 1H); 8.41 (d, J=2.4 Hz, 1H); 8.35 (d, J=8.8 Hz, 1H); 8.13 (d, J=9.2 Hz, 1H); 7.91 (dd, J=2.4, 8.8 Hz, 1H); 7.78 (d, J=2.8 Hz, 1H); 7.74 (d, J=9.6 Hz, 1H); 7.56 (d, J=8.8 Hz, 1H); 6.38 (d, J=9.6 Hz, 1H); 6.29 (s, 1H); 4.79 (m, 1H); 3.68 (d, J=12.4 Hz, 2H); 3.00 (m, 2H); 2.96 (s, 6H); 1.88 (m, 2H); 1.80 (m, 2H); 1.32 (s, 9H). IS-MS m/e: 628.3 (m+1). Analysis for C$_{31}$H$_{35}$Cl$_2$N$_5$O$_5$: Calc: C, 59.24; H, 5.61; N, 11.14; Found: C, 59.06; H, 5.61; N, 11.41.

B. 5-Chloro-N-(5-chloropyridin-2-yl)-2-[4-(dimethylamino)-2-(piperidin-4-yloxy)-benzoylamino]benzamide Using methods substantially equivalent to those described in Example 4-G, 5-chloro-N-(5-chloropyridin-2-yl)-2-[4-(dimethylamino)-2-(piperidin-4-yloxy)-benzoylamino]benzamide (152 mg, 0.29 mmol, 99%) was prepared from 2-[2-

(1-tert-butoxycarbonylpiperidin-4-yloxy)-4-(dimethylamino)benzoylamino]-N-(5-chlorpyridin-2-yl)-5-chlorobenzamide.

$^1$NMR (300 MHz, DMSO-$d_6$): δ 8.41 (s, 1H); 8.40 (d, J=9.0 Hz, 1H); 8.17 (d, J=9.0 Hz, 1H); 7.94 (dd, J=2.6, 9.3 Hz, 1H); 7.76 (d, J=2.1 Hz, 1H); 7.72 (d, J=6.3 Hz, 1H); 7.55 (dd, J=2.1, 9.0 Hz, 1H); 6.36 (d, J=9.0 Hz, 1H); 6.26 (s, 1H); 4.62 (m, 1H); 2.77 (m, 2H); 2.49 (m, 2H); 1.84 (m, 2H); 1.63 (m, 2H). IS-MS m/e: 528.1 (m+1). Analysis for $C_{26}H_{27}Cl_2N_5O_3$: Calc: C, 56.67; H, 5.11; N, 12.47; Found: C, 56.61; H, 5.01; N, 12.62.

EXAMPLE 94

Preparation of 5-Chloro-N-(5-chloropyridin-2-yl)-2-[2-[2-(dimethylamino)ethoxy]-4-(methylthio)benzoylamino]benzamide Hydrochloride.

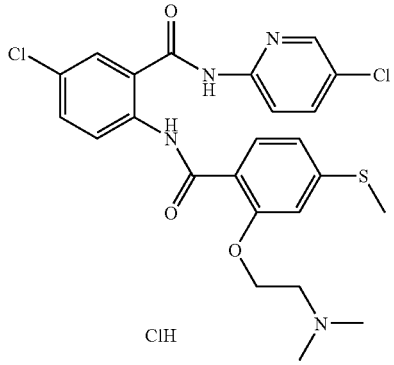

A. Methyl 2-[2-(tert-butoxycarbonylamino)ethoxy]-4-(methylthio)benzoate

Methyl 2-[2-(tert-butoxycarbonylamino)ethoxy]-4-(methylthio)benzoate was prepared (12.6 g, 76%) as described in Example 21-C from methyl 2-hyroxy-4-(methylthio)benzoate and 2-(tert-butoxycarbonylamino)ethanol.

IR(CHCl$_3$): 1707, 1595, 1249, 1162 cm$^{-1}$. $^1$NMR (300 MHz, DMSO-$d_6$) δ ppm: 7.78 (d, J=8.3 Hz, 1H), 7.26 (s, 1H), 6.83 (dd, J=1.5, 8.3 Hz, 1H), 6.78 (d, J=1.5 Hz, 1H), 4.11 (m, 2H), 3.89 (s, 3H), 3.57 (m, 2H), 2.49 (s, 3H), 1.45 (s, 9H). IS-MS, m/e: 342.1 (m+1).

B. 2-[2-(tert-Butoxycarbonylamino)ethoxy]-4-(methylthio)benzoic acid

The methyl 2-[2-(tert-butoxycarbonylamino)ethoxy]-4-(methylthio)benzoate was added to a solution of KOH (9.05 g, 161.2 mmol) in EtOH (200 mL) and H1120 (200 mL).

The reaction was heated to 70° C. for two hours. Ethanol was removed in vacuo, and the remaining aqueous solution was diluted with CH$_2$Cl$_2$ (500 mL) and saturated citric acid (200 mL). The organic layer was partitioned, dried over Na$_2$SO$_4$, and concentrated to yield 2-[2-(tert-butoxycarbonylamino)ethoxy]-4-(methylthio)benzoic acid (9.1 g, 87%).

IR(CHCl$_3$): 1711, 1597, 1412, 1162 cm$^{-1}$. $^1$NMR (300 MHz, DMSO-$d_6$) δ ppm: 8.05 (d, J=8.3 Hz, 1H), 7.26 (s, 1H), 6.93 (dd, J=1.5, 8.3 Hz, 1H), 6.84 (d, J=1.5 Hz, 1H), 5.05 (s, 1H), 4.28 (t, J=5.7 Hz, 2H), 3.62 (dt, J=5.7, 10.9 Hz, 2H), 2.52 (s, 3H), 1.45 (s, 9H). IS-MS, m/e: 328.2 (m+1). Analysis for $C_{15}H_{21}NO_5S$: Calcd: C, 55.03; H, 6.47; N, 4.28; Found: C, 54.80; H, 6.21; N, 4.50.

C. 2-[2-[2-(tert-Butoxycarbonylamino)ethoxy]-4-(methylthio)benzoylamino]-5-chloro-N-(5-chloropyridin-2-yl)benzamide 2-[2-[2-(tert-Butoxycarbonylamino)ethoxy]-4-(methylthio)benzoylamino]-5-chloro-N-(5-chloropyridin-2-yl)benzamide was prepared by methods described in example 4-E from 2-[2-(tert-butoxycarbonylamino)ethoxy]-4-(methylthio)benzoic acid and N-(5-chloropyridin-2-yl)-2-amino-5-chlorobenzamide (3 g, 92%). IR (CHCl$_3$): 1665, 1500, 1375, 1296 cm$^{-1}$.

$^1$NMR (300 MHz, DMSO-$d_6$) δ ppm: 11.28 (s, 1H), 11.25 (s, 1H), 8.44 (m, 2H), 8.20 (d, J=9.0 Hz, 1H), 7.96 (dd, J=2.6, 9.0 Hz 1H), 7.88 (m, 2H), 7.62 (dd, J=2.6, 9.0 Hz, 1H), 7.07 (s, 1H), 6.96 (dd, J=1.1, 8.3 Hz, 1H), 4.30 (t, J=6.0 Hz, 2H), 3.40 (m, 2H), 2.50 (s, 3H), 1.31 (s, 9H). IS-MS, m/e: 591.4 (m+1). Analysis for $C_{27}H_{28}Cl_2N_4O_5S$: Calcd: C, 54.83; H, 4.77; N, 9.47; Found: C, 54.64; H, 4.78; N, 9.49.

D. 2-[2-(2-Aminoethoxy)-4-(methylthio)benzoylamino]-5-chloro-N-(5-chloro-pyridin-2-yl)benzamide

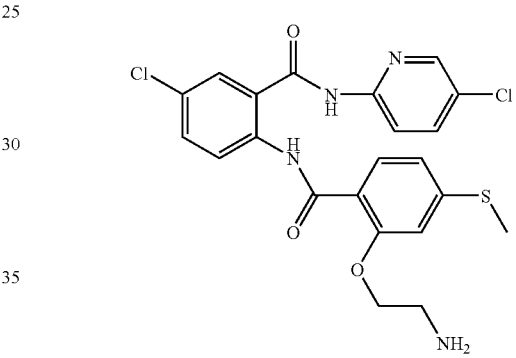

Using the procedure described in example 4-G, 2-[2-[2-(tert-butoxycarbonyl-amino)ethoxy]-4-(methylthio)benzoylamino]-5-chloro-N-(5-chloropyridin-2-yl)-benzamide gave 2-[2-(2-aminoethoxy)-4-(methylthio)benzoylamino]-5-chloro-N-(5-chloropyridin-2-yl)benzamide (200 mg, 87%).

$^1$NMR (300 MHz, DMSO-$d_6$) δ ppm: 8.41 (d, J=1.5 Hz, 1H), 8.31 (d, J=8.9 Hz, 1H), 8.08 (d, J=8.8 Hz, 1H), 7.94 (dd, J=2.7, 9.0 Hz, 1H), 7.82 (m, 2H), 7.59 (dd, J=2.7, 9.0 Hz, 1H), 7.00 (d, J=1.2 Hz, 1H), 6.93 (dd, J=1.2, 8.23 Hz, 1H), 4.27 (m, 2H), 3.27 (s, 3H), 3.0 (m, 2H), 2.51 (s, 3H). IS-MS, m/e: 491.2 (m+1).

E. 5-Chloro-N-(5-chloropyridin-2-yl)-2-[2-[2-(dimethylamino)ethoxy]-4-(methylthio)benzoylamino] benzamide hydrochloride To a mixture of 2-[2-(2-aminoethoxy)-4-(methylthio)benzoylamino]-5-chloro-N-(5-chloropyridin-2-yl)benzamide (1.25 g, 2.47 mmol), paraformaldehyde (312 mg, 10.4 mmol) and methanol (30 mL) was added acetic acid to obtain a pH of 4.0. Sodium cyanoborohydride (311 mg, 4.95 mmol) was added to this mixture. After stirring overnight, the reaction was concentrated, dissolved in 10% MeOH/CHCl$_3$, and passed through an SCX column. The eluent was concentrated and chromatographed on silica gel (1:10 EtOAc:CH$_2$Cl$_2$ to 1:10 MeOH:CH$_2$Cl$_2$) to give impure product. The impure product was dissolved in 5% MeOH/CH$_2$Cl$_2$ and 1 N HCl and stirred for one hour. The mixture was basified with 50% satd sodium carbonate and extracted with $CH_2Cl_2$. The organic layer was concentrated and purified by HPLC on a Vydac C18 column [preparative: gradient 20% $CH_3$ CN/(0.01% HCl in $H_2O$) to 80% $CH_3$ CN/(0.01% HCl in $H_2O$) over 6 h on a 5×25 cm column; analytical: 5% $CH_3$ CN/(0.1% TFA in $H_2O$) to 70% $CH_3$ CN/(0.1% TFA in $H_2O$) on a 0.46×25 cm column] to give the title product as a white solid (329 mg, 62%).

$^1$NMR (300 MHz, DMSO-$d_6$) δ ppm: 11.34 (s, 1H), 11.06 (s, 1H), 10.34 (s, 1H), 8.47 (d, J=2.6 Hz, 1H), 8.39 (d, J=9.0 Hz, 1H), 8.11 (d, J=9.0 Hz, 1H), 7.98 (dd, J=2.6, 8.7 Hz, 1H), 7.89 (d, J=2.6 Hz, 1H), 7.84 (d, J=8.3 Hz, 1H), 7.64 (dd, J=2.6, 9.0 Hz, 1H), 7.07 (d, J=1.5 Hz, 1H), 7.01 (dd, J=1.5, 8.3 Hz, 1H), 4.66 (t, J=4.9 Hz, 2H), 3.61 (m, 2H), 2.78 (s, 6H), 2.56 (s, 3H). IS-MS, m/e: 519.2 (m+1). Analysis for $C_{24}H_{25}Cl_2N_4O_3S$—HCl: Calcd: C, 51.85; H, 4.53; N, 10.08; Found: C, 51.82; H, 4.42; N, 9.87.

EXAMPLE 95

Preparation of 2-[2-(2-Aminoethoxy)-4-(methylthio) benzoylamino]-N-(5-chloro-pyridin-2-yl)-5-fluorobenzamide.

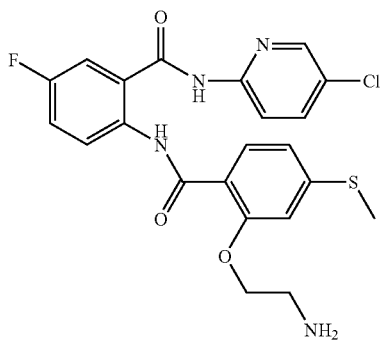

A. 2-[2-[2-(tert-Butoxycarbonylamino)ethoxy]-4-(methylthio)benzoylamino]-N-(5-chloropyridin-2-yl)-5-fluorobenzamide 2-[2-[2-(tert-Butoxycarbonylamino)ethoxy]-4-(methylthio)benzoylamino]-N-(5-chloropyridin-2-yl)-5-fluorobenzamide was prepared by methods described in Example 4-E from 2-[2-[2-(tert-butoxycarbonylamino)ethoxy]-4-(methylthio)benzoic acid and N-(5-chloropyridin-2-yl)-2-amino-5-fluorobenzamide (2.80 g, 89%).

$^1$NMR (300 MHz, DMSO-$d_6$) δ ppm: 11.21 (s, 1H), 11.12 (s, 1H), 8.44 (d, J=2.6 Hz, 1H), 8.36 (dd, J=4.9, 9.0 Hz, 1H), 8.21 (d, J=9.0 Hz, 1H), 7.96 (dd, 2.6, 8.7 Hz, 1H), 7.88 (d, 8.3 Hz, 1H), 7.66 (dd, J=3.0, 9.0 Hz, 1H), 6.94 (dt, J=1.5, 8.3 Hz, 1H), 7.06 (s, 1H), 6.96 (m, 2H), 4.29 (t, J=6.0 Hz, 2H), 3.42 (m, 2H), 2.55 (s, 3H), 1.31 (s, 9H). IS-MS, m/e: 575.2 (m+1). Analysis for $C_{27}H_{28}ClFN_4O_5S$: Calcd: C, 56.39; H, 4.91; N, 9.74; Found: C, 56.17; H, 4.78; N, 10.02.

B. 2-[2-(2-Aminoethoxy)-4-(methylthio)benzoylamino]-N-(5-chloropyridin-2-yl)-5-fluorobenzamide Using the procedure described in Example 4-G, 2-[4-methylmercapto-2-(2-tert-butoxycarbonylaminoethoxy)benzoylamino]-N-(5-chloropyridin-2-yl)-5-fluorobenzamide gave 2-[2-(2-aminoethoxy)-4-(methylthio)benzoylamino]-N-(5-chloropyridin-2-yl)-5-fluorobenzamide (190 mg, 85%).

$^1$NMR IS-MS, m/e: 475.1 (m+1). Analysis for $C_{22}H_{20}ClFN_4O_3S$: Calcd: C, 55.64; H, 4.24; N, 11.80; Found: C, 55.62; H, 4.17; N, 11.72.

EXAMPLE 96

Preparation of 2-[2-(2-Aminoethoxy)-4-methylsulfinylbenzoylamino]-N-(5-chloropyridin-2-yl)-5-chlorobenzamide.

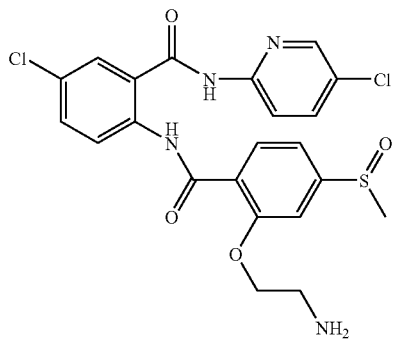

A. 2-[2-[2-(tert-Butoxycarbonylamino)ethoxy]-4-methylsulfinylbenzoylamino]-5-chloro-N-(5-chloropyridin-2-yl)benzamide To a solution of 2-[2-[2-(tert-butoxycarbonylamino)ethoxy]-4-(methylthio)-benzoylamino]-N-(5-chloropyridin-2-yl)-5-chlorobenzamide (893 mg, 1.51 mmol), camphorsulfonic acid (92 mg, 0.40 mmol) and $CHCl_3$ (8.5 mL) was added tert-butyl hydroperoxide (0.30 mL, 3.02 mmol). After stirring overnight, the mixture was chromatographed (10% EtOAc/$CH_2Cl_2$ to 10% MeOH/$CH_2Cl_2$) to give the desired product as a white solid (517 mg, 56%).

$^1$NMR (300 MHz, DMSO-$d_6$) δ ppm: 11.27 (s, 1H), 8.44 (d, J=2.6 Hz, 1H), 8.39 (d, J=8.7 Hz, 1H), 8.18 (d, J=9.0 Hz, 1H), 8.07 (d, J=8.7 Hz, 1H), 7.94 (dd, J=2.6, 8.7 Hz, 1H), 7.90 (d, J=2.2 Hz, 1H), 7.64 (dd, J=2.6, 8.7 Hz, 1H), 7.49 (d, J=1.1 Hz, 1H), 7.39 (dd, J=1.1, 8.7 Hz, 1H), 4.30 (m, 2H), 3.41 (m, 2H), 2.81 (s, 3H), 1.29 (s, 9H). IS-MS, m/e: 607.2 (m+1). Analysis for $C_{27}H_{28}Cl_2N_4O_6S$: Calcd: C, 53.38; H, 4.65; N, 9.22; Found: C, 53.31; H, 4.46; N, 9.31.

B. 2-[2-(2-Aminoethoxy)-4-methylsulfinylbenzoylamino]-N-(5-chloropyridin-2-yl)-5-chlorobenzamide Using the procedure described in example 4-G, 2-[2-[2-(tert-butoxycarbonyl-amino)ethoxy)-4-methylsulfinylbenzoylamino]-N-(5-chloropyridin-2-yl)-5-chloro-benzamide gave 2-[2-(2-aminoethoxy)-4-methylsulfinylbenzoylamino]-N-(5-chloro-pyridin-2-yl)-5-chlorobenzamide (381 mg, 98%).

$^1$NMR IS-MS, m/e: 507.0 (m+1). Analysis for $C_{22}H_{20}Cl_2N_4O_4S$: Calcd: C, 52.08; H, 3.97; N, 11.04; Found: C, 51.90; H, 3.93; N, 10.90.

EXAMPLE 97

Preparation of 2-[2-(2-Aminoethoxy)-4-methylsulfinylbenzoylamino]-N-(5-chloro-pyridin-2-yl)-5-fluorobenzamide.

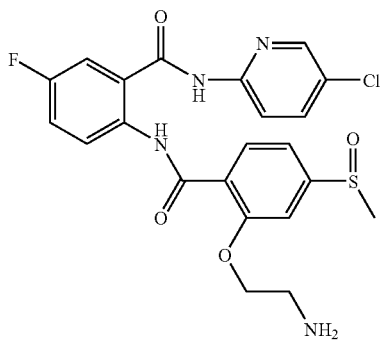

A. 2-[2-(2-tert-Butoxycarbonylaminoethoxy)-4-methylsulfinylbenzoylamino]-N-(5-chloropyridin-2-yl)-5-fluorobenzamide Using a procedure analogous to Example 96-A, 2-[2-[2-(tert-butoxycarbonyl-amino)ethoxy]-4-(methylthio)benzoylamino]-N-(5-chloropyridin-2-yl)-5-fluoro-benzamide gave 2-[2-(2-tert-butoxycarbonylaminoethoxy)-4-methylsulfinylbenzoylamino]-N-(5-chloropyridin-2-yl)-5-fluorobenzamide (485 mg, 54%).

$^1$NMR (300 MHz, DMSO-d$_6$) δ ppm: 11.19 (s, 1H), 11.14 (s, 1H), 8.44 (d, J=2.6 Hz, 1H), 8.31 (dd, J=5.3, 9.0 Hz, 1H), 8.19 (d, J=9.0 Hz, 1H), 8.05 (d, J=7.9 Hz, 1H), 7.94 (dd, J=2.6, 9.0 Hz, 1H), 7.69 (dd, J=2.6, 9.0 Hz, 1H), 7.48 (d, J=1.1 Hz, 1H), 7.45 (dd, J=2.6, 7.9 Hz, 1H), 7.36 (d, J=1.1 Hz, 1H), 6.95 (m, 1H), 4.30 (m, 2H), 3.42 (m, 2H), 2.80 (s, 3H), 1.29 (s, 9H). IS-MS, m/e: 591.4 (m+1). Analysis for C$_{27}$H$_{28}$ClFN$_4$O$_6$S: Calcd: C, 54.87; H, 4.77; N, 9.48; Found: C, 54.83; H, 4.73; N, 9.62.

B. 2-[2-(2-Aminoethoxy)-4-methylsulfinylbenzoylamino]-N-(5-chloropyridin-2-yl)-5-fluorobenzamide Using the procedure described in example 4-G, 2-[2-(2-tert-butoxycarbonylamino-ethoxy)-4-methylsulfinylbenzoylamino]-N-(5-chloropyridin-2-yl)-5-fluorobenzamide gave 2-[2-(2-aminoethoxy)-4-methylsulfinylbenzoylamino]-N-(5-chloropyridin-2-yl)-5-fluorobenzamide (330 mg, 87%).

$^1$NMR IS-MS, m/e: 491.2 (m+1). Analysis for C$_{22}$H$_{20}$ClFN$_4$O$_4$S: Calcd: C, 52.86; H, 4.23; N, 11.21; Found: C, 52.51; H, 3.88; N, 10.99.

EXAMPLE 98

Preparation of 2-[4-(Dimethylamino)-2-(piperidin-4-yloxy)benzoylamino]-N-(5-chloropyridin-2-yl)-5-fluorobenzamide.

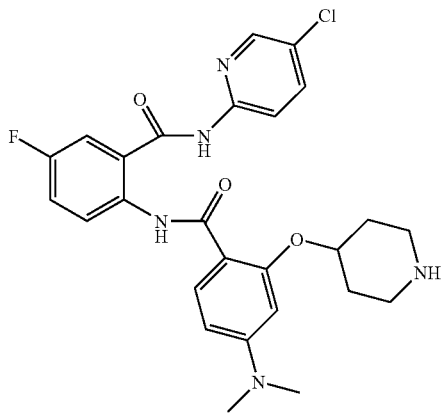

Using methods substantially equivalent to those described in Example 4-E & 4-G, 2-[4-(dimethylamino)-2-(piperidin-4-yloxy)benzoylamino]-N-(5-chloropyridin-2-yl)-5-fluorobenzamide (158 mg, 0.31 mmol, 100%) was prepared from 2-(1-tert-butoxy-carbonylpiperidin-4-yloxy)-4-(dimethylamino)benzoic acid and N-(5-chloropyridin-2-yl)-2-amino-5-fluorobenzamide.

$^1$NMR (400 MHz, DMSO-d$_6$): δ 10.67 (br s, 2H); 8.41 (d, J=2.0 Hz, 1H); 8.31 (dd, J=4.8, 9.2 Hz, 1H); 8.18 (d, J=9.2 Hz, 1H); 7.94 (dd, J=2.8, 8.8 Hz, 1H); 7.73 (d, J=9.2 Hz, 1H); 7.57 (dd, J=3.0, 9.0 Hz, 1H); 7.37 (dt, J=2.8, 9.2 Hz, 1H); 6.36 (dd, J=2.2, 9.0 Hz, 1H); 6.27 (d, J=2.0 Hz, 1H); 4.65 (m, 1H); 2.95 (s, 6H); 2.82 (m, 2H); 2.54 (m, 2H); 1.87 (m, 2H); 1.67 (m, 2H); 1.07 (s, 1H). IS-MS m/e: 512.5 (m+1). Analysis for C$_{26}$H$_{27}$ClFN$_5$O$_{3.0.75}$H$_2$O: Calc: C, 59.43; H, 5.47; N, 13.33; Found: C, 59.14; H, 5.23; N, 13.21.

EXAMPLE 99

Preparation of 2-[2-(3-Aminopropoxy)-4-(pyrrolidin-1-yl)-benzoylamino]-N-(5-chloropyridin-2-yl)-5-chlorobenzamide.

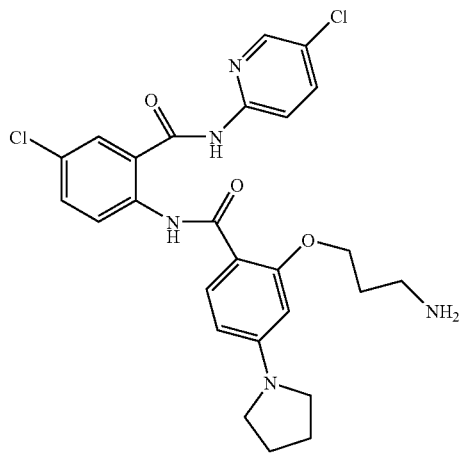

A. Methyl 2-[3-(tert-butoxycarbonylamino)pro-poxy]-4-(pyrrolidin-1-yl)benzoate A mixture of methyl 4-fluoro-2-[3-(tert-butoxycarbony-lamino)propoxy]benzoate (8.148 g, 25 mmol) and pyrroli-dine (20.87 mL, 250 mmol) was purged with nitrogen and heated to 80° C. for 3 hours. The reaction was concentrated in vacuo. After diluting with EtOAc, the mixture was cooled to 0° C., acidified with satd citric acid, and extracted with EtOAc. The organic layer was washed with satd citric acid and water, dried ($Na_2SO_4$), and concentrated. The resulting residue was absorbed onto silica gel and chromatographed (20% EtOAc/hexane to 35% EtOAc/hexane). The resulting product was triturated with $Et_2O$/hexane to give the desired product as a white solid (9.05 g, 99%).
$^1$NMR (300 MHz, $CDCl_3$) δ ppm: 7.85 (d, J=8.7 Hz, 1H), 6.24 (d, J=8.7 Hz, 1H), 6.20 (s, 1H), 4.19 (t, J=5.7 Hz, 0.4H), 4.12 (t, J=5.7 Hz, 1.6H), 3.90 (m, 0.7H), 3.84 (s, 2.3H), 3.77 (m, 0.8H), 3.41 (m, 3.2H), 2.25 (m, 0.8H), 2.08 (m, 3.2H), 1.45 (s, 9H). IS-MS, m/e: 379.1 (m+1).

B. 2-[3-(tert-Butoxycarbonylamino)propoxy]-4-(pyr-rolidin-1-yl)benzoic acid

Using a procedure analogous to Example 21-D, methyl 2-[3-(tert-butoxycarbonyl-amino)propoxy]-4-(pyrrolidin-1-yl)benzoate gave the desired product as a white solid (7.65 g, 88%).
$^1$NMR (300 MHz, $CDCl_3$) δ ppm: 7.97 (d, J=8.7 Hz, 1H); 6.30 (dd, J=1.8, 8.7 Hz, 1H), 6.13 (s, 1H), 4.82 (br s, 1H), 4.24 (t, J=6.3 Hz, 2H), 3.37 (m, 6H), 2.11 (m, 6H), 1.43 (s, 9H). IS-MS, m/e: 365.1 (m+1). Analysis for $C_{19}H_{28}N_2O_5$: Calcd: C, 61.86; H, 7.79; N, 7.59; Found: C, 61.79; H, 7.57; N, 7.51.

C. 2-[3-(tert-Butoxycarbonylamino)propoxy]-4-(pyr-rolidin-1-yl)benzoylamino]-5-chloro-N-(5-chloropy-ridin-2-yl)benzamide Using methods substantially equivalent to those described in Example 4-E, 2-[3-(tert-butoxycarbonylamino)propoxy]-4-(pyrrolidin-1-yl)benzoylamino]-5-chloro-N-(5-chloropy-ridin-2-yl)benzamide (1.60 g, 2.54 mmol, 34%) was prepared from 2-[3-(tert-butoxycarbonylamino)propoxy]-4-(pyrroli-din-1-yl)benzoic acid and N-(5-chloropyridin-2-yl)-2-amino-5-chlorobenzamide.
$^1$NMR (400 MHz, DMSO-$d_6$): δ 11.27 (s, 1H); 11.00 (s, 1H); 8.43 (m, 2H); 8.14 (d, J=8.4 Hz, 1H); 7.96 (d, J=8.8 Hz, 1H); 7.78 (m, 2H); 7.54 (d, J=8.8 Hz, 1H); 6.80 (m, 1H); 6.22 (d, J=8.8 Hz, 1H); 6.07 (s, 1H); 4.23 (t, J=6.2 Hz, 2H); 3.29 (m, 4H); 2.95 (m, 2H); 1.95 (m, 4H); 1.86 (m, 2H); 1.31 (s, 9H). IS-MS m/e: 628.4 (m+1). Analysis for $C_{31}H_{35}Cl_2N_5O_5$. 0.30$H_2O$: Calc: C, 58.73; H, 5.66; N, 11.05; Found: C, 58.36; H, 5.25; N, 10.71.

D. 2-[2-(3-Aminopropoxy)-4-(pyrrolidin-1-yl)-ben-zoylamino]-N-(5-chloropyridin-2-yl)-5-chlorobenza-mide Using methods substantially equivalent to those described in Example 4-G, 2-[2-(3-aminopropoxy)-4-(pyrrolidin-1-yl)-benzoylamino]-N-(5-chloropyridin-2-yl)-5-chloroben-zamide (1.56 g, 2.96 mmol, 100%) was prepared from 2-[3-(tert-butoxy-carbonylamino)propoxy]-4-(pyrrolidin-1-yl) benzoylamino]-5-chloro-N-(5-chloropyridin-2-yl) benzamide.
$^1$NMR (400 MHz, DMSO-$d_6$): δ 8.44 (d, J=1.6 Hz, 1H); 8.41 (d, J=8.8 Hz, 1H); 8.10 (d, J=8.8 Hz, 1H); 7.96 (dd, J=2.4, 9.2 Hz, 1H); 7.78 (d, J=9.2 Hz, 1H); 7.56 (dd, J=1.6, 10.4 Hz, 1H); 6.24 (d, J=8.0 Hz, 1H); 6.11 (s, 1H); 4.32 (t, J=4.8 Hz, 2H); 3.29 (m, 4H); 2.86 (m, 2H); 2.05 (m, 2H); 1.94 (m, 4H). Analysis for $C_{26}H_{27}Cl_2N_5O_3$.155$CH_2Cl_2$: Calc: C, 51.50; H, 4.47; N, 10.32; Found: C, 51.22; H, 4.14; N, 10.47.

EXAMPLE 100

Preparation of 5-Chloro-N-(5-chloropyridin-2-yl)-2-[4-isopropyl-2-(piperidin-3-yl-methoxy)benzoy-lamino]benzamide Dihydrochloride.

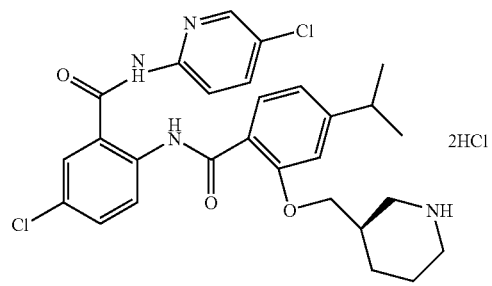

A. Methyl 4-isopropyl-2-hydroxybenzoate

The 4-isopropyl-2-methoxymethoxybenzoic acid (5.3 g, 23.6 mmol) was dissolved in methylene chloride (75 mL) and MeOH (75 mL). Acetyl chloride (1 mL) was added to gener-ate HCl. The reaction mixture was stirred for 2 h. The reaction was washed with water (2×150 mL), dried ($MgSO_4$), and concentrated under vacuum. The crude product was dissolved in methylene chloride (100 mL) and MeOH (30 mL), and to this solution a 2 M hexane solution of trimethylsilyldiaz-omethane (11.8 mL, 23.6 mmol) was added dropwise. After 1 h, the solvent was removed under vacuum, giving the title compound as an oil.
$^1$NMR

B. Methyl 2-(1-tert-butoxycarbonypiperidin-3-yl-methoxy)-4-isopropylbenzoate The methyl 4-isopropyl-2-hydroxybenzoate (4.4 g, 22.7 mmol) was dissolved in THF (100 mL). Then 3-hydroxym-ethyl-N-tert-butoxycarbonylpiperidine (4.88 g, 22.7 mmol) and triphenylphosphine (7.14 g, 27.24 mmol) were added. The mixture was placed in an ice bath, and then diisopropyl azodicarboxylate (4.59 g, 22.7 mmol) in methylene chloride (15 mL) was added dropwise. The reaction mixture was allowed to warm gradually to room temperature. After 16 h, the solvent was removed under vacuum. The solid residue was subjected directly to flash chromatography on silica (0 to 30% EtOAc in hexane gradient), giving the title compound (3.34 g, 43% yield) as an oil.
$^1$NMR

C. 2-(1-tert-Butoxycarbonylpiperidin-3-ylmethoxy)-4-isopropylbenzoic acid

The methyl 2-(1-tert-butoxycarbonypiperidin-3-yl-methoxy)-4-isopropylbenzoate (1.53 g, 3.90 mmol) was dis-solved in THF (15 mL) and LiOH.$H_2O$ (0.36 g, 8.58 mmol) in water (5 mL) was added. The mixture was heated at 65° C. for 24 h. The reaction mixture was concentrated in vacuo and redissolved in a mixture of EtOAc (100 mL) and cold dilute HCl. The mixture was shaken in a separatory funnel. The layers were separated and the organic layer was washed with cold water (100 mL), dried (MgSO$_4$), and concentrated to give 1.23 g of the title compound as an oil.
$^1$NMR D. 5-Chloro-N-(5-chloropyridin-2-yl)-2-[4-isopropyl-2-(piperidin-3-ylmethoxy)-benzoylamino]benzamide hydrochloride Using methods substantially equivalent to those described in Example 60-I and J, 5-chloro-N-(5-chloropyridin-2-yl)-2-[4-isopropyl-2-(piperidin-3-ylmethoxy)-benzoylamino]benzamide trifluoroacetate (150 mg, 0.20 mmol, 6%) was prepared from 2-(N-tert-butoxycarbonylpiperidin-3-yl)-4-isopropylmethoxybenzoic acid and N-(5-chloropyridin-2-yl)-2-amino-5-chlorobenzamide. This product was subjected to reverse phase HPLC to obtain 60 mg of the title compound as the hydrochloride salt.
$^1$NMR

EXAMPLE 101

Preparation of N-(5-Chloropyridin-2-yl)-5-fluoro-2-[4-isopropyl-2-(piperidin-3-yl-methoxy)benzoylamino]benzamide Dihydrochloride.

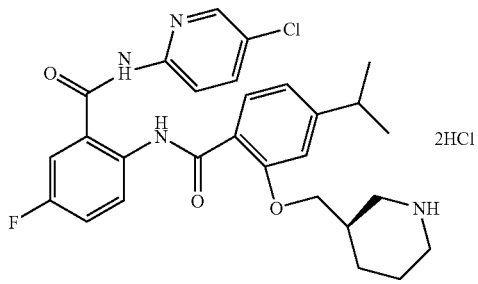

Using methods substantially equivalent to those described in example 60-I & J, 2-[4-isopropyl-2-(piperidin-3-yl-methoxy)benzoylamino]-N-(5-chloropyridin-2-yl)-5-fluorobenzamide hydrochloride (92 mg, 0.15 mmol, 14%) was prepared from 4-isopropyl-2-(N-tert-butoxycarbonylpiperidin-3-yl)methoxybenzoic acid and N-(5-chloropyridin-2-yl)-2-amino-5-fluorobenzamide after reverse phase HPLC purification.
$^1$NMR

EXAMPLE 102

Preparation of 2-[2-(2-Aminoethoxy)-4-methylsulfonylbenzoylamino]-5-chloro-N-(5-chloropyridin-2-yl) benzamide.

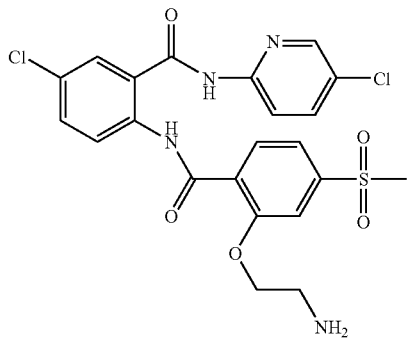

A. 2-[2-(2-tert-Butoxycarbonylaminoethoxy)-4-methylsulfonylbenzoylamino]-5-chloro-N-(5-chloropyridin-2-yl)benzamide To a solution of 2-[2-(2-tert-butoxycarbonylaminoethoxy)-4-(methylthio)-benzoylamino]-N-(5-chloropyridin-2-yl)-5-chlorobenzamide (414 mg, 0.70 mmol) and CHCl$_3$ (10 mL), at 0° C., was added mCPBA (567 mg, 1.91 mmol). After stirring for 30 minutes, Ca(OH)$_2$ (249 mg, 3.36 mmol) was added. The reaction was warmed to room temperature and filtered. The filtrate was concentrated and chromatographed (10% EtOAc/CH$_2$Cl$_2$) to give the desired product as a white solid (340 mg, 78%).
$^1$NMR (300 MHz, DMSO-d$_6$) δ ppm: 11.27 (s, 1H), 8.44 (d, 2.3 Hz, 1H), 8.35 (d, J=9.0 Hz, 1H), 8.18 (d, J=9.0 Hz, 1H), 8.07 (d, J=7.9 Hz, 1H), 7.95 (dd, J=2.6, 8.7 Hz, 1H), 7.90 (d, J=2.6 Hz, 1H), 7.70 (s, 1H), 7.67 (dd, J=2.6, 8.7 Hz, 1H), 7.61 (dd, J=1.5, 8.3 Hz, 1H), 6.94 (m, 2H), 4.34 (m, 2H), 3.42 (m, 2H), 3.29 (s, 3H), 1.29 (s, 9H). IS-MS, m/e: 623.3 (m+1). Analysis for C$_{27}$H$_{28}$Cl$_2$ N$_4$O$_7$S: Calcd: C, 52.01; H, 4.53; N, 8.99; Found: C, 52.20; H, 4.42; N, 8.85.

B. 2-[2-(2-Aminoethoxy)-4-methylsulfonylbenzoylamino]-5-chloro-N-(5-chloro-pyridin-2-yl)benzamide Using the procedure described in Example 4-G, 2-[2-(2-tert-butoxycarbonyl-aminoethoxy)-4-methylsulfonylbenzoylamino]-5-chloro-N-(5-chloropyridin-2-yl)-benzamide gave 2-[2-(2-aminoethoxy)-4-methylsulfonylbenzoylamino]-5-chloro-N-(5-chloropyridin-2-yl)benzamide (220 mg, 89%).

$^1$NMR (300 MHz, DMSO-d$_6$) δ ppm: 8.42 (d, J=2.6 Hz, 1H), 8.28 (d, J=9.0 Hz, 1H), 8.12 (d, J=9.0 Hz, 1H), 8.01 (d, J=7.9 Hz, 1H), 7.94 (dd, J=2.6, 9.0 Hz, 1H), 7.88 (d, J=2.6 Hz, 1H), 7.67 (d, J=1.5 Hz, 1H), 7.62 (m, 2H), 6.80 (br s, 2H), 4.28 (t, J=5.6 Hz, 2H), 3.28 (s, 3H), 2.94 (t, J=5.6 Hz, 2H). S-MS, nim/e: 523.1 (m+1). Analysis for C$_{22}$H$_{20}$Cl$_2$ N$_4$O$_5$S: Calcd: C, 50.49; H, 3.85; N, 10.70; Found: C, 50.23; H, 3.73; N, 10.46.

EXAMPLE 103

Preparation of 2-[2-(2-Aminoethoxy)-4-methylsulfonylbenzoylamino]-N-(5-chloro-pyridin-2-yl)-5-fluorobenzamide.

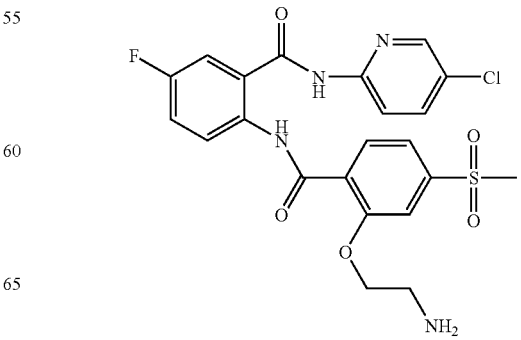

A. 2-[2-(2-tert-Butoxycarbonylaminoethoxy)-4-methylsulfonylbenzoylamino]-N-(5-chloropyridin-2-yl)-5-fluorobenzamide Using a procedure analogous to Example 102-A, 2-[2-(2-tert-butoxycarbonyl-aminoethoxy)-4-(methylthio)benzoylamino]-N-(5-chloropyridin-2-yl)-5-fluorobenzamide gave 2-[2-(2-tert-butoxycarbonylaminoethoxy)-4-methylsulfonylbenzoylamino]-N-(5-chloropyridin-2-yl)-5-fluorobenzamide (370 mg, 87%).

$^1$NMR (300 MHz, DMSO-d$_6$) δ ppm: 11.18 (s, 1H), 11.14 (s, 1H), 8.44 (d, J=2.3 Hz, 1H), 8.27 (dd, J=5.0, 9.0 Hz, 1H), 8.18 (d, J=9.0 Hz, 1H), 8.05 (d, J=7.9 Hz, 1H), 7.96 (d, J=2.3, 9.0 Hz, 1H), 7.70 (m, 2H), 7.60 (dd, J=1.5, 7.9 Hz, 1H), 7.45 (m, 1H), 6.96 (m, 1H), 4.33 (m, 2H), 3.43 (m, 2H), 3.28 (s, 3H), 1.30 (s, 9H). IS-MS, m/e: 607.2 (m+1). Analysis for C$_{27}$H$_{28}$ClFN$_4$O$_7$S: Calcd: C, 53.42; H, 4.65; N, 9.23; Found: C, 53.30; H, 4.78; N, 9.17.

B. 2-[2-(2-aminoethoxy)-4-methylsulfonylbenzoylamino]-N-(5-chloropyridin-2-yl)-5-fluorobenzamide Using the procedure described in example 4-G, 2-[2-(2-tert-butoxycarbonylamino-ethoxy)-4-methylsulfonylbenzoylamino]-5-chloro-N-(5-chloropyridin-2-yl)benzamide gave 2-[2-(2-aminoethoxy)-4-methylsulfonylbenzoylamino]-N-(5-chloropyridin-2-yl)-5-fluorobenzamide (25 mg, 88%).

$^1$NMR IS-MS, m/e: 507.1 (m+1). Analysis for C$_{22}$H$_{20}$ClFN$_4$O$_5$S: Calcd: C, 52.13; H, 3.98; N, 11.05; Found: C, 52.20; H, 3.96; N, 10.93.

EXAMPLE 104

Preparation of 5-Fluoro-2-[2-(1-methylpiperidin-4-yloxy)-4-(pyrrolidin-1-yl)-benzoylamino]-N-(pyridin-2-yl)benzamide Hydrochloride.

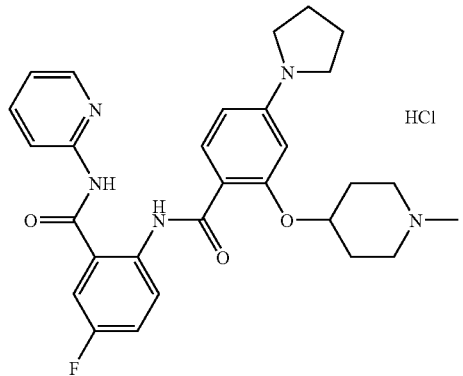

Using methods substantially equivalent to those described in Example 91-G, and isolating the product as a salt by evaporating an ethanolic HCl solution, 5-fluoro-2-[2-(1-methylpiperidin-4-yloxy)-4-(pyrrolidin-1-yl)benzoylamino]-N-(pyridin-2-yl)-benzamide hydrochloride was prepared from 6-fluoro-2-[2-(1-methylpiperidin-4-yloxy)-4-(pyrrolidin-1-yl)phenyl]-4H-3,1-benzoxazin-4-one and 2-aminopyridine.

$^1$NMR IS-MS 518 (m+1)

EXAMPLE 105

Preparation of 2-[2-(3-Aminopropoxy)-4-(methylthio)benzoylamino]-N-(5-chloro-pyridin-2-yl)-5-fluorobenzamide.

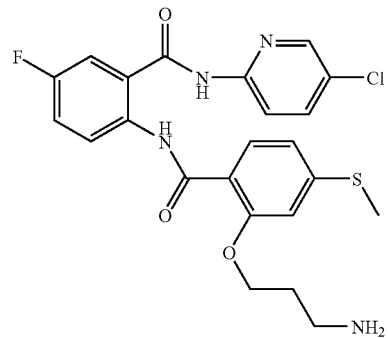

A. Methyl 2-(3-tert-butoxycarbonylaminopropoxy)-4-(methylthio)benzoate

Methyl 2-(3-tert-butoxycarbonylaminopropoxy)-4-(methylthio)benzoate (7.0 g, 82%) was obtained as described in Example 21-C from methyl 2-hydroxy-4-(methylthio)-benzoate and 3-(tert-butoxycarbonylamino)propanol.

$^1$NMR (300 MHz, DMSO-d$_6$) δ ppm: 7.82 (d, J=8.3 Hz, 1H), 6.80 (m, 2H), 6.0 (s, 1H), 4.11 (t, 5.3 Hz, 2H), 3.88 (s, 3H), 3.42 (m, 2H), 2.50 (s, 3H), 2.05 (m, 2H), 1.44 (s, 9H). IS-MS, m/e: 356.4 (m+1). Analysis for C$_{17}$H$_{25}$NO$_5$S: Calcd: C, 57.44; H, 7.09; N, 3.94; Found: C, 57.41; H, 7.04; N, 4.24.

B. 2-(3-tert-Butoxycarbonylaminopropoxy)-4-(methylthio)benzoic acid

Using a procedure analogous to Example 94-B, methyl 2-(3-tert-butoxycarbonyl-aminopropoxy)-4-(methylthio) benzoate gave 2-(3-tert-butoxycarbonylaminopropoxy)-4-(methylthio)benzoic acid (6.04 g, 93%).

$^1$NMR (300 MHz, DMSO-d$_6$) δ ppm: 8.03 (d, J=8.3 Hz, 1H), 6.92 (dd, J=1.5, 8.3 Hz, 1H), 6.83 (d, 1.5 Hz, 1H), 4.85 (m, 1H), 4.27 (t, J=6.4 Hz, 2H), 3.35 (m, 2H), 2.52 (s, 3H), 2.10 (m, 2H), 1.42 (s, 9H). IS-MS, m/e: 342.1 (m+1). Analysis for C$_{16}$H$_{23}$NO$_5$S: Calcd: C, 56.29; H, 6.79; N, 4.10; Found: C, 56.33; H, 6.49; N, 4.38.

C. 2-[2-(3-tert-Butoxycarbonylaminopropoxy)-4-(methylthio)benzoylamino]-N-(5-chloropyridin-2-yl)-5-fluorobenzamide 2-[2-(3-tert-Butoxycarbonylaminopropoxy)-4-(methylthio)benzoylamino]-N-(5-chloropyridin-2-yl)-5-fluorobenzamide was prepared by methods described in Example 4-E from 2-(3-tert-butoxycarbonylaminopropoxy)-4-(methylthio)benzoic acid and N-(5-chloropyridin-2-yl)-2-amino-5-fluorobenzamide (1.53 g, 47%).

$^1$NMR (300 MHz, DMSO-d$_6$).8 ppm: 11.22 (s, 1H), 11.02 (s, 1H), 8.44 (d, J=2.6 Hz, 1H), 8.36 (m, 1H), 8.15 (d, J=9.0 Hz, 1H), 7.97 (dd, J=2.6, 9.0 Hz, 1H), 7.86 (d, J=8.3 Hz, 1H), 7.65 (dd, J=3.0, 9.4 Hz, 1H), 7.44 (m, 1H), 6.95 (m, 2H), 6.82 (m, 1H), 4.27 (t, J=6.4 Hz, 2H), 3.02 (m, 2H), 2.53 (s, 3H), 1.90 (m, 2H), 1.33 (s, 9H). IS-MS, m/e: 589.2 (m+1). Analysis for C$_{28}$H$_{30}$ClFN$_4$O$_5$S: Calcd: C, 57.09; H, 5.13; N, 9.51; Found: C, 56.95; H, 5.09; N, 9.45.

D. 2-[2-(3-Aminopropoxy)-4-(methylthio)benzoylamino]-N-(5-chloropyridin-2-yl)-5-fluorobenzamide Using the procedure described in Example 4-G, 2-[2-(3-tert-butoxycarbonyl-aminopropoxy)-4-(methylthio)benzoylamino]-N-(5-chloropyridin-2-yl)-5-fluoro-benzamide gave 2-[2-(3-aminopropoxy)-4-(methylthio)benzoylamino]-N-(5-chloro-pyridin-2-yl)-5-fluorobenzamide (206 mg, 92%).
[1]NMR IS-MS, m/e: 489.5 (m+1).

EXAMPLE 106

Preparation of 2-[2-(3-Aminopropoxy)-4-(methylthio)benzoylamino]-5-chloro-N-(5-chloropyridin-2-yl)benzamide.

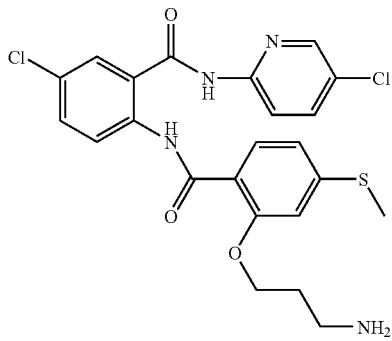

A. 2-[2-(3-tert-Butoxycarbonylaminopropoxy)-4-(methylthio)benzoylamino]-5-chloro-N-(5-chloropyridin-2-yl)benzamide 2-[2-(3-tert-Butoxycarbonylaminopropoxy)-4-(methylthio)benzoylamino]-5-chloro-N-(5-chloropyridin-2-yl)benzamide was prepared by methods described in Example 4-E from 2-(3-tert-butoxycarbonylaminopropoxy)-4-(methylthio)benzoic acid and N-(5-chloropyridin-2-yl)-2-amino-5-chlorobenzamide (1.63 g, 49%).
[1]NMR (300 MHz, DMSO-$d_6$) δ ppm: 11.29 (s, 1H), 11.10 (s, 1H), 8.41 (s, 1H), 8.11 (d, J=9.0 Hz, 1H), 7.94 (dd, J=2.4, 9.0 Hz, 1H), 7.83 (d, J=9.0 Hz, 1H), 7.59 (dd, J=2.4, 9.0 Hz, 1H), 7.17 (m, 2H), 6.93 (m, 2H), 6.79 (m, 1H), 4.23 (t, J=6.3 Hz, 2H), 2.94 (m, 2H), 2.50 (s, 3H), 1.84 (m, 2H), 1.29 (s, 9H). IS-MS, m/e: 605.2 (m+1). Analysis for $C_{28}H_{30}Cl_2N_4O_5S$. Calcd: C, 55.54; H, 4.99; N, 9.25. Found: C, 55.81; H, 5.01; N, 9.50.

B. 2-[2-(3-Aminopropoxy)-4-(methylthio)benzoylamino]-5-chloro-N-(5-chloro-pyridin-2-yl)benzamide Using the procedure described in Example 4-G, 2-[2-(3-tert-butoxycarbonyl-aminopropoxy)-4-(methylthio)benzoylamino]-5-chloro-N-(5-chloropyridin$^{-2}$-yl)-benzamide gave 2-[2-(3-aminopropoxy)-4-(methylthio)benzoylamino]-5-chloro-N-(5-chloro-pyridin-2-yl)benzamide (199 mg, 87%).
[1]NMR IS-MS, m/e: 505.1 (m+1). Analysis for $C_{23}H_{22}Cl_2N_4O_3S$. Calcd: C, 54.66; H, 4.39; N, 11.09. Found: C, 54.96; H, 4.44; N, 10.96.

EXAMPLE 107

Preparation of 2-[2-(3-Aminopropoxy)-4-methylsulfonylbenzoylamino]-5-chloro-N-(5-chloropyridin-2-yl)benzamide

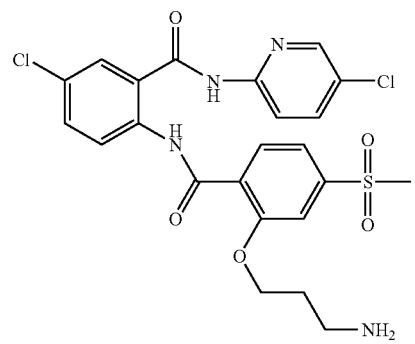

A. 2-[2-(3-tert-Butoxycarbonylaminopropoxy)-4-methylsulfonylbenzoylamino]-5-chloro-N-(5-chloro-pyridin-2-yl)benzamide Using a procedure analogous to Example 102-A, 2-[2-(3-tert-butoxycarbonyl-aminopropoxy)-4-(methylthio)benzoylamino]-5-chloro-N-(5-chloropyridin-2-yl)-benzamide gave 2-[2-(3-tert-butoxycarbonylaminopropoxy)-4-methylsulfonyl-benzoylamino]-5-chloro-N-(5-chloropyridin-2-yl)benzamide (307 mg, 69%).
[1]NMR (300 MHz, DMSO-$d_6$) δ ppm: 11.26 (s, 1H), 11.11 (s, 1H), 8.41 (d, J=1.8 Hz, 1H), 8.29 (d, J=8.7 Hz, 1H), 8.09 (d, J=8.7 Hz, 1H), 7.94 (m, 2H), 7.85 (s, 1H), 7.60 (m, 3H), 6.80 (m, 1H), 4.25 (t, J=6.0 Hz, 2H), 3.29 (s, 3H), 2.97 (m, 2H), 1.85 (m, 2H), 1.28 (s, 9H). IS-MS, m/e: 637.1 (m+1). Analysis for $C_{28}H_{30}Cl_2N_4O_7S$. Calcd: C, 52.75; H, 4.74; N, 8.79. Found: C, 52.63; H, 4.85; N, 8.70.

B. 2-[2-(3-Aminopropoxy)-4-methylsulfonylbenzoylamino]-5-chloro-N-(5-chloropyridin-2-yl)benzamide Using a procedure analogous to Example 4-G, 2-[2-(3-tert-butoxycarbonylamino-propoxy)-4-methylsulfonylbenzoylamino]-5-chloro-N-(5-chloropyridin-2-yl)benzamide gave 2-[2-(3-aminopropoxy)-4-methylsulfonylbenzoylamino]-5-chloro-N-(5-chloro-pyridin-2-yl)benzamide (232 mg, 100%). [1]NMR IS-MS, m/e: 537.2 (m+1).

EXAMPLE 108

Preparation of 2-[2-(3-Aminopropoxy)-4-methylsulfonylbenzoylamino]-N-(5-chloropyridin-2-yl)-5-fluorobenzamide

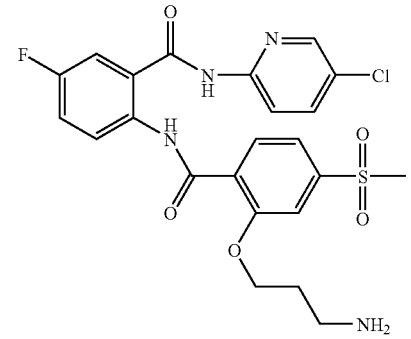

A. 2-[2-(3-tert-Butoxycarbonylaminopropoxy)-4-methylsulfonylbenzoylamino]-N-(5-chloropyridin-2-yl)-5-fluorobenzamide Using a procedure analogous to Example 102-A, 2-[2-(3-tert-butoxycarbonyl-aminopropoxy)-4-(methylthio)benzoylamino]-N-(5-chloropyridin-2-yl)-5-fluoro-benzamide gave 2-[2-(3-tert-butoxycarbonylaminopropoxy)-4-methylsulfonylbenzoyl-amino]-N-(5-chloropyridin-2-yl)-5-fluorobenzamide (328 mg, 75%).

$^1$NMR (300 MHz, DMSO-$d_6$) $\delta$ ppm: 11.19 (s, 1H), 11.00 (s, 1H), 8.41 (d, J=1.8 Hz, 1H), 8.21 (m, 1H), 8.10 (d, J=9.0 Hz, 1H), 7.94 (m, 2H), 7.85 (s, 1H), 7.60 (m, 3H), 7.41 (m, 1H), 6.82 (m, 1H), 4.25 (m, 1H), 3.29 (s, 3H), 2.98 (m, 2H), 1.87 (m, 2H), 1.28 (s, 9H). IS-MS, m/e: 621.5 (m+1). Analysis for $C_{28}H_{30}ClFN_4O_7S$. Calcd: C, 54.15; H, 4.87; N, 9.02. Found: C, 54.75; H, 5.05; N, 9.27.

B. 2-[2-(3-Aminopropoxy)-4-methylsulfonylbenzoylamino]-N-(5-chloropyridin-2-yl)-5-fluorobenzamide Using a procedure analogous to Example 4-G, 2-[2-(3-tert-butoxycarbonylamino-propoxy)-4-methylsulfonylbenzoylamino]-N-(5-chloropyridin-2-yl)-5-fluorobenzamide gave 2-[2-(3-aminopropoxy)-4-methylsulfonylbenzoylamino]-N-(5-chloropyridin-2-yl)-5-fluorobenzamide (242 mg, 95%).

$^1$NMR IS-MS, m/e: 521.2 (m+1).

EXAMPLE 109

Preparation of 2-[2-(3-Aminopropoxy)-4-methylsulfinylbenzoylamino]-5-chloro-N-(5-chloropyridin-2-yl)benzamide

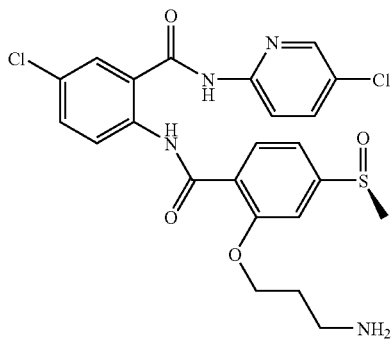

A. 2-[2-(3-tert-Butoxycarbonylaminopropoxy)-4-methylsulfinylbenzoylamino]-N-(5-chloropyridin-2-yl)-5-chlorobenzamide Using a procedure analogous to Example 96-A, 2-[2-(3-tert-butoxycarbonyl-aminopropoxy)-4-(methylthio)benzoylamino]-5-chloro-N-(5-chloropyridin-2-yl)-benzamide gave 2-[2-(3-tert-butoxycarbonylaminopropoxy)-4-methylsulfinylbenzoyl-amino]-N-(5-chloropyridin-2-yl)-5-chlorobenzamide (437 mg, 70%).

$^1$NMR (300 MHz, DMSO-$d_6$) $\delta$ ppm: 11.29 (s, 1H), 11.17 (s, 1H), 8.44 (d, J=2.6 Hz, 1H), 8.37 (d, J=9.0 Hz, 1H), 8.13 (d, J=9.0 Hz, 1H), 8.02 (d, J=8.3 Hz, 1H), 7.96 (dd, J=2.6, 9.0 Hz, 1H), 7.88 (d, J=2.6 Hz, 1H), 7.64 (dd, J=2.6, 8.3 Hz, 1H), 7.46 (s, 1H), 7.36 (d, J=1.5 Hz, 1H), 6.81 (m, 1H), 4.28 (t, J=6.4 Hz, 2H), 3.00 (m, 2H), 2.79 (s, 3H), 1.91 (m, 2H), 1.32 (s, 9H). IS-MS, m/e: 621.5 (m+1). Analysis for $C_{28}H_{30}Cl_2N_4O_6S$. Calcd: C, 54.11; H, 4.87; N, 9.01. Found: C, 54.36; H, 4.86; N, 8.97.

B. 2-[2-(3-Aminopropoxy)-4-methylsulfinylbenzoylamino]-5-chloro-N-(5-chloropyridin-2-yl)benzamide Using a procedure analogous to Example 4-G, 2-[2-(3-tert-butoxycarbonylamino-propoxy)-4-methylsulfinylbenzoylamino]-N-(5-chloropyridin-2-yl)-5-chlorobenzamide gave 2-[4-methylsulfinyl-2-(3-aminopropoxy)benzoylamino]-N-(5-chloropyridin-2-yl)-5-chlorobenzamide (308 mg, 92%).

$^1$NMR IS-MS, m/e: 521.2 (m+1).

EXAMPLE 110

Preparation of 2-[2-(3-Aminopropoxy)-4-methylsulfinylbenzoylamino]-N-(5-chloro-pyridin-2-yl)-5-fluorobenzamide

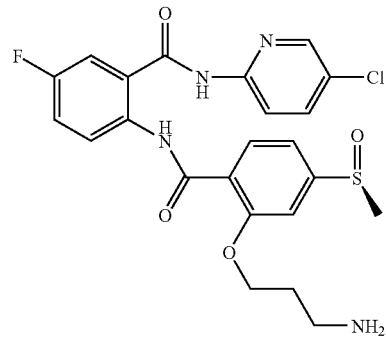

A. 2-[2-(3-tert-butoxycarbonylaminopropoxy)-4-methylsulfinylbenzoylamino]-N-(5-chloropyridin-2-yl)-5-fluorobenzamide Using a procedure analogous to Example 96-A, 2-[2-(3-tert-butoxycarbonyl-aminopropoxy)-4-(methylthio)benzoylamino]-N-(5-chloropyridin-2-yl)-5-fluoro-benzamide gave 2-[2-(3-tert-butoxycarbonylaminopropoxy)-4-methylsulfinylbenzoyl-amino]-N-(5-chloropyridin-2-yl)-5-fluorobenzamide (519 mg, 75%).

$^1$NMR (300 MHz, DMSO-$d_6$) $\delta$ ppm: 11.21 (s, 1H), 11.05 (s, 1H), 8.44 (d, J=2.6 Hz, 1H), 8.30 (m, 1H), 8.15 (d, J=9.0 Hz, 1H), 8.02 (d, J=7.9 Hz, 1H), 7.96 (dd, J=2.6, 8.7 Hz, 1H), 7.67 (dd, J=3.0, 9.0 Hz, 1H), 7.46 (m, 2H), 7.36 (dd, J=1.1, 8.3 Hz, 1H), 6.80 (m, 1H), 4.27 (t, J=6.4 Hz, 2H), 3.02 (m, 2H), 2.79 (s, 3H), 1.91 (m, 2H), 1.32 (s, 9H). IS-MS, m/e: 605.3 (m+1). Analysis for $C_{28}H_{30}ClFN_4O_6S$. Calcd: C, 55.58; H, 5.00; N, 9.26. Found: C, 55.46; H, 4.94; N, 9.36.

B. 2-[2-(3-aminopropoxy)-4-methylsulfinylbenzoylamino]-N-(5-chloropyridin-2-yl)-5-fluorobenzamide Using a procedure analogous to Example 4-G, 2-[2-(3-tert-butoxycarbonylamino-propoxy)-4-methylsulfinylbenzoylamino]-N-(5-chloropyridin-2-yl)-5-fluorobenzamide gave 2-[2-(3-aminopropoxy)-4-methylsulfinylbenzoylamino]-N-(5-chloropyridin-2-yl)-5-fluorobenzamide (355 mg, 88%).

$^1$NMR IS-MS, m/e: 505.1 (m+1).

EXAMPLE 111

Preparation of 2-[4-(tert-Butyl)-2-(piperidin-4-yloxy)benzoylamino]-5-chloro-N-(pyridin-2-yl)benzamide Hydrochloride/trifluoroacetate

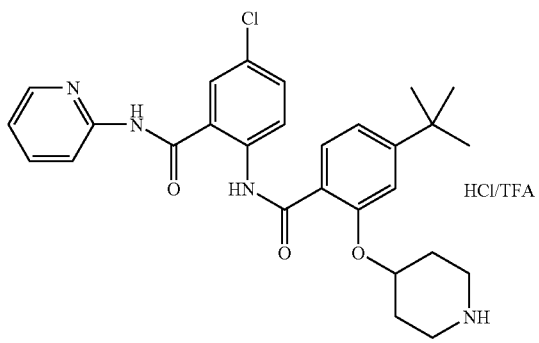

A. N-(Pyridin-2-yl)-5-chloro-2-nitrobenzamide

By methods substantially equivalent to those described in Example 16-A, N-(pyridin-2-yl)-5-chloro-2-nitrobenzamide (8.6 g, 42%) was prepared from 5-chloro-2-nitrobenzoic acid and 2-aminopyridine.

$^1$NMR IS-MS, m/e 278.0 (m+1) Analysis for $C_{12}H_8ClN_3O_3$. Calcd: C, 51.91; H, 2.90; N, 15.13. Found: C, 52.53; H, 2.85; N, 15.05.

B. N-(Pyridin-2-yl)-2-amino-5-chlorobenzamide

By methods substantially equivalent to those described in Example 2-B, N-(pyridin-2-yl)-2-amino-5-chlorobenzamide (2.4 g, 67%) was prepared from N-(pyridin-2-yl)-5-chloro-2-nitrobenzamide.

$^1$NMR IS-MS, m/e 248.3 (m+1) Analysis for $C_{12}H_{10}ClN_3O$. Calcd: C, 58.19; H, 4.07; N, 16.96. Found: C, 58.39; H, 4.07; N, 17.08.

C. 2-[4-(tert-Butyl)-2-(1-Boc-piperidin-4-yloxy)benzoylamino]-5-chloro-N-(pyridin-2-yl)benzamide By methods substantially equivalent to those described in Example 16-F, 2-[4-(tert-butyl)-2-(1-Boc-piperidin-4-yloxy)benzoylamino]-5-chloro-N-(pyridin-2-yl)-benzamide (0.44 g, 57%) was prepared from 4-(tert-butyl)-2-(1-Boc-piperidin-4-yloxy)-benzoyl chloride and N-(pyridin-2-yl)-2-amino-5-chlorobenzamide.

$^1$NMR IS-MS, m/e 607.3 (m+1) Analysis for $C_{33}H_{39}ClN_4O_5$. Calcd: C, 65.28; H, 6.47; N, 9.23. Found: C, 65.21; H, 6.64; N, 8.93.

D. 2-[4-(tert-Butyl)-2-(piperidin-4-yloxy)benzoylamino]-5-chloro-N-(pyridin-2-yl)-benzamide hydrochloride/trifluoroacetate By methods substantially equivalent to those described in Example 85-D, 2-[4-(tert-butyl)-2-(piperidin-4-yloxy)benzoylamino]-5-chloro-N-(pyridin-2-yl)-benzamide hydrochloride (0.16 g, 73%) was prepared from 2-[4-(tert-butyl)-2-(1-Boc-piperidin-4-yloxy)benzoylamino]-5-chloro-N-(pyridin-2-yl)benzamide. The product was purified by preparative RPHPLC, eluting with a gradient of 20% through 40% acetonitrile in 0.05% aq HCl, over 180 min.

$^1$NMR IS-MS, m/e 507.2 (m+1) Analysis for $C_{28}H_{32}ClN_4O_3 \cdot 0.7HCl \cdot 0.7TFA \cdot H_2O$. Calcd: C, 55.93; H, 5.65; N, 8.87; Cl, 9.55; F, 6.32. Found: C, 55.53; H, 5.28; N, 8.92; Cl, 9.04; F, 6.12.

EXAMPLE 112

Preparation of 2-[4-(tert-Butyl)-2-(piperidin-4-yloxy)benzoylamino]-5-chloro-N-(5-methylpyridin-2-yl)benzamide Hydrochloride

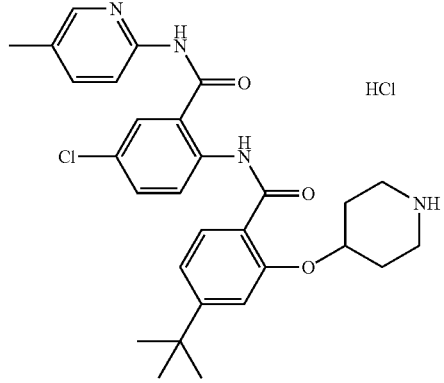

A. N-(5-Methylpyridin-2-yl)-5-chloro-2-nitrobenzamide

By methods substantially equivalent to those described in Example 16-A, N-(5-methylpyridin-2-yl)-5-chloro-2-nitrobenzamide (11.4 g, 53%) was prepared from 5-chloro-2-nitrobenzoic acid and 2-amino-5-methylpyridine.

IS-MS, m/e 292.0 (m+1) Analysis for $C_{13}H_{10}ClN_3O_3$. Calcd: C, 53.53; H, 3.46; N, 14.40. Found: C, 53.76; H, 3.41; N, 14.35.

B. N-(5-Methylpyridin-2-yl)-2-amino-5-chlorobenzamide

By methods substantially equivalent to those described in Example 2-B, N-(5-methylpyridin-2-yl)-2-amino-5-chlorobenzamide (2.4 g, 67%) was prepared from N-(5-methylpyridin-2-yl)-5-chloro-2-nitrobenzamide.

$^1$NMR IS-MS, m/e 262.0 (m+1) Analysis for $C_{13}H_{12}ClN_3O$. Calcd: C, 59.66; H, 4.62; N, 16.06. Found: C, 59.89; H, 4.57; N, 15.99.

C. 2-[4-(tert-Butyl)-2-(1-Boc-piperidin-4-yloxy)benzoylamino]-5-chloro-N-(5-methylpyridin-2-yl)benzamide By methods substantially equivalent to those described in Example 16-F, 2-[4-(tert-butyl)-2-(1-Boc-piperidin-4-yloxy)benzoylamino]-5-chloro-N-(5-methyl-pyridin-2-yl)benzamide (0.50 g, 76%) was prepared from 4-(tert-butyl)-2-(1-Boc-piperidin-4-yloxy)benzoyl chloride and N-(5-methylpyridin-2-yl)-2-amino-5-chloro-benzamide.

$^1$NMR IS-MS, m/e 621.5 (m+1) Analysis for $C_{34}H_{41}ClN_4O_5$. Calcd: C, 65.74; H, 6.65; N, 9.02. Found: C, 66.00; H, 6.80; N, 8.80.

D. 2-[4-(tert-Butyl)-2-(piperidin-4-yloxy)benzoylamino]-5-chloro-N-(5-methyl-pyridin-2-yl)benzamide hydrochloride By methods substantially equivalent to those described in Example 16-G, 2-[4-(tert-butyl)-2-(piperidin-4-yloxy)benzoylamino]-5-chloro-N-(5-methylpyridin-2-yl)-benzamide hydrochloride (0.17 g, 40%) was prepared from 2-[4-(tert-butyl)-2-(1-Boc-piperidin-4-yloxy)benzoylamino]-5-chloro-N-(5-methylpyridin-2-yl)benzamide. The product was purified by preparative RPHPLC, eluting with a gradient of 20% through 40% acetonitrile in 0.05% aq HCl, over 180 min.

$^1$NMR IS-MS, m/e 521.3 (m+1) Analysis for $C_{29}H_{34}ClN_4O_3 \cdot 1.7HCl1.5H_2O$. Calcd: C, 57.00; H, 6.38; N, 9.17; Cl, 15.67. Found: C, 57.08; H, 6.00; N, 9.29; Cl, 15.55.

EXAMPLE 113

Preparation of 2-[4-(1-Aminoethyl)-2-(piperidin-3-yloxy)benzoylamino]-N-(5-chloro-pyridin-2-yl)benzamide Tris(trifluoroacetate)

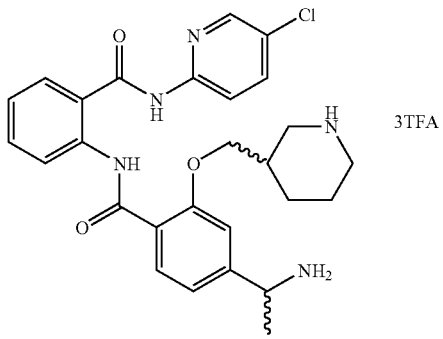

A. 3-(Acetyl)phenyl methoxymethyl ether

To a stirred solution of 3-hydroxyacetophenone (20.40 g, 150 mmol) in $CH_2Cl_2$ (450 mL) at 0° C. under $N_2$ was added N,N-diisopropylethylamine (52.25 mL, 300 mmol) followed by methyl chloromethyl ether (MOM chloride) (13.67 mL, 180 mmol) over a period of 30 min. The reaction was stirred at 0° C. for 30 min and then at room temperature for 2 h. The reaction was quenched with $H_2O$ (500 mL). The organic solution was separated, washed with $H_2O$ (2×500 mL), 0.5 N NaOH (2×100 mL), and again with H1120 (200 mL). The organic solution was dried ($Na_2 SO_4$) and concentrated. The resulting residue was purified by filtration through a pad of silica gel using n-hexanes through 2-5% EtOAc/n-hexanes to give the desired product (17.30 g, 64%); TLC Rf: 0.45 (20% EtOAc/n-hexanes).

$^1$H NMR (400 MHz, CDCl$_3$): δ 7.62 (dd, 1H, J=1.6 and 8.4 Hz); 7.59 (d, 1H, J=1.6 Hz); 7.38 (t, 1H, J=6 Hz); 5.23 (s, 2H); 3.49 (s, 3H); 2.60 (s, 3H). IS-MS (m/e): 180 (m) Analysis for $C_{10}H_{12}O_3$. Calcd: C, 66.65; H, 6.71. Found: C, 67.73; H, 6.87.

B. Methoxymethyl 3-(2-methyl-1,3-dioxolan-2-yl)phenyl ether

A mixture of 3-(acetyl)phenyl methoxymethyl ether (3.6 g, 20 mmol), ethylene glycol (3.72 g, 60 mmol) and pyridinium tosylate (0.075 g, 0.3 mmol, 3 mol %) in benzene (200 mL) was azeotropically refluxed for 8 h. The reaction was concentrated and the resulting residue was diluted with ethyl ether (150 mL) and washed with saturated aqueous bicarbonate (2×50 mL) and brine (100 mL). The ethyl ether solution was dried ($K_2 CO_3$) and concentrated. The residue was suspended in n-hexanes and the by-product was precipitated. The n-hexane solution was then separated and concentrated to obtain the desired product (2.69 g, 61%); TLC Rf: 0.5 (30% EtOAc/n-hexanes).

$^1$H NMR (400 MHz, CDCl$_3$): δ 7.33 (t, 1H, J=7.6 Hz); 7.22 (ddd, 1H, J=1.6, 2.4 and 7.6 Hz); 7.19 (bs, 1H); 7.06 (dd, 1H, J=1.2 and 8.0 Hz); 5.26 (s, 2H); 4.10 (m, 2H); 3.86 (m, 2H); 3.56 (s, 3H); 1.73 (s, 3H). IS-MS (m/e): 225 (m+1) Analysis for $C_{12}H_{16}O_4$. Calcd: C, 64.27; H, 7.19. Found: C, 64.46; H, 7.09.

C. Lithium 2-(methoxymethoxy)-4-(2-methyl-1,3-dioxolan-2-yl)benzoate

A dry reaction flask equipped with a magnetic stirring bar and a rubber septum was charged with methoxymethyl 3-(2-methyl-1,3-dioxolan-2-yl)phenyl ether (4.75 g, 21.20 mmol) and ethyl ether (85 mL). The solution was placed under $N_2$ and cooled to −10° C. Then tert-BuLi (1.7 M in pentane, 14.96 mL, 25.45 mmol) was added over a period of 25 min. After the reaction had stirred for 3.5 h, $CO_2$ gas was bubbled in for 15 minutes, during which the precipitate color changed from yellow to faint yellow. The resulting reaction was stirred at room temperature for 3 h, diluted with ethyl ether (100 mL), filtered, washed with ethyl ether (2×50 mL) and dried to obtain the desired lithium salt (5.25 g, 90%).

$^1$H NMR (400 MHz, D$_2$O): δ 7.23 (d, 1H, J=8 Hz); 7.03 (d, 1H, J=0.8 Hz); 7.00 (d, 1H, J=8 Hz); 5.08 (s, 2H); 3.93 (m, 2H); 3.71 (m, 2H); 3.31 (s, 3H); 1.51 (s, 3H). IS-MS (m/e): 275 (m+1) Analysis for $C_{13}H_{15} LiO_6$. Calcd: C, 56.95; H, 5.51. Found: C, 55.92, H, 5.37.

D. N-(5-Chloropyridin-2-yl)-2-[2-(methoxymethoxy)-4-(2-methyl-1,3-dioxolan-2-yl)benzoylamino]benzamide To a suspension of lithium 2-(methoxymethoxy)-4-(2-methyl-1,3-dioxolan-2-yl)-benzoate (0.08 g, 0.29 mmol) in $CH_2Cl_2$ (2 mL) at 0° C. was added DMF (2 drops) followed by oxalyl chloride (0.025 mL, 0.29 mmol). Vigorous bubbling occurred. The reaction was stirred at room temperature for 30 min and then the solvent was removed under reduced pressure. The residue was suspended in $CH_2Cl_2$ (10 mL) and cooled to 0° C. Pyridine (0.07 mL, 0.87 mmol) and N-(5-chloropyridiri-2-yl)-2-aminobenzamide (0.072 g, 0.29 mmol) were added and the reaction was stirred at room temperature for 6 h. The reaction was quenched with $H_2O$:EtOAc (10 mL each) and extracted with EtOAc (3×30 mL). The organic solution was washed with 2 NHC (cold), $H_2O$ (10 mL), 2 N NaOH (cold) and $H_2O$ (10 mL), dried (Na$_2$ SO$_4$), and concentrated. The resulting residue was purified by silica gel flash chromatography (n-hexanes through 30% EtOAc/n-hexanes) to obtain the desired product (0.110 g, 76%); TLC Rf: 0.42 (40% EtOAc/n-hexanes).

$^1$H NMR (400 MHz, CDCl$_3$): δ 11.61 (s, 1H); 8.80 (s, 1H); 8.71 (d, 1H, J=7.6 Hz); 8.25 (d, 1H, J=8.8 Hz); 8.17 (d, 2H, J=8.4 Hz); 7.70 (dd, 1H, J=2.4 and 8.8 Hz); 7.61 (dd, 1H, J=1.6 and 7.6 Hz); 7.52 (dt, 1H, J=1.6 and 7.2 Hz); 7.39 (d, 1H, 1.2 Hz); 7.21 (dd, 1H, J=1.2 and 8 Hz); 7.11 (dt, 1H, J=1.2 and 7.2 Hz); 5.49 (s, 2H); 4.03 (m, 2H); 3.77 (m, 2H); 3.51 (s, 3H); 1.64 (s, 3H). IS-MS (m/e): 498 (m) Analysis for C$_{25}$H$_{24}$ClN$_3$O$_6$. Calcd: C, 60.30; H, 4.86; N, 8.44. Found: C, 60.20; H, 5.00; N, 8.15.

E. 2-[4-Acetyl-2-(methoxymethoxy)benzoylamino]-N-(5-chloropyridin-2-yl)-benzamide To a solution of N-(5-chloropyridin-2-yl)-2-[2-(methoxymethoxy)-4-(2-methyl-1,3-dioxolan-2-yl)benzoylamino]benzamide (4.37 g, 8.78 mmol) in THF (150 mL) at 0° C. was added 5 N HCl (28 mL, 140 mmol). The resulting solution was stirred at room temperature for 6 h. The solution was concentrated to the half of its original volume, diluted with H$_2$O (300 mL) and basified with 2 N NaOH (~pH 9). The solid obtained was filtered, washed with H$_2$O (3×50 mL), and dried to give the expected product (3.82 g, 96%), TLC Rf: 0.38 (40% EtOAc/n-hexanes).

$^1$H NMR (400 MHz, CDCl$_3$): δ 11.79 (s, 1H); 8.75 (d, 1H, J=8.4 Hz); 8.54 (bs, 1H); 8.28 (d, 2H, J=8.4 Hz); 7.86 (d, 1H, J=1.2 Hz); 7.74-7.57 (m, 5H); 7.21 (t, 1H, J=7.2 Hz); 5.48 (s, 2H); 3.26 (s, 3H); 2.60 (s, 3H). IS-MS (m/e):454 (m) Analysis for C$_{23}$H$_{20}$ClN$_3$O$_5$. Calcd: C, 60.86; H, 4.44; N, 9.26; Cl, 7.81. Found: C, 61.04; H, 4.33; N, 9.25; Cl, 8.40.

F. 2-[4-(1-Aminoethyl)-2-(methoxymethoxy)benzoylamino]-N-(5-chloropyridin-2-yl)benzamide A mixture of 2-[4-acetyl-2-(methioxymethoxy)benzoylamino]-N-(5-chloropyridin-2-yl)benzamide (2.4 g, 5.28 mmol) and 3 Å molecular sieves (5 g) was evacuated for 15 min under N$_2$. Methanol and methylene chloride (90 mL each) were added. The reaction mixture was refluxed for 6 h and then cooled to room temperature. After the addition of NaCNBH$_3$ (0.331 g, 5.28 mmol) the reaction mixture was stirred at 60° C. for 4-6 h and then at room temperature for 16 h. The reaction was filtered through a pad of diatomaceous earth and concentrated. The resulting residue was dissolved in CH$_2$Cl$_2$ (200 mL) and extracted with 2 N HCl (cold) (3×100 mL). The aqueous acidic solution was then basified with 2 N NaOH (about pH 9), extracted with EtOAc (5×100 mL), dried (Na$_2$SO$_4$) and concentrated to give the requisite product (1.4 g, 60%), TLC Rf: 0.36 (2 N NH$_3$/MeOH in CH$_2$Cl$_2$). $^1$H NMR (400 MHz, CDCl$_3$): δ 11.62 (s, 1H); 8.73 (d, 1H, J=8 Hz); 8.55 (s, 1H); 8.24 (d, 1H, J=8.8 Hz); 8.23 (s, 1H); 8.16 (d, 1H, J=8.0 Hz); 7.70 (dd, 1H, J=2.4 and 8.8 Hz); 7.61 (dd, 1H, J=1.6 and 7.6 Hz); 7.54 (dt, 1H, J=1.6 and 8.8 Hz); 7.29 (s, 1H); 7.17-7.09 (m, 2H); 5.51 (s, 2H); 41.19 (m, 1H); 3.51 (s, 3H). IS-MS (m/e): 454 (m)

G. 2-[4-(1-Aminoethyl)-2-hydroxybenzoylamino]-N-(5-chloropyridin-2-yl)-benzamide To a solution of 2-[4-(1-aminoethyl)-2-(methoxymethoxy) benzoylamino]-N-(5-chloropyridin-2-yl)benzamide (0.205 g, 0.45 mmol) in CH$_2$Cl$_2$ (4.1 mL) was added trifluoroacetic acid (4.1 mL) followed by H$_2$O (4.1 mL). The reaction was stirred at room temperature for 20-30 min. Then the volatile solvent was removed under a reduced pressure and the residue was diluted with H$_2$O (20 mL) and carefully neutralized with solid NaHCO$_3$. The aqueous solution was extracted with EtOAc (5×25 mL), dried (Na$_2$SO$_4$) and concentrated to afford the expected product (0.180 g, 97%), TLC Rf: 0.36 (5% 2 N NH$_3$/MeOH in CH$_2$Cl$_2$). $^1$H NMR (400 MHz, CD$_3$OD): δ 8.44 (d, 1H, J=8.0 Hz); 8.31 (d, 1H, J=2.4 Hz); 8.23 (d, 1H, J=8.8 Hz); 7.93 (d, 1H, J=8.8 Hz); 7.86-7.82 (m, 2H); 7.59 (dt, 1H, J=2.0 and 8.8 Hz); 7.29 (dt, 1H, J=0.8 and 7.6 Hz); 7.00 (m, 2H); 4.39 (q, 1H, J=7.2 Hz); 1.58 (d, 3H, J=6.8 Hz). IS-MS (m/e): 411 (m+1) and 409 (m−1) H. Wang's Resin-linked 2-[4-(1-aminoethyl)-2-hydroxybenzoylamino]-N-(5-chloro-pyridin-2-yl)benzamide

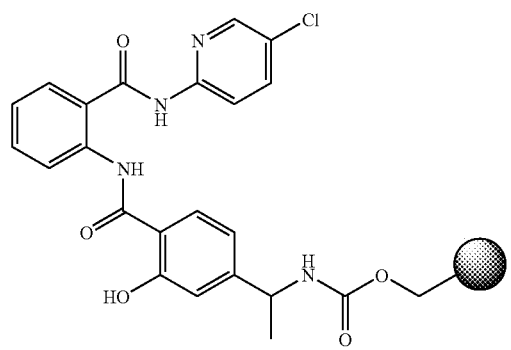

To a screw-capped vial was placed Wang-p-nitrophenyl carbonate resin (0.173 g, 1.43 mmol/g, 0.243 mmol), 2-[4-(1-aminoethyl)-2-hydroxybenzoylamino]-N-(5-chloro-pyridin-2-yl)benzamide (0.102 g, 0.292 mmol) and CH$_2$Cl$_2$: NMP (1 mL each), followed by N,N-diisopropylethylamine (0.084 mL, 0.486 mmol). The vial was capped well and shaken for 2 days. The resulting resin was filtered using a fritted funnel, washed with CH$_2$Cl$_2$, THF, MeOH (3×10 mL, each) and dried to afford the desired resin (0.217 g, 1.38 mmol/g).

I. 2-[4-(1-Aminoethyl)-2-(piperidin-3-yloxy)benzoylamino]-N-(5-chloropyridin-2-yl)benzamide trifluoroacetate A vial which was equipped with a sintered glass filter was charged with Wang's resin-linked 2-[4-(1-aminoethyl)-2-(hydroxy)benzoylamino]-N-(5-chloropyridin-2-yl)-benzamide (1.38 mmol/g, 0.150 g, 0.207 mmol), Ph$_3$P (0.271 g, 1.035 mmol), 3-hydroxy-methyl-1-tert-butoxycarbonylpiperidine (0.222 g, 1.035 mmol) and THF (14 mL). The resulting mixture was shaken well and to it was added diethylisopropylamine (0.203 mL, 1.035 mmol). The vial was capped and shaken for 4 days. The resin was filtered, washed with THF, CH$_2$Cl$_2$ and MeOH (3×5 mL, each) and further treated with trifluoroacetic acid and CH$_2$Cl$_2$ (1 mL, each) at room temperature for 30 min. After the filtration, the resin was washed with CH$_2$Cl$_2$ (3×4 mL) and the filtrate was collected and concentrated. The resulting trifluoroacetate salt was purified by preparative RPHPLC using acetonitrile and 0.1% aqueous TFA to yield the title product (24.3 mg).

MS (m/e): 508 (m+1), 506 (m−1) $^1$H NMR (400 MHz, CD$_3$OD): δ 8.40 (d, 1H, J=8.4 Hz); 8.35 (bs, 1H); 8.11 (d, 1H, J=8.8 Hz); 7.92 (d, 1H, J=8.0 Hz); 7.84 (dt, 2H, J=2.4 and 8.8 Hz); 7.60 (dt, 1H, J=1.6 and 8.4 Hz); 7.35 (bs, 1H); 7.30 (dt, 1H, J=1.2 and 7.6 Hz); 7.17 (d, 1H, J=7.6 Hz); 4.53 (m, 1H); 4.30 (m, 1H); 4.22 (m, 1H); 3.55 (m, 1H); 3.35 (m, 2H); 2.92 (m, 1H); 2.80 (m, 1H); 2.50 (m, 1H); 1.90 (m, 2H); 1.63 (d, 3H, 6.4 Hz); 1.47 (m, 1H).

EXAMPLE 114

Preparation of 5-Fluoro-N-(5-methylisoxazol-3-yl)-2-[2-(1-methylpiperidin-4-yloxy)-4-(pyrrolidin-1-yl)benzoylamino]benzamide

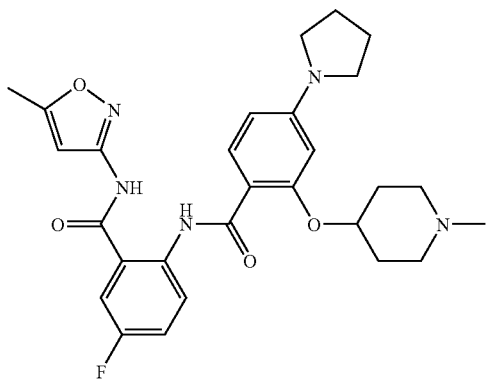

Using methods substantially equivalent to those described in Example 91-G, 5-fluoro-N-(5-methylisoxazol-3-yl)-2-[2-(1-methylpiperidin-4-ylxy)-4-(pyrrlidin-1-yl)-benzoylamino]benzamide was prepared from 6-fluoro-2-[2-(1-methylpiperidin-4-yloxy)-4-(pyrrolidin-1-yl)phenyl]-4H-3,1-benzoxazin-4-one and 3-amino-5-methylisoxazole.
$^1$NMR IS-MS, m/e 522 (m+1)

EXAMPLE 115

Preparation of 2-[2-(3-Aminopropoxy)-4-(morpholin-4-yl)benzoylamino]-N-(5-chloropyridin-2-yl)-5-fluorobenzamide

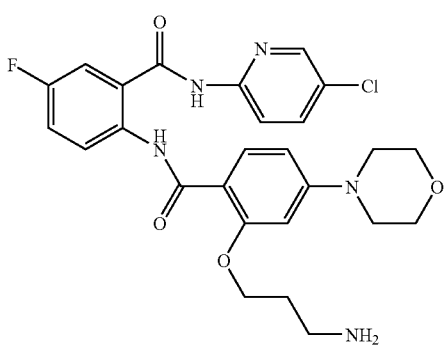

A. Methyl 2-[3-(tert-butoxycarbonylamino)propoxy]-4-(morpholin-4-yl)benzoate Using methods substantially equivalent to those described in Example 4-F, methyl 2-[3-(tert-butoxycarbonylamino)propoxy]-4-(morpholin-4-yl)benzoate (2.39 g, 6.06 mmol, 16%) was prepared from methyl 2-[3-(tert-butoxycarbonylamino)propoxy]-4-fluorobenzoate and morpholine.
$^1$NMR (300 MHz, DMSO-d$_6$): δ 7.60 (d, J=9.0 Hz, 1H); 6.84 (m, 1H); 6.50 (d, J=9.0 Hz, 1H); 6.46 (s, 1H); 3.98 (t, J=5.9 Hz, 2H); 3.68 (m, 4H); 3.22 (m, 4H); 3.10 (q, J=6.3 Hz, 2H); 1.79 (t, J=6.3 Hz, 2H); 1.33 (s, 9H). IS-MS, m/e 395.2 (m+1). Analysis for C$_{20}$H$_{30}$N$_2$O$_6$. Calc: C, 60.90; H, 7.67; N, 7.10. Found: C, 60.61; H, 7.45; N, 7.08.

B. 2-[3-(tert-Butoxycarbonylamino)propoxy]-4-(morpholin-4-yl)benzoic acid

The methyl 2-[3-(tert-butoxycarbonylamino)propoxy]-4-(morpholin-4-yl)benzoate (2.34 g, 5.93 mmol) was diluted with ethanol (60 mL) and water (60 mL). Potassium hydroxide pellets (1.64 g, 29.2 mmol) were added and the resulting mixture was heated to 70° C. After 2 hours, the reaction was concentrated in vacuo. The residue was diluted with methylene chloride (200 mL) and extracted with saturated aqueous citric acid (2×50 mL). The organic layer was dried over sodium sulfate, filtered, and concentrated to give the desired product (2.24 g, 5.90 mmol, 99%). $^1$NMR (300 MHz, DMSO-d$_6$): δ 7.59 (d, J=8.7 Hz, 1H); 6.85 (m, 1H); 6.49 (m, 2H); 4.00 (t, J=5.9 Hz, 2H); 3.68 (m, 4H); 3.21 (m, 4H); 3.07 (m, 2H); 1.79 (t, J=6.2 Hz, 2H); 1.33 (s, 9H). IS-MS m/e: 381.4 (m+1).

C. 2-[2-[3-(tert-Butoxycarbonylamino)propoxy]-4-(morpholin-4-yl)benzoylamino]-N-(5-chloropyridin-2-yl)-5-fluorobenzamide Using a procedure analogous to Example 4-C, 2-[3-(tert-butoxycarbonylamino)-propoxy]-4-(morpholin-4-yl)benzoic acid and N-(5-chloropyridin-2-yl)-2-amino-5-fluorobenzamide gave the desired product as a solid (2.56 g, 70%).
$^1$NMR IS-MS, m/e: 628.2 (m+1).

D. 2-[2-(3-Aminopropoxy)-4-(morpholin-4-yl)benzoylamino]-N-(5-chloropyridin-2-yl)-5-fluorobenzamide 2-[2-(3-Aminopropoxy)-4-(morpholin-4-yl)benzoylamino]-N-(5-chloropyridin-2-yl)-5-fluorobenzamide was prepared by methods described in example 4-G from 2-[2-[3-(tert-butoxycarbonylamino)propoxy]-4-(morpholin-4-yl)benzoylamino]-N-(5-chloropyridin-2-yl)-5-fluorobenzamide (1.82 g, quant.). $^1$NMR (300 MHz, DMSO-d$_6$) δ ppm: 8.41 (m, 2H), 8.16 (d, J=9.0 Hz, 1H), 7.98 (dd, J=2.6, 9.0 Hz, 1H), 7.83 (d, J=2.6 Hz, 1H), 7.60 (dd, J=2.6, 9.0 Hz, 1H), 7.40 (m, 1H), 6.33 (m, 2H), 4.29 (t, J=6.4 Hz, 2H), 3.73 (m, 4H), 3.27 (m, 4H), 2.57 (t, J=6.4 Hz, 2H), 1.80 (m, 2H). IS-MS, m/e: 528.1 (m+1).

EXAMPLE 116

Preparation of N-(5-Chloropyrimidin-2-yl)-5-fluoro-2-[2-(1-methylpiperidin-4-yloxy)-4-(pyrrolidin-1-yl)benzoylamino]benzamide Hydrochloride

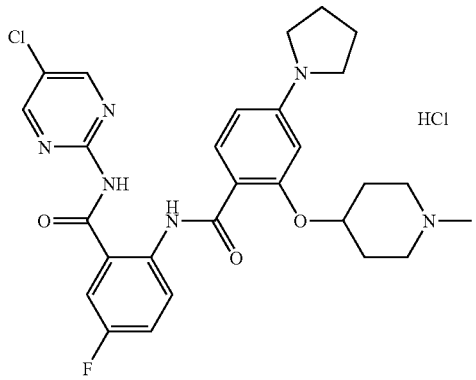

Using methods substantially equivalent to those described in Example 91-G, except using potassium t-butoxide as the base and isolating the product as a salt by evaporating an ethanolic HCl solution, N-(5-chloropyrimidin-2-yl)-5-fluoro-2-[2-(1-methylpiperidin-4-yloxy)-4-(pyrrolidin-1-yl)benzoylamino]benzamide hydrochloride was prepared from 6-fluoro-2-[4-(pyrrolidin-1-yl)-2-(1-methylpiperidin-4-yloxy)phenyl]-4H-3,1-benzoxazin-4-one and 2-amino-5-chloropyrimidine. [1]NMR IS-MS, m/e 553 (m+1)

EXAMPLE 117

Preparation of 5-Fluoro-2-[2-(1-methylpiperidin-4-yloxy)-4-(pyrrolidin-1-yl)-benzoylamino]-N-[4-(methylthio)phenyl]benzamide Hydrochloride

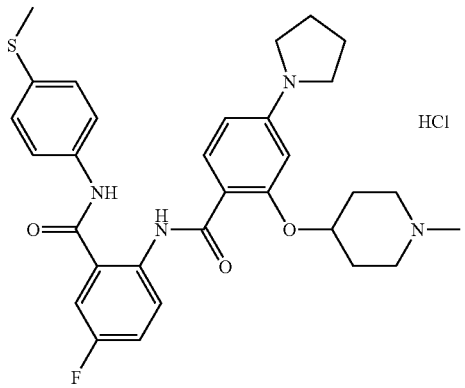

Using methods substantially equivalent to those described in Example 116, 5-fluoro-2-[2-(1-methylpiperidin-4-yloxy)-4-(pyrrolidin-1-yl)benzoylamino]-N-[4-(methylthio)phenyl]benzamide hydrochloride was prepared from 6-fluoro-2-[2-(1-methylpiperidin-4-yloxy)-4-(pyrrolidin-1-yl)phenyl]-4H-3,1-benzoxazin-4-one and 4-(methylthio)aniline.
[1]NMR IS-MS, m/e 563 (m+1)

EXAMPLE 118

Preparation of N-(3,4-Dichlorophenyl)-5-fluoro-2-[2-(1-methylpiperidin-4-yloxy)-4-(pyrrolidin-1-yl)benzoylamino]benzamide

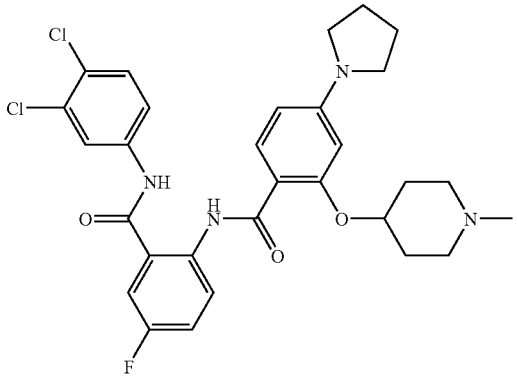

Using methods substantially equivalent to those described in Example 91-G, except using potassium t-butoxide as the base; N-(3,4-dichlorophenyl)-5-fluoro-2-[2-(1-methylpiperidin-4-yloxy)-4-(pyrrolidin-1-yl)benzoylamino]benzamide was prepared from 6-fluoro-2-[2-(1-methylpiperidin-4-yloxy)-4-(pyrrolidin-1-yl)phenyl]-4H-3,1-benzoxazin-4-one and 3,4-dichloroaniline.
[1]NMR IS-MS, m/e 585 (m+)

EXAMPLE 119

Preparation of N-(4-Chloro-2-methylphenyl)-5-fluoro-2-[2-(1-methylpiperidin-4-yloxy)-4-(pyrrolidin-1-yl)benzoylamino]benzamide Hydrochloride

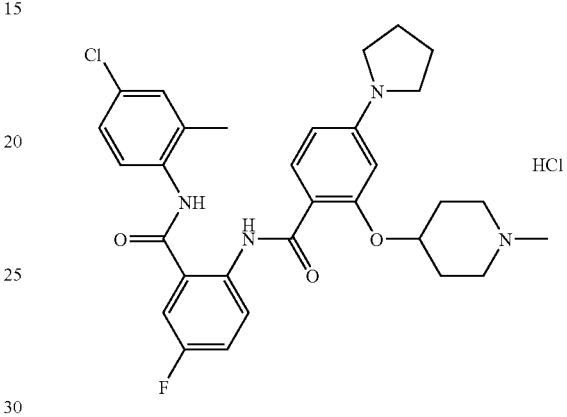

Using methods substantially equivalent to those described in Example 116, N-(4-chloro-2-methylphenyl)-5-fluoro-2-[2-(1-methylpiperidin-4-yloxy)-4-(pyrrolidin-1-yl)benzoylamino]benzamide hydrochloride was prepared from 6-fluoro-2-[2-(1-methyl-piperidin-4-yloxy)-4-(pyrrolidin-1-yl)phenyl]-4H-3,1-benzoxazin-4-one and 4-chloro-2-methylaniline.
[1]NMR IS-MS, m/e 565 (m+)

EXAMPLE 120

Preparation of 5-Fluoro-2-[2-(1-methylpiperidin-4-yloxy)-4-(pyrrolidin-1-yl)-benzoylamino]-N-(5-trifluoromethylpyridin-2-yl)benzamide Hydrochloride

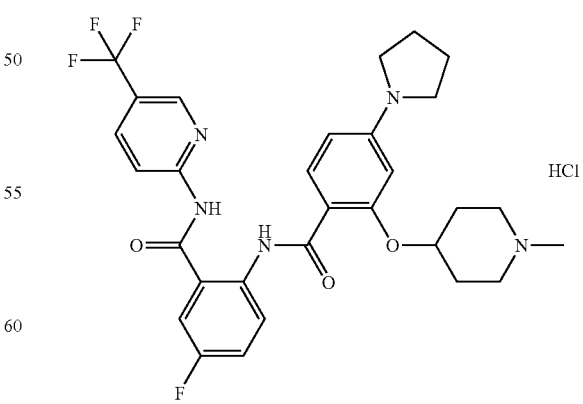

Using methods substantially equivalent to those described in Example 116, 5-fluoro-2-[2-(1-methylpiperidin-4-yloxy)-4-(pyrrolidin-1-yl)benzoylamino]-N-(5-trifluoromethylpyridin-2-yl)benzamide hydrochloride was prepared from 6-fluoro-2-[2-(1-methylpiperidin-4-yloxy)-4-(pyrrolidin-1-yl)phenyl]-4H-3,1-benzoxazin-4-one and 2-amino-5-(trifluoromethyl)aniline.

$^1$NMR IS-MS, m/e 586 (m+1)

EXAMPLE 121

Preparation of N-(2,4-Dichlorophenyl)-5-fluoro-2-[2-(1-methylpiperidin-4-yloxy)-4-(pyrrolidin-1-yl)benzoylamino]benzamide

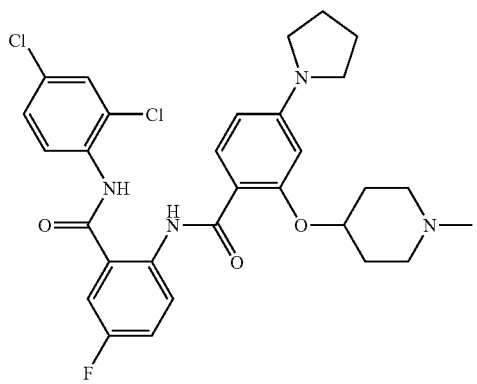

Using methods substantially equivalent to those described in Example 118, N-(2,4-dichlorophenyl)-5-fluoro-2-[2-(1-methylpiperidin-4-yloxy)-4-(pyrrolidin-1-yl)-benzoylamino]benzamide was prepared from 6-fluoro-2-[2-(1-methylpiperidin-4-yloxy)-4-(pyrrolidin-1-yl)phenyl]-4H-3,1-benzoxazin-4-one and 2,4-dichloroaniline.

$^1$NMR IS-MS, m/e 585 (m+)

EXAMPLE 122

Preparation of 5-Fluoro-2-[2-(1-methylpiperidin-4-yloxy)-4-(pyrrolidin-1-yl)-benzoylamino]-N-(2,4,6-trichlorophenyl)benzamide

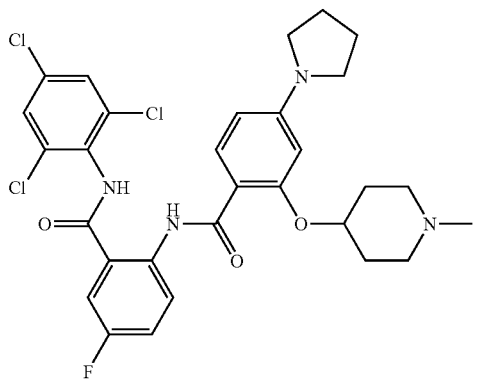

Using methods substantially equivalent to those described in Example 118, 5-fluoro-2-[2-(1-methylpiperidin-4-yloxy)-4-(pyrrolidin-1-yl)benzoylamino]-N-(2,4,6-tri-chlorophenyl)benzamide was prepared from 6-fluoro-2-[2-(1-meth-ylpiperidin-4-yloxy)-4-(pyrrolidin-1-yl)phenyl]-4H-3,1-benzoxazin-4-one and 2,3,5-trichloroaniline.

$^1$NMR IS-MS, m/e 621 (m+2)

EXAMPLE 123

Preparation of N-(5-Chloropyridin-2-yl)-2-[4-fluoro-2-(piperidin-4-yloxy)-benzoylamino]benzamide Trifluoroacetate

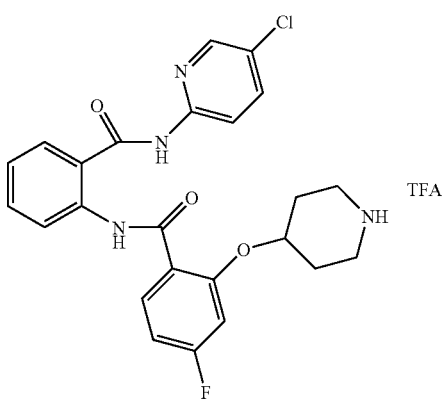

Using the procedure described in Example 4-G, 2-[4-fluoro-2-(1-tert-butoxy-carbonylpiperidin-4-yloxy)benzoylamino]-N-(5-chloropyridin-2-yl)benzamide yielded the title compound as a solid.

IR(CHCl$_3$): 1675, 1504, 1374, 1177 cm$^{-1}$; $^1$H-NMR (400 MHz, DMSO-d$_6$): δ 11.17 (s, 1H); 10.95 (s, 1H); 8.43 (s, 1H); 8.35 (m, 1H); 8.27 (d, J=8.0 Hz, 1H); 8.10 (d, J=9.2 Hz, 1H); 7.93 (d, J=8.8 Hz, 1H); 7.81 (d, J=7.2 Hz, 2H); 7.57 (t, J=8.0 Hz, 1H); 7.25-7.21 (m, 2H); 6.93 (t, J=8.0 Hz, 1H); 4.86 (m, 1H); 3.17 (m, 2H); 3.04 (m, 2H); 2.06 (m, 2H); 1.99 (m, 2H); MS-FD m/e: 469.1 (m+1). Analysis for C$_{24}$H$_{22}$ClFN$_4$O$_3$CF$_3$CO$_2$H. Calc: C, 53.57; H, 3.98; N, 9.61. Found: C, 53.89; H, 3.81; N, 9.50.

EXAMPLE 124

Preparation of N-(5-Chloropyridin-2-yl)-2-[2-[3-(dimethylamino)propoxy]-4-(morpholin-4-yl)benzoylamino]-5-fluorobenzamide

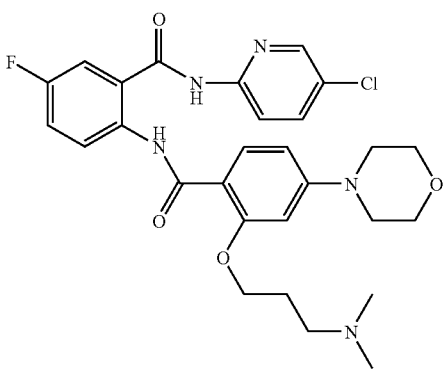

A mixture of 2-[2-(3-aminopropoxy)-4-(morpholin-4-yl)benzoylamino]-N-(5-chloropyridin-2-yl)-5-fluorobenzamide (400 mg, 0.76 mmol), paraformaldehyde (96 mg, 3.19 mmol) and MeOH (75 mL) was adjusted to pH 5-6 with AcOH. Sodium cyanoborohydride (96 mg, 1.57 mmol) was added. After stirring overnight, the reaction was acidified with 1 N HCl (pH=2) and stirred for 2 hours. Methylene chloride was added to the mixture and it was basified with 50% satd $Na_2CO_3$. The organic layer was dried ($Na_2SO_4$) and concentrated to give the desired product (418 mg, 99%).

$^1$NMR (300 MHz, DMSO-$d_6$) δ ppm: 11.34 (br s, 0.7H), 11.13 (br s, 1H), 10.96 (br s, 0.3H), 8.43 (m, 2H), 8.16 (d, J=8.6 Hz, 1H), 7.98 (dd, J=2.6, 9.0 Hz, 1H), 7.83 (d, J=8.6 Hz, 1H), 7.61 (dd, J=3.0, 9.0 Hz, 1H), 7.41 (m, 1H), 6.62 (dd, J=1.5, 9.0 Hz, 1H), 6.57 (d, J=1.5 Hz, 1H), 4.25 (t, J=6.8 Hz, 2H), 3.73 (m, 4H), 3.26 (m, 4H), 2.17 (t, J=6.8 Hz, 2H), 1.98 (s, 6H), 1.86 (m, 2H). IS-MS, m/e: 556.2 (m+1). Analysis for $C_{28}H_{31}ClFN_5O_4$. Calcd: C, 60.48; H, 5.62; N, 12.60. Found: C, 60.18; H, 5.58; N, 12.74.

EXAMPLE 125

Preparation of N-(1,3-Dimethylpyrazol-4-yl)-5-fluoro-2-[2-(1-methylpiperidin-4-yloxy)-4-(pyrrolidin-1-yl)benzoylamino]benzamide

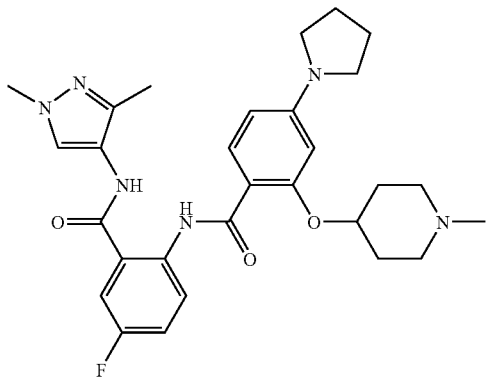

Using methods substantially equivalent to those described in Example 118, N-(1,3-dimethylpyrazol-4-yl)-5-fluoro-2-[2-(1-methylpiperidin-4-yloxy)-4-(pyrrolidin-1-yl)benzoylamino]benzamide hydrochloride was prepared from 6-fluoro-2-[4-(pyrrolidin-1-yl)-2-(1-methylpiperidin-4-yloxy)phenyl]-4H-3,1-benzoxazin-4-one and 5-amino-1,3-dimethylpyrazole.

IS-MS, m/e 535 (m+1)

EXAMPLE 126

Preparation of 5-fluoro-2-[2-(1-methylpiperidin-4-yloxy)-4-(pyrrolidin-1-yl)-benzoylamino]-N-(3-nitropyridin-2-yl)benzamide

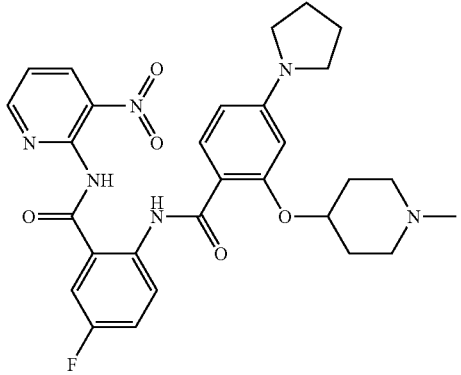

Using methods substantially equivalent to those described in Example 118, 5-fluoro-2-[2-(1-methylpiperidin-4-yloxy)-4-(pyrrolidin-1-yl)benzoylamino]-N-(3-nitro-pyridin-2-yl)benzamide hydrochloride was prepared from 6-fluoro-2-[4-(pyrrolidin-1-yl)-2-(1-methylpiperidin-4-yloxy)phenyl]-4H-3,1-benzoxazin-4-one and 2-amino-3-nitro-pyridine.

IS-MS, m/e 563 (m+1)

EXAMPLE 127

Preparation of 5-Fluoro-2-[2-(1-methylpiperidin-4-yloxy)-4-(pyrrolidin-1-yl)-benzoylamino]-N-(4-nitrophenyl)benzamide

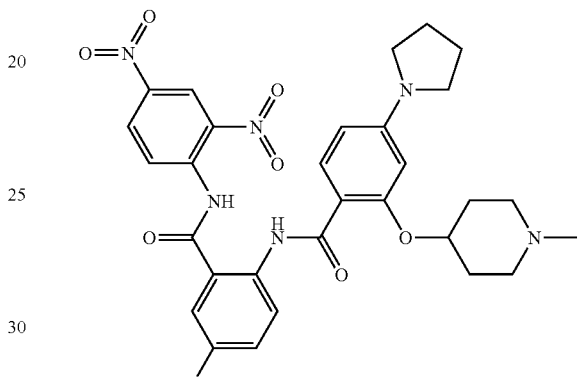

Using methods substantially equivalent to those described in Example 118, 5-fluoro-2-[2-(1-methylpiperidin-4-yloxy)-4-(pyrrolidin-1-yl)benzoylamino]-N-(4-nitro-phenyl)benzamide hydrochloride was prepared from 6-fluoro-2-[4-(pyrrolidin-1-yl)-2-(1-methylpiperidin-4-yloxy)phenyl]-4H-3,1-benzoxazin-4-one and 4-nitroaniline.

IS-MS, m/e 562 (m+1)

EXAMPLE 128

Preparation of N-(4-Acetylphenyl)-5-fluoro-2-[2-(1-methylpiperidin-4-yloxy)-4-(pyrrolidin-1-yl)benzoylamino]benzamide

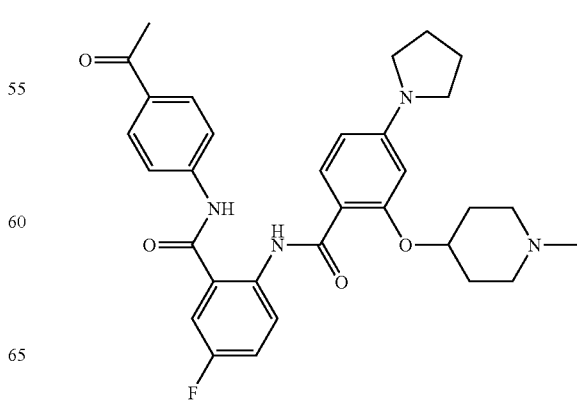

Using methods substantially equivalent to those described in Example 118, N-(4-acetylphenyl)-5-fluoro-2-[2-(1-methylpiperidin-4-yloxy)-4-(pyrrolidin-1-yl)-benzoylamino]benzamide trifluoroacetate was prepared from 6-fluoro-2-[4-(pyrrolidin-1-yl)-2-(1-methylpiperidin-4-yloxy)phenyl]-4H-3,1-benzoxazin-4-one and 4-acetylaniline.

IS-MS, m/e 558 (m+1)

EXAMPLE 129

Preparation of N-(3,5-dichloropyridin-2-yl)-5-fluoro-2-[2-(1-methylpiperidin-4-yloxy)-4-(pyrrolidin-1-yl)benzoylamino]benzamide

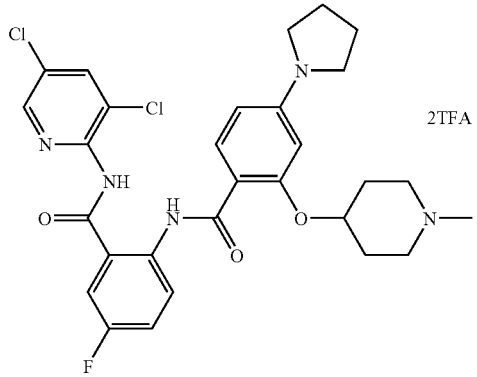

Using methods substantially equivalent to those described in Example 118, N-(3,5-dichloropyridin-2-yl)-5-fluoro-2-[2-(1-methylpiperidin-4-yloxy)-4-(pyrrolidin-1-yl)benzoylamino]benzamide trifluoroacetate was prepared from 6-fluoro-2-[4-(pyrrolidin-1-yl)-2-(1-methylpiperidin-4-yloxy)phenyl]-4H-3,1-benzoxazin-4-one and 3,5-dichloropyridine.

IS-MS, m/e 586 (m+1)

EXAMPLE 130

Preparation of 5-Fluoro-2-[2-(1-methylpiperidin-4-yloxy)-4-(pyrrolidin-1-yl)-benzoylamino]-N-(3-methylpyridin-2-yl)benzamide

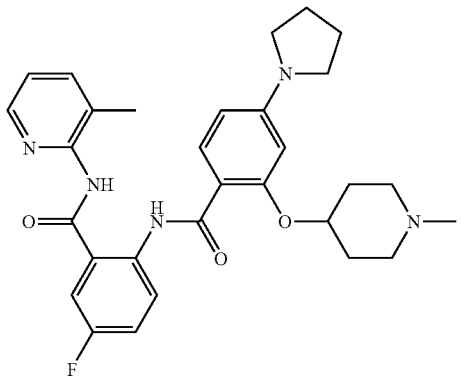

Using methods substantially equivalent to described in Example 118, 5-fluoro-2-[2-(1-methylpiperidin-4-yloxy)-4-(pyrrolidin-1-yl)benzoylamino]-N-(3-methylpyridin-2-yl) benzamide trifluoroacetate was prepared from 6-fluoro-2-[4-(pyrrolidin-1-yl)-2-(1-methylpiperidin-4-yloxy)phenyl]-4H-3,1-benzoxazin-4-one and 2-amino-3-methylpyridine.

IS-MS, m/e 532 (m+1)

EXAMPLE 131

Preparation of N-(4,6-Dimethylpyridin-2-yl)-5-fluoro-2-[2-(1-methylpiperidin-4-yloxy)-4-(pyrrolidin-1-yl)benzoylamino]benzamide

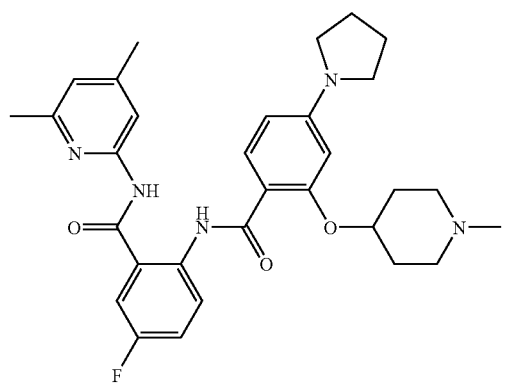

Using methods substantially equivalent to those described in Example 118, N-(4,6-dimethylpyridin-2-yl)-5-fluoro-2-[2-(1-methylpiperidin-4-yloxy)-4-(pyrrolidin-1-yl)benzoylamino]benzamide trifluoroacetate was prepared from 6-fluoro-2-[4-(pyrrolidin-1-yl)-2-(1-methylpiperidin-4-yloxy)phenyl]-4H-3,1-benzoxazin-4-one and 4,6-dimethylpyridine.

IS-MS, m/e 546 (m+1)

EXAMPLE 132

Preparation of 5-fluoro-N-(4-methoxy-2-nitrophenyl)-2-[2-(1-methylpiperidin-4-yloxy)-4-(pyrrolidin-1-yl)benzoylamino]benzamide

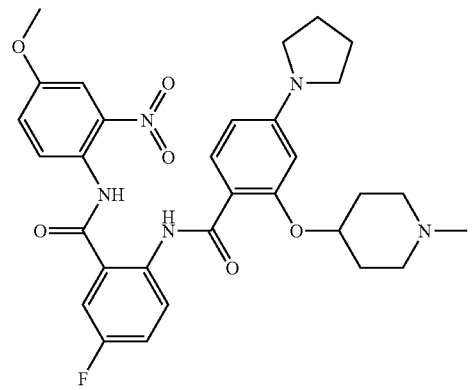

Using methods substantially equivalent to those described in Example 118, 5-fluoro-N-(4-methoxy-2-nitrophenyl)-2-[2-(1-methylpiperidin-4-yloxy)-4-(pyrrolidin-1-yl)benzoylamino]benzamide trifluoroacetate was prepared from 6-fluoro-2-[4-(pyrrolidin-1-yl)-2-(1-methylpiperidin-4-yloxy)phenyl]-4H-3,1-benzoxazin-4-one and 4-methoxy-2-nitroaniline.

IS-MS, m/e 592 (m+1)

EXAMPLE 133

Preparation of N-(4-Bromo-2-chlorophenyl)-5-fluoro-2-[2-(1-methylpiperidin-4-yloxy)-4-(pyrrolidin-1-yl)benzoylamino]benzamide

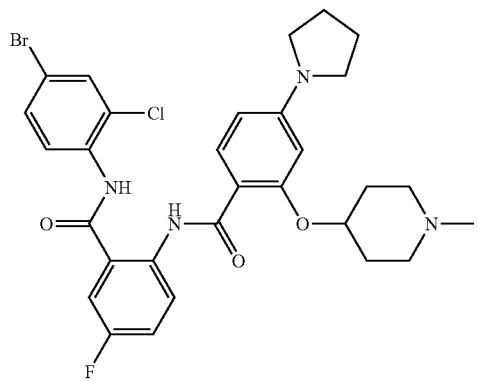

Using methods substantially equivalent to those described in Example 118, N-(4-bromo-2-chlorophenyl)-5-fluoro-2-[2-(1-methylpiperidin-4-yloxy)-4-(pyrrolidin-1-yl)benzoylamino]benzamide trifluoroacetate was prepared from 6-fluoro-2-[4-(pyrrolidin-1-yl)-2-(1-methylpiperidin-4-yloxy)phenyl]-4H-3,1-benzoxazin-4-one and 4-bromo-2-chloroaniline.

IS-MS, m/e 631 (m+2)

EXAMPLE 134

Preparation of N-(2-Chloro-4-nitrophenyl)-5-fluoro-2-[2-(1-methylpiperidin-4-yloxy)-4-(pyrrolidin-1-yl)benzoylamino]benzamide

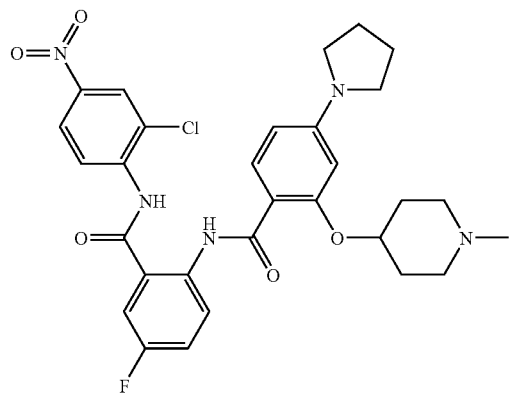

Using methods substantially equivalent to those described in Example 118, N-(2-chloro-4-nitrophenyl)-5-fluoro-2-[2-(1-methylpiperidin-4-yloxy)-4-(pyrrolidin-1-yl)benzoylamino]benzamide trifluoroacetate was prepared from 6-fluoro-2-[4-(pyrrolidin-1-yl)-2-(1-methylpiperidin-4-yloxy)phenyl]-4H-3,1-benzoxazin-4-one and 2-chloro-4-nitroaniline.

IS-MS, m/e 596 (m+1)

EXAMPLE 135

Preparation of 5-Fluoro-2-[2-(1-methylpiperidin-4-yloxy)-4-(pyrrolidin-1-yl)-benzoylamino]-N-(2-methoxyphenyl)benzamide

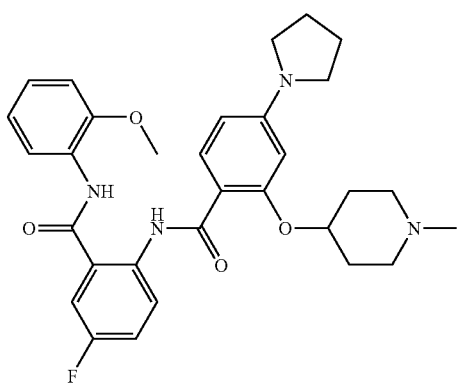

Using methods substantially equivalent to those described in Example 118, 5-fluoro-2-[2-(1-methylpiperidin-4-yloxy)-4-(pyrrolidin-1-yl)benzoylamino]-N-(2-methoxyphenyl)benzamide trifluoroacetate was prepared from 6-fluoro-2-[4-(pyrrolidin-1-yl)-2-(1-methylpiperidin-4-yloxy)phenyl]-4H-3,1-benzoxazin-4-one and 2-methoxyaniline.

IS-MS, m/e 547 (m+1)

EXAMPLE 136

Preparation of N-(5-Chloropyridin-2-yl)-2-[2-(piperidin-4-yloxy)-4-(pyrrolidin-1-yl)-benzoylamino]benzenesulfonamide

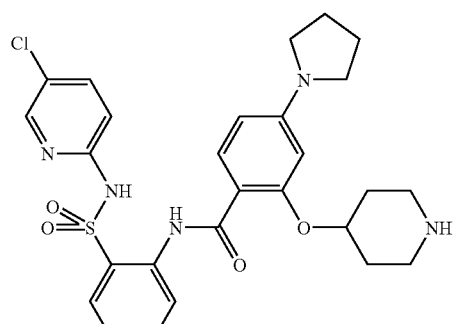

A.
N-(5-Chloropyridin-2-yl)-2-nitrobenzenesulfonamide

Using a procedure similar to Example 16-F, N-(5-chloropyridin-2-yl)-2-nitro-benzenesulfonamide was prepared from 2-nitrobenzenesulfonyl chloride and 2-amino-5-chloropyridine.

FD-MS, m/e (m+1) 313.9

B. 2-Amino-N-(5-chloropyridin-2-yl)benzenesulfonamide

To a solution of N-(5-chloropyridin-2-yl)-2-nitrobenzenesulfonamide in THF (300 mL) and CH$_3$OH (150 mL) at room temperature was added Ni(OAc)$_2$.4H$_2$O (9.62 g, 38.6 mmol). The mixture was stirred until all the solid dissolved. The dark green solution was then cooled to 0° C. and NaBH$_4$ (2.92 g, 72.3 mmoles) was added portionwise. The reaction was stirred at room temperature for 10 min. The solvent was stripped away and the residue partitioned between EtOAc (300 mL) and a mixture of H$_2$O (150 mL) and conc NH$_4$OH (150 mL). The aqueous layer was further extracted with EtOAc (3×200 mL). The combined extracts were washed once with brine, dried (Na$_2$SO$_4$), filtered and the solvent removed. Chromatography using 10-20% Et$_2$O/CHCl$_3$ afforded 1.6 g (5.64 mmoles, 29% yield) of product as a gray solid.

TLC (20% Et$_2$O/CHCl$_3$) R$_f$=0.31 $^1$NMR IS-MS, m/e 284.1 Analysis for C$_{11}$H$_{10}$ClN$_3$O$_2$S. Calcd: C, 46.56; H, 3.55; N, 14.81. Found: C, 46.46; H, 3.64; N, 14.59.

C. 2-[2-(1-tert-Butoxycarbonylpiperidin-4-yloxy)-4-(pyrrolidin-1-yl)benzoylamino]-N-(5-chloropyridin-2-yl)benzenesulfonamide To a solution of 2-(1-tert-butoxycarbonylpiperidin-4-yloxy)-4-(pyrrolidin-1-yl)-benzoic acid (781 mg, 2.0 mmol), DMF (catalytic) and pyridine (178 µL, 2.2 mmol) in CH$_2$Cl$_2$ (20 mL) at 0° C. was added dropwise 2 M oxalyl chloride in CH$_2$Cl$_2$ (1.1 mL, 2.2 mmol). This mixture was allowed to warm to room temperature and stirred for 30 min. The acid chloride solution was then added to a solution of 2-amino-N-(5-chloro-pyridin-2-yl)benzenesulfonamide (624 mg, 2.2 mmol) and pyridine (178 µL, 2.2 mmol) in CH$_2$Cl$_2$ (20 mL). The reaction was stirred at room temperature for 6 h. The reaction mixture was partitioned between saturated NaHCO$_3$ (200 mL) and EtOAc (3×300 mL). The extracts were washed with H$_2$O (200 mL) and brine, dried (Na$_2$SO$_4$), filtered, and the solvent removed. Flash chromatography with 3-10% acetone/CHCl$_3$ afforded 620 mg (0.945 mmol, 47% yield) of product.

TLC (10% acetone/CHCl$_3$) R$_f$=0.55 $^1$NMR IS-MS, m/e 656.3 Analysis for C$_{32}$H$_{38}$ClN$_5$O$_6$S. Calcd: C, 58.57; H, 5.84; N, 10.67. Found: C, 58.15; H, 5.96; N, 10.06.

D. N-(5-chloropyridin-2-yl)-2-[2-(piperidin-4-yloxy)-4-(pyrrolidin-1-yl)-benzoylamino]benzenesulfonamide To a solution of 2-[2-(1-tert-butoxycarbonylpiperidin-4-yloxy)-4-(pyrrolidin-1-yl)benzoylamino]-N-(5-chloropyridin-2-yl)benzsulfonamide (620 mg, 0.945 mmol) in CH$_2$Cl$_2$ (15 mL) was added trifluoroacetic acid (2.5 mL). This mixture was stirred at room temperature overnight. The solvent was removed in vacuo and the residue purified by flash chromatography using 5% 2 M NH$_3$ in CH$_3$OH and 15% CH$_3$OH in CHCl$_3$. The chromatography product crystallized from CH$_2$Cl$_2$ affording 120 mg (0.216 mmol, 23% yield) of product.

$^1$NMR IS-MS, m/e 556.3

EXAMPLE 137

Preparation of 2-[2-[2-(tert-Butoxycarbonylamino) ethoxy]-4-methoxybenzoyl-amino]-N-(4-methoxyphenyl)-4-nitrobenzamide

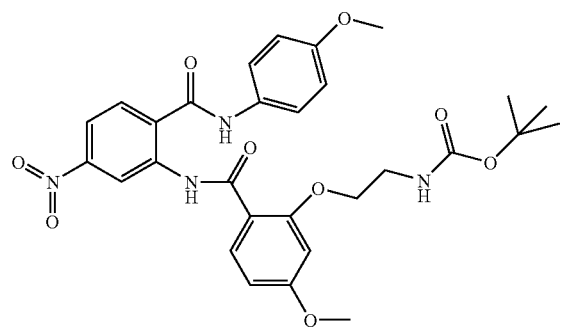

A. 2-Amino-N-(4-methoxyphenyl)-4-nitrobenzamide

Using a procedure analogous to Example 16-F, 4-nitroisatoic anhydride and 4-methoxyaniline gave the desired product as a greenish-yellow solid (2.73 g, 95%).

$^1$NMR (300 MHz, DMSO-d$_6$) δ ppm: 7.76 (d, J=8.7 Hz, 1H), 7.58 (m, 3H), 7.32 (dd, J=2.1, 8.7 Hz, 1H), 6.90 (d, J=9.3 Hz, 2H), 3.72 (s, 3H). IS-MS, m/e: 286 (m–1).

B. Methyl 2-(2-tert-butoxycarbonylaminoethoxy)-4-methoxybenzoate

Using a procedure similar to that in Example 21-C, methyl 2-(2-tert-butoxy-carbonylaminoethoxy)-4-methoxybenzoate was produced from methyl 2-hydroxy-4-methoxybenzoate and 2-(tert-butoxycarbonylamino)ethanol.

C. 2-(2-tert-Butoxycarbonylaminoethoxy)-4-methoxybenzoic acid

Using a procedure analogous to Example 21-D, methyl 2-(2-tert-butoxycarbonyl-aminoethoxy)-4-methoxy benzoate gave the desired product as a white solid (14.52 g, 99%).

$^1$NMR (300 MHz, CDCl$_3$) δ ppm: 8.14 (d, J=8.7 Hz, 1H), 6.66 (dd, J=2.1, 8.7 Hz, 1H), 6.54 (d, J=2.1 Hz, 1H), 5.02 (br s, 1H), 4.28 (t, J=5.1 Hz, 2H), 3.88 (s, 3H), 3.64 (m, 2H), 1.46 (s, 9H). FD-MS, m/e: 311 (m+1) Analysis for C$_{15}$H$_{21}$NO$_6$. Calcd: C, 57.87; H, 6.80; N, 4.50. Found: C, 57.94; H, 6.73; N, 4.68.

D. 2-[2-[2-(tert-butoxycarbonylamino)ethoxy]-4-methoxybenzoylamino]-N-(4-methoxyphenyl)-4-nitrobenzamide Using methods substantially equivalent to those described in Example 4-E, 2-[2-[2-(tert-butoxycarbonylamino) ethoxy]-4-methoxybenzoylamino]-N-(4-methoxyphenyl)-4-nitrobenzamide (833 mg, 1.43 mmol, 44%) was prepared from 2-(2-tert-butoxy-carbonylaminoethoxy)-4-methoxybenzoic acid and 2-amino-N-(4-methoxyphenyl)-4-nitrobenzamide.

IR(CHCl$_3$): 1703, 1662, 1606, 1533, 1511, 1260 cm$^{-1}$.
$^1$NMR (300 MHz, DMSO-d$_6$): δ 11.48 (s, 1H); 10.67 (s, 1H); 9.37 (s, 1H); 8.76 (m, 1H); 8.02-7.93 (m, 3H); 7.65 (d, J=9.0 Hz, 2H); 6.92 (d, J=9.0 Hz, 2H); 6.76 (s, 1H); 6.67 (d, J=8.7 Hz, 1H); 4.25 (t, J=5.6 Hz, 2H); 3.81 (s, 3H); 3.71 (s, 3H); 3.33 (d, J=5.7 Hz, 2H); 1.25 (s, 9H). FD-MS m/e: 580.0 (m). Analysis for C$_{29}$H$_{32}$N$_4$O$_9$. Calc: C, 59.99; H, 5.56; N, 9.65. Found: C, 59.74; H, 5.48; N, 9.62.

EXAMPLE 138

Preparation of 2-[2-(2-Aminoethoxy)-4-methoxy-benzoylamino]-N-(4-methoxy-phenyl)-4-nitrobenzamide

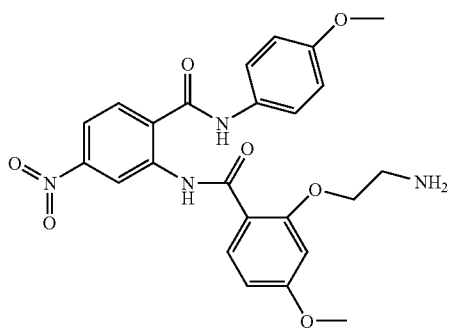

Using methods substantially equivalent to those described in Example 4-G except 1 N NaOH was used as the base, 2-[2-(2-aminoethoxy)-4-methoxybenzoylamino]-N-(4-methoxyphenyl)-4-nitrobenzamide (262 mg, 0.55 mmol; 42%) was prepared from 2-[2-[2-(tert-butoxycarbonylamino) ethoxy]-4-methoxybenzoylamino]-N-(4-methoxy-phenyl)-4-nitrobenzamide.

$^1$NMR (300 MHz, DMSO-d$_6$): δ 9.32 (s, 1H); 8.02-7.92 (m, 3H); 7.62 (d, J=8.7 Hz, 2H); 6.92 (d, J=9.0 Hz, 2H); 6.71 (s, 1H); 6.67 (d, J=8.7 Hz, 2H); 4.18 (t, J=5.7 Hz, 2H); 3.80 (s, 3H); 3.71 (s, 3H); 2.88 (t, J=5.4 Hz, 2H). IS-MS m/e: 481.2 (m+1). Analysis for C$_{24}$H$_{24}$N$_4$O$_7$. Calc: C, 59.96; H, 5.04; N, 11.66. Found: C, 60.17; H, 5.13; N, 11.73.

EXAMPLE 139

Preparation of 4-Amino-2-[2-[2-(thiophen-2-ylcarbonylamino)ethoxy]-4-methoxy-benzoylamino]-N-(4-methoxyphenyl)benzamide

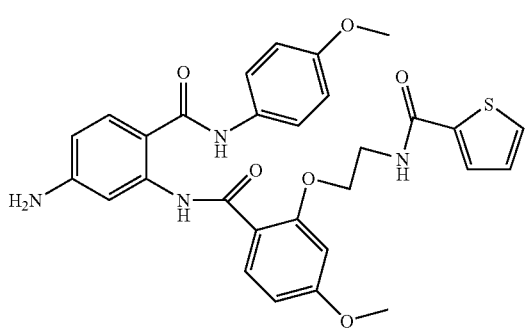

A. 2-[4-Methoxy-2-[2-(thiophen-2-ylcarbonylamino) ethoxy]benzoylamino]-N-(4-methoxyphenyl)-4-nitrobenzamide A mixture of 2-[2-(2-aminoethoxy)-4-methoxybenzoylamino]-N-(4-methoxy-phenyl)-4-nitrobenzamide (227 mg, 0.47 mmol), P-EPC resin (2.09 g, 1.78 mmol), and thiophene-2-carboxylic acid (144 mg, 1.12 mmol) in methylene chloride (15 mL) was shaken in a screw top vial overnight. The reaction was filtered and the solids were washed with 10% methanol in chloroform. The filtrate was concentrated to yield the desired product (265 mg, 0.45 mmol, 95%) as a greenish solid.

$^1$NMR (300 MHz, DMSO-d$_6$): δ 11.51 (s, 1H); 10.65 (s, 1H); 9.31 (s, 1H); 8.55 (s, 1H); 8.02-7.92 (m, 3H); 7.65 (d, J=6.9 Hz, 4H); 6.97 (m, 1H); 6.90 (d, J=8.7 Hz, 2H); 6.82 (s, 1H); 6.66 (d, J=9.0 Hz, 1H); 4.41 (t, J=6.0 Hz, 2H); 3.77 (s, 3H); 3.67 (s, 3H); 3.61 (d, J=5.7 Hz, 2H). IS-MS m/e: 591.4 (m+1).

B. 4-Amino-2-[2-[2-(thiophen-2-ylcarbonylamino) ethoxy]-4-methoxybenzoyl-amino]-N-(4-methoxyphenyl)benzamide The 2-[2-[4-methoxy-2-(thiophen-2-ylcarbonylamino) ethoxy]benzoylamino]-N-(4-methoxyphenyl)-4-nitrobenzamide (258 mg, 0.44 mmol) was diluted with methanol (20 mL) and THF (20 mL). Nickel acetate tetrahydrate (220 mg, 0.88 mmol) was added and the mixture was cooled to 0° C. Sodium borohydride (72 mg, 1.90 mmol) was then added in portions. Vigorous bubbling occurred and the reaction turned black. After 15 minutes, the reaction was concentrated in vacuo. The crude residue was diluted with EtOAc (60 mL), water (20 mL), and concentrated ammonium hydroxide (10 mL). The resulting mixture was stirred for 5 minutes and then it was poured into a separatory funnel and the layers were separated. The organic layer was washed with water (20 mL) and brine (20 mL) and then dried over magnesium sulfate, filtered and concentrated to give the desired product (201 mg, 0.36 mmol, 81%) as a grey solid.

$^1$NMR (300 MHz, DMSO-d$_6$): δ 11.85 (s, 1H); 9.89 (s, 1H); 8.57 (s, 1H); 7.85-7.80 (m, 2H); 7.68 (d, J=4.8 Hz, 1H); 7.56-7.49 (m, 4H); 7.01 (t, J=4.2 Hz, 1H); 6.82 (d, J=8.7 Hz, 2H); 6.76 (s, 1H); 6.61 (d, J=8.4 Hz, 1H); 6.30 (d, J=7.5 Hz, 1H); 5.78 (br s, 2H); 4.33 (t, J=5.9 Hz, 2H); 3.77 (s, 3H); 3.64 (s, 3H); 3.29 (m, 2H). IS-MS m/e: 561.2 (m+1).

EXAMPLE 140

Preparation of 2-[4-Methoxy-2-(piperidin-4-yloxy) benzoylamino]-N-(4-methoxy-phenyl)-4-nitrobenzamide

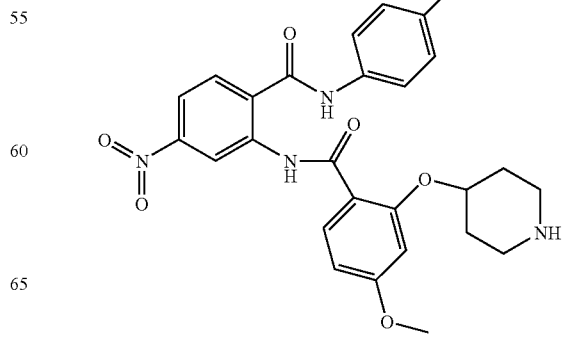

A. Methyl 2-(1-tert-butoxycarbonylpiperidin-4-yloxy)-4-methoxybenzoate

Using a procedure similar to that used in Example 21-C, methyl 2-(1-tert-butoxy-carbonylpiperidin-4-yloxy)-4-methoxybenzoate (10.38 g, 71%) was prepared from methyl 2-hydroxy-4-methoxybenzoate and 4-hydroxy-1-tert-butoxycarbonylpiperidine.

B. 2-(1-tert-Butoxycarbonylpiperidin-4-yloxy)-4-methoxybenzoic acid

Using a procedure analogous to Example 21-D, methyl 2-(1-tert-butoxycarbonyl-piperidin-4-yloxy)-4-methoxybenzoate gave the desired product as a white solid (9.95 g, 98%).

$^1$NMR (300 MHz, CDCl$_3$) δ ppm: 8.17 (d, J=8.7 Hz, 1H), 6.68 (dd, J=2.1, 8.7 Hz, 1H), 6.55 (d, J=2.1 Hz, 1H), 4.72 (m, 1H), 3.89 (s, 3H), 3.85 (m, 2H), 3.30 (m, 2H), 2.11 (m, 2H), 1.87 (m, 2H), 1.49 (s, 9H). Analysis for C$_{18}$H$_{25}$NO$_6$. Calcd: C, 61.52; H, 7.17; N, 3.99. Found: C, 61.55; H, 7.26; N, 3.80.

C. 2-[2-(1-tert-Butoxycarbonylpiperidin-4-yloxy)-4-methoxybenzoylamino]-N-(4-methoxyphenyl)-4-nitrobenzamide Using methods substantially equivalent to those described in example 4-E, 2-[2-(1-tert-butoxycarbonylpiperidin-4-yloxy)-4-methoxybenzoylamino]-N-(4-methoxy-phenyl)-4-nitrobenzamide (1.64 g, 2.64 mmol, 93%) was prepared from 2-(1-tert-butoxy-carbonylpiperidin-4-yloxy)-4-methoxybenzoic acid and N-(4-methoxyphenyl)-2-amino-4-nitrobenzamide.

IR(CHCl$_3$): 1670, 1533, 1245 cm$^{-1}$. $^1$NMR (300 MHz, DMSO-d$_6$): δ 11.17 (s, 1H); 10.69 (s, 1H); 9.33 (s, 1H); 8.02-7.96 (m, 2H); 7.87 (d, J=9.0 Hz, 1H); 7.62 (d, J=9.0 Hz, 2H); 6.91 (d, J=9.0 Hz, 2H); 6.74 (s, 1H); 6.67 (d, J=8.7 Hz, 1H); 4.74 (m, 1H); 3.80 (s, 3H); 3.71 (s, 3H); 3.68 (m, 2H); 2.99 (m, 2H); 1.83 (br s, 2H); 1.33 (s, 9H). IS-MS m/e: 621.6 (m+1). Analysis for C$_{32}$H$_{36}$N$_4$O$_9$. Calc: C, 61.93; H, 5.85; N, 9.03. Found: C, 62.17; H, 6.04; N, 9.03.

D. 2-[4-Methoxy-2-(piperidin-4-yloxy)benzoylamino]-N-(4-methoxyphenyl)-4-nitrobenzamide Using methods substantially equivalent to those described in example 4-G, except that 1 N NaOH was used as the base, 2-[4-methoxy-2-(piperidin-4-yloxy)benzoylamino]-N-(4-methoxyphenyl)-4-nitrobenzamide (1.08 g, 2.07 mmol, 82%) was prepared from 2-[2-(1-tert-butoxycarbonylpiperidin-4-yloxy)-4-methoxybenzoylamino]-N-(4-methoxy-phenyl)-4-nitrobenzamide. IR(CHCl$_3$): 1606, 1532, 1511, 1254 cm$^{-1}$.

$^1$NMR (300 MHz, DMSO-d$_6$): δ 9.42 (s, 1H); 8.04-7.95 (m, 2H); 7.85 (d, J=8.7 Hz, 1H); 7.63 (d, J=8.7 Hz, 2H); 6.92 (d, J=8.7 Hz, 2H); 6.69-6.64 (m, 2H); 4.58 (m, 1H); 3.79 (s, 3H); 3.71 (s, 3H); 2.70 (d, J=12.3 Hz, 2H); 2.42 (m, 2H); 1.81-1.76 (m, 2H); 1.58-1.54 (m, 2H). IS-MS m/e: 521.2 (m+1). Analysis for C$_{27}$H$_{28}$N$_4$O$_7$. Calc: C, 62.30; H, 5.42; N, 10.76. Found: C, 62.09; H, 5.61; N, 10.55.

EXAMPLE 141

Preparation of 4-Amino-N-(4-methoxyphenyl)-2-[4-methoxy-2-[1-(thiophen-2-yl-carbonyl)piperidin-4-yloxy]benzoylamino]benzamide

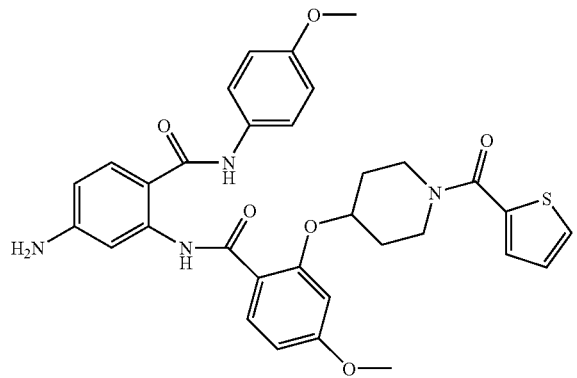

A. N-(4-Methoxyphenyl)-2-[4-methoxy-2-[1-(thiophen-2-ylcarbonyl)piperidin-4-yloxy]benzoylamino]-4-nitrobenzamide Using methods substantially equivalent to those described in Example 139-A, N-(4-methoxyphenyl)-2-[4-methoxy-2-[1-(thiophen-2-ylcarbonyl)piperidin-4-yloxy]-benzoylamino]-4-nitrobenzamide (192 mg, 0.30 mmol, 78%) was prepared from N-(4-methoxyphenyl)-2-[4-methoxy-2-(piperidin-4-yloxy)benzoylamino]-4-nitro-benzamide and thiophene 2-carboxylic acid.

$^1$NMR (300 MHz, DMSO-d$_6$): δ 11.19 (s, 1H); 10.68 (s, 1H); 9.34 (s, 1H); 8.04-7.95 (m, 2H); 7.90 (d, J=9.0 Hz, 1H); 7.71 (d, J=4.8 Hz, 1H); 7.57 (d, J=8.7 Hz, 2H); 7.29 (d, J=3.3 Hz, 1H); 7.07 (t, J=4.2 Hz, 1H); 6.81 (d, J=9.0 Hz, 3H); 6.68 (d, J=9.3 Hz, 1H); 4.91 (m, 1H); 3.99 (d, J=7.2 Hz, 4H); 3.81 (s, 3H); 3.66 (s, 3H); 1.95 (m, 4H). IS-MS m/e: 631.2 (m+1).

B. 4-Amino-N-(4-methoxyphenyl)-2-[4-methoxy-2-[1-(thiophen-2-ylcarbonyl)-piperidin-4-yloxy]benzoylamino]benzamide Using methods substantially equivalent to those described in example 139-B, 4-amino-N-(4-methoxyphenyl)-2-[4-methoxy-2-[1-(thiophen-2-ylcarbonyl)piperidin-4-yloxy]benzoylamino]benzamide was prepared from N-(4-methoxyphenyl)-2-[4-methoxy-2-[1-(thiophen-2-ylcarbonyl)piperidin-4-yloxy]benzoylamino]-4-nitrobenzamide.

$^1$NMR (300 MHz, DMSO-d$_6$): δ 11.68 (s, 1H); 9.84 (s, 1H); 7.86 (s, 1H); 7.74-7.68 (m, 2H); 7.47 (d, J=8.7 Hz, 2H); 7.23 (s, 1H); 7.05 (s, 1H); 6.83-6.69 (m, 3H); 6.62 (d, J=8.1 Hz, 1H); 6.29 (d, J=8.4 Hz, 1H); 5.80 (s, 2H); 4.83 (m, 1H); 3.84 (m, 2H); 3.78 (s, 3H); 3.64 (s, 3H); 3.39 (m, 2H); 1.90 (br s, 4H). IS-MS m/e: 601.4 (m+1). Analysis for C$_{32}$H$_{32}$N$_4$O$_6$S. Calc: C, 63.98; H, 5.37; N, 9.33. Found: C, 64.28; H, 5.55; N, 9.03.

EXAMPLE 142

Preparation of N-(5-Chloropyridin-2-yl)-4-fluoro-2-[4-(ethylsulfonyl)-2-(3-amino-propyloxy)benzoylamino]benzamide

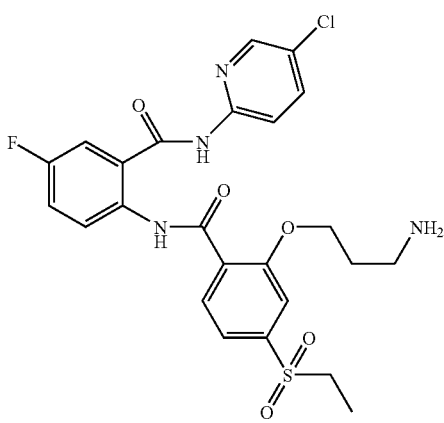

A. Methyl 2-Hydroxy-4-(ethylthio)benzoate

To a solution of methyl 4-fluoro-2-(methoxymethoxy)benzoate (10.6 g, 50 mmol) and DMSO (20 mL), under nitrogen, was added sodium ethanethiolate (5.8 g, 55 mmol) in portions. The exothermic reaction was stirred for 19 h, diluted with water, and extracted with ethyl acetate. The organic layer was concentrated; and the residue was dissolved in ether, filtered through diatomaceus earth, and concentrated to give intermediate methyl 4-(ethylthio)-2-(methoxymethoxy)benzoate.

To this intermediate was added methylene chloride (75 mL), TFA (377 mL), and water (377 mL); and the mixture was stirred for 0.5 h. The reaction was concentrated and chromatographed (silica gel, 5% ethyl acetate/hexane) to give the title compound (5.8 g, 55%).

$^1$NMR (250 MHz, CDCl$_3$): δ 10.87 (s, 1H); 7.71 (d, J=8.5 Hz, 1H); 6.84 (d, J=1.8 Hz, 1H); 6.76 (dd, J=1.8, 8.5 Hz, 1H); 3.96 (s, 3H); 3.02 (q, J=7.3 Hz, 2H); 1.40 (t, J=7.3 Hz, 3H). IS-MS, m/e 213.1 (m+1).

B. Methyl 2-(3-t-Butoxycarbonylaminopropoxy)-4-(ethylthio)benzoate

Using a procedure analogous to Example 21-C, methyl 2-hydroxy-4-(ethylthio)-benzoate and 3-t-butoxycarbonylaminopropanol gave the title compound as a solid (10.41 g, 85%).

$^1$NMR (250 MHz, CHCl$_3$): δ 7.85 (d, J=8.2 Hz, 1H), 6.80 (m, 2H), 6.12 (br s, 1H), 4.14 (t, 5.8 Hz, 2H), 3.91 (s, 3H), 3.43 (m, 2H), 3.03 (q, J=7.3 Hz, 2H), 2.09 (m, 2H), 1.48 (s, 9H), 1.39 (t, J=7.3 Hz, 3H). IS-MS, m/e: 370.1 (m+1).

C. 2-(3-t-Butoxycarbonylaminopropoxy)-4-(ethylthio)benzoic Acid

Using a procedure analogous to Example 94-B, methyl 2-(3-t-butoxycarbonyl-aminopropoxy)-4-(ethylthio)benzoate gave the title compound as a solid (8.28 g, 96%).

$^1$NMR (250 MHz, CDCl$_3$): δ 8.04 (d, J=8.5 Hz, 1H), 6.97 (dd, J=1.5, 8.5 Hz, 1H), 6.88 (d, J=1.5 Hz, 1H), 4.94 (br s, 1H), 4.27 (t, J=6.4 Hz, 2H), 3.05 (q, J=7.3 Hz, 2H), 2.11 (m, 2H), 1.44 (s, 9H), 1.40 (t, J=7.3 Hz, 3H). IS-MS, m/e: 356.3 (m+1). Analysis for C$_{17}$H$_{25}$NO$_5$S. Calcd: C, 57.44; H, 7.09; N, 3.94. Found: C, 57.60; H, 7.05; N, 4.02.

D. N-(5-Chloropyridin-2-yl)-4-fluoro-2-[4-ethylthio-2-(3-(t-butoxycarbonylamino)-propyloxy)benzoylamino]benzamide Using a procedure analogous to Example 4-E, N-(5-chloropyridin-2-yl)-4-fluoro-2-aminobenzamide and 4-(ethylthio)-2-(3-(t-butoxycarbonylamino)propyloxy)benzoic acid gave the title compound as a solid (0.93 g, 44%).

$^1$NMR (300 MHz, CDCl$_3$) ES-MS, m/e 603.2 (m+1). Analysis for C$_{29}$H$_{32}$ClFN$_4$O$_5$S. Calcd: C, 57.75; H, 5.35; N, 9.29. Found: C, 57.40; H, 5.23; N, 9.11.

E. N-(5-Chloropyridin-2-yl)-4-fluoro-2-[4-ethylsulfonyl-2-(3-aminopropyloxy)-benzoylamino]benzamide Using a sequential procedures analogous to Example 102-A and Example 4-G, N-(5-chloropyridin-2-yl)-4-fluoro-2-[4-ethylthio-2-(3-(t-butoxycarbonyamino)-propyloxy) benzoylamino]benzamide gave the title compound as a solid (0.6 g, 54%).

$^1$NMR (300 MHz, CD$_3$OD) ES-MS, m/e 535.1 (m+1). Analysis for C$_{24}$H$_{24}$ClFN$_4$O$_5$S. Calcd: C, 53.88; H, 4.52; N, 10.47. Found: C, 53.48; H, 4.52; N, 10.30.

EXAMPLE 143

Preparation of 2-[2-(3-Aminopropoxy)-4-methoxybenzoylamino]-N-(4-methoxy-phenyl)-4-nitrobenzamide

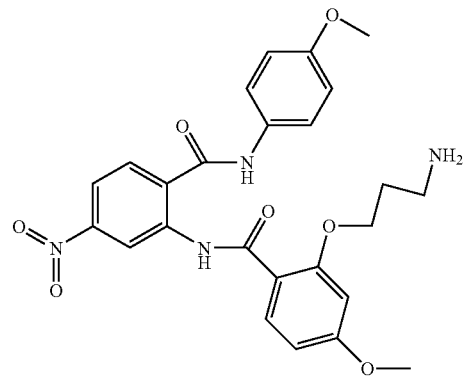

A. 1-tert-Butoxycarbonylamino-3-bromopropane

To a solution of 3-bromopropylamine hydrobromide (100 g, 457 mmol) in water (250 mL) was added a solution of di-tert-butyl dicarbonate (49.84 g, 228 mmol) in dichloromethane (600 mL). The resulting biphasic mixture was stirred vigorously, then a solution of sodium hydroxide (36.56 g, 914 mmol) in water (250 mL) was added and the mixture stirred at room temperature for 3 to 16 hours. The organic layer was washed sequentially with water, 0.2 N HCl until the pH reached 1, then again with water until the pH reached 6 to 7. The organic layer was dried over sodium sulfate and concentrated in vacuo to provide 45.18 grams (83%) of 1-tert-butoxycarbonylamino-3-bromopropane as a pale orange oil.

$^1$NMR FAB-MS, m/z 238.0 (m+1), 240.0 (m+1). Analysis for $C_8H_{16}BrNO_2$. Calcd: C, 40.35; H, 6.77; N, 5.88. Found: C, 40.12; H, 6.62; N, 6.06.

B. Methyl 2-(3-tert-butoxycarbonylaminopropoxy)-4-methoxybenzoate

To a solution of methyl 4-methoxysalicylate (11.48 g, 63 mmol) in dimethylformamide (30 mL) was added solid $K_2CO_3$ (13.06 g, 94.5 mmol), 1-tert-butoxycarbonylamino-3-bromopropane (22.5 g, 94.5 mmol), and freshly ground potassium iodide (1.5 g). The resulting slurry was placed under a nitrogen atmosphere and stirred for 2.5 days. The slurry was diluted with water (250 mL), washed with 1 N NaOH (2×250 mL), water (250 mL), and brine (250 mL), then dried over sodium sulfate and concentrated in vacuo. The crude mixture was purified on a preparative HPLC chromatograph using two silica columns and a hexanes through 1:1 hexanes:EtOAc gradient to provide methyl 2-(3-tert-butoxycarbonylaminopropoxy)-4-methoxybenzoate (19.93 g, 93.3%) as a colorless oil.

$^1$NMR FAB-MS, m/z 340.2 (m+1). Analysis for $C_{17}H_{25}NO_6$. Calcd: C, 60.16; H, 7.43; N, 4.13. Found: C, 59.92; H, 7.42; N, 4.18.

C. 2-(3-tert-Butoxycarbonylaminopropoxy)-4-methoxybenzoic acid

Methyl 2-(3-tert-butoxycarbonylaminopropoxy)-4-methoxybenzoate (18.61 g, 54.8 mmol) was suspended in 3:1 tetrahydrofuran:water (100 mL), then solid LiOH monohydrate (5.06 g, 121 mmol) was added and the mixture was stirred at 50° C. for 24 hours. The mixture was diluted with water (350 mL) and washed with diethyl ether (2×250 mL). The aqueous layer was acidified to pH 1-2 with 1 N sodium bisulfate and the resulting slurry was extracted with EtOAc (2×300 mL). The combined EtOAc layers were washed with brine, dried, then concentrated in vacuo to give a solid white mass. Recrystallization from EtOAc provided 2-(3-tert-butoxycarbonylaminopropoxy)-4-methoxybenzoic acid as white needles (15.52 g, 87%).

$^1$NMR FAB-MS, m/z 312.2 (m+1). Analysis for $C_{15}H_{21}NO_6$. Calcd: C, 57.87; H, 6.80; N, 4.50. Found: C, 58.09; H, 6.88; N, 4.57.

D. 2-[2-(3-tert-Butoxycarbonylaminopropoxy)-4-methoxybenzoylamino]-N-(4-methoxyphenyl)-4-nitrobenzamide Using methods substantially equivalent to those described in Example 4-E, 2-[2-(3-tert-butoxycarbonylaminopropoxy)-4-methoxybenzoylamino]-N-(4-methoxy-phenyl)-4-nitrobenzamide (984 mg, 1.65 mmol, 58%) was prepared from 4-methoxy-2-(3-tert-butoxycarbonylaminopropoxy)benzoic acid and N-(4-methoxyphenyl)-2-amino-4-nitrobenzamide.

IR(CHCl$_3$): 1606, 1533, 1250 cm$^{-1}$. $^1$NMR (300 MHz, DMSO-d$_6$): δ 11.40 (s, 1H); 10.69 (s, 1H); 9.41 (s, 1H); 7.99 (m, 1H); 7.64 (d, J=8.7 Hz, 2H); 6.94 (d, J=9.0 Hz, 2H); 6.67 (m, 3H); 4.23 (t, J=5.9 Hz, 2H); 3.81 (s, 3H); 3.73 (s, 3H); 2.93 (m, 2H); 1.83 (m, 2H); 1.30 (s, 9H). FD-MS m/e: 594.0 (m).

E. 2-[2-(3-Aminopropoxy)-4-methoxybenzoylamino]-N-(4-methoxyphenyl)-4-nitrobenzamide Using methods substantially equivalent to those described in example 4-G except 1 N NaOH was used as the base, 2-[2-(3-aminopropoxy)-4-methoxybenzoylamino]-N-(4-methoxyphenyl)-4-nitrobenzamide (1.214 g, 2.45 mmol, 100%) was prepared from 2-[2-(3-tert-butoxycarbonylaminopropoxy)-4-methoxybenzoylamino]-N-(4-methoxy-phenyl)-4-nitrobenzamide.

IR(KBr): 1602, 1532, 1262 cm$^{-1}$. $^1$NMR (300 MHz, DMSO-d$_6$): δ 11.43 (s, 1H); 10.72 (s, 1H); 9.38 (s, 1H); 8.00 (m, 3H); 7.64 (d, J=9.0 Hz, 2H); 6.95 (d, J=9.0 Hz, 2H); 6.72 (d, J=6.9 Hz, 2H); 4.34 (t, J=5.9 Hz, 2H); 3.83 (s, 3H); 3.74 (s, 3H); 2.85 (m, 2H); 2.07 (m, 2H). IS-MS m/e: 495 (m+1). Analysis for $C_{27}H_{27}F_3N_4O_9$. Calc: C, 53.29; H, 4.47; N, 9.21. Found: C, 53.31; H, 4.23; N, 9.16.

EXAMPLE 144

Preparation of 4-Amino-2-[4-methoxy-2-[3-(thiophen-2-ylcarbonylamino)-propoxy]benzoylamino]-N-(4-methoxyphenyl)benzamide

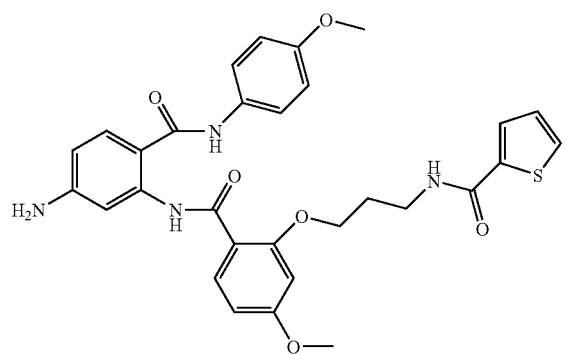

A. 2-[4-Methoxy-2-[3-(thiophen-2-ylcarbonylamino)propoxy]benzoylamino]-N-(4-methoxyphenyl)-4-nitrobenzamide Using methods substantially equivalent to those described in Example 139-A, 2-[4-methoxy-2-[3-(thiophen-2-ylcarbonylamino)propoxy]benzoylamino]-N-(4-methoxyphenyl)-4-nitrobenzamide (162 mg, 0.27 mmol, 81%) was prepared from 2-[2-(3-aminopropoxy)-4-methoxybenzoylamino]-N-(4-methoxyphenyl)-4-nitro-benzamide and thiophene 2-carboxylic acid.

IR(CHCl$_3$): 1606, 1511, 1258 cm$^{-1}$. $^1$NMR (300 MHz, DMSO-d$_6$): δ 11.43 (s, 1H); 10.67 (s, 1H); 9.39 (s, 1H); 8.40 (m, 1H); 8.04-7.94 (m, 3H); 7.67-7.61 (m, 4H); 7.05 (t, J=4.4 Hz, 2H); 6.89 (d, J=9.0 Hz, 2H); 6.69-6.65 (m, 2H); 4.29 (t, J=6.3 Hz, 2H); 3.78 (s, 3H); 3.69 (s, 3H); 3.23 (d, J=6.0 Hz, 2H); 1.98 (t, J=6.6 Hz, 2H). IS-MS m/e: 605.2 (m+1). Analysis for $C_{30}H_{28}N_4O_8 \cdot 1.0H_2O$. Calc: C, 57.87; H, 4.86; N, 9.00. Found: C, 57.77; H, 4.52; N, 8.98.

B. 4-Amino-2-[4-methoxy-2-[3-(thiophen-2-ylcarbonylamino)propoxy]-benzoylamino]-N-(4-methoxyphenyl)benzamide Using methods substantially equivalent to those described in Example 139-B, 4-amino-2-[4-methoxy-2-[3-(thiophen- 2-ylcarbonylamino)propoxy]-benzoylamino]-N-(4-methoxyphenyl)benzamide (114 mg, 0.20 mmol, 100%) was prepared from 2-[4-methoxy-2-[3-(thiophen-2-ylcarbonylamino)propoxy]benzoylamino]-N-(4-methoxyphenyl)-4-nitrobenzamide.

IR(CHCl$_3$): 1642, 1606, 1511 cm$^{-1}$. $^1$NMR (400 MHz, DMSO-d$_6$): δ 11.79 (s, 1H); 9.48 (s, 1H); 8.41 (m, 1H); 7.87 (s, 1H); 7.77 (d, J=8.8 Hz, 1H); 7.67-7.63 (m, 2H); 7.52-7.48 (m, 3H); 7.04 (t, J=4.4 Hz, 1H); 6.80 (d, J=9.2 Hz, 2H); 6.62 (m, 2H); 6.28 (d, J=8.4 Hz, 1H); 5.78 (br s, 2H); 4.19 (t, J=6.6 Hz, 2H); 3.76 (s, 3H); 3.65 (s, 3H); 3.27 (m, 2H); 1.71 (m, 2H). IS-MS m/e: 575.2 (m+1).

EXAMPLE 145

Preparation of 2-[4-Methoxy-2-[1-(3-methoxybenzyl)piperidin-4-yloxy]-benzoylamino]-N-(4-methoxyphenyl)-4-nitrobenzamide

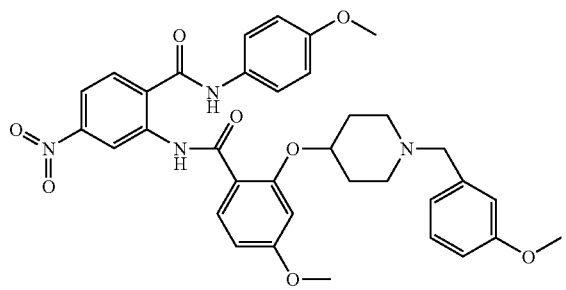

Using methods substantially equivalent to those described in Example 94-E, 2-[4-methoxy-2-[1-(3-methoxybenzyl)piperidin-4-yloxy]benzoylamino]-N-(4-methoxy-phenyl)-4-nitrobenzamide (62 mg, 0.097 mmol, 65%) was prepared from 2-[4-methoxy-2-(piperidin-4-yloxy)benzoylamino]-N-(4-methoxyphenyl)-4-nitrobenzamide and 3-methoxybenzaldehyde.

$^1$NMR (400 MHz, DMSO-d$_6$): δ 11.13 (s, 1H); 10.67 (s, 1H); 8.03-7.79 (m, 2H); 7.86 (d, J=8.8 Hz, 1H); 7.63 (d, J=9.2 Hz, 2H); 7.16 (t, J=7.6 Hz, 1H); 6.91-6.64 (m, 7H); 4.59 (m, 1H); 3.79 (s, 3H); 3.66 (s, 3H); 3.65 (s, 3H); 3.27 (s, 2H); 2.51 (m, 2H); 2.07 (m, 2H); 1.83 (m, 4H). IS-MS m/e: 641.3 (m+1).

EXAMPLE 146

Preparation of 2-[2-[1-(2,6-Dimethoxybenzyl)piperidin-4-yloxy)-4-methoxy-benzoylamino]-N-(4-methoxyphenyl)-4-nitrobenzamide

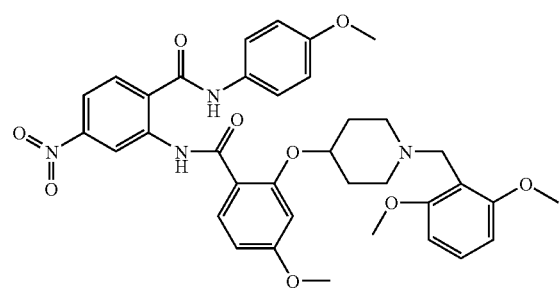

Using methods substantially equivalent to those described in Example 94-E, 2-[2-(1-(2,6-dimethoxybenzyl)piperidin-4-yloxy)-4-methoxybenzoylamino]-N-(4-methoxyphenyl)-4-nitrobenzamide (78 mg, 0.12 mmol, 78%) was prepared from 2-[4-methoxy-2-(piperidin-4-yloxy)benzoylamino]-N-(4-methoxyphenyl)-4-nitro-benzamide and 2,6-dimethoxybenzaldehyde.

$^1$NMR (400 MHz, DMSO-d$_6$): δ 11.10 (s, 1H); 10.63 (s, 1H); 9.32 (s, 1H); 8.04-7.96 (m, 2H); 7.83 (d, J=8.4 Hz, 1H); 7.60 (d, J=6.0 Hz, 2H); 7.15 (m, 1H); 6.83 (d, J=6.0 Hz, 2H); 6.69 (s, 1H); 6.64 (d, J=8.4 Hz, 1H); 6.56 (d, J=8.0 Hz, 2H); 4.52 (m, 1H); 3.77 (s, 3H); 3.68 (s, 3H); 3.65 (s, 6H); 3.29 (s, 2H); 2.56 (s, 2H); 2.04 (m, 2H); 1.76 (m, 4H). IS-MS m/e: 671.6 (m+1).

EXAMPLE 147

Preparation of 2-[4-Methoxy-2-(1-(2-methylbenzyl)piperidin-4-yloxy)-benzoylamino]-N-(4-methoxyphenyl)-4-nitrobenzamide

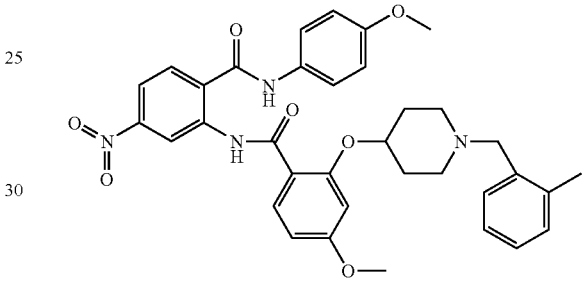

Using methods substantially equivalent to those described in Example 94-E, 2-[4-methoxy-2-(1-(2-methylbenzyl)piperidin-4-yloxy)benzoylamino]-N-(4-methoxy-phenyl)-4-nitrobenzamide (66 mg, 0.11 mmol, 70%) was prepared from 2-[4-methoxy-2-(piperidin-4-yloxy)benzoylamino]-N-(4-methoxyphenyl)-4-nitrobenzamide and 2-methyl-benzaldehyde.

$^1$NMR (400 MHz, DMSO-d$_6$): δ 11.13 (s, 1H); 10.66 (s, 1H); 9.34 (s, 1H); 8.05-7.96 (m, 2H); 7.86 (d, J=8.8 Hz, 1H); 7.61 (d, J=9.2 Hz, 2H); 7.10 (s, 4H); 6.77 (d, J=9.2 Hz, 2H); 6.71-6.64 (m, 2H); 4.60 (m, 1H); 3.79 (s, 3H); 3.64 (s, 3H); 2.52 (m, 2H); 2.23 (s, 3H); 2.10 (m, 2H); 1.83 (m, 4H). IS-MS m/e: 625.6 (m+1).

EXAMPLE 148

Preparation of 2-[2-[4-Methoxy-1-(2-methoxybenzyl)piperidin-4-yloxy]-benzoylamino]-N-(4-methoxyphenyl)-4-nitrobenzamide

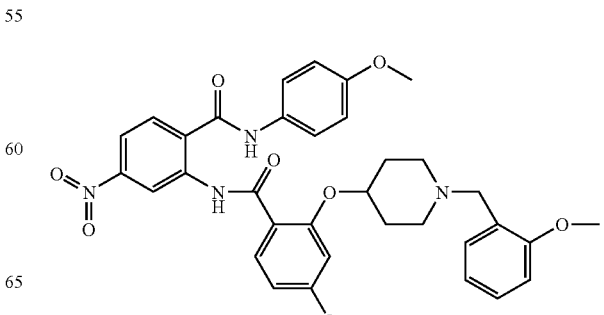

Using methods substantially equivalent to those described in Example 94-E, 2-[4-methoxy-2-[1-(2-methoxybenzyl)piperidin-4-yloxy]benzoylamino]-N-(4-methoxy-phenyl)-4-nitrobenzamide (83 mg, 0.13 mmol, 86%) was prepared from 2-[4-methoxy-2-(piperidin-4-yloxy)benzoylamino]-N-(4-methoxyphenyl)-4-nitrobenzamide and 2-methoxybenzaldehyde.

$^1$NMR (400 MHz, DMSO-$d_6$): δ 11.14 (s, 1H); 10.68 (s, 1H); 9.37 (s, 1H); 8.04-8.00 (m, 2H); 7.86 (d, J=8.8 Hz, 1H); 7.64 (d, J=6.4 Hz, 2H); 7.21 (m, 2H); 6.92-6.82 (m, 2H); 6.71-6.67 (m, 2H); 4.63 (m, 1H); 3.79 (s, 3H); 3.68 (s, 3H); 3.66 (s, 3H); 3.30 (s, 2H); 2.52 (m, 2H); 2.11 (m, 2H); 1.84 (m, 4H). IS-MS m/e: 641.3 (m+1).

EXAMPLE 149

Preparation of 2-[2-(1-Benzylpiperidin-4-yloxy)-4-methoxybenzoylamino]-N-(4-methoxyphenyl)-4-nitrobenzamide

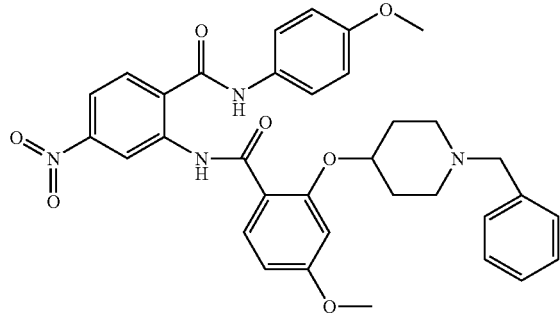

Using methods substantially equivalent to those described in example 94-E, 2-[2-(1-benzylpiperidin-4-yloxy)-4-methoxybenzoylamino]-N-(4-methoxyphenyl)-4-nitrobenzamide (60 mg, 0.098 mmol, 65%) was prepared from 2-[4-methoxy-2-(piperidin-4-yloxy)benzoylamino]-N-(4-methoxyphenyl)-4-nitrobenzamide and benzaldehyde.

$^1$NMR (400 MHz, DMSO-$d_6$): δ 11.14 (s, 1H); 9.38 (s, 1H); 8.06-7.98 (m, 2H); 7.86 (d, J=8.8 Hz, 1H); 7.63 (d, J=8.8 Hz, 2H); 7.28-7.19 (m, 5H); 6.81 (d, J=9.2 Hz, 2H); 6.70-6.65 (m, 2H); 4.60 (m, 1H); 3.79 (s, 3H); 3.66 (s, 3H); 3.29 (s, 2H); 2.50 (m, 2H); 2.08 (m, 2H); 1.84 (m, 4H). IS-MS m/e: 611.3 (m+1).

EXAMPLE 150

Preparation of 2-[4-Methoxy-2-[1-(4-methoxybenzyl)piperidin-4-yloxy]-benzoylamino]-N-(4-methoxyphenyl)-4-nitrobenzamide

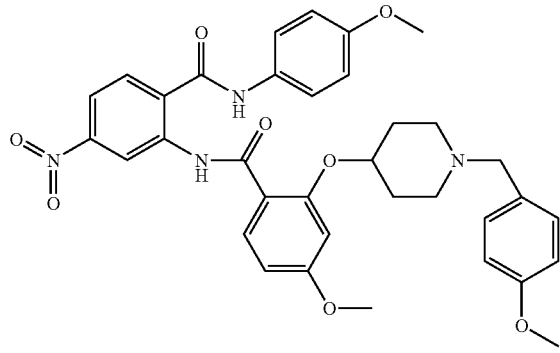

Using methods substantially equivalent to those described in example 94-E, 2-[4-methoxy-2-(1-(4-methoxybenzyl)piperidin-4-yloxy)benzoylamino]-N-(4-methoxy-phenyl)-4-nitrobenzamide (69 mg, 0.11 mmol, 72%) was prepared from 2-[4-methoxy-2-(piperidin-4-yloxy)benzoylamino]-N-(4-methoxyphenyl)-4-nitrobenzamide and 4-methoxybenzaldehyde.

$^1$NMR (400 MHz, DMSO-$d_6$): δ 11.13 (s, 1H); 10.67 (s, 1H); 9.36 (s, 1H); 8.06-7.97 (m, 2H); 7.85 (d, J=7.2 Hz, 1H); 7.63 (d, J=8.0 Hz, 2H); 7.09 (d, J=8.0 Hz, 2H); 6.83-6.64 (m, 6H); 4.59 (m, 1H); 3.78 (s, 3H); 3.67 (s, 6H); 3.29 (s, 2H); 2.46 (m, 2H); 2.04 (m, 2H); 1.82 (m, 4H). IS-MS m/e: 641.3 (m+1).

EXAMPLE 151

Preparation of 2-[2-[1-(2-Fluorobenzyl)piperidin-4-yloxy)-4-methoxybenzoylamino]-N-(4-methoxyphenyl)-4-nitrobenzamide

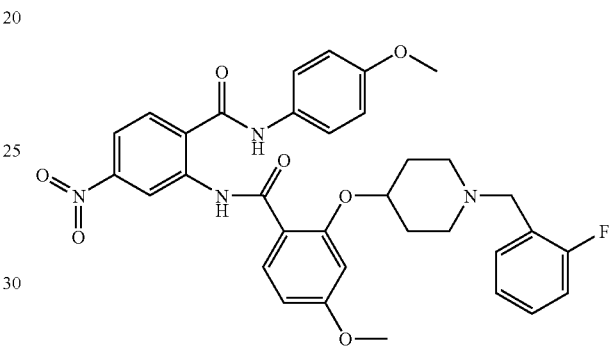

Using methods substantially equivalent to those described in Example 94-E, 2-[2-[1-(2-fluorobenzyl)piperidin-4-yloxy]-4-methoxybenzoylamino]-N-(4-methoxy-phenyl)-4-nitrobenzamide (63 mg, 0.10 mmol, 67%) was prepared from 2-[4-methoxy-2-(piperidin-4-yloxy)benzoylamino]-N-(4-methoxyphenyl)-4-nitrobenzamide and 2-fluoro-benzaldehyde.

$^1$NMR (300 MHz, DMSO-$d_6$): δ 11.12 (s, 1H); 10.66 (s, 1H); 9.36 (s, 1H); 8.05-7.96 (m, 2H); 7.84 (d, J=8.1 Hz, 1H); 7.62 (d, J=8.1 Hz, 2H); 7.29-7.23 (m, 2H); 7.11-7.06 (m, 2H); 6.82 (d, J=8.1 Hz, 2H); 6.70 (s, 1H); 6.64 (d, J=8.7 Hz, 1H); 4.59 (m, 1H); 3.78 (s, 3H); 3.67 (s, 3H); 3.42 (s, 2H); 2.50 (m, 2H); 2.12 (m, 2H); 1.83 (m, 4H). IS-MS m/e: 629.3 (m+1).

EXAMPLE 152

Preparation of 2-[2-[3-(2-Fluorobenzyl)aminopropoxy]-4-methoxybenzoylamino]-N-(4-methoxyphenyl)-4-nitrobenzamide

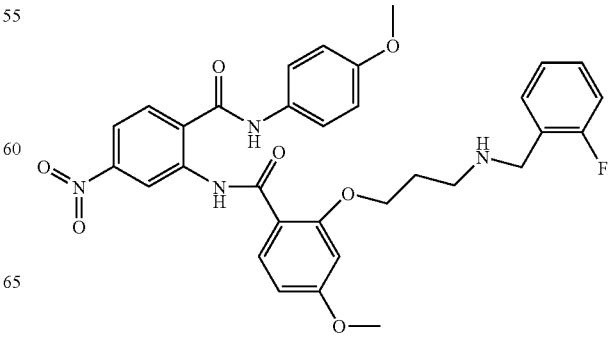

Using methods substantially equivalent to those described in Example 94-E except that sodium borohydride was the reducing agent, 2-[2-[3-(2-fluorobenzyl)aminopropoxy]-4-methoxybenzoylamino]-N-(4-methoxyphenyl)-4-nitrobenzamide (20 mg, 0.033 mmol, 22%) was prepared from 2-[2-(3-aminopropoxy)-4-methoxybenzoylamino]-N-(4-methoxyphenyl)-4-nitrobenzamide and 2-fluorobenzaldehyde.

$^1$NMR (400 MHz, DMSO-d$_6$): δ 11.43 (s, 1H); 10.67 (s, 1H); 9.37 (d, J=2.4 Hz, 1H); 7.99 (m, 3H); 7.61 (d, J=8.8 Hz, 2H); 7.17 (m, 2H); 6.94 (d, J=9.2 Hz, 2H); 6.87 (d, J=8.8 Hz, 2H); 6.69 (m, 2H); 4.36 (m, 2H); 3.78 (s, 3H); 3.67 (s, 3H); 3.56 (m, 2H); 2.46 (s, 2H); 2.07 (m, 2H). IS-MS m/e: 603.3 (m+1).

EXAMPLE 153

Preparation of 2-[2-[3-(2-Chlorobenzyl)aminopropoxy]-4-methoxybenzoylamino]-N-(4-methoxyphenyl)-4-nitrobenzamide

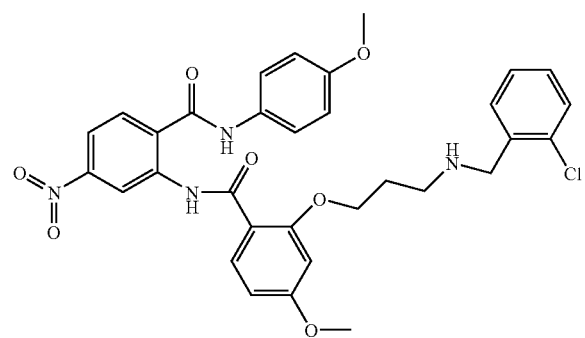

Using methods substantially equivalent to those described in example 94-E except that sodium borohydride was the reducing agent, 2-[2-[3-(2-chlorobenzyl)amino-propoxy]-4-methoxybenzoylamino]-N-(4-methoxyphenyl)-4-nitrobenzamide (34 mg, 0.055 mmol, 37%) was prepared from 2-[2-(3-aminopropoxy)-4-methoxybenzoylamino]-N-(4-methoxyphenyl)-4-nitrobenzamide and 2-chlorobenzaldehyde.

$^1$NMR (400 MHz, DMSO-d$_6$): δ 11.44 (s, 1H); 10.66 (s, 1H); 9.35 (s, 1H); 8.02 (d, J=9.2 Hz, 1H); 7.95 (d, J=8.8 Hz, 1H); 7.84 (d, J=8.0 Hz, 1H); 7.62 (d, J=8.8 Hz, 2H); 7.40 (d, J=3.6 Hz, 2H); 7.31 (m, 2H); 6.87 (d, J=8.8 Hz, 2H); 6.70 (s, 1H); 6.67 (d, J=9.2 Hz, 2H); 4.36 (m, 2H); 3.78 (s, 3H); 3.60 (s, 3H); 3.29 (s, 2H); 2.09 (m, 2H). IS-MS m/e: 619.5 (m+1).

EXAMPLE 154

Preparation of 2-[4-Methoxy-2-[3-(4-methoxybenzyl)aminopropoxy]benzoylamino]-N-(4-methoxyphenyl)-4-nitrobenzamide

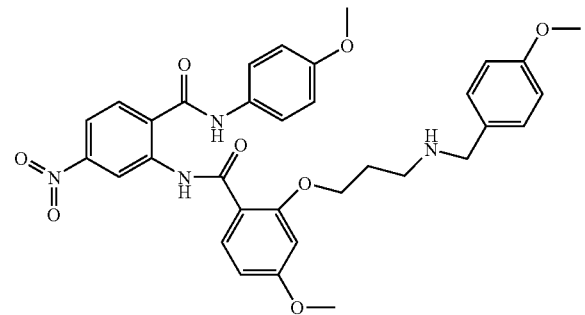

Using methods substantially equivalent to those described in Example 94-E except that sodium borohydride was the reducing agent, 2-[4-methoxy-2-[3-(4-methoxybenzyl)-aminopropoxy]benzoylamino]-N-(4-methoxyphenyl)-4-nitrobenzamide (48 mg, 0.078 mmol, 52%) was prepared from 2-[2-(3-aminopropoxy)-4-methoxybenzoylamino]-N-(4-methoxyphenyl)-4-nitrobenzamide and 4-methoxybenzaldehyde.

$^1$NMR (300 MHz, DMSO-d$_6$): δ 11.43 (s, 1H); 10.67 (s, 1H); 9.39 (s, 1H); 7.99 (m, 3H); 7.63 (d, J=8.8 Hz, 2H); 7.53 (d, J=8.8 Hz, 2H); 6.89 (d, J=11.6 Hz, 4H); 6.70 (m, 2H); 4.34 (m, 2H); 3.78 (s, 3H); 3.74 (s, 3H); 3.68 (s, 3H); 3.46 (s, 2H); 2.02 (m, 2H). IS-MS m/e: 615.3 (m+1).

EXAMPLE 155

Preparation of 2-[4-Methoxy-2-[3-(3-methoxybenzyl)aminopropoxy]benzoylamino]-N-(4-methoxyphenyl)-4-nitrobenzamide

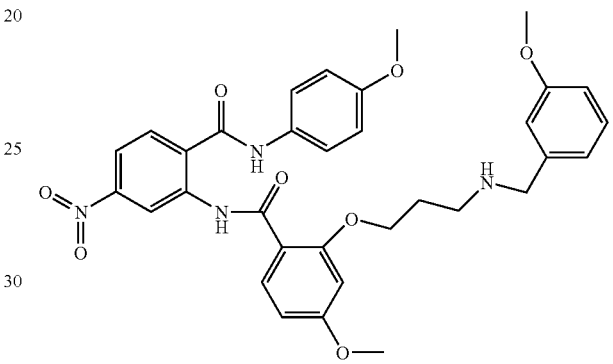

Using methods substantially equivalent to those described in Example 94-E except that sodium borohydride was the reducing agent, 2-[4-methoxy-2-[3-(3-methoxybenzyl)-aminopropoxy]benzoylamino]-N-(4-methoxyphenyl)-4-nitrobenzamide (26 mg, 0.042 mmol, 28%) was prepared from 2-[2-(3-aminopropoxy)-4-methoxybenzoylamino]-N-(4-methoxyphenyl)-4-nitrobenzamide and 3-methoxybenzaldehyde.

$^1$NMR (400 MHz, DMSO-d$_6$): δ 9.37 (d, J=1.8 Hz, 1H); 7.99 (m, 3H); 7.63 (d, J=9.2 Hz, 2H); 7.26 (t, J=7.8 Hz, 1H); 7.15 (m, 2H); 6.94 (m, 4H); 6.89 (d, J=8.8 Hz, 2H); 6.70 (s, 1H); 6.68 (d, J=13.6 Hz, 1H); 4.36 (m, 2H); 3.78 (s, 3H); 3.70 (s, 3H); 3.68 (s, 3H); 3.51 (m, 2H); 3.30 (s, 2H); 2.05 (m, 2H). IS-MS m/e: 615.3 (m+1).

EXAMPLE 156

Preparation of 2-[2-[3-(2,6-Dimethoxybenzyl)aminopropoxy]-4-methoxybenzoyl-amino]-N-(4-methoxyphenyl)-4-nitrobenzamide

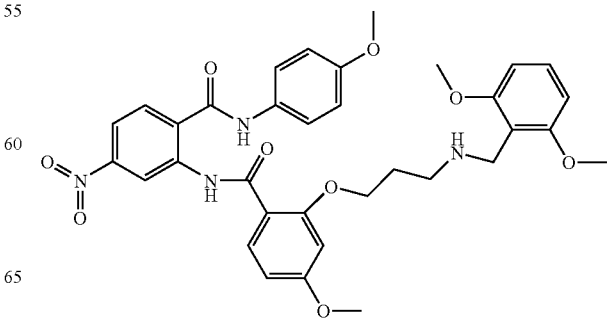

Using methods substantially equivalent to those described in Example 94-E except that sodium borohydride was the reducing agent, 2-[2-[3-(2,6-dimethoxybenzyl)amino-propoxy]-4-methoxybenzoylamino]-N-(4-methoxyphenyl)-4-nitrobenzamide (59 mg, 0.092 mmol, 61%) was prepared from 2-[2-(3-aminopropoxy)-4-methoxybenzoylamino]-N-(4-methoxyphenyl)-4-nitrobenzamide and 2,6-dimethoxybenzaldehyde.

$^1$NMR (400 MHz, DMSO-d$_6$): δ 9.38 (d, J=2.0 Hz, 1H); 7.98 (m, 3H); 7.62 (d, J=9.2 Hz, 2H); 6.90 (t, J=8.4 Hz, 1H); 6.61 (m, 6H); 4.28 (q, J=7.6 Hz, 2H); 3.79 (s, 3H); 3.69 (s, 3H); 3.63 (s, 6H); 3.45 (m, 2H); 2.03 (m, 2H). IS-MS m/e: 645.5 (m+1).

EXAMPLE 157

Preparation of 2-[4-Methoxy-2-(3-(2-methylbenzyl)aminopropoxy)benzoylamino]-N-(4-methoxyphenyl)-4-nitrobenzamide

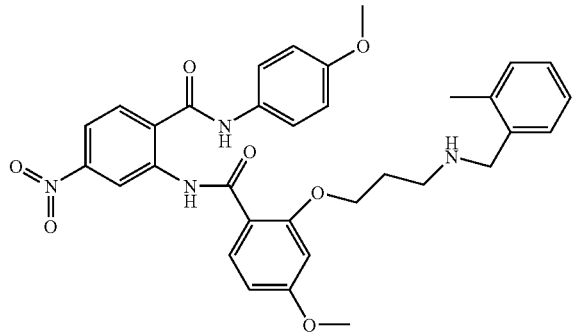

Using methods substantially equivalent to those described in Example 94-E except that sodium borohydride was the reducing agent, 2-[4-methoxy-2-(3-(2-methylbenzyl)-aminopropoxy)benzoylamino]-N-(4-methoxyphenyl)-4-nitrobenzamide (50 mg, 0.084 mmol, 56%) was prepared from 2-[2-(3-aminopropoxy)-4-methoxybenzoylamino]-N-(4-methoxyphenyl)-4-nitrobenzamide and 2-methylbenzaldehyde.

$^1$NMR (300 MHz, DMSO-d$_6$): δ 11.43 (s, 1H); 10.67 (s, 1H); 9.36 (s, 1H); 7.98 (m, 3H); 7.62 (d, J=9.0 Hz, 2H); 6.87 (d, J=9.3 Hz, 2H); 6.69 (s, 1H); 6.67 (d, J=10.8 Hz, 1H); 4.35 (m, 2H); 3.77 (s, 3H); 3.67 (s, 3H); 3.63 (s, 6H); 3.54 (t, J=5.9 Hz, 2H); 3.26 (s, 2H); 2.30 (s, 3H); 2.06 (t, J=3.9 Hz, 2H). IS-MS m/e: 599.4 (m+1).

EXAMPLE 158

Preparation of 2-[4-Methoxy-2-[3-(2-methoxybenzyl)aminopropoxy]benzoylamino]-N-(4-methoxyphenyl)-4-nitrobenzamide

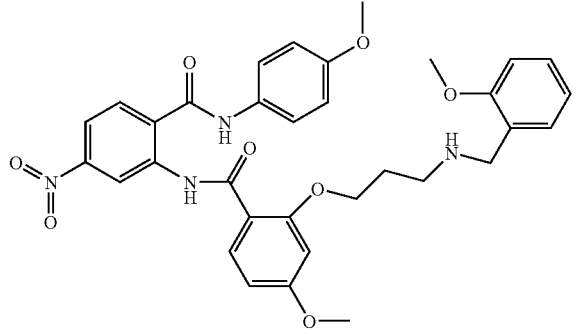

Using methods substantially equivalent to those described in Example 94-E except that sodium borohydride was the reducing agent, 2-[4-methoxy-2-[3-(2-methoxybenzyl)-aminopropoxy]benzoylamino]-N-(4-methoxyphenyl)-4-nitrobenzamide (52 mg, 0.085 mmol, 56%) was prepared from 2-[2-(3-aminopropoxy)-4-methoxybenzoylamino]-N-(4-methoxyphenyl)-4-nitrobenzamide and 2-methoxybenzaldehyde.

$^1$NMR (300 MHz, DMSO-d$_6$): δ 11.44 (s, 1H); 10.66 (s, 1H); 9.38 (s, 1H); 7.95 (m, 3H); 7.62 (d, J=8.7 Hz, 2H); 7.08 (m, 2H); 6.88 (d, J=9.0 Hz, 2H); 6.72 (m, 4H); 4.30 (t, J=7.2 Hz, 2H); 4.26-3.68 (m, 11H); 3.50 (s, 2H); 1.86 (m, 2H). IS-MS m/e: 615.3 (m+1).

EXAMPLE 159

Preparation of 2-[2-(3-Benzylaminopropoxy)-4-methoxybenzoylamino]-N-(4-methoxyphenyl)-4-nitrobenzamide

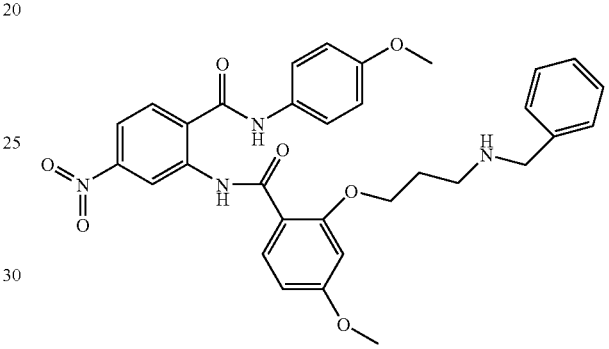

Using methods substantially equivalent to those described in Example 94-E except that sodium borohydride was the reducing agent, 2-[2-(3-benzylaminopropoxy)-4-methoxybenzoylamino]-N-(4-methoxyphenyl)-4-nitrobenzamide (45 mg, 0.077 mmol, 51%) was prepared from 2-[2-(3-aminopropoxy)-4-methoxybenzoylamino]-N-(4-methoxyphenyl)-4-nitrobenzamide and benzaldehyde.

$^1$NMR (300 MHz, DMSO-d$_6$): δ 11.43 (s, 1H); 10.67 (s, 1H); 9.38 (s, 1H); 8.01 (d, J=8.8 Hz, 1H); 7.95 (m, 2H); 7.61 (m, 4H); 7.36 (m, 3H); 6.88 (d, J=9.2 Hz, 2H); 6.69 (s, 1H); 6.67 (d, J=8.8 Hz, 1H); 4.34 (m, 2H); 3.77 (s, 3H); 3.51 (m, 2H); 3.27 (s, 2H); 2.04 (m, 2H). IS-MS m/e: 585.5 (m+1).

EXAMPLE 160

Preparation of N-(5-Chloropyridin-2-yl)-4-methoxycarbonyl-2-[4-methylthio-2-(3-aminopropoxy)benzoylamino]benzamide

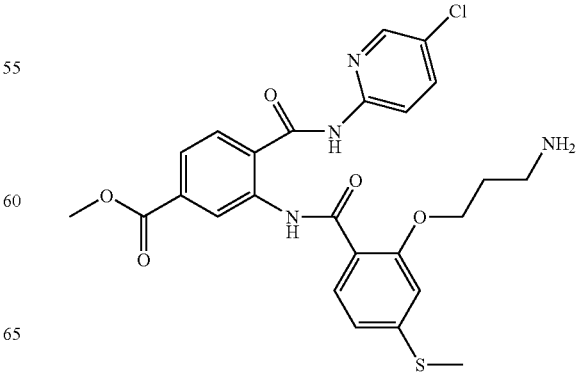

A. N-(5-Chloropyridin-2-yl)-4-methoxycarbonyl-2-[4-methylthio-2-(3-(t-butoxy-carbonylamino)propoxy)benzoylamino]benzamide Using a procedure analogous to Example 4-E, N-(5-chloropyridin-2-yl)-4-methoxycarbonyl-2-aminobenzamide and 4-(methylthio)-2-(3-(t-butoxycarbonylamino)-propoxy)benzoic acid gave the title compound as a white solid (12 g, 50%).

$^1$NMR (300 MHz, DMSO-$d_6$): δ 1.32 (s, 9H), 1.87 (m, 2H), 2.54 (s, 3H), 2.97 (m, 2H), 3.91 (s, 3H), 4.28 (t, J=6.6 Hz, 2H), 6.80 (m, 1H), 6.99 (m, 2H), 7.76 (dd, J=1.5, 8.1 Hz, 1H), 7.89 (s, 1H), 7.92 (s, 1H), 7.98 (dd, J=2.6, 8.8 Hz, 1H), 8.18 (d, J=8.8 Hz, 1H), 8.45 (d, J=2.6 Hz, 1H), 9.03 (d, J=0.7 Hz, 1H), 11.15 (s, 1H), 11.38 (s, 1H). FIA-MS, m/e 629.2 (m+1). Analysis for $C_{30}H_{33}ClN_4O_7S$. Calcd: C, 57.27; H, 5.29; N, 8.91. Found: C, 57.36; H, 5.03; N, 9.18.

B. N-(5-Chloropyridin-2-yl)-4-methoxycarbonyl-2-[4-methylthio-2-(3-amino-propoxy)benzoylamino]benzamide Using a procedure analogous to Example 4-G, N-(5-chloropyridin-2-yl)-4-methoxycarbonyl-2-[4-methylthio-2-(3-t-butoxycarbonylamino)propoxy)benzoylamino]-benzamide gave the title compound as a light yellow solid (680 mg, 90%).

$^1$NMR (300 MHz, DMSO-$d_6$): δ 1.79 (m, 2H), 2.57 (m, 5H), 3.91 (s, 3H), 4.32 (t, J=6.6 Hz, 2H), 6.96 (dd, J=1.5, 8.4 Hz, 1H), 7.02 (s, 1H), 7.74 (dd, J=1.8, 8.1 Hz, 1H), 7.91 (m, 2H), 7.98 (dd, J=2.6, 8.8 Hz, 1H), 8.17 (d, J=8.8 Hz, 1H), 8.43 (d, J=2.6 Hz, 1H), 9.06 (d, J=1.5 Hz, 1H). FIA-MS, m/e 529.1 (m+1). Analysis for $C_{25}H_{25}ClN_4O_5S$. Calcd: C, 56.76; H, 4.76; N, 10.59. Found: C, 56.99; H, 4.92; N, 10.74.

EXAMPLE 161

Preparation of N-(5-Chloropyridin-2-yl)-4-carboxy-2-[4-methylthio-2-(3-amino-propoxy)benzoylamino]benzamide Hydrochloride

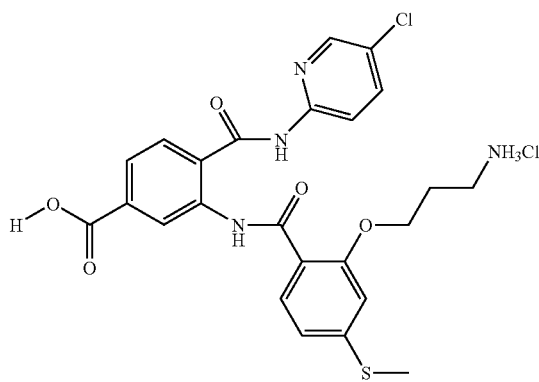

To a mixture of N-(5-chloropyridin-2-yl)-4-methoxycarbonyl-2-[4-methylthio-2-(3-aminopropoxy)benzoylamino]benzamide (480 mg, 0.91 mmol), MeOH (10 mL) and water (7 mL) was added LiOH (109 mg, 4.54 mmol). The reaction mixture was heated to 65° C. for 45 min and then cooled to room temperature. To the mixture was added 5N HCl (1.8 mL, 9 mmol), and the resulting solid was filtered with $CH_2Cl_2$ and 20% $Et_2O$/hexanes washes to give the title compound as a white solid (213 mg, 55%).

$^1$NMR (300 MHz, DMSO-$d_6$): δ 2.13 (m, 2H), 2.55 (s, 3H), 2.93 (m, 2H), 4.39 (t, J=6.2 Hz, 2H), 6.99 (dd, J=1.1, 8.4 Hz, 1H), 7.04 (s, 1H), 7.75 (dd, J=1.5, 8.1 Hz, 1H), 7.89 (m, 3H), 8.01 (dd, J=2.6, 8.8 Hz, 1H), 8.15 (d, J=8.8 Hz, 1H), 8.46 (d, J=2.9 Hz, 1H), 8.95 (d, J=1.1 Hz, 1H), 11.14 (s, 1H), 11.36 (s, 1H), 13.30 (br s, 1H). FIA-MS, m/e 515.3 (m+1). Analysis for $C_{24}H_{23}ClN_4O_5S$·HCl. Calcd: C, 52:27; H, 4.39; N, 10.16. Found: C, 52.59; H, 4.73; N, 9.65.

EXAMPLE 162

Preparation of N-(5-Chloropyridin-2-yl)-4-methoxycarbonyl-2-[4-methylsulfinyl-2-(3-aminopropoxy)benzoylamino]benzamide

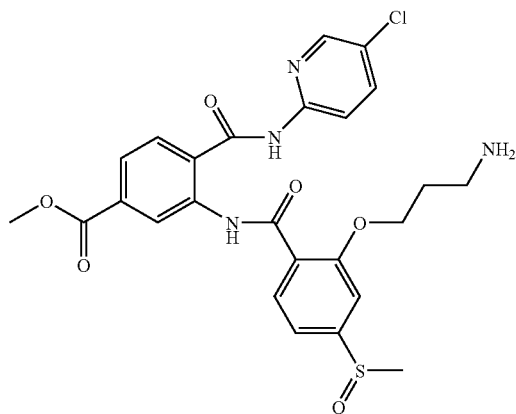

A. N-(5-Chloropyridin-2-yl)-4-methoxycarbonyl-2-[4-methylsulfinyl-2-(3-(t-butoxy-carbonylamino)propoxy)benzoylamino]benzamide Using a procedure analogous to Example 23, N-(5-chloropyridin-2-yl)-4-methoxycarbonyl-2-[4-methylthio-2-(3-t-butoxycarbonylamino)propoxy)benzoylamino]-benzamide gave the title compound as a white solid (1.4 g, 68%).

$^1$NMR (300 MHz, DMSO-$d_6$): δ 1.31 (s, 9H), 1.90 (m, 2H), 2.80 (s, 3H), 2.99 (m, 2H), 3.91 (s, 3H), 4.29 (t, J=6.2 Hz, 2H), 7.38 (d, J=8.1 Hz, 1H), 7.47 (s, 1H), 7.79 (dd, J=1.5, 8.1 Hz, 1H), 7.93 (d, J=8.1 Hz, 1H), 7.98 (dd, J=2.6, 8.8 Hz, 1H), 8.05 (d, J=8.1 Hz, 1H), 8.17 (d, J=8.8 Hz, 1H), 8.44 (d, J=2.6 Hz, 1H), 8.97 (s, 1H), 11.18 (s, 1H), 11.37 (s, 1H). FIA-MS, m/e 645.5 (m+1). Analysis for $C_{30}H_{33}ClN_4O_8S$. Calcd: C, 55.85; H, 5.16; N, 8.68. Found: C, 55.55; H, 4.97; N, 8.65.

B. N-(5-Chloropyridin-2-yl)-4-methoxycarbonyl-2-[4-methylsulfinyl-2-(3-amino-propoxy)benzoylamino]benzamide Using a procedure analogous to Example 4-G, N-(5-chloropyridin-2-yl)-4-methoxycarbonyl-2-[4-methylsulfinyl-2-(3-t-butoxycarbonylamino)propyloxy)benzoyl-amino]benzamide gave the title compound as a white solid (950 mg, 83%).

$^1$NMR (300 MHz, DMSO-$d_6$): δ 1.84 (m, 2H), 2.65 (t, J=6.6 Hz, 2H), 2.81 (s, 3H), 3.91 (s, 3H), 4.31 (t, J=6.2 Hz, 2H), 7.36 (dd, J=1.5, 8.1 Hz, 1H), 7.46 (d, =1.5 Hz, 1H), 7.73

(dd, J=1.5, 8.1 Hz, 1H), 7.93 (dd, J=2.6, 8.8 Hz, 1H), 7.99 (d, J=8.1 Hz, 1H), 8.04 (d, J=8.1 Hz, 1H), 8.17 (d, J=8.8 Hz, 1H), 8.40 (s, 1H), 9.04 (d, J=1.5 Hz, 1H).
FIA-MS, m/e 545.2 (m+1). Analysis for $C_{25}H_{25}ClN_4O_6S$. Calcd: C, 55.10; H, 4.62; N, 10.28. Found: C, 55.36; H, 4.65; N, 10.00.

EXAMPLE 163

Preparation of N-(5-Chloropyridin-2-yl)-4-carboxy-2-[4-methylsulfinyl-2-(3-amino-propoxy)benzoylamino]benzamide Hydrochloride

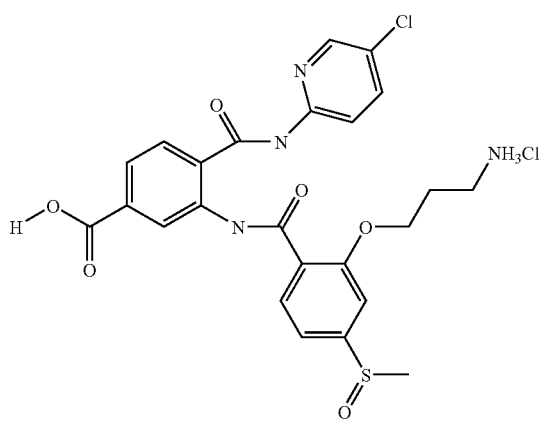

Using a procedure analogous to Example 161, N-(5-chloropyridin-2-yl)-4-methoxycarbonyl-2-[4-methylsulfinyl-2-(3-aminopropoxy)benzoylamino]benzamide gave the title compound as a white solid (240 mg, 46%).
$^1$NMR (300 MHz, DMSO-$d_6$): δ 2.12 (m, 2H), 2.82 (s, 3H), 2.94 (m, 2H), 4.39 (t, J=5.9 Hz, 2H), 7.39 (dd, J=1.1, 8.1 Hz, 1H), 7.51 (d, J=1.1 Hz, 1H) 7.78 (dd, J=1.5, 8.1 Hz, 1H), 7.86 (br s, 1H), 7.92 (d, J=8.1 Hz, 1H), 8.00 (m, 2H), 8.14 (d, J=8.8 Hz, 1H), 8.46 (d, J=2.6 Hz, 1H), 8.87 (d, J=1.1 Hz, 1H), 11.15 (s, 1H), 11.34 (s, 1H), 13.4 (br s, 1H). FIA-MS, m/e 531.1 (m+1). Analysis for $C_{24}H_{23}ClN_4O_6S$—HCl.0.75H$_2$O. Calcd: C, 49.53; H, 4.59; N, 9.36. Found: C, 49.27; H, 4.21; N, 9.63.

EXAMPLE 164

Preparation of N-(5-Chloropyridin-2-yl)-4-methoxycarbonyl-2-[4-methylsulfonyl-2-(3-aminopropoxy)benzoylamino]benzamide A. N-(5-Chloropyridin-2-yl)-4-methoxycarbonyl-2-[4-methylsulfonyl-2-(3-(t-butoxycarbonylamino)propoxy)benzoylamino]benzamide Using a procedure analogous to Example 25, N-(5-chloropyridin-2-yl)-4-methoxycarbonyl-2-[4-methylthio-2-(3-t-butoxycarbonylamino)propoxy)benzoylamino]-benzamide gave the title compound as a white solid (1.82 g, 86%).

$^1$NMR (300 MHz, DMSO-$d_6$): δ 1.31 (s, 9H), 1.89 (m, 2H), 3.00 (m, 2H), 3.29 (s, 3H), 3.91 (s, 3H), 4.30 (t, J=6.2 Hz, 2H), 6.81 (m, 1H), 7.64 (m, 2H), 7.81 (dd, J=1.5, 8.1 Hz, 1H), 7.96 (m, 2H), 8.05 (d, J=8.1 Hz, 1H), 8.16 (d, J=8.8 Hz, 1H), 8.45 (d, J=2.6 Hz, 1H), 8.91 (s, 1H), 11.16 (s, 1H), 11.35 (s, 1H). FIA-MS, m/e 661.1 (m+1). Analysis for $C_{30}H_{33}ClN_4O_9S$. Calcd: C, 54.50; H, 5.03; N, 8.47. Found: C, 55.03; H, 4.88; N, 8.37.

B. N-(5-Chloropyridin-2-yl)-4-methoxycarbonyl-2-[4-methylsulfonyl-2-(3-aminopropoxy)benzoylamino]benzamide Using a procedure analogous to Example 4-G, N-(5-chloropyridin-2-yl)-4-methoxycarbonyl-2-[4-methylsulfonyl-2-(3-t-butoxycarbonylamino)propoxy)benzoyl-amino]benzamide gave the title compound as a white solid (1.3 g, 88%).

$^1$NMR (300 MHz, DMSO-$d_6$): δ 1.88 (m, 2H), 2.73 (t, J=6.2 Hz, 2H), 3.29 (s, 3H), 3.90 (s, 3H), 4.31 (t, J=6.2 Hz, 2H), 7.61 (m, 2H), 7.68 (dd, J=1.5, 8.1 Hz, 1H), 7.90 (dd, J=2.6, 8.8 Hz, 1H), 8.05 (m, 2H), 8.19 (d, J=8.8 Hz, 1H), 8.36 (d, J=2.6 Hz, 1H), 9.01 (d, J=1.5 Hz, 1H). FIA-MS, m/e 561.2 (m+1). Analysis for $C_{25}H_{25}ClN_4O_7S$. Calcd: C, 53.52; H, 4.49; N, 9.99. Found: C, 53.61; H, 4.57; N, 9.86.

EXAMPLE 165

Preparation of N-(5-Chloropyridin-2-yl)-4-carboxy-2-[4-methylsulfonyl-2-(3-amino-propoxy)benzoylamino]benzamide

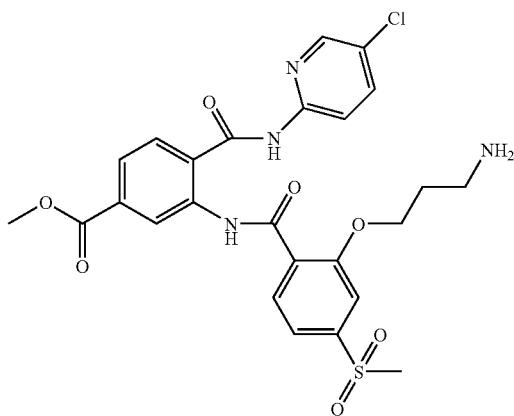

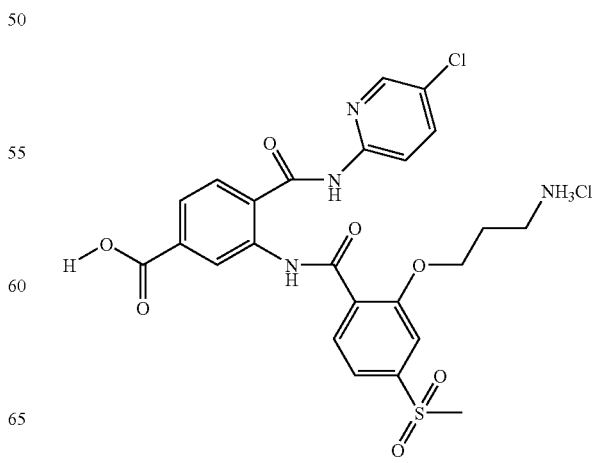

Using a procedure analogous to Example 161, N-(5-chloropyridin-2-yl)-4-methoxycarbonyl-2-[4-methylsulfonyl-2-(3-aminopropoxy)benzoylamino]benzamide gave the title compound as a white solid (380 mg, 73%).

$^1$NMR (300 MHz, DMSO-$d_6$): δ 2.12 (m, 2H), 2.94 (m, 2H), 3.30 (s, 3H), 4.40 (t, J=5.9 Hz, 2H), 7.67 (m, 2H), 7.80 (dd, J=1.5, 8.1 Hz, 1H), 7.85 (br s, 1H), 7.93 (d, J=8.4 Hz, 1H), 8.00 (m, 2H), 8.14 (d, J=8.8 Hz, 1H), 8.46 (d, J=2.6 Hz, 1H), 8.82 (s, 1H), 11.14 (s, 1H), 11.32 (s, 1H), 13.35 (br s, 1H). FIA-MS, m/e 547.1 (m+1). Analysis for $C_{24}H_{23}ClN_4O_7S·HCl·0.5H_2O$. Calcd: C, 48.66; H, 4.25; N, 9.46. Found: C, 48.63; H, 3.99; N, 9.15.

EXAMPLE 166

Preparation of N-(5-Chloropyridin-2-yl)-4-iodo-2-[4-methylsulfonyl-2-(4-piperidinyloxy)benzoylamino]benzamide

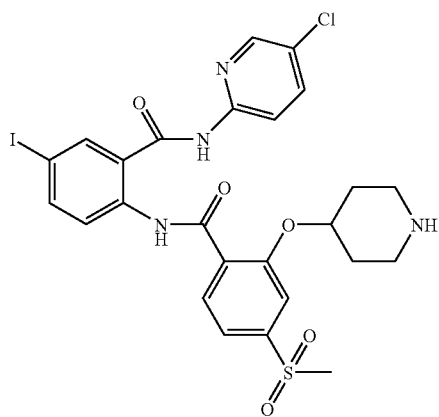

A. N-(5-Chloropyridin-2-yl)-4-iodo-2-[4-methylthio-2-(1-t-butoxycarbonylpiperidin-4-yloxy)benzoylamino]benzamide Using a procedure analogous to Example 4-E, N-(5-chloropyridin-2-yl)-4-iodo-2-aminobenzamide and 4-methylthio-2-(1-t-butoxycarbonylpiperidin-4-yloxy)benzoic acid gave the title compound as a white solid (3.03 g, 84%).

$^1$NMR (300 MHz, DMSO-$d_6$): δ 1.36 (s, 9H), 1.78 (m, 2H), 1.88 (m, 2H), 2.55 (s, 3H), 3.04 (m, 2H), 3.67 (m, 2H), 4.86 (m, 1H), 6.95 (dd, J=1.8, 8.4 Hz, 1H), 7.07 (s, 1H), 7.81 (d, J=8.4 Hz, 1H), 7.92 (m, 2H), 8.11 (s, 1H), 8.12 (d, J=8.8 Hz, 1H), 8.22 (d, J=8.8 Hz, 1H), 8.43 (d, J=2.6 Hz, 1H), 10.97 (s, 1H), 11.37 (s, 1H). ES-MS, m/e 723.28 (m+1). Analysis for $C_{30}H_{32}ClIN_4O_5S$. Calcd: C, 49.84; H, 4.46; N, 7.75. Found: C, 49.81; H, 4.46; N, 7.66.

B. N-(5-Chloropyridin-2-yl)-4-iodo-2-[4-methylsulfonyl-2-(1-t-butoxycarbonyl-piperidin-4-yloxy)benzoylamino]benzamide Using a procedure analogous to Example 25, N-(5-chloropyridin-2-yl)-4-iodo-2-[4-methylthio-2-(1-t-butoxycarbonyl)piperidino-4-yloxy)benzoylamino]benzamide gave the title compound as a white solid (2.41 g, 82%).

$^1$NMR (300 MHz, DMSO-$d_6$): δ 1.36 (s, 9H), 1.72 (m, 2H), 1.87 (m, 2H), 3.13 (m, 2H), 3.29 (s, 3H), 3.55 (m, 2H), 4.91 (m, 1H), 7.60 (dd, J=1.5, 8.1 Hz, 1H), 7.69 (s, 1H), 7.93 (m, 2H), 7.98 (d, J=8.1 Hz, 1H), 8.15 (m, 3H), 8.44 (d, J=2.6 Hz, 1H), 11.07 (s, 1H), 11.36 (s, 1H). ES-MS, m/e 755.1 (m+1). FAB+/MS, exact m/e: calc. 755.0803 ($C_{30}H_{33}ClIN_4O_7S$); found 755.0793.

C. N-(5-Chloropyridin-2-yl)-4-iodo-2-[4-methylsulfonyl-2-(4-piperidinyloxy)-benzoylamino]benzamide Using a procedure analogous to Example 4-G, N-(5-chloropyridin-2-yl)-4-iodo-2-[4-methylthio-2-(1-t-butoxycarbonylpiperidin-4-yloxy)benzoylamino]benzamide gave the title compound as a white solid (207 mg, 79%).

$^1$NMR (300 MHz, DMSO-$d_6$): δ 1.53 (m, 2H), 1.80 (m, 2H), 2.47 (m, 2H), 2.75 (m, 2H), 3.29 (s, 3H), 4.68 (m, 1H), 7.56 (s, 1H), 7.61 (s, 1H), 7.83 (m, 2H), 7.90 (d, J=2.6 Hz, 1H), 8.13 (d, J=8.8 Hz, 1H), 8.20 (d, J=1.8 Hz, 1H), 8.27 (d, J=8.8 Hz, 1H), 8.36 (d, J=2.2 Hz, 1H). ES-MS, m/e: 655.0 (m+1).

EXAMPLE 167

Preparation of N-(5-Chloropyridin-2-yl)-4-cyano-2-[4-methylsulfonyl-2-(4-piperidinyloxy)benzoylamino]benzamide

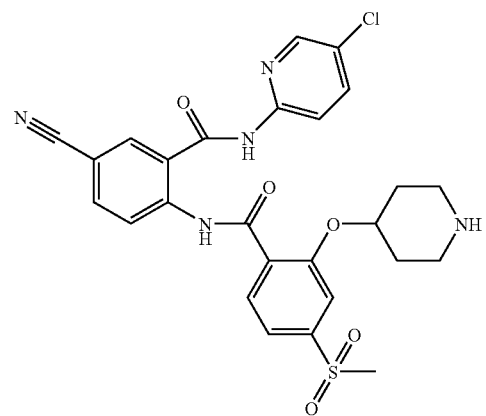

A. N-(5-Chloropyridin-2-yl)-4-cyano-2-[4-methylsulfonyl-2-(1-t-butoxycarbonyl-piperidin-4-yloxy)benzoylamino]benzamide A mixture of N-(5-chloropyridin-2-yl)-4-iodo-2-[4-methylsulfonyl-2-(1-t-butoxy-carbonylpiperidin-4-yloxy)benzoylamino]benzamide (755 mg, 1.0 mmol), Zn(CN)$_2$ (82 mg, 0.7 mmol), Pd(PPh$_3$)$_4$ (58 mg, 0.05 mmol) and DMF (3 ml) was degassed and vented with nitrogen. The mixture was heated to 80° C. for 4 h, cooled to room temperature, diluted with water and filtered. The solid was suspended in CH$_2$Cl$_2$, with sonication, chromatographed (60 g SiO$_2$, CH$_2$Cl$_2$ to 15% EtOAc/CH$_2$Cl$_2$), triturated with Et$_2$O, and filtered to give the title compound as a white solid (634 mg, 97%).

$^1$NMR (300 MHz, DMSO-$d_6$): δ 1.35 (s, 9H), 1.73 (m, 2H), 1.89 (m, 2 h), 3.13 (m, 2H), 3.31 (s, 3H), 3.56 (m, 2H), 4.92 (m, 1H), 7.61 (dd, J=1.1, 8.1 Hz, 1H), 7.71 (s, 1H), 7.96 (dd, J=2.6, 8.8 Hz, 1H), 8.02 (d, J=8.8 Hz, 1H), 8.05 (dd, J=1.8, 8.8 Hz, 1H), 8.11 (d, J=9.1 Hz, 1H), 8.34 (d, J=1.8 Hz, 1H), 8.46 (d, J=2.2 Hz, 1H), 8.59 (d, J=8.4 Hz, 1H), 11.34 (s, 1H), 11.44 (s, 1H). ES-MS, m/e 654.4 (m+1). Analysis for $C_{31}H_{32}Cl_7N_5O_7S$. Calcd: C, 56.92; H, 4.93; N, 10.71. Found: C, 56.61; H, 4.76; N, 10.48.

B. N-(5-Chloropyridin-2-yl)-4-iodo-2-[4-methylsulfonyl-2-(4-piperidinyloxy)-benzoylamino]benzamide Using a procedure analogous to Example 4-G, N-(5-chloropyridin-2-yl)-4-cyano-2-[4-methylsulfonyl-2-(1-t-butoxycarbonylpiperidin-4-yloxy)benzoylamino]benzamide gave the title compound as a white solid.

$^1$NMR (300 MHz, DMSO-d$_6$): δ 1.41 (m, 2H), 1.74 (m, 2H), 2.41 (m, 2H), 2.80 (m, 2H), 3.27 (s, 3H), 4.47 (m, 1H), 7.49 (m, 2H), 7.65 (dd, J=0.7, 7.4 Hz, 1H), 7.76 (m, 2H), 8.18 (d, J=2.2 Hz, 1H), 8.21 (d, J=7.7 Hz, 1H), 8.35 (d, J=1.8 Hz, 1H), 8.65 (d, J=9.1 Hz, 1H). FAB+/MS, exact m/e: calc. 554.1265 ($C_{26}H_{24}ClN_5O_5S$+H); found 554.1263.

EXAMPLE 168

N-(5-Chloropyridin-2-yl)-5-fluoro-2-[4-(4-methylhexahydro-1,4-diazepin-1-yl)-2-(4-oxocyclohexyloxy)benzoylamino]benzamide Trifluoroacetate

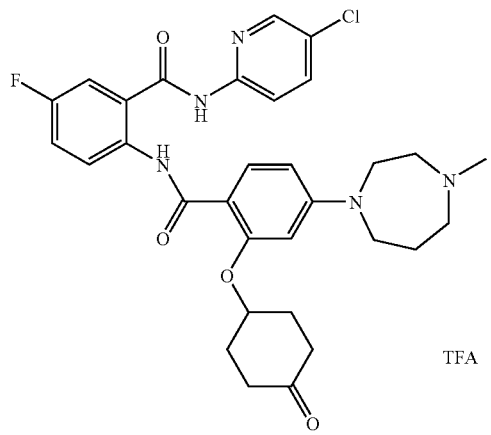

A. N-(5-Chloropyridin-2-yl)-5-fluoro-2-(2-acetoxy-4-fluorobenzoylamino)-benzamide 5-Fluoro-2-amino-N-(5-chloropyridin-2-yl)benzamide (5.32 g, 20 mmol) was added to a solution of 2 mL dry pyridine and 2-acetoxy-4-fluorobenzoyl chloride (21 mmol) in 100 mL dry methylene chloride under dry nitrogen with magnetic stirring. The reaction was allowed to stir overnight at room temperature and then was diluted with 500 mL of methylene chloride. The methylene chloride solution was washed with cold 1 M HCl, cold saturated NaHCO$_3$, and brine; and then was dried over sodium sulfate. The solvent was evaporated, and the crude product was crystallized from acetone to give 2:92 g of off-white product.

$^1$H NMR ESMS [M+H]$^+$446.1 calcd from $C_{21}H_{15}ClF_2N_3O_4$ 446 ESMS [M–H]$^-$444.2 calcd from $C_{21}H_{13}ClF_2N_3O_4$ 444 Analysis for $C_{21}H_{14}ClF_2N_3O_4$. Calcd: C, 56.58; H, 3.17; N, 9.43. Found: C, 53.76; H, 3.08; N, 8.66.

B. N-(5-Chloropyridin-2-yl)-5-fluoro-2-(4-fluoro-2-hydroxybenzoylamino)-benzamide N-(5-Chloropyridin-2-yl)-5-fluoro-2-(2-acetoxy-4-fluorobenzoylamino)-benzamide (2.75 g, 6 mmol) was dissolved in 75 mL of methanol under nitrogen. The solution was cooled in an ice-water bath and 0.5M NaOH (13 mL, 6.5 mmol) was added.

The reaction mixture was stirred overnight warming to room temperature. HCl (6.5 mL, 1M, 6.5 mmol) was added. The mixture was diluted with additional water; and the precipitated solid was filtered, washed with water, and dried over KOH in vacuo at 35° C. to give 2.15 g of white solid (89% yield).

$^1$H NMR ESMS [M+H]$^{+404.4}$ calcd from $C_{19}H_{12}ClF_2N_3O_3$ 404 ESMS [M–H]$^-$402.2 calcd from $C_{19}H_{11}ClF_2N_3O_3$ 402 Analysis for $C_{21}H_{14}ClF_2N_3O_4$. Calcd: C, 56.52; H, 3.00; N, 10.41. Found: C, 56.34; H, 2.93; N, 9.99.

C. N-(5-Chloropyridin-2-yl)-5-fluoro-2-[4-fluoro-2-(1,4-dioxa-spiro[4.5]decan-8-yloxy)benzoylamino]benzamide N-(5-Chloropyridin-2-yl)-5-fluoro-2-(4-fluoro-2-hydroxybenzoylamino)-benzamide (1.62 g, 4 mmol), 8-hydroxy-1,4-dioxa-spiro[4.5]decane (630 mg, 4 mmol), and triphenylphosphine (1.04 g, 4 mmol) were dissolved in 4 mL dry DMF, 2 mL dry methylene chloride, and 6 mL dry THF. The resulting slurry was sonicated for 5 min, and then diisopropyl azodicarboxylate (DIAD, 0.8 mL, 4 mmol) was added; and the mixture was sonicated for 2 h. Ether (40 mL) was added, and the mixture was cooled in the freezer overnight. Triphenylphosphine oxide was filtered off, and the resulting solution was concentrated to dryness under reduced pressure. Flash chromatography on silica gel gave the crude product (1.53 g) as a viscous, colorless oil which was used without further purification.

D. N-(5-Chloropyridin-2-yl)-5-fluoro-2-[4-(4-methylhexahydro-1,4-diazepin-1-yl)-2-(1,4-dioxa-spiro[4.5]decan-8-yloxy)benzoylamino]benzamide N-(5-Chloropyridin-2-yl)-5-fluoro-2-[4-fluoro-2-(1,4-dioxa-spiro[4.5]decan-8-yl-oxy)benzoylamino]benzamide (1.5 g, 2.8 mmol) and 1.5 mL 1-methylhexahydro-1,4-diazepine were dissolved in 1.5 mL of dry DMSO and heated overnight in a pressure tube at 100° C. under Ar. The solution was cooled and poured into 1 L of ethyl acetate. The ethyl acetate solution was washed once with brine, dried over sodium sulfate and evaporated to dryness under reduced pressure at 40° C. to give the intermediate ketal as a yellow oil which was used without further purification.

E. N-(5-Chloropyridin-2-yl)-5-fluoro-2-[4-(4-methylhexahydro-1,4-diazepin-1-yl)-2-(4-oxocyclohexyloxy)benzoylamino]benzamide N-(5-Chloropyridin-2-yl)-5-fluoro-2-[4-(4-methylhexahydro-1,4-diazepin-1-yl)-2-(1,4-dioxa-spiro[4.5]decan-8-yloxy)benzoylamino]benzamide (2.8 mmol) in was dissolved in 48 mL THF with magnetic stirring. The solution was cooled to ice water bath temperature and 5M HCl (9 mL) was added. The reaction mixture was allowed to stir overnight, warming to room temperature. Water (160 mL) was added and the pH of the mixture was adjusted to 12. The alkaline solution was extracted with methylene chloride. The extracts were washed with brine, dried over sodium sulfate, and evaporated under reduced pressure to give 1.64 g of a yellow glass. This material was dissolved in ether. A solution of trifluoroacetic acid (0.154 mL, 2.0 mmol) in ether was added with magnetic stirring. The resulting precipitate was filtered, washed with ether, and dried in vacuo over KOH pellets at room temperature to yield 550 mg of the title product as an off-white solid TFA salt.

1 HNMR ESMS [M+H]$^+$ 594.5 calcd from $C_{31}H_{34}$ ClFN$_5$O$_4$ 594 ESMS [M–H]$^-$592.5 calcd from $C_{31}H_{32}$ ClFN$_5$O$_4$ 592 Analysis for $C_{31}H_{33}$ ClFN$_5$O$_4$·$C_2$HF$_3$O$_2$. Calcd: C, 55.98; H, 4.84; N, 9.89. Found: C, 55.15; H, 4.93; N, 9.64.

EXAMPLE 169

Preparation of 5-Chloro-N-(5-chloropyridin-2-yl)-2-[2-(4-oxocyclohexyloxy)-4-(pyrrolidin-1-yl)benzoylamino]benzamide

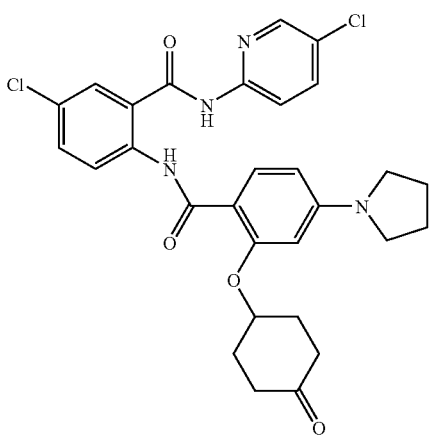

A. 2-(2-Acetoxy-4-fluorobenzoylamino)-5-chloro-N-(5-chloropyridin-2-yl)-benzamide To a stirred solution of 2-acetoxy-4-fluorobenzoic acid (852 mg, 4.9 mmol) in dry dichloromethane (40 mL) under dry nitrogen were added sequentially dry DMF (8 drops), dry pyridine (0.5 mL) and oxalyl chloride (0.5 mL). After stirring 1.5 h at room temperature, the reaction mixture was evaporated to dryness to afford 2-acetoxy-4-fluoro-benzoyl chloride.

The acid chloride (4.9 mmol) was dissolved in dry dichloromethane (40 mL) and treated with dry pyridine (0.5 mL) and 2-amino-5-chloro-N-(5-chloropyridin-2-yl)-benzamide (1.27 g). The reaction mixture was stirred at room temperature overnight before it was evaporated to dryness and taken up in ethyl acetate and water. After filtration of a small amount of insoluble material, 1 M HCl was added to bring the aqueous phase to about 0.5 M HCl. After separation of the phases, the organic phase was washed with sodium bicarbonate solution, then brine, and dried over sodium sulfate. The solution was evaporated to afford a tan solid (1.72 g), which was triturated with ether to afford a first crop (0.63 g) of the title compound as a tan solid. Evaporation of the ethereal mother liquour and trituration with ether afforded a second crop (0.41 g) of the title compound as a tan solid. Combined yield (1.04 g).
$^1$NMR

B. 5-Chloro-N-(5-chloropyridin-2-yl)-2-(4-fluoro-2-hydroxybenzoylamino)-benzamide 2-(2-Acetoxy-4-fluorobenzoylamino)-5-chloro-N-(5-chloropyridin-2-yl)-benzamide (1.04 g, 2.17 mmol) was dissolved in methanol (25 mL) under nitrogen. The solutions was cooled in an ice-water bath and 0.5 M NaOH (5 mL, 2.5 mmol) was added.

The reaction mixture was stirred overnight, warming to room temperature. The reaction mixture was evaporated to dryness and taken up in ethyl acetate and water, which did not afford a homogeneous mixture, but a sold precipitate and an aqueous layer. After addition of additional ethyl acetate and 1 M HCl, the separated organic phase was evaporated to a small volume. The resulting solid was filtered, washed with water and dried under vacuum over KOH, first at room temperature to afford the title phenol (870 mg, 92%) as a light tan solid ($^1$NMR) which was further dried under vacuum over KOH at 40° C. prior to the next step.

C. 5-Chloro-N-(5-chloropyridin-2-yl)-2-[2-(1,4-dioxa-spiro[4.5]decan-8-yloxy)-4-fluorobenzoylamino]benzamide Using a procedure similar to that of Example 64A, part C, 5-chloro-N-(5-chloro-pyridin-2-yl)-2-(4-fluoro-2-hydroxybenzoylamino)benzamide (860 mg) was O-alkylated to afford the title compound (220 mg, 19%) as a white solid.
$^1$NMR

D. 5-Chloro-N-(5-chloropyridin-2-yl)-2-[2-(1,4-dioxa-spiro[4.5]decan-8-yloxy)-4-(pyrrolidino-1-yl)benzoylamino]benzamide 5-Chloro-N-(5-chloropyridin-2-yl)-2-[2-(1,4-dioxa-spiro[4.5]decan-8-yloxy)-4-fluorobenzoylamino]benzamide (220 mg, 0.38 mmol) under nitrogen was treated with pyrrolidine (2 mL, 24 mmol), and the stirred reaction mixture was heated 3 h in an 80° C. oil bath. After cooling to room temperature, water was added, and the solid product was filtered, washed with water, and dried under vacuum over KOH overnight to afford the crude product (170 mg) as an off white solid.
ESMS: 1223.2 [M+H+M]$^+$; 610 [M–H]$^-$

E. 5-Chloro-N-(5-chloropyridin-2-yl)-2-[2-(4-oxocyclohexyloxy)-4-(pyrrolidin-1-yl)benzoylamino]benzamide Using a procedure similar to that of Example 64A, part D, the ketal of 5-chloro-N-(5-chloropyridin-2-yl)-2-[2-(1,4-dioxa-spiro[4.5]decan-8-yloxy)-4-(pyrrolidino-1-yl)-benzoylamino]benzamide was hydrolyzed. After the diluted, acidic reaction mixture was adjusted to pH 8, the THF was evaporated; and the resulting was filtered, washed with water and dried under vacuum over KOH at room temperature to afford a cream colored solid (144 mg). Examination by TLC showed ketal hydrolysis incomplete; to the product was resubmitted to the hydrolysis conditions for an additional 6 h, leading to the isolation of a light yellow solid (127 mg) which was triturated with ether and dried under vacuum to afford the title ketone as a white solid (91 mg).
ESMS: 567 [M+H]$^+$; 565 [M–H]$^-$

EXAMPLE 170

Preparation of 2-[4-(1-Amino-1-methyl)ethyl-2-(4-oxocyclohexyloxy)benzoylamino]-5-chloro-N-(5-chloropyridin-2-yl)benzamide Dihydrochloride

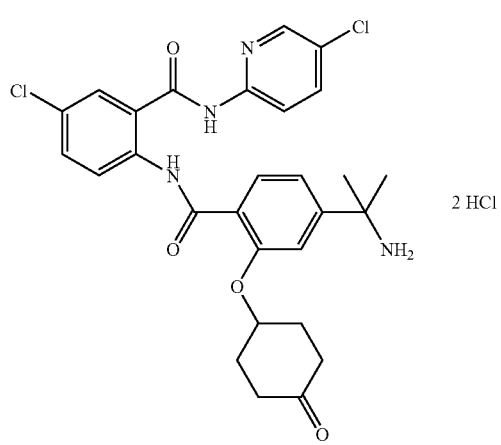

A. Methyl 4-(1-tert-butyloxycarbonylamino-1-methyl)ethyl-2-(1,4-dioxa-spiro[4.5]decan-8-yloxy)benzoate Using a procedure similar to that of Example 60, part H, methyl 4-(1-tert-butyloxycarbonylamino-1-methyl)ethyl-2-hydroxybenzoate (0.58 g) was O-alkylated to afford the title compound.

B. 2-[4-(1-tert-Butyloxycarbonylamino-1-methyl)ethyl-2-(1,4-dioxa-spiro[4.5]decan-8-yloxy)benzoylamino]-5-chloro-N-(5-chloropyridin-2-yl)benzamide Using a procedure similar to that of Example 60, part I, first paragraph, methyl 4-(1-tert-butyloxycarbonylamino-1-methyl)ethyl-2-(1,4-dioxa-spiro[4.5]decan-8-yloxy)-benzoate (0.635 g) was converted into lithium 4-(1-tert-butyloxycarbonylamino-1-methyl)ethyl-2-(1,4-dioxa-spiro[4.5]decan-8-yloxy)benzoate.

Using a procedure similar to that of Example 60, part I, second paragraph, the lithium benzoate was converted into the corresponding benzoyl chloride.

Using a procedure similar to that of Example 60, part I, third paragraph, and 2-amino-5-chloro-N-(5-chloropyridin-2-yl)benzamide, the benzoyl chloride was converted into the title compound.

C. 2-[4-(1-Amino-1-methyl)ethyl-2-(4-oxocyclohexyloxy)benzoylamino]-5-chloro-N-(5-chloropyridin-2-yl)benzamide Dihydrochloride Using a procedure similar to that of Example 64A, part D, the ketal of 2-[4-(1-tert-butyloxycarbonylamino-1-methyl)ethyl-2-(1,4-dioxa-spiro[4.5]decan-8-yloxy)benzoylamino]-5-chloro-N-(5-chloropyridin-2-yl)benzamide was hydrolyzed using 5 M HCl.

Using a procedure similar to that of Example 60, part J, the BOC group was removed. The resulting salt was purified by reversed phase chromatography to provide the product as a dihydrochloride. $^1$NMR, MS

EXAMPLE 171

Preparation of 2-[4-(1-Amino-1-methyl)ethyl-2-(4-oxocyclohexyloxy)benzoylamino]-N-(5-chloropyridin-2-yl)-5-fluorobenzamide Dihydrochloride

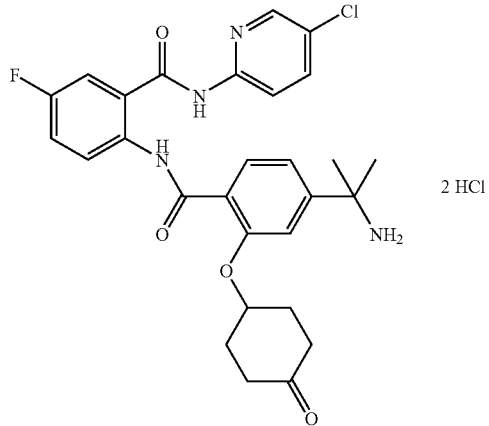

A. 2-[4-(1-tert-Butyloxycarbonylamino-1-methyl)ethyl-2-(1,4-dioxa-spiro[4.5]decan-8-yloxy)benzoylamino]-N-(5-chloropyridin-2-yl)-5-fluorobenzamide Using a procedure similar to that of Example 60, part I, third paragraph, and 2-amino-N-(5-chloropyridin-2-yl)-5-fluorobenzamide, 4-(1-tert-butyloxycarbonylamino-1-methyl)ethyl-2-(1,4-dioxa-spiro[4.5]decan-8-yloxy)benzoyl chloride was converted into the title compound.

B. 2-[4-(1-Amino-1-methyl)ethyl-2-(4-oxocyclohexy)benzoylamino]-N-(5-chloropyridin-2-yl)-5-fluorobenzamide Dihydrochloride Using a procedure similar to that of Example 64A, part D, the ketal of 2-[4-(1-tert-butyloxycarbonylamino-1-methyl)ethyl-2-(1,4-dioxa-spiro[4.5]decan-8-yloxy)benzoylamino]-N-(5-chloropyridin-2-yl)-5-fluorobenzamide was hydrolyzed using 5 M HCl.

Using a procedure similar to that of Example 60, part J, the BOC group was removed. The resulting salt was purified by reversed phase chromatography to provide the product as a dihydrochloride.
$^1$NMR, MS

EXAMPLE 172

Preparation of N-(5-Chloropyridin-2-yl)-2-[2-[1-(4-pyridinyl)piperidin-4-yl-carbonylamino]benzoylamino]benzamide Hydrochloride

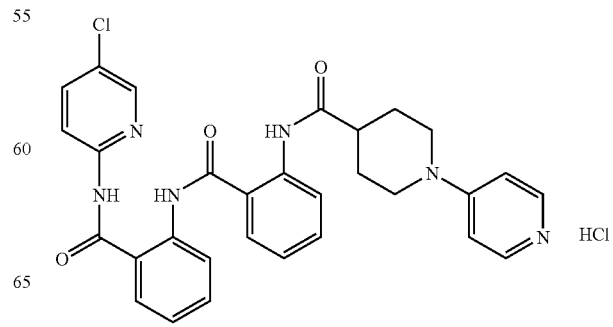

A. N-(5-Chloropyridin-2-yl)-2-[(2-nitrobenzoyl) amino]benzamide

By methods substantially equivalent to those described in Example 16-F, N-(5-chloropyridin-2-yl)-2-[(2-nitrobenzoyl) amino]benzamide (0.48 g, 75%) was prepared from N-(5-chloropyridin-2-yl)-2-aminobenzamide and 2-nitrobenzoyl chloride.

[1]NMR IS-MS, m/e 397.1 (m+1) Analysis for $C_{19}H_{13}ClN_4O_4$. Calcd: C, 57.51; H, 3.30; N, 14.12. Found: C, 57.52; H, 3.47; N, 13.88.

B. N-(5-Chloropyridin-2-yl)-2-[(2-aminobenzoyl) amino]benzamide

By methods substantially equivalent to those described in Example 139-B, N-(5-chloropyridin-2-yl)-2-[(2-aminobenzoyl)amino]benzamide (0.33 g, 96%) was prepared from N-(5-chloropyridin-2-yl)-2-[(2-nitrobenzoyl)amino]benzamide.

[1]NMR IS-MS, m/e 367.1 (m+1)

C. N-(5-Chloropyridin-2-yl)-2-[2-[1-(4-pyridinyl) piperidin-4-ylcarbonylamino]-benzoylamino]benzamide hydrochloride By methods substantially equivalent to those described in Example 16-F, N-(5-chloropyridin-2-yl)-2-[2-[1-(4-pyridinyl)piperidin-4-ylcarbonylamino]benzoyl-amino]benzamide hydrochloride (0.208 g, 46%) was prepared from N-(5-chloropyridin-2-yl)-2-[(2-aminobenzoyl)amino]benzamide and 1-(4-pyridinyl)piperidin-2-ylcarbonyl chloride.

[1]NMR IS-MS, m/e 555.2 (m+1) Analysis for $C_{30}H_{27}ClN_6O_3 \cdot HCl \cdot 0.5H_2O$. Calcd: C, 59.97; H, 4.87; N, 14.00. Found: C, 59.96; H, 4.78; N, 13.97.

TABLE 2

Examples 201-256

Compounds of formula I which may be denoted by the following formula I-2

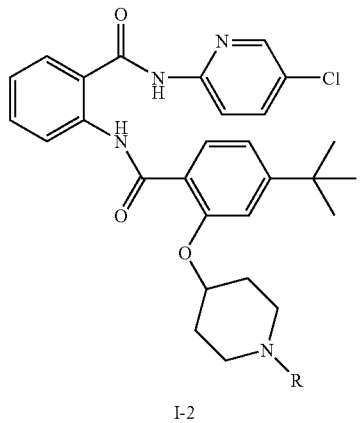

I-2 in which R has the indicated value of $R^a$ were prepared according to the indicated procedure from a requisite corresponding compound of formula I and the reagents and conditions appropriate for the indicated procedure or by a procedure otherwise noted.

EXAMPLE 201

R=BOC; Procedure:

Under a nitrogen atmosphere, 2-(1-tert-butoxycarbonylpiperidin-4-yloxy)-4-tert-butyl benzoic acid (1.52 g, 4 mmol) was dissolved in dry dichloromethane (25 mL) and dimethylformamide (0.25 mL) catalyst was added. Subsequently oxalyl chloride (0.423 mL, 4.85 mmol) was added portionwise via syringe. Vigorous gas evolution took place.

The mixture was stirred at room temperature for about 10 minutes until gas evolution nearly ceased, then the volatiles were evaporated under vacuum. The resulting milky-white residue was redissolved in 4:1 dichloromethane:toluene, concentrated again in vacuo, then dissolved in amylene-stabilized chloroform (10 mL) and transferred to an addition funnel. The acid chloride solution was added dropwise to a stirring ice-cold solution of 2-amino-N-(5-chloropyridin-2-yl)benzamide (1.0 g, 4 mmol) and pyridine (1.15 g, 14.5 mmol) in amylene-stabilized chloroform (20 mL). The mixture was then allowed to warm to room temperature with stirring overnight. The mixture was diluted with dichloromethane, washed once each with saturated sodium bicarbonate solution, water, and brine, then dried and concentrated in vacuo to provide a crusty brown foam.

The foam was purified on a 6 mm Chromatotron plate using 1:1 ether:hexanes. A mass of white solid precipitated from the eluted fractions. This material was washed several times with petroleum ether, then dried under high vacuum to provide 1.75 grams (71%) of 2-[2-(1-tert-butoxycarbonylpiperidin-4-yloxy)-4-(tert-butyl)benzoylamino]-N-(5-chloro-pyridin-2-yl)benzamide as a white solid.

[1]NMR IS-MS, m/z 607.3 (m+) Analysis for $C_{33}H_{39}ClN_4O_5$. Calcd: C, 65.28; H, 6.48; N, 9.23. Found: C, 65.51; H, 6.78; N, 9.31.

EXAMPLE 202

R=H; Procedure:

The 2-[2-(1-tert-butoxycarbonylpiperidin-4-yloxy)-4-(tert-butyl)benzoylamino]-N-(5-chloropyridin-2-yl)benzamide (1.57 g, 2.58 mmol) was dissolved in 20 mL of a 4 N HCl in dioxane solution at room temperature, resulting in a modest evolution of gas. After 1 hour stirring at room temperature, the solvent and HCl gas were evaporated in vacuo, then the resulting white solid was resuspended in 75 mL 2:1 EtOAc:dichloromethane and evaporated a second time. The pasty white solid was dissolved in a solution of $K_2 CO_3$ (11.2 g) in water (75 mL), dichloromethane was added (75 mL), and the mixture vigorously stirred overnight. The mixture was partitioned, the aqueous layer back-extracted twice with dichloromethane, then the combined organic layers washed with brine. The organic layer was dried and concentrated in vacuo to provide 2-[4-tert-butyl)-2-(piperidin-4-yloxy)benzoylamino]-N-(5-chloropyridin-2-yl)benzamide (1.32 g, 100%) as an off-white crystalline solid.

[1]NMR IS-MS, m/z 507.3 (m+); 505.3 (m−1).

General Procedure A for Reductive Alkylation of Secondary Amines Such as the Compound Described in Example 202:

The 2-[4-(tert-butyl)-2-(piperidin-4-yloxy)benzoylamino]-N-(5-chloropyridin-2-yl)benzamide (30 mg, 59 pmunol) is placed in a 4 mL screw-cap vial, then the aldehyde (180 micromoles, 3 eq) or the ketone (at least 180 micromoles, at least 3 eq) is added directly to the amine. The amine and aldehyde component mixture are then dissolved in 1 mL of freshly prepared 95:5 anhydrous MeOH:AcOH. To this solution is added 0.5 mL freshly prepared sodium cyanoborohydride solution (15.1 mg/mL in 95:5 anhydrous MeOH: AcOH, 120 micromoles, 2 equivalents). The vial is capped and shaken overnight at room temperature on an orbital platform shaker (350 rpm). The crude reaction mixture is then applied to a solid phase extraction (SPE) cartridge (strong cation exchange (SCX), 6 cc volume, 1 gram of packing material from Varian Sample Preparation Products, Harbor City, Calif.) that has been pre-washed with methanol (2×5 mL). The cartridge is next washed with methanol (3-4×5 mL). The product is eluted with 0.5 M ammonia in methanol (2×5 mL). The resulting solution is concentrated in vacuo to afford the alkylated product, generally in 60-95% yield.

EXAMPLE 203

R=4-Methylbenzyl; Procedure A; IS-MS m/z 611.3 (m+1), 609 (m−1).

EXAMPLE 204

R=2-Nitrobenzyl; Procedure A; IS-MS m/z 642.3 (m+1).

EXAMPLE 205

R=2,3-Methylenedioxybenzyl; Procedure A; IS-MS m/z 641.3 (m+1), 639.4 (m−1).

General Procedure B for Acylation of Secondary Amines Such as the Compound Described in Example 202:

The 2-[4-tert-butyl)-2-(piperidin-4-yloxy)benzoylamino]-N-(5-chloropyridin-2-yl)benzamide (30 mg, 59 pnol) in a 4 mL screw cap vial is dissolved in amylene-stabilized chloroform (1 mL). An isocyanate or isothiocyanate (1.3 equivalents) is then added directly to the amine solution and the resulting mixture shaken for 2-20 h at room temperature on an orbital shaker (350 rpm). Excess acylating agent is scavenged by adding aminomethylated polystyrene resin (100 mg 2.25 mmol/g loading) and amylene stabilized chloroform (1 mL) to the reaction vial. This slurry is shaken overnight, then filtered through a disposable polypropylene frit. Concentration of the filtrate affords clean product.

EXAMPLE 206

R=(2-Fluorophenyl)aminocarbonyl; Procedure B; IS-MS m/z 644.4 (m+1).

EXAMPLE 207

R=Benzyl; Procedure A; IS-MS m/z 597.5 (m+1), 595.6 (m−1).

EXAMPLE 208

R=2-Fluorobenzyl; Procedure A; IS-MS m/z 615.3 (m+1), 613.5 (m−1).

EXAMPLE 209

R=2-Chlorobenzyl; Procedure A; IS-MS m/z 631.3 (m+1), 629.7 (m−1).

EXAMPLE 210

R=2-Methoxybenzyl; Procedure A; IS-MS m/z 627.3 (m+1), 625.5 (m−1).

EXAMPLE 211

R=2-Ethoxybenzyl; Procedure A; IS-MS m/z 641.3 (m+1), 639.5 (m−1).

EXAMPLE 212

R=2-Hydroxybenzyl; Procedure A; IS-MS m/z 613.3 (m+1), 61-1.4 (m−1).

EXAMPLE 213

R=2-Methylbenzyl; Procedure A; IS-MS m/z 611.3 (m+1).

EXAMPLE 214

R=3-Methylbenzyl; Procedure A; IS-MS m/z 611.3 (m+1), 609.4 (m−1).

EXAMPLE 215

R=Thien-2-ylmethyl; Procedure A; IS-MS m/z 603.3 (m+1).

EXAMPLE 216

R=3-Methylthien-2-ylmethyl; Procedure A; IS-MS m/z 617.4 (m+1), 615.6 (m−1).

EXAMPLE 217

R=Thien-3-ylmethyl; Procedure A; IS-MS m/z 603.3 (m+1).

EXAMPLE 218

R=Cyclopropylmethyl; Procedure A; IS-MS m/z 561.3 (m+1), 559.4 (m−1).

EXAMPLE 219

R=2-Carboxybenzyl; Procedure A; IS-MS m/z 641.3 (m+1), 639.4 (m−1).

EXAMPLE 220

R=Imidazol-2-ylmethyl; Procedure A; IS-MS m/z 587.3 (m+1), 585.3 (m−1).

EXAMPLE 221

R=2-Pyridinylmethyl; Procedure A; IS-MS m/z 598.4 (m+1), 596.5 (m−1).

EXAMPLE 222

R=2-Cyanobenzyl; Procedure A; IS-MS m/z 622.5 (m+1).

EXAMPLE 223

R=Thiazol-2-ylmethyl; Procedure A; IS-MS m/z 604.3 (m+1), 602.4 (m−1).

EXAMPLE 224

R=5-Methylimidazol-4-ylmethyl; Procedure A; IS-MS m/z 601.4 (m+1), 599.4 (m−1).

EXAMPLE 225

R=2-Methoxycarbonylbenzyl; Procedure A; IS-MS m/z 655.5 (m+1), 653.5 (m−1).

EXAMPLE 226

R=Methyl; Procedure A; IS-MS m/z 521.4 (m+1).

EXAMPLE 227

R=2-Methoxyethyl; Procedure A, modified such that the aqueous solution of methoxyacetaldehyde was passed over a diatomaceous earth column before addition to the amine; IS-MS m/z 562.2 (m+1), 563.3 (m−1).

General Procedure C for Acylation of Secondary Amines Such as the Compound Described in Example 202:

To 2-[4-(tert-butyl)-2-(piperidin-4-yloxy)benzoylamino]-N-(5-chloropyrdin-2-yl)benzamide (30 mg, 59 pmnol) in a 4 mL screw cap vial is added polymer-supported carbodiimide (P-EPC, 280 mg @0.85 mmol/g, 4 eq) and a carboxylic acid of choice (120 micromoles, 2 eq), followed by 3 mL of 4:1 (amylene stabilized) chloroform:tert-butyl alcohol. Where acid hydrochloride salts are used, piperidinomethyl polystyrene resin (100 mg @2.6-2.8 mmol/g) is added to effect reaction. The vial is capped, shaken overnight at room temperature, then the mixture is filtered. Retentates are washed with amylene stabilized chloroform (3 mL), and the combined filtrate and wash are concentrated in vacuo to afford the amide derivative of the compound of Example 202.

EXAMPLE 228

R=2-Oxo-2-(2-thiophenyl)acetyl; Procedure C; IS-MS m/z 645.0 (m+1), 643.0 (m−1).

EXAMPLE 229

R=Isopropyl; Procedure A; IS-MS m/z 549.4 (m+1).

EXAMPLE 230

R=Propyl; Procedure A; IS-MS m/z 549.2 (m+1), 547.3 (m−1).

General Procedure D for Alkylation of Secondary Amines Such as the Compound Described in Example 202 with Epoxides:

To 2-[4-(tert-butyl)-2-(piperidin-4-yloxy)benzoylamino]-N-(5-chloropyridin-2-yl)benzamide (30 mg, 59 μmol) in a 4 mL screw cap vial is added a selected epoxide (120 micromoles, 2 eq) and methanol (350 microliters). The vial is capped, heated to 60° C. for 16-24 h, then the mixture is diluted with methanol and purified via SCX solid phase extraction as described in general procedure A to afford the (hydroxyethyl)alkylamine.

EXAMPLE 231

R=2-Hydroxypropyl; Procedure D; IS-MS m/z 565.1 (m+1), 563.1 (m−1).

EXAMPLE 232

R=2-Phenylpropyl; Procedure A; IS-MS m/z 625.1 (m+1), 623.1 (m−1).

EXAMPLE 233

R=2-Methylbutyl; Procedure A; IS-MS m/z 577.1 (m+1), 575.1 (m−1).

EXAMPLE 234

R=(Methoxyethyl)aminothiocarbonyl; Procedure B; IS-MS m/z 624.0 (m+1), 622.1 (m−1).

EXAMPLE 235

R=(3-Diethylaminopropyl)aminothiocarbonyl; Procedure B; IS-MS m/z 679.1 (m+1), 677.2 (m−1).

EXAMPLE 236

R=2-hydroxy-3,3,3-trifluoropropyl; Procedure D; IS-MS m/z 619.0 (m+1), 617.1 (m−1).

EXAMPLE 237

R=2-Phenylethyl; Procedure A; IS-MS m/z 611.1 (m+1), 609.1 (m−1).

EXAMPLE 238

R=(3-Dimethylaminopropyl)aminothiocarbonyl; Procedure B; IS-MS m/z 651.1 (m+1), 649.1 (m−1).

EXAMPLE 239

R=3-(Morpholin-4-yl)propylaminothiocarbonyl Procedure B; IS-MS m/z 693.1 (m+1), 691.1 (m−1).

EXAMPLE 240

R=(3-Pyridinylmethyl)aminothiocarbonyl; Procedure B; IS-MS m/z 657.0 (m+1), 655.1 (m−1).

EXAMPLE 241

R=2-(2-Furanyl)-2-oxoacetyl; Procedure C; IS-MS m/z 629.0 (m+1), 627.1 (m−1).

EXAMPLE 242

R=1-Methylpyrazol-5-ylcarbonyl; Procedure C; IS-MS m/z 615.0 (m+1), 613.1 (m−1).

EXAMPLE 243

R=3,3-Dimethylbutyl; Procedure A; IS-MS m/z 591.1 (m+1), 589.2 (m−1).

EXAMPLE 244

R=3-Carboxypropionyl; Procedure C using succinic anyhdride with polymer-supported base and without polymer-supported carbodiimide; IS-MS m/z 607.0 (m+1), 605.1 (m−1).

EXAMPLE 245

R=1-Methylpyrrol-2-ylcarbonyl; Procedure C; IS-MS m/z 614.2 (m+1).

EXAMPLE 246

R=(Dimethylamino)acetyl; Procedure C; IS-MS m/z 592.2 (m+1), 590.3 (m−1).

EXAMPLE 247

R=3-Methylbutyl; Procedure A; IS-MS m/z 577.2 (m+1), 575.3 (m−1).

EXAMPLE 248

R=Pyruvoyl; Procedure C; IS-MS m/z 577.2 (m+1), 575.3 (m−1).

EXAMPLE 249

R=E/Z-3-(Furan-2-yl)prop-2-enyl; Procedure A; IS-MS m/z 613.2 (m+1).

EXAMPLE 250

R=E/Z-3-Phenylprop-2-enyl; Procedure A; IS-MS m/z 623.2 (m+1).

EXAMPLE 251

R=3-Phenylpropyl; Procedure A; IS-MS m/z 625.3 (m+1).

EXAMPLE 252

R=n-Butyl; Procedure A; IS-MS m/z 563.2 (m+1).

EXAMPLE 253

R=2-(Thien-2-yl)ethylaminocarbonyl; Procedure B; IS-MS m/z 660.2 (m+1).

EXAMPLE 254

R=Tetrazol-1-ylacetyl; Procedure C; IS-MS m/z 617.1 (m+1), 615.2 (m−1).

EXAMPLE 255

R=(3-Methoxypropyl)aminothiocarbonyl; Procedure B; IS-MS m/z 638.2 (m+1).

EXAMPLE 256

R=2-Hydroxy-3,3-dimethylbutyl; Procedure D; IS-MS m/z 607.2 (m+1), 605.3 (m−1).

TABLE 3

Examples 301-319

Compounds of formula I which may be denoted by the following formula I-3

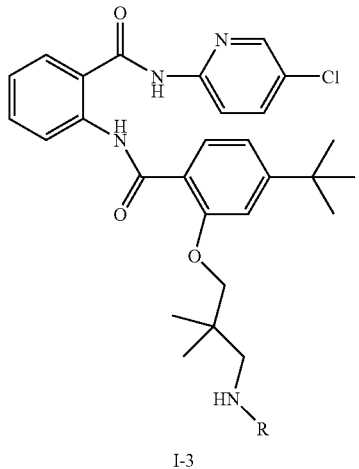

I-3 in which R has the indicated value of $R^a$ were prepared according to the indicated procedure from a requisite corresponding compound of formula I and the reagents and conditions appropriate for the indicated procedure or by a procedure otherwise noted.

EXAMPLE 301

R=BOC; Procedure:

A. Methyl 2-(3-tert-butoxycarbonylamino-2,2-dimethylpropoxy)-4-(tert-butyl)-benzoate Using methods substantially equivalent to Example 21-C, except that the Mitsonobu reaction was allowed to proceed for 7 to 10 days, methyl 2-(3-tert-butoxy-carbonylamino-2,2-dimethylpropoxy)-4-(tert-butyl)benzoate (10.85 g, 39%) as a pale yellow brittle foam was prepared from methyl 4-(tert-butyl)salicylate (14.72 g, 70.8 mmol) and 3-(tert-butoxycarbonylamino)-2,2-dimethylpropanol (14.37 g, 70.8 mmol). $^1$NMR IR (KBr): 3339, 1722, 1691 cm$^{-1}$. IS-MS, m/z 394.2 (m+1), 392.4 (m−1). Analysis for $C_{22}H_{35}NO_5$. Calcd: C, 67.15; H, 8.96; N, 3.56. Found: C, 61.13; H, 8.11; N, 3.24.

B. 2-(3-tert-Butoxycarbonylamino-2,2-dimethylpropoxy)-4-(tert-butyl)benzoic acid Using methods substantially equivalent to those described in Example 21-D, 2-(3-tert-butoxycarbonylamino-2,2-dimethylpropoxy)-4-(tert-butyl)benzoic acid (10.6 g, 102%) was prepared from methyl-2-(3-tert-butoxycarbonylamino-2,2-dimethylpropoxy)-4-(tert-butyl)benzoate (10.8 g, 27.4 mmol).

C. 2-[2-(3-tert-Butoxycarbonylamino-2,2-dimethyl-propoxy)-4-(tert-butyl)benzoyl-amino]-N-(5-chloro-pyridin-2-yl)benzamide Using methods substantially equivalent to those described in Example 201, 2-[2-(3-tert-butoxycarbonylamino-2,2-dimethylpropoxy)-4-(tert-butyl)benzoylamino]-N-(5-chloropyridin-2-yl)benzamide was prepared from 2-(3-tert-butoxycarbonylamino-2,2-dimethylpropoxy)-4-(tert-butyl)benzoic acid and N-(5-chloropyridin-2-yl)-2-amino-benzamide to provide, after silica gel purification, 1.98 g (80.5%) of a yellow foam.
$^1$NMR IS-MS, m/z 609.3 (m+1), 607.5 (m−1) Analysis for $C_{33}H_{41}ClN_4O_5$. Calcd: C, 65.07; H, 6.78; N, 9.20. Found: C, 64.46; H, 6.63; N, 8.90.

EXAMPLE 302

R═H; Procedure:
2-[2-(3-tert-butoxycarbonylamino-2,2-dimethylpropoxy)-4-(tert-butyl)benzoyl-amino]-N-(5-chloropyridin-2-yl)benzamide (1.50 g, 2.48 mmol) was dissolved in TFA (5 mL) and stirred at room temperature for 3 h. The TFA was removed in vacuo to give a yellow oil. The free base was obtained from the salt by loading onto 3 SCX columns (60 cc, 10 g; prewashed with MeOH). The columns were washed with 9:1 $CHCl_3$:MeOH, and the free amine eluted with 3:1 $CHCl_3$:2 N $NH_3$ in MeOH to provide 2-[2-(3-amino-2,2-dimethylpropoxy)-4-(tert-butyl)benzoylamino]-N-(5-chlropyridin-2-yl)benzamide (1.08 g, 86.4%) as a pale yellow foam.
$^1$NMR IS-MS m/z 504.3 (m+1), 502.4 (m−1).

EXAMPLE 303

R=1-Methylpyrrol-2-ylcarbonyl; Procedure C; IS-MS m/z 616.4 (m+1), 614.4 (m−1).

EXAMPLE 304

R=3-Methylthien-2-ylcarbonyl; Procedure C; IS-MS m/z 633.3 (m+1), 631.5 (m−1).

EXAMPLE 305

R=3-Thienylcarbonyl; Procedure C; IS-MS m/z 619.6 (m+1), 617.5 (m−1).

EXAMPLE 306

R=2-Fluorobenzoyl; Procedure C; IS-MS m/z 631.3 (m+1), 629.5 (m−1).

EXAMPLE 307

R=2-Oxo-2-(2-thienyl)acetyl; Procedure C; IS-MS m/z 647.5 (m+1), 645.6 (m−1).

EXAMPLE 308

R=(3-Thienyl)acetyl; Procedure C; IS-MS m/z 633.4 (m+1), 631.4 (m−1).

EXAMPLE 309

R=2-Methylbenzoyl; Procedure C; IS-MS m/z 627.4 (m+1), 625.5 (m−1).

EXAMPLE 310

R=3-(2-Pyridinyl)-1-oxopropyl; Procedure C; IS-MS m/z 642.3 (m+1), 640.4 (m−1).

EXAMPLE 311

R=2-Thienylcarbonyl; Procedure C; IS-MS m/z 642.3 (m+1), 640.4 (m−1).

EXAMPLE 312

R=(2-Thienyl)acetyl; Procedure C; IS-MS m/z 633.6 (m+1), 631.3 (m−1).

General Procedure G for Alkylation of Primary Amines Such as the Compound Described in Example 302:
To an aldehyde (98 mmol, 2 eq) in a 1 mL screw cap vial is added 2-[2-(3-amino-2,2-dimethylpropoxy)-4-(tert-butyl)benzoylamino]-N-(5-chloropyridin-2-yl)benzamide (25 mg, 49 mmol) as a solution in MeOH (0.25 mL). The vial is capped and allowed to stand at room temperature. After 1 h, excess solid $NaBH_4$ is added, and the vials are left capped at room temperature overnight. The reaction is diluted with MeOH (0.5 mL) and $CHCl_3$ (0.5 mL) and a drop of AcOH is added. The solution is applied to a prewashed (MeOH) 10 cc, 0.5 g SCX solid phase extraction cartridge, and the cartridge is washed with 2×5 mL of $CHCl_3$:MeOH (9:1). The product is eluted with 2×5 mL of $CHCl_3$:2 N $NH_3$ in MeOH, and the solvent is removed in vacuo to give the purified product.

EXAMPLE 313

R=2-Fluorobenzyl; Procedure G; IS-MS m/z 617.4 (m+1), 615.2 (m−1).

EXAMPLE 314

R=3-Methylthien-2-ylmethyl; Procedure G; IS-MS m/z 619.5 (m+1), 617.6 (m−1).

EXAMPLE 315

R=2,3-Dimethoxybenzyl; Procedure G; IS-MS m/z 659.4 (m+1), 657.4 (m−1).

EXAMPLE 316

R=2-Methoxybenzyl; Procedure G; IS-MS m/z 629.3 (m+1), 627.5 (m−1).

EXAMPLE 317

R=2-Methylbenzyl; Procedure G; IS-MS m/z 613.5 (m+1), 611.4 (m−1).

EXAMPLE 318

R=2,3-Methylenedioxybenzyl; Procedure G; IS-MS m/z 643.4 (m+1), 641.4 (m−1).

EXAMPLE 319

R=2-Hydroxy-6-methoxybenzyl; Procedure G; IS-MS m/z 645.6 (m+1), 643.5 (m−1).

PREPARATION 401

Preparation of 2-[2-(3-Bromopropyl)-4-isopropyl-benzoylamino]-N-(5-chloropyridin-2-yl)benzamide

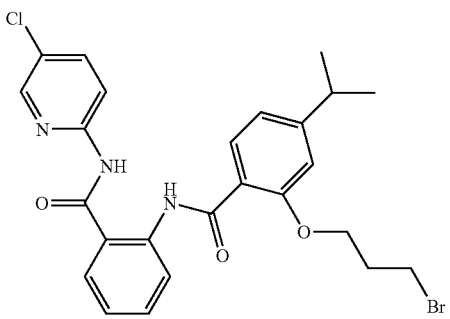

N-(5-Chloropyridin-2-yl)-2-(2-hydroxy-4-isopropylbenzoylamino)benzamide (2.55 g, 6.23 mmol), 3-bromo-1-propanol (867 mg, 0.564 mL, 6.23 mmol) and triphenyl-phosphine (1.63 g, 6.23 mmol) were dissolved in dry THF (25 mL) under a nitrogen atmosphere, then cooled on ice. To the chilled solution was then added dropwise diisopropyl azidodicarboxylate (1.26 g, 1.23 mL, 6.23 mmol) via syringe over a 15 minute period. The mixture was stirred on ice for 15 minutes more, then it was allowed to warm to room temperature with stirring overnight. The reaction was concentrated in vacuo, redissolved in dichloromethane (200 mL), washed twice with saturated sodium bicarbonate, once with brine, then dried and concentrated to provide a yellow oil. This oil was partially purified by flash chromatography on about 250 g silica (isocratic 95:5 dichloromethane:EtOAc) to yield 2.4 g of a pale yellow oil. This material was divided in half and each portion applied to a 4 mm chromatotron plate equilibrated with dichloromethane. The product was eluted with 95:5 dichloromethane:EtOAc and the clean fractions were pooled and concentrated to provide 2.34 g (71%) of 2-[2-(3-bromopropyl)-4-isopropylbenzoylamino]-N-(5-chloropyridin-2-yl)benzamide as a crystalline white solid.

[1]NMR IS-MS, m/z 530.1/532.1 (m+1) Analysis for $C_{25}H_{25}BrClN_3O_3$. Calcd: C, 56.57; H, 4.75; N, 7.92. Found: C, 56.27; H, 4.73; N, 8.03.

TABLE 4

Examples 402-509

Compounds of formula I which may be denoted by the following formula I-4

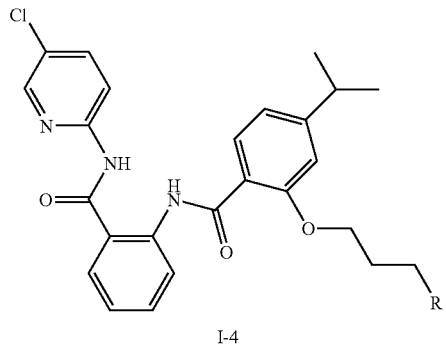

I-4 in which R has the indicated value of $NR^aR^b$ were prepared from an amine of formula $HNR^aR^b$ according to the indicated procedure from the above intermediate corresponding to a compound of formula I-4 in which R is bromo and the reagents and conditions appropriate for the indicated procedure or by a procedure otherwise noted.

General Procedure E for Alkylation Using Bromoalkyl Ethers Such as the Compound of Preparation 401 Above:

To 2-[2-(3-bromopropyl)-4-isopropylbenzoylamino]-N-(5-chloropyridin-2-yl)-benzamide (22 mg, 42 μmol) in a 4 mL screw cap vial is added a primary or secondary amine of choice (120 μmol, 3 equiv) and dimethylformamide (0.25 mL). The vial is capped, and the reaction mixture is heated at 60° C. for 16-36 hours and then allowed to cool to room temperature. Excess primary amines are scavenged by the addition of resin-supported aldehyde (formylmethyl polystyrene, 120 mg@about 1 mmol/g), resin-supported base (piperidinomethylpolystyrene, 100 mg@2.6-2.8 mmol/g), and amylene stabilized chloroform (3 mL). Excess secondary amines are scavenged in the same fashion, except that resin-supported isocyanate (methylisocyanate polystyrene resin, Novabiochem, San Diego, Calif., 150 mg@1 mmol/g) is used instead of aldehyde resin. The resulting slurry is shaken at room temperature on an orbital shaker (350 rpm) overnight, then applied to a pre-washed (1:1 chloroform:MeOH) 6 cc, 1 gram SCX solid phase extraction cartridge. The remaining slurry in the vial is washed with chloroform (3 mL) and the wash is added to the cartridge. The cartridge containing resin slurry is washed once with 5 mL of 1:1 chloroform:MeOH, three times with 5 mL portions of MeOH, then allowed to dry overnight. The dried resin over the SCX media is discarded and the cartridge rinsed once with MeOH (5 mL). The product is eluted with two 5 mL portions of 0.5 M $NH_3$ in MeOH and the eluent is concentrated in vacuo. The residue is then dissolved in 4 mL 1:1 chloroform:MeOH, filtered (0.45 micron teflon filter, Gelman Sciences), and concentrated in vacuo to provide the desired product.

EXAMPLE 402

R=4-Morpholinyl; Procedure E; IS-MS m/z 537.0 (m+1), 535.1 (m−1).

EXAMPLE 403

R=4-Thiomorpholinyl; Procedure E; IS-MS m/z 553.0 (m+1), 551.1 (m−1).

EXAMPLE 404

R=Piperidin-1-yl; Procedure E; IS-MS m/z 535.0 (m+1), 533.1 (m−1).

EXAMPLE 405

R=4-Hydroxypiperidin-1-yl; Procedure E; IS-MS m/z 551.0 (m+1), 549.1 (m−1).

EXAMPLE 406

R=Azetidin-1-yl; Procedure E; IS-MS m/z 507.0 (m+1), 505.0 (m−1).

EXAMPLE 407

R=Pyrrolidin-1-yl; Procedure E; IS-MS m/z 521.0 (m+1), 519.1 (m−1).

EXAMPLE 408

R=3-Carbamoylpiperidin-1-yl; Procedure E; IS-MS m/z 578.0 (m+1), 576.0 (m−1).

EXAMPLE 409

R=Cyclopropylamino; Procedure E; IS-MS m/z 507.0 (m+1), 505.1 (m−1).

EXAMPLE 410

R=Cyclobutylamino; Procedure E; IS-MS m/z 521.0 (m+1), 519.1 (m−1).

EXAMPLE 411

R=Cyclopentylamino; Procedure E; IS-MS m/z 535.1 (m+1), 533.1 (m−1).

EXAMPLE 412

R=Cyclohexylamino; Procedure E; IS-MS m/z 549.1 (m+1), 547.1 (m−1).

EXAMPLE 413

R=(3-Methylcyclohexyl)amino; Procedure E; IS-MS m/z 563.1 (m+1), 561.2 (m−1).

EXAMPLE 414

R=(4-Methylcyclohexyl)amino; Procedure E; IS-MS m/z 563.1 (m+1), 561.2 (m−1).

EXAMPLE 415

R=(5-Hydroxy-1,3,3-trimethylcyclohexylmethyl)amino; Procedure E; IS-MS m/z 621.1 (m+1), 619.2 (m−1).

EXAMPLE 416

R=Cyclooctylamino; Procedure E; IS-MS m/z 577.1 (m+1), 575.2 (m−1).

EXAMPLE 417

R=N-Methyl-N-(2-hydroxyethyl)amino; Procedure E; IS-MS m/z 525.0 (m+1), 523.1 (m−1).

EXAMPLE 418

R=(1-Ethylpyrrolidin-2-ylmethyl)amino; Procedure E; IS-MS m/z 578.1 (m+1), 576.2 (m−1).

EXAMPLE 419

R=N-Propyl-N-(hydroxyethyl)amino; Procedure E; IS-MS m/z 553.1 (m+1), 551.1 (m−1).

EXAMPLE 420

R=2-(1-Pyrrolidinyl)ethylamino; Procedure E; IS-MS m/z 564.1 (m+1), 562.1 (m−1).

EXAMPLE 421

R=(2-Furanylmethyl)amino; Procedure E; IS-MS m/z 547.0 (m+1), 545.1 (m−1).

EXAMPLE 422

R=Cycloheptylamino; Procedure E; IS-MS m/z 563.1 (m+1), 561.2 (m−1).

EXAMPLE 423

R=Octahydroazocin-1-yl; Procedure E; IS-MS m/z 563.1 (m+1), 561.2 (m−1).

EXAMPLE 424

R=1-(Hydroxymethyl)-3-(methylthio)propylamino; Procedure E; IS-MS m/z 585.0 (m+1), 583.1 (m−1).

EXAMPLE 425

R=1,3-Thiazolidin-1-yl; Procedure E; IS-MS m/z 539.0 (m+1), 537.1 (m−1).

EXAMPLE 426

R=(S)-2-(2-Hydroxyethyl)pyrrolidin-1-yl; Procedure E; IS-MS m/z 551.0 (m+1), 549.1 (m−1).

EXAMPLE 427

R=3-Hydroxypyrrolidin-1-yl; Procedure E; IS-MS m/z 537.0 (m+1), 535.1 (m−1).

EXAMPLE 428

R=(2-Tetrahydrofuranylmethyl)amino; Procedure E; IS-MS m/z 551.0 (m+1), 549.1 (m−1).

EXAMPLE 429

R=4-Phenylpiperazin-1-yl; Procedure E; IS-MS m/z 612.1 (m+1), 610.1 (m−1).

EXAMPLE 430

R=4-(4-Pyridyl)piperazin-1-yl; Procedure E; IS-MS m/z 613.1 (m+1), 611.1 (m−1).

EXAMPLE 431

R=4-(2-Methoxyphenyl)piperazin-1-yl; Procedure E; IS-MS m/z 642.2 (m+1), 640.1 (m−1).

EXAMPLE 432

R=3,4-Didehydropiperidin-1-yl; Procedure E; IS-MS m/z 533.0 (m+1), 531.1 (m−1).

EXAMPLE 433

R=4-Methylpiperazin-1-yl; Procedure E; IS-MS m/z 550.1 (m+1), 548.1 (m−1).

EXAMPLE 434

R=4-[2-(1-Pyrrolidinyl)-2-oxoethyl]piperazin-1-yl; Procedure E; IS-MS m/z 647.1 (m+1), 645.2 (m−1).

EXAMPLE 435

R=4-(2-Hydroxyethyl)piperazin-1-yl; Procedure E; IS-MS m/z 580.1 (m+1), 578.1 (m−1).

EXAMPLE 436

R=2,6-Dimethylmorpholin-4-yl; Procedure E; IS-MS m/z 565.1 (m+1), 563.1 (m−1).

EXAMPLE 437

R=2-Methylpiperidin-1-yl; Procedure E; IS-MS m/z 549.1 (m+1), 547.1 (m−1).

EXAMPLE 438

R=2,2,6,6-Tetramethylpiperidin-4-ylamino; Procedure E; IS-MS m/z 606.1 (m+1), 604.2 (m−1).

EXAMPLE 439

R=2-Hydroxymethylpiperidin-1-yl; Procedure E; IS-MS m/z 565.1 (m+1), 563.1 (m−1).

EXAMPLE 440

R=2-(2-Hydroxyethyl)piperidin-1-yl; Procedure E; IS-MS m/z 579.1 (m+1), 577.1 (m−1).

EXAMPLE 441

R=3,5-Dimethylpiperidin-1-yl; Procedure E; IS-MS m/z 563.1 (m+1), 561.2 (m−1).

EXAMPLE 442

R=3-Hydroxymethylpiperidin-1-yl; Procedure E; IS-MS m/z 565.0 (m+1), 563.1 (m−1).

EXAMPLE 443

R=4-Methylpiperidin-1-yl; Procedure E; IS-MS m/z 549.1 (m+1), 547.1 (m−1).

EXAMPLE 444

R=4-(2-Hydroxyethyl)piperidin-1-yl; Procedure E; IS-MS m/z 579.1 (m+1), 577.1 (m−1).

EXAMPLE 445

R=4-(2-Pyridinyl)piperazin-1-yl; Procedure A; IS-MS m/z 613.1 (m+1), 611.1 (m−1).

EXAMPLE 446

R=2-Pyridinylmethylamino; Procedure E; IS-MS m/z 558.0 (m+1), 556.1 (m−1).

EXAMPLE 447

R=3-Pyridinylmethylamino; Procedure E; IS-MS m/z 558.0 (m+1), 556.1 (m−1).

EXAMPLE 448

R=4-(1-Piperidinyl)piperidin-1-yl; Procedure E; IS-MS m/z 618.1 (m+1), 616.2 (m−1).

EXAMPLE 449

R=N-Methyl-N-(1-methylpiperidin-4-yl)amino; Procedure E; IS-MS m/z 578.1 (m+1), 576.1 (m−1).

EXAMPLE 450

R=2-(1-Piperidinyl)ethylamino; Procedure E; IS-MS m/z 578.1 (m+1), 576.2 (m−1).

EXAMPLE 451

R=Hexahydroazepin-1-yl; Procedure E; IS-MS m/z 549.1 (m+1), 547.1 (m−1).

EXAMPLE 452

R=2,2,5-Trimethylhexahydroazepin-1-yl; Procedure E; IS-MS m/z 591.1 (m+1), 589.1 (m−1).

EXAMPLE 453

R=1,1-Dimethyl-2-hydroxyethylamino; Procedure E; IS-MS m/z 539.0 (m+1), 537.1 (m−1).

EXAMPLE 454

R=Isopropylamino; Procedure E; IS-MS m/z 509.1 (m+1), 507.1 (m−1).

EXAMPLE 455

R=Benzylamino; Procedure E; IS-MS m/z 557.1 (m+1), 555.1 (m−1).

EXAMPLE 456

R=2-(Acetylamino)ethylamino; Procedure E; IS-MS m/z 552.1 (m+1), 550.1 (m−1).

EXAMPLE 457

R=2-(Dimethylamino)ethylamino; Procedure E; IS-MS m/z 538.1 (m+1), 536.2 (m−1).

EXAMPLE 458

R=2-Methoxyethylamino; Procedure E; IS-MS m/z 525.1 (m+1), 523.1 (m−1).

EXAMPLE 459

R=2-Hydroxyethylamino; Procedure E; IS-MS m/z 511.1 (m+1), 509.1 (m−1).

EXAMPLE 460

R=Propargylamino; Procedure E; IS-MS m/z 505.0 (m+1), 503.1 (m−1).

EXAMPLE 461

R=3-Hydroxypropylamino; Procedure E; IS-MS m/z 525.1 (m+1), 523.1 (m−1).

EXAMPLE 462

R=4-Hydroxybutylamino; Procedure E.

EXAMPLE 463

R=N,N-Dimethylamino; Procedure E; IS-MS m/z 495.1 (m+1), 493.1 (m−1).

EXAMPLE 464

R=N-Ethyl-(2-dimethylamino)ethylamino; Procedure E; IS-MS m/z 566.1 (m+1), 564.2 (m−1).

EXAMPLE 465

R=(S)-2-(Methoxymethyl)pyrrolidin-1-yl; Procedure E; IS-MS m/z 565.1 (m+1), 563.2 (m−1).

EXAMPLE 466

R=1-Hydroxymethylcyclopentylamino; Procedure E; IS-MS m/z 565.1 (m+1), 563.2 (m−1).

EXAMPLE 467

R=1,2-Diethylpyrazolidin-4-ylamino; Procedure E; IS-MS m/z 593.1 (m+1), 591.2 (m−1).

EXAMPLE 468

R=(S)-2-(1-Pyrrolidinylmethyl)pyrrolidin-1-yl; Procedure E; IS-MS m/z 604.1 (m+1), 602.2 (m−1).

EXAMPLE 469

R=1-Methyl-2-(dimethylamino)ethylamino; Procedure E; IS-MS m/z 552.1 (m+1), 550.2 (m−1).

EXAMPLE 470

R=2-(Methylthio)ethylamino; Procedure E; IS-MS m/z 541.0 (m+1), 539.1 (m−1).

EXAMPLE 471

R=N-Methyl-N-[2-(dimethylamino)ethyl]amino; Procedure E; IS-MS m/z 552.1 (m+1), 550.2 (m−1).

EXAMPLE 472

R=1-Isopropyl-2-methylpropylamino; Procedure E; IS-MS m/z 565.1 (m+1), 563.2 (m−1).

EXAMPLE 473

R=2-[2-(Pyrrolidin-1-yl)ethyl]piperidin-1-yl; Procedure E; IS-MS m/z 632.2 (m+1), 630.2 (m−1).

EXAMPLE 474

R=N-Methyl-N-(3-pyridinylmethyl)amino; Procedure E; IS-MS m/z 572.1 (m+1), 570.2 (m−1).

EXAMPLE 475

R=N-Ethyl-N-(4-pyridinylmethyl)amino; Procedure E; IS-MS m/z 586.1 (m+1), 584.1 (m−1).

EXAMPLE 476

R=4-(1-Pyrrolidinyl)piperidin-1-yl; Procedure E; IS-MS m/z 604.1 (m+1), 602.2 (m−1).

EXAMPLE 477

R=4-(Furan-2-ylcarbonyl)piperazin-1-yl; Procedure E; IS-MS m/z 630.1 (m+1), 628.1 (m−1).

EXAMPLE 478

R=4-(2-Chlorophenyl)piperazin-1-yl; Procedure E; IS-MS m/z 646.1 (m+1), 644.1 (m−1).

EXAMPLE 479

R=4-(3-Chlorophenyl)piperazin-1-yl; Procedure E; IS-MS m/z 646.1 (m+1), 644.1 (m−1).

EXAMPLE 480

R=4-(3-Methylphenyl)piperazin-1-yl; Procedure E; IS-MS m/z 626.1 (m+1), 624.2 (m−1).

EXAMPLE 481

R=4-(2-Pyrimidinyl)piperazin-1-yl; Procedure E; IS-MS m/z 614.1 (m+1), 612.2 (m−1).

EXAMPLE 482

R=4-(2-Pyrazinyl)piperazin-1-yl; Procedure E; IS-MS m/z 614.1 (m+1), 612.2 (m−1).

EXAMPLE 483

R=2,2-Dimethyl-3-(dimethylamino)propylamino; Procedure E; IS-MS m/z 580.2 (m+1), 578.2 (m−1).

EXAMPLE 484

R=2-hydroxy-1-(hydroxymethyl)ethylamino; Procedure E; IS-MS m/z 541.1 (m+1), 539.1 (m−1).

EXAMPLE 485

R=4-Acetylpiperazin-1-yl; Procedure E; IS-MS m/z 578.1 (m+1), 576.2 (m−1).

EXAMPLE 486

R=4-Methylhexahydro-1,4-diazepin-1-yl; Procedure E; IS-MS m/z 564.1 (m+1), 562.2 (m−1).

EXAMPLE 487

R=2,2-Dimethyl-3-hydroxypropylamino; Procedure E; IS-MS m/z 553.1 (m+1), 551.2 (m−1).

EXAMPLE 488

R=(R)-2-Hydroxymethylpyrrolidin-1-yl; Procedure E; IS-MS m/z 551.1 (m+1), 549.2 (m−1).

EXAMPLE 489

R=(S)-2-Hydroxy-1-methylethylamino; Procedure E; IS-MS m/z 525.1 (m+1), 523.2 (m−1).

EXAMPLE 490

R=(R)-2-Hydroxy-1-methylethylamino; Procedure E; IS-MS m/z 525.1 (m+1), 523.2 (m−1).

EXAMPLE 491

R=(S)-2-Hydroxymethylpropylamino; Procedure E; IS-MS m/z 539.1 (m+1), 537.2 (m−1).

EXAMPLE 492

R=(R)-2-Hydroxymethylpropylamino; Procedure E; IS-MS m/z 539.1 (m+1), 537.2 (m−1).

EXAMPLE 493

R=(S)-2-Hydroxypropylamino; Procedure E; IS-MS m/z 525.1 (m+1), 523.2 (m−1).

EXAMPLE 494

R=(R)-2-Hydroxypropylamino; Procedure E; IS-MS m/z 525.1 (m+1), 523.2 (m−1).

EXAMPLE 495

R=(S)-Hexahydro-2-oxoazepin-3-ylamino; Procedure E; IS-MS m/z 578.1 (m+1), 576.2 (m−1).

EXAMPLE 4965

R=Cis-2,6-Dimethyl-piperidin-1-yl; Procedure E; IS-MS m/z 563.1 (m+1), 561.2 (m−1).

EXAMPLE 497

R=1,3,3-Trimethyl-6-azabicyclo[3.2.1]octan-6-yl; Procedure E; IS-MS m/z 603.2 (m+1), 601.2 (m−1).

EXAMPLE 498

R=trans-4-Hydroxycyclohexylamino; Procedure E; IS-MS m/z 565.1 (m+1), 563.2 (m−1).

EXAMPLE 499

R=(S)-3-(Acetylamino)pyrrolidin-1-yl; Procedure E; IS-MS m/z 578.1 (m+1), 576.2 (m−1).

EXAMPLE 500

R=N-Methyl-N-(2-methoxyethyl)amino; Procedure E; IS-MS m/z 539.1 (m+1), 537.2 (m−1).

EXAMPLE 501

R=4-Cyclopentylpiperazin-1-yl; Procedure E; IS-MS m/z 604.2 (m+1), 602.2 (m−1).

EXAMPLE 502

R=4-Hydroxymethylpiperidin-1-yl; Procedure E; IS-MS m/z 565.1 (m+1), 563.2 (m−1).

EXAMPLE 503

R=(S)-3-(Dimethylamino)pyrrolidin-1-yl; Procedure E; IS-MS m/z 564.1 (m+1), 562.2 (m−1).

EXAMPLE 504

R=(S)-1-Hydroxymethyl-2,2-dimethylpropylamino; Procedure E; IS-MS m/z 567.1 (m+1), 565.2 (m−1).

EXAMPLE 505

R=(S)-1-Hydroxmethyl-3-methylbutylamino; Procedure E; IS-MS m/z 567.1 (m+1), 565.2 (m−1).

EXAMPLE 506

R=(S)-1-Hydroxymethyl-2-methylpropylamino; Procedure E; IS-MS m/z 553.1 (m+1), 551.2 (m−1).

EXAMPLE 507

R=(R)-α-Methylbenzylamino; Procedure E; IS-MS m/z 571.1 (m+1), 569.2 (m−1).

EXAMPLE 508

R=(S)-α-Methylbenzylamino; Procedure E; IS-MS m/z 571.1 (m+1), 569.2 (m−1).

EXAMPLE 509

R=(R)-α-(Hydroxymethyl)benzylamino; Procedure E; IS-MS m/z 587.1 (m+1), 585.1 (m−1).

Preparation 600

Preparation of N-(5-Chloropyridin-2-yl)-2-[2-(oxiranylmethyl)-4-isopropylbenzoyl-amino]benzamide

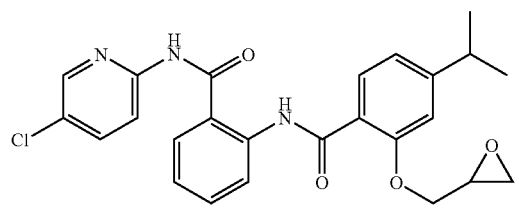

Using methods substantially equivalent to those described in Example 201, N-(5-chloropyridin-2-yl)-2-[2-(oxiranylmethyl)-4-isopropylbenzoylamino]benzamide was prepared from glycidol and N-(5-chloropyridin-2-yl)-2-[2-hydroxy-4-isopropyl-benzoylamino]benzamide. This compound contained diisopropyl hydrazodicarboxylate as a contaminant (about 30%) after two rounds of silica gel flash chromatography, first with hexanes through 6:4 hexanes:EtOAc, then with 95:5 dichloromethane:EtOAc. Partially purified material was carried on directly to the next transformation.

IS-MS, m/z 466.2 (m+1), 464.3 (m−1).

TABLE 6

Examples 601-630

Compounds of formula I which may be denoted by the following formula I-6

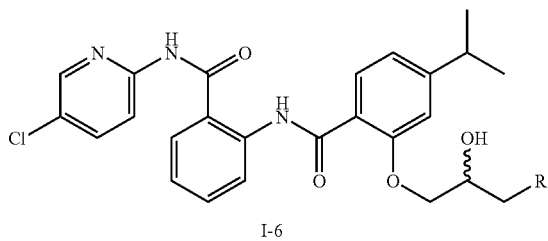

I-6 in which R has the indicated value of NR$^a$R$^b$ were prepared according to the indicated procedure from a requisite amine of formula HNR$^a$R$^b$ and the above described epoxide and the reagents and conditions appropriate for the indicated procedure or by a procedure otherwise noted.

General Procedure F for Alkylation Using Epoxide Ethers Such as the Compound of Preparation 600 Above:

Procedure F is substantially equivalent to that described in general procedure E, except that 2 or more equivalents of nucleophilic amine are employed and the piperidinomethylpolystyrene resin is omitted.

EXAMPLE 601

R=Thiomorpholin-4-yl; Procedure F; IS-MS m/z 569.0 (m+1), 567.0 (m−1).

EXAMPLE 602

R=1-Piperidinyl; Procedure F; IS-MS m/z 551.0 (m+1), 549.1 (m−1).

EXAMPLE 603

R=Morpholin-4-yl; Procedure F; IS-MS m/z 553.0 (m+1), 551.1 (m−1).

EXAMPLE 604

R=4-Hydroxypiperidin-1-yl; Procedure F; IS-MS m/z 567.0 (m+1), 565.1 (m−1).

EXAMPLE 605

R=1-Pyrrolidinyl; Procedure F; IS-MS m/z 537.0 (m+1), 535.1 (m−1).

EXAMPLE 606

R=1-Azetidinyl; Procedure F; IS-MS m/z 523.0 (m+1), 521.1 (m−1).

EXAMPLE 607

R=3-Carbamoylpiperidin-1-yl; Procedure F; IS-MS m/z 594.0 (m+1), 592.2 (m−1).

EXAMPLE 608

R=4-Pyridinylmethylamino; Procedure F; IS-MS m/z 574.0 (m+1), 572.1 (m−1).

EXAMPLE 609

R=Octahydroazocin-1-yl; Procedure F; IS-MS m/z 579.1 (m+1), 577.2 (m−1).

EXAMPLE 610

R=1,3-Thiazolidin-3-yl; Procedure F; IS-MS m/z 555.0 (m+1), 553.1 (m−1).

EXAMPLE 611

R=(S)-2-Hydroxymethylpyrrolidin-1-yl; Procedure F; IS-MS m/z 567.1 (m+1), 565.1 (m−1).

EXAMPLE 612

R=4-Phenylpiperazin-1-yl; Procedure F; IS-MS m/z 628.1 (m+1), 626.1 (m−1).

EXAMPLE 613

R=4-[2-(1-Pyrrolidinyl)-2-oxoethyl]piperazin-1-yl; Procedure F; IS-MS m/z 663.1 (m+1), 661.2 (m−1).

EXAMPLE 614

R=2,6-Dimethylmorpholin-4-yl; Procedure F; IS-MS m/z 581.1 (m+1), 579.1 (m−1).

EXAMPLE 615

R=Hexahydroazepin-1-yl; Procedure F; IS-MS m/z 565.1 (m+1), 563.2 (m−1).

EXAMPLE 616

R=3,3,5-Trimethylhexahydroazepin-1-yl; Procedure F; IS-MS m/z 607.1 (m+1), 605.2 (m−1).

EXAMPLE 617

R=(S)-2-Methoxymethylpyrrolidin-1-yl; Procedure F; IS-MS m/z 581.1 (m+1), 579.1 (m−1).

EXAMPLE 618

R=1-Hydroxymethylcyclopentylamino; Procedure F; IS-MS m/z 581.1 (m+1), 579.1 (m−1).

EXAMPLE 619

R=4-(Pyrrolidin-1-yl)piperazin-1-yl; Procedure F; IS-MS m/z 620.1 (m+1), 618.2 (m−1).

EXAMPLE 620

R=4-(2-Pyrimidinyl)piperazin-1-yl; Procedure F; IS-MS m/z 630.1 (m+1), 628.1 (m−1).

EXAMPLE 621

R=4-(2-Pyrazinyl)piperazin-1-yl; Procedure F; IS-MS m/z 630.1 (m+1), 628.1 (m−1).

EXAMPLE 622

R=4-Acetylpiperazin-1-yl; Procedure F; IS-MS m/z 594.1 (m+1), 592.1 (m−1).

EXAMPLE 623

R=(S)-1-Hydroxymethyl-2-methylpropylamino; Procedure F; IS-MS m/z 569.1 (m+1), 567.1 (m−1).

EXAMPLE 624

R=(S)-1-Hydroxymethylethylamino; Procedure F; IS-MS m/z 541.0 (m+1), 539.1 (m−1).

EXAMPLE 625

R=(R)-1-Hydroxymethylethylamino; Procedure F; IS-MS m/z 541.0 (m+1), 539.1 (m−1).

EXAMPLE 626

R=(S)-Hexahydro-2-oxoazepin-3-ylamino; Procedure F; IS-MS m/z 594.1 (m+1), 592.1 (m−1).

EXAMPLE 627

R=Cis-2,6-Dimethylpiperidin-1-yl; Procedure F; IS-MS m/z 579.1 (m+1), 577.2 (m−1).

EXAMPLE 628

R=4-Cyclopentylpiperazin-1-yl; Procedure F; IS-MS m/z 620.1 (m+1), 618.2 (m−1).

EXAMPLE 629

R=4-Hydroxymethylpiperidin-1-yl; Procedure F; IS-MS m/z 581.1 (m+1), 579.1 (m−1).

EXAMPLE 630

R=(S)-3-(Dimethylamino)pyrrolidin-1-yl; Procedure F; IS-MS m/z 580.1 (m+1), 578.1 (m−1).

Preparation 700

Preparation of 2-[2-(2-Bromoethoxy)-4-isopropyl-benzoylamino]-N-(5-chloropyridin-2-yl)benzamide

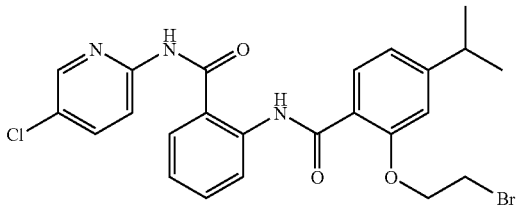

Using methods substantially equivalent to those described in Preparation 401 except that the Mitsonobu reaction was performed with 2-bromoethanol, 2-[2-(2-bromo-ethoxy)-4-isopropylbenzoylamino]-N-(5-chloropyridin-2-yl)benzamide (2.6 g, 5 mmol, 68%) was prepared from N-(5-chloro-pyridin-2-yl)-2-[2-hydroxy-4-isopropylbenzoyl-amino] benzamide.

TABLE 7

Examples 701-799

Compounds of the formula I which may be denoted by the following formula I-7

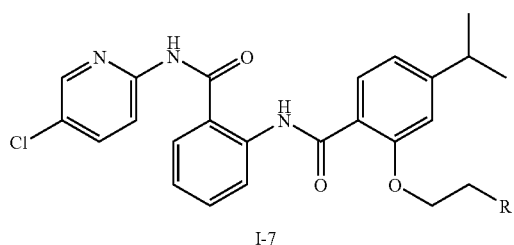

I-7 in which R has the indicated value of $NR^aR^b$ were prepared according to the indicated procedure from a requisite corresponding amine of formula $HNR^aR^b$ and the above bromide corresponding to a compound of formula I-7 in which R is bromo and the reagents and conditions appropriate for the indicated procedure or by a procedure otherwise noted.

EXAMPLE 701

R=Cyclobutylamino; Procedure E; IS-MS m/z 507.2 (m+1), 505.3 (m−1).

EXAMPLE 702

R=Cyclopentylamino; Procedure E; IS-MS m/z 521.2 (m+1), 519.3 (m−1).

EXAMPLE 703

R=Cyclohexylamino; Procedure E; IS-MS m/z 535.2 (m+1), 533.3 (m−1).

EXAMPLE 704

R=(3-Methyl)cyclohexylamino; Procedure E; IS-MS m/z 549.3 (m+1), 547.3 (m−1).

EXAMPLE 705

R=(4-Methyl)cyclohexylamino; Procedure E; IS-MS m/z 549.2 (m+1), 547.3 (m−1).

EXAMPLE 706

R=N-Methyl-N-(2-hydroxyethyl)amino; Procedure E; IS-MS m/z 511.2 (m+1), 509.3 (m−1).

EXAMPLE 707

R=N-Propyl-N-(2-hydroxyethyl)amino; Procedure E; IS-MS m/z 539.2 (m+1), 537.3 (m−1).

EXAMPLE 708

R=2-(1-Pyrrolidinyl)ethylamino; Procedure E; IS-MS m/z 550.2 (m+1), 548.3 (m−1).

EXAMPLE 709

R=2-Furanylmethylamino; Procedure E; IS-MS m/z 533.2 (m+1), 531.1 (m−1).

EXAMPLE 710

R=Cycloheptylamino; Procedure E; IS-MS m/z 549.3 (m+1), 547.3 (m−1).

EXAMPLE 711

R=Octahydroazocin-1-yl; Procedure E; IS-MS m/z 549.3 (m+1), 547.3 (m−1).

EXAMPLE 712

R=1-Azetidinyl; Procedure E; IS-MS m/z 493.2 (m+1), 491.3 (m−1).

EXAMPLE 713

R=1,3-Thiazolidin-3-yl; Procedure E; IS-MS m/z 525.2 (m+1), 523.1 (m−1).

EXAMPLE 714

R=1-Pyrrolidinyl; Procedure E; IS-MS m/z 507.2 (m+1), 505.3 (m−1).

EXAMPLE 715

R=(S)-2-Hydroxymethylpyrrolidin-1-yl; Procedure E; IS-MS m/z 537.2 (m+1), 535.3 (m−1).

EXAMPLE 716

R=2-Thienylmethylamino; Procedure E; IS-MS m/z 549.2 (m+1), 547.2 (m−1).

EXAMPLE 717

R=3,4-Didehydropiperidin-1-yl; Procedure E; IS-MS m/z 519.2 (m+1), 517.3 (m−1).

EXAMPLE 718

R=4-Methylpiperazin-1-yl; Procedure E; IS-MS m/z 536.2 (m+1), 534.3 (m−1).

EXAMPLE 719

R=4-[2-(1-Pyrrolidinyl)-2-oxoethyl]piperazin-1-yl; Procedure E; IS-MS m/z 633.3 (m+1), 631.3 (m−1).

EXAMPLE 720

R=4-(2-Hydroxyethyl)piperazin-1-yl; Procedure E; IS-MS m/z 566.2 (m+1), 564.3 (m−1).

EXAMPLE 721

R=Morpholin-4-yl; Procedure E; IS-MS m/z 523.2 (m+1), 521.3 (m−1).

EXAMPLE 722

R=2,6-Dimethylmorpholin-4-yl; Procedure E; IS-MS m/z 551.2 (m+1), 549.3 (m−1).

EXAMPLE 723

R=Thiomorpholin-4-yl; Procedure E; IS-MS m/z 539.2 (m+1), 537.3 (m−1).

EXAMPLE 724

R=1-Piperidinyl; Procedure E; IS-MS m/z 521.2 (m+1), 519.3 (m−1).

EXAMPLE 725

R=3,5-Dimethylpiperidin-1-yl; Procedure E; IS-MS m/z 549.3 (m+1), 547.3 (m−1).

EXAMPLE 726

R=4-Hydroxypiperidin-1-yl; Procedure E; IS-MS m/z 537.2 (m+1), 535.3 (m−1).

EXAMPLE 727

R=4-Methylpiperidin-1-yl; Procedure E; IS-MS m/z 535.2 (m+1), 533.3 (m−1).

EXAMPLE 728

R=4-(2-Hydroxyethyl)piperidin-1-yl; Procedure E; IS-MS m/z 565.2 (m+1), 563.3 (m−1).

EXAMPLE 729

R=4-(2-Pyridinyl)piperazin-1-yl; Procedure E; IS-MS m/z 599.3 (m+1), 597.3 (m−1).

EXAMPLE 730

R=2-Pyridinylmethylamino; Procedure E; IS-MS m/z 544.2 (m+1), 542.3 (m−1).

EXAMPLE 731

R=3-Pyridinylmethylamino; Procedure E; IS-MS m/z 544.2 (m+1), 542.3 (m−1).

EXAMPLE 732

R=4-(1-Piperidinyl)piperidin-1-yl; Procedure E; IS-MS m/z 604.3 (m+1), 602.4 (m−1).

EXAMPLE 733

R=N-Methyl-N-(1-methylpiperidin-4-yl)amino; Procedure E; IS-MS m/z 564.3 (m+1), 562.4 (m−1).

EXAMPLE 734

R=2-(1-Piperidinyl)ethylamino; Procedure E; IS-MS m/z 564.3 (m+1), 562.3 (m−1).

EXAMPLE 735

R=Hexahydroazepin-1-yl; Procedure E; IS-MS m/z 535.2 (m+1), 533.3 (m−1).

EXAMPLE 736

R=1,1-Dimethyl-2-hydroxyethylamino; Procedure E; IS-MS m/z 525.2 (m+1), 523.3 (m−1).

EXAMPLE 737

R=Isopropylamino; Procedure E; IS-MS m/z 495.2 (m+1), 493.3 (m−1).

EXAMPLE 738

R=Benzylamino; Procedure E; IS-MS m/z 543.2 (m+1), 541.3 (m−1).

EXAMPLE 739

R=2-(Acetylamino)ethylamino; Procedure E; IS-MS m/z 538.2 (m+1), 536.3 (m−1).

EXAMPLE 740

R=2-(N,N-Dimethylamino)ethylamino; Procedure E; IS-MS m/z 524.2 (m+1), 522.3 (m−1).

EXAMPLE 741

R=2-Methoxyethylamino; Procedure E; IS-MS m/z 511.2 (m+1), 509.3 (m−1).

EXAMPLE 742

R=2-Hydroxyethylamino; Procedure E; IS-MS m/z 497.2 (m+1), 495.3 (m−1).

EXAMPLE 743

R=Propargylamino; Procedure E; IS-MS m/z 491.2 (m+1), 489.2 (m−1).

EXAMPLE 744

R=3-Hydroxypropylamino; Procedure E; IS-MS m/z 511.2 (m+1), 509.3 (m−1).

EXAMPLE 745

R=4-Hydroxybutylamino; Procedure E; IS-MS m/z 525.2 (m+1), 523.3 (m−1).

EXAMPLE 746

R=N,N-Dimethylamino; Procedure E; IS-MS m/z 481.2 (m+1), 479.3 (m−1).

EXAMPLE 747

R=N-[2-(N,N-Dimethylamino)ethyl]-N-ethylamino; Procedure E; IS-MS m/z 552.3 (m+1), 550.3 (m−1).

EXAMPLE 748

R=(S)-2-Methoxymethylpyrrolidin-1-yl; Procedure E; IS-MS m/z 551.2 (m+1), 549.3 (m−1).

EXAMPLE 749

R=1-Hydroxymethylcyclopentylamino; Procedure E; IS-MS m/z 551.2 (m+1), 549.3 (m−1).

EXAMPLE 750

R=(S)-2-(1-Pyrrolidinylmethyl)pyrrolidin-1-yl; Procedure E; IS-MS m/z 590.3 (m+1), 588.4 (m−1).

EXAMPLE 751

R=1,2-Diethylpyrazolidin-4-ylamino; Procedure E; IS-MS m/z 579.3 (m+1), 577.3 (m−1).

EXAMPLE 752

R=2-(Methylthio)ethylamino; Procedure E; IS-MS m/z 527.2 (m+1), 525.3 (m−1).

EXAMPLE 753

R=N-[2-(Dimethylamino)ethyl]-N-methylamino; Procedure E; IS-MS m/z 538.3 (m+1), 536.3 (m−1).

EXAMPLE 754

R=1-Isopropyl-2-methylpropylamino; Procedure E; IS-MS m/z 551.3 (m+1), 549.3 (m−1).

EXAMPLE 755

R=N-Methyl-N-(3-pyridinylmethyl)amino; Procedure E; IS-MS m/z 558.2 (m+1), 556.3 (m−1).

EXAMPLE 756

R=N-Ethyl-N-(4-pyridinylmethyl)amino; Procedure E; IS-MS m/z 572.2 (m+1), 570.3 (m−1).

EXAMPLE 757

R=4-(1-Pyrrolidinyl)piperidin-1-yl; Procedure E; IS-MS m/z 590.3 (m+1), 588.3 (m−1).

EXAMPLE 758

R=4-Carbamoylpiperidin-1-yl; Procedure E; IS-MS m/z 564.2 (m+1), 562.3 (m−1).

EXAMPLE 759

R=4-(2-Furoyl)piperazin-1-yl; Procedure E; IS-MS m/z 616.3 (m+1), 614.3 (m−1).

EXAMPLE 760

R=4-(2-Pyrimidinyl)piperazin-1-yl; Procedure E; IS-MS m/z 600.3 (m+1), 589.3 (m−1).

EXAMPLE 761

R=2,2-Dimethyl-(3-dimethylamino)propylamino; Procedure E; IS-MS m/z 566.3 (m+1), 564.4 (m−1).

EXAMPLE 762

R=2-Hydroxy-1-(hydroxymethyl)ethylamino; Procedure E; IS-MS m/z 527.2 (m+1), 525.3 (m−1).

EXAMPLE 763

R=2-(2-Thienyl)ethylamino; Procedure E; IS-MS m/z 563.2 (m+1), 561.3 (m−1).

EXAMPLE 764

R=4-Acetylpiperazin-1-yl; Procedure E; IS-MS m/z 564.2 (m+1), 562.3 (m−1).

EXAMPLE 765

R=4-Methylhexahydro-1,4-diazepin-1-yl; Procedure E; IS-MS m/z 550.3 (m+1), 548.3 (m−1).

EXAMPLE 766

R=2,2-Dimethyl-3-hydroxypropylamino; Procedure E; IS-MS m/z 539.2 (m+1), 537.3 (m−1).

EXAMPLE 767

R=(R)-2-Hydroxypropylamino; Procedure E; IS-MS m/z 511.2 (m+1), 509.3 (m−1).

EXAMPLE 768

R=(S)-2-Hydroxypropylamino; Procedure E; IS-MS m/z 511.2 (m+1), 509.3 (m−1).

EXAMPLE 769

R=(S)-Hexahydro-2-oxoazepin-3-ylamino; Procedure E; IS-MS m/z 564.2 (m+1), 562.3 (m−1).

EXAMPLE 770

R=cis-2,6-Dimethylpiperidin-1-yl; Procedure E; IS-MS m/z 549.3 (m+1).

EXAMPLE 771

R=(S)-3-Acetamidopyrrolidin-1-yl; Procedure E; IS-MS m/z 564.2 (m+1), 562.3 (m−1).

EXAMPLE 772

R=N-Methyl-N-(2-methoxyethyl)amino; Procedure E; IS-MS m/z 525.2 (m+1), 523.3 (m−1).

EXAMPLE 773

R=4-Cyclopentylpiperazin-1-yl; Procedure E; IS-MS m/z 590.3 (m+1), 588.4 (m−1).

EXAMPLE 774

R=(S)-3-Dimethylaminopyrrolidin-1-yl; Procedure E; IS-MS m/z 550.2 (m+1), 548.3 (m−1).

EXAMPLE 775

R=4-Hydroxymethylpiperidin-1-yl; Procedure E; IS-MS m/z 551.2 (m+1), 549.3 (m−1).

EXAMPLE 776

R=(R)-2-Hydroxymethylpyrrolidin-1-yl; Procedure E; IS-MS m/z 537.2 (m+1), 535.3 (m−1).

EXAMPLE 777

R=(S)-1-Hydroxymethyl-3-(methylthio)propylamino; Procedure E;
IS-MS m/z 571.2 (m+1), 569.3 (m−1).

EXAMPLE 778

R=(R)-α-(Hydroxymethyl)benzylamino; Procedure E.

EXAMPLE 779

R=(S)-1-Hydroxymethyl-3-methylbutylamino; Procedure E; IS-MS m/z 553.2 (m+1), 551.3 (m−1).

EXAMPLE 780

R=(S)-1-Hydroxymethyl-2-methylpropylamino; Procedure E; IS-MS m/z 539.2 (m+1), 537.3 (m−1).

EXAMPLE 781

R=(S)-α-Methylbenzylamino; Procedure E; IS-MS m/z 557.2 (m+1), 555.3 (m−1).

EXAMPLE 782

R=(R)-α-Methylbenzylamino; Procedure E; IS-MS m/z 557.2 (m+1), 555.3 (m−1).

EXAMPLE 783

R=(S)-1-Methyl-2-hydroxyethylamino; Procedure E; IS-MS m/z 511.2 (m+1), 509.3 (m−1).

EXAMPLE 784

R=(R)-1-Methyl-2-hydroxyethylamino; Procedure E; IS-MS m/z 511.2 (m+1), 509.3 (m−1).

EXAMPLE 785

R=(S)-1-Hydroxymethylpropylamino; Procedure E; IS-MS m/z 525.2 (m+1), 523.3 (m−1).

EXAMPLE 786

R=(R)-1-Hydroxymethylpropylamino; Procedure E; IS-MS m/z 525.2 (m+1), 523.3 (m−1).

EXAMPLE 787

R=trans-4-Hydroxycyclohexylamino; Procedure E; IS-MS m/z 551.2 (m+1), 549.3 (m−1).

EXAMPLE 788

R=(S)-1-Hydroxymethyl-2,2-dimethylpropylamino; Procedure E; IS-MS m/z 553.3 (m+1), 551.3 (m−1).

EXAMPLE 789

R=1-Ethylpyrrolidin-2-ylmethylamino; Procedure E; IS-MS m/z 564.3 (m+1), 562.3 (m−1).

EXAMPLE 790

R=3-Hydroxypyrrolidin-1-yl; Procedure E; IS-MS m/z 523.2 (m+1), 521.3 (m−1).

EXAMPLE 791

R=Tetrahydrofuran-2-ylmethylamino; Procedure E; IS-MS m/z 537.2 (m+1), 535.3 (m−1).

EXAMPLE 792

R=2-Methylpiperidin-1-yl; Procedure E; IS-MS m/z 535.2 (m+1), 533.3 (m−1).

EXAMPLE 793

R=2-Hydroxymethylpiperidin-1-yl; Procedure E; IS-MS m/z 551.2 (m+1), 549.3 (m−1).

EXAMPLE 794

R=2-(2-Hydroxyethyl)piperidin-1-yl; Procedure E; IS-MS m/z 565.3 (m+1), 563.3 (m−1).

EXAMPLE 795

R=3-Carbamoylpiperidin-1-yl; Procedure E; IS-MS m/z 564.2 (m+1), 562.3 (m−1).

EXAMPLE 796

R=3,3,5-Trimethylhexahydroazepin-1-yl; Procedure E; IS-MS m/z 577.3 (m+1), 575.3 (m−1).

EXAMPLE 797

R=2-(Dimethylamino)-1-methylethylamino; Procedure E; IS-MS m/z 538.3 (m+1), 536.3 (m−1).

EXAMPLE 798

R=2-Methylpyrrolidin-1-yl; Procedure E; IS-MS m/z 521.2 (m+1), 519.3 (m−1).

EXAMPLE 799

R=3-Hydroxymethylpiperidin-1-yl; Procedure E; IS-MS m/z 551.2 (m+1), 549.3 (m−1).

TABLE 8

Examples 801-811

Compounds of the formula I which may be denoted by the following formula I-8

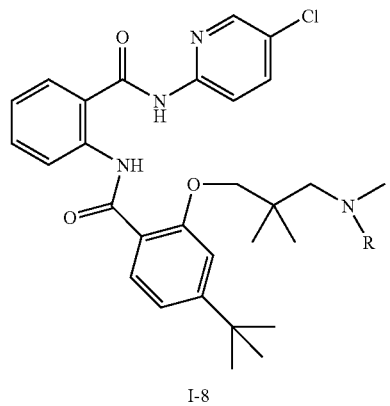

I-8 in which R has the indicated value of $R^a$ were prepared according to the indicated procedure from a requisite corresponding compound of formula I and the reagents and conditions appropriate for the indicated procedure or by a procedure otherwise noted.

EXAMPLE 801

R=BOC; Procedure:

A. Methyl 2-[3-[(tert-Butoxycarbonyl)(methyl)amino]-2,2-dimethylpropoxy]-4-tert-butylbenzoate To a solution of methyl 2-(3-tert-butoxycarbonylamino-2,2-dimethylpropoxy)-4-tert-butylbenzoate (2.50 g, 6.35 mmol) in THF at 0° C. under $N_2$ was added methyl iodide (4.51 g, 31.8 mmol, 5 eq), followed by sodium bis(trimethylsilyl)amide (12.7 mL, 12.7 mmol, 1.0 M in THF). The cooling bath was allowed to slowly warm to room temperature. The reaction was stirred at room temerature for 2.5 days, then diluted with dichloromethane, washed with water and brine, dried, and concentrated in vacuo to give 1.60 g (61.8%) of the desired product as a viscous oil which was used without further purification.

B. 2-[3-[(tert-Butoxycarbonyl)(methyl)amino]-2,2-dimethylpropoxy]-4-tert-butylbenzoic acid Using methods substantially equivalent to those described in Example 21-D, methyl 2-[3-[(tert-butoxycarbonyl)(methyl)amino]-2,2-dimethylpropoxy]-4-tert-butylbenzoate (1.60 g, 3.93 mmol) was hydrolized to give 2-[3-[(tert-butoxycarbonyl)-(methyl)amino]-2,2-dimethylpropoxy]-4-tert-butylbenzoic acid (1.34 g, 87.0%) as a white foam.

IS-MS, m/z 394.5 (m+1), 392.4 (m−1); Analysis for $C_{22}H_{35}NO_5$: Calcd: C, 67.15; H, 8.96; N, 3.56; Found: C, 66.86; H, 8.88; N, 3.54.

C. 2-[2-[3-[(tert-Butoxycarbonyl)(methyl)amino]-2,2-dimethylpropoxy]-4-tert-butylbenzoylamino]-N-(5-chloropyridin-2-yl)benzamide Using methods substantially equivalent to those described in Example 201, 2-[2-[3-[(tert-butoxycarbonyl)(methyl)amino]-2,2-dimethylpropoxy]-4-tert-butylbenzoyl-amino]-N-(5-chloropyridin-2-yl)benzamide was prepared from 2-[3-[(tert-butoxy-carbonyl)(methyl)amino]-2,2-dimethylpropoxy]-4-tert-butylbenzoic acid (1.30 g, 3.30 mmol) and N-(5-chloropyridin-2-yl)-2-aminobenzamide (0.817 g, 3.30 mmol) to provide, after silica gel purification, 1.57 g (76.2%) of a white foam.

$^1$NMR IS-MS, m/z 623.5 (m+1), 622.0 (m−1); Analysis for $C_{34}H_{43}ClNO_5$: Calcd: C, 65.53; H, 6.95; N, 8.99; Found: C, 65.45; H, 6.96; N, 8.78.

EXAMPLE 802

R═H; Procedure:

Using methods substantially equivalent to those described in Example 302, 2-[4-tert-butyl-2-(2,2-dimethyl-3-methylamino-propoxy)benzoylamino]-N-(5-chloro-pyridin-2-yl)benzamide was prepared from 2-[2-[3-[(tert-butoxycarbonyl)(methyl)-amino]-2,2-dimethylpropoxy]-4-tert-butylbenzoylamino]-N-(5-chloropyridin$^{-2}$-yl)-benzamide to provide 0.806 g (96.1%) of the desired product as a white foam.

$^1$NMR IS-MS, m/z 523.3 (m+1), 521.4 (m−1).

EXAMPLE 803

R=Cyclobutyl; Procedure A, except that an additional silica gel purification was performed at the end. IS-MS, m/z 577.2 (m+1), 575.2 (m−1).

EXAMPLE 804

R=Cyclopentyl; Procedure A, except that an additional silica gel purification was performed at the end. IS-MS, m/z 591.2 (m+1), 589.3 (m−1).

EXAMPLE 805

R=2-Hydroxybenzyl; Procedure A, except that an additional silica gel purification was performed at the end. IS-MS, m/z 629.2 (m+1), 627.2 (m−1).

EXAMPLE 806

R=2-Methylbenzyl; Procedure A, except that an additional silica gel purification was performed at the end. IS-MS, m/z 627.2 (m+1), 625.3 (m−1).

EXAMPLE 807

R=2-Thienylmethyl; Procedure A, except that an additional silica gel purification was performed at the end. IS-MS, m/z 619.1 (m+1), 617.2 (m−1).

EXAMPLE 808

R=2-Carboxybenzyl; Procedure A, except that an additional silica gel purification was performed at the end. IS-MS, m/z 657.2 (m+1), 655.2 (m−1).

EXAMPLE 809

R=2-Fluorophenylaminocarbonyl; Procedure B, except that no scavenging was conducted, and the compound was purified via SCX solid phase extraction. IS-MS, m/z 660.1 (m+1), 658.2 (m−1).

EXAMPLE 810

R=2-Fluorophenylcarbonyl; Procedure C, except that the compound was purified via silical gel chromatography. IS-MS, m/z 645.1 (m+1), 643.2 (m−1).

EXAMPLE 811

R=3-Methylthiophen-2-ylcarbonyl; Procedure C, except that the compound was purified via silica gel chromatography. IS-MS, m/z 647.1 (m+1), 645.2 (m−1).

TABLE 9

Examples 901-910

Compounds of formula I which may be denoted by the following formula I-9

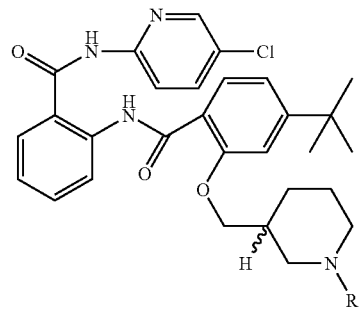

I-9 in which R has the indicated value of $R^a$ were prepared according to the indicated procedure from a requisite corresponding compound of formula I and the reagents and conditions appropriate for the indicated procedure or by a procedure otherwise noted.

EXAMPLE 901

R=Boc; Procedure:

A. Methyl 2-(1-tert-Butoxycarbonylpiperidin-3-yl-methoxy)-4-tert-butylbenzoate In a manner substantially equivalent to Example 21-C, methyl 4-tert-butyl-2-hydroxybezoate (2.08 g, 10.0 mmol)

and 1-Boc-3-hydroxymethylpiperidine (2.15 g, 10.0 mmol) were reacted to give the desired product (1.30 g, 32.1%).

B. 2-(1-tert-Butoxycarbonylpiperidin-3-ylmethoxy)-4-tert-butylbenzoic acid

In a manner substantially equivalent to Example 21-D, methyl 2-(1-tert-butoxy-carbonylpiperidin-3-ylmethoxy)-4-tert-butylbenzoate (1.30 g, 3.21 mmol) yielded 1.25 g (99.2%) of the desired product as an off-white foam.

C. 2-[2-(1-tert-butoxycarbonylpiperidin-3-yl-methoxy)-4-tert-butylbenzoylamino]-N-(5-chloropyridin-2-yl)benzamide In a manner substantially equivalent to Example 201, 2-(1-tert-butoxycarbonyl-piperidin-3-ylmethoxy)-4-tert-butylbenzoic acid (1.25 g, 3.19 mmol) and N-(5-chloropyridin-2-yl)-2-aminobenzamide (0.791 g, 3.19 mmol) yielded 0.396 g (20%) of 2-[2-(1-tert-butoxycarbonylpiperidin-3-yl-methoxy)-4-tert-butylbenzoylamino]-N-(5-chloropyridin-2-yl)benzamide as a white foam.
[1]NMR IS-MS, m/z 621.9 (m+1), 619.8 (m−1).

EXAMPLE 902

R=H; Procedure:
In a manner substantially equivalent to example 302, 2-[4-tert-butyl-2-(piperidin-3-ylmethoxy)benzoylamino]-N-(5-chloropyridin-2-yl)benzamide was prepared from 2-[2-(1-tert-butoxycarbonylpiperidin-3-ylmethoxy)-4-tert-butylbenzoylamino]-N-(5-chloropyridin-2-yl)benzamide (0.375 g, 0.604 mmol) to give 0.311 g (98.7%) of the desired product as an off-white solid.
[1]NMR
IS-MS, m/z 521.4 (m+1), 519.4 (m−1).

EXAMPLE 903

R=2-Fluorophenylcarbonyl; Procedure C; IS-MS, m/z 643.2 (m+1), 641.2 (m−1).

EXAMPLE 904

R=2-Fluorophenylaminocarbonyl; Procedure B, except that no scavanging was conducted, and the compound was purified via SCX solid phase extraction; IS-MS, m/z 658.2 (m+1), 656.3 (m−1).

EXAMPLE 905

R=2-Hydroxybenzyl; Procedure A; IS-MS, m/z 627.2 (m+1), 625.3 (m−1).

EXAMPLE 906

R=2-Carboxybenzyl; Procedure A; IS-MS, m/z 655.2 (m+1), 653.3 (m−1).

EXAMPLE 907

R=2-Methylbenzyl; Procedure A; IS-MS, m/z 625.2 (m+1), 6523.3 (m−1).

EXAMPLE 908

R=Imidazol-2-ylmethyl; Procedure A; IS-MS, m/z 601.2 (m+1), 599.3 (m−1).

EXAMPLE 909

R=Thiophen-3-ylmethyl; Procedure A; IS-MS, m/z 617.2 (m+1), 615.2 (m−1).

EXAMPLE 910

R=Cyclopropylmethyl; Procedure A; IS-MS, m/z 575.2 (m+1), 573.3 (m−1).

TABLE 10

Examples 1001-1002

Compounds of formula I which may be denoted by the following formula I-10

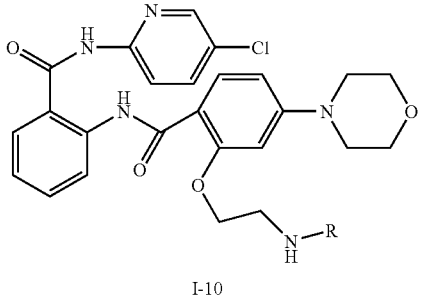

I-10 in which R has the indicated value of $R^a$ were prepared according to the indicated procedure from a requisite corresponding compound of formula I and the reagents and conditions appropriate for the indicated procedure or by a procedure otherwise noted.

EXAMPLE 1001

R=BOC; Procedure:
In a manner substantially equivalent to Example 201, 2-(2-tert-butoxycarbonyl-aminoethoxy)-4-(4-morpholinyl)benzoic acid (0.610 g, 1.66 mmol) and N-(5-chloro-pyridin-2-yl)-2-aminobenzamide (0.411 g, 1.66 mmol) yielded 0.503 g (50.7%) of 2-[2-(2-tert-butoxycarbonylaminoethoxy)-4-(4-morpholinyl)benzoylamino]-N-(5-chloro-pyridin-2-yl)benzamide as a white solid.
[1]NMR IS-MS, m/z 596.1 (m+1), 594.2 (m−1); Analysis for $C_{30}H_{34}N_5O_6$ Cl: Calcd: C, 60.45; H, 5.75; N, 11.75; Found: C, 60.48; H, 5.58; N, 11.70.

EXAMPLE 1002

R=H; Procedure:
In a manner substantially equivalent to Example 302, 2-[2-(2-aminoethoxy)-4-(4-morpholinyl)benzoylamino]-N-(5-chloropyridin-2-yl)benzamide was prepared from 2-[2-(2-tert-butoxycarbonylaminoethoxy)-4-(4-morpholinyl) benzoylamino]-N-(5-chloropyridin-2-yl)benzamide (0.210 g, 0.352 mmol) to give 0.147 g (94.3%) of the desired product as a white solid.
[1]NMR IS-MS, m/z 496.0 (m+1), 494.0 (m−1); Analysis for $C_{25}H_{26}N_5O_4$ Cl: Calcd: C, 60.54; H, 5.28; N, 14.12; Found: C, 60.13; H, 5.35; N, 13.72.

TABLE 11

Examples 1101-1108

Compounds of formula I which may be denoted by the following formula I-11

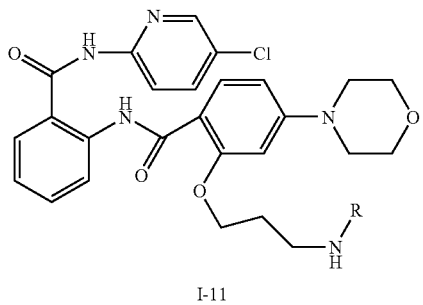

I-11 in which R has the indicated value of $R^a$ were prepared according to the indicated procedure from a requisite corresponding compound of formula I and the reagents and conditions appropriate for the indicated procedure or by a procedure otherwise noted.

EXAMPLE 1101

R=BOC; Procedure:

In a manner substantially equivalent to Example 201, 2-(3-tert-butoxycarbonylaminopropoxy)-4-(4-morpholinylbenzoic acid (1.25 g, 3.29 mmol) and N-(5-chloropyridin-2-yl)-2-aminobenzamide (0.815 g, 3.29 mmol) yielded 0.59 g (29.5%) of 2-[2-(3-tert-butoxycarbonylaminopropoxy)-4-(4-morpholinyl)benzoylamino]-N-(5-chloropyridin-2-yl)benzamide as a white solid.

$^1$NMR IS-MS, m/z 610.2 (m+1), 608.3 (m-1).

EXAMPLE 1102

R=H; Procedure:

In a manner substantially equivalent to Example 302, 2-[2-(3-aminopropoxy)-4-(4-morpholinyl)benzoylamino]-N-(5-chloropyridin-2-yl)benzamide was prepared from 2-[2-(3-tert-butoxycarbonylaminopropoxy)-4-(4-morpholinyl) benzoylamino]-N-(5-chloropyridin-2-yl)benzamide (0.568 g, 0.931 mmol) to give 0.445 g (93.5%) of the desired product as an off-white solid.

$^1$NMR (300 MHz, DMSO-d6): IS-MS, m/z 510.3 (m+1), 508.2 (m-1).

EXAMPLE 1103

R=2-Fluorophenylaminocarbonyl; Procedure B, except the crude material was purified via SCX solid phase extraction followed by silica gel chromatography.

IS-MS, m/z 647.0 (m+1), 645.1 (m-1).

EXAMPLE 1104

R=2-Fluorophenylaminothiocarbonyl; Procedure B, the crude material was purified via SCX solid phase extraction followed by silica gel chromatography.

IS-MS, m/z 662.9 (m+1), 661.0 (m-1).

EXAMPLE 1105

R=3-Methylthiophen-2-ylcarbonyl; Procedure C, except the crude material was purified via SCX solid phase extraction followed by silica gel chromatography.

IS-MS, m/z 633.9 (m+1), 632.0 (m-1).

EXAMPLE 1106

R=2-Thiophenecarbonyl; Procedure C, except the crude material was purified via SCX solid phase extraction followed by silica gel chromatography. IS-MS, m/z 619.9 (m+1), 618.0 (m-1).

EXAMPLE 1107

R=3-Thiophenecarbonyl; Procedure C, except the crude material was purified via SCX solid phase extraction followed by silica gel chromatography. IS-MS, m/z 619.9 (m+1), 618.0 (m-1).

EXAMPLE 1108

R=2-Methylbenzyl; Procedure A. The crude material was purified as described, followed by silica gel chromatography. IS-MS, m/z 614.0 (m+1), 612.1 (m-1).

TABLE 12

Examples 1201-1209

Compounds of the formula I which may be denoted by the following formula I-12

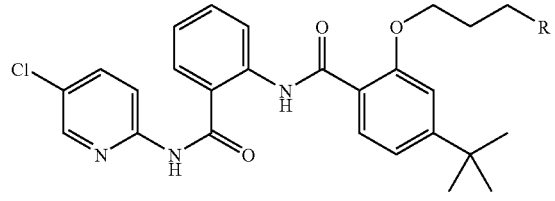

I-12 in which R has the indicated value of $NR^aR^b$ were prepared according to the indicated procedure from a requisite corresponding compound of formula I and the reagents and conditions appropriate for the indicated procedure or by a procedure otherwise noted.

EXAMPLE 1201

R=NH—BOC; Procedure:

A. Methyl 2-(3-tert-Butoxycarbonylaminopropoxy)-4-tert-butylbenzoate

Methyl 4-tert-butyl-2-hydroxybenzoate (2.41 g, 11.6 mmol) was dissolved in DMF (15 mL) and $K_2CO_3$ (2.39 g, 17.4 mmol) and N-Boc-3-bromopropylamine (4.14 g, 17.4 mmol) was added using DMF (10 mL) to aid the transfer. Potassium iodide (0.30 g) was added, and the reaction stirred at room temperature under nitrogen for 18 hr. The DMF was removed in vacuo and the residue taken up in ethyl acetate and washed with water and brine, dried, and the solvent removed in vacuo to give a viscous brown oil. Purification by chromaotgraphy over silica on a preparative scale apparatus, eluting with a gradient of hexane to hexane:ethyl acetate (70:30) gave 1.91 g (45.2%) of a viscous yellow oil.

B. 2-(3-tert-Butoxycarbonylaminopropoxy)-4-tert-butylbenzoic acid

In a manner substantially equivalent to 21-D, methyl 2-(3-tert-butoxycarbonyl-aminopropoxy)-4-tert-butylbenzoate (1.90 g, 5.20 mmol) gave the desired product (1.78 g, 97.4%) as a viscous oil.

C. 2-[2-(3-tert-Butoxycarbonylaminopropoxy)-4-tert-butylbenzoylamino]-N-(5-chloropyridin-2-yl)benzamide In a manner substantially equivalent to Example 201, 2-(3-tert-butoxycarbonylaminopropoxy)-4-tert-butylbenzoic acid (1.74 g, 4.95 mmol) and N-(5-chloropyridin-2-yl)-2-aminobenzamide (1.23 g, 4.95 mmol) yielded 1.55 g (53.8%) of the desired product as a white solid.
$^1$NMR IS-MS, m/z 581.1 (m+1), 579.2 (m−1); Analysis for $C_{31}H_{37}ClN_4O_5$: Calcd: C, 64.07; H, 6.42; N, 9.64; Found: C, 64.92; H, 6.30; N, 9.47.

EXAMPLE 1202

R=NH$_2$; Procedure:
In a manner substantially equivalent to Example 302, 2-[2-(3-tert-butoxycarbonyl-aminopropoxy)-4-tert-butylbenzoylamino]-N-(5-chloropyridin-2-yl)benzamide (1.50 g, 2.58 mmol) gave 1.18 g (95.2%) of the desired product as a white foam.
$^1$NMR IS-MS, m/z 481.1 (m+1), 479.2 (m−1). Analysis for $C_{26}H_{29}ClN_4O_3$: Calcd: C, 64.93; H, 6.08; N, 11.65; Found: C, 64.58; H, 5.72; N, 11.40.

EXAMPLE 1203

R=2-Fluorophenylcarbonylamino; Procedure C, with purification by silica gel chromatography. IS-MS, m/z 603.0 (m+1), 601.0 (m−1).

EXAMPLE 1204

R=3-Methylthiophen-2-ylcarbonylamino; Procedure C, with purification by silica gel chromatography. IS-MS, m/z 605.0 (m+1), 603.0 (m−1).

EXAMPLE 1205

R=2-Hydroxybenzylamino; Procedure A, with additional purification via silica gel chromatography. IS-MS, m/z 587.1 (m+1), 585.1 (m−1).

EXAMPLE 1206

R=Bis(3-thiophenylmethyl)amino; Procedure A, except that purification was effected by recrystallization from acetonitrile. IS-MS, m/z 673.0 (m+1), 671.1 (m−1).

EXAMPLE 1207

R=Bis(2-methylbenzyl)amino; Procedure A, with additional purification via silica gel chromatography. IS-MS, m/z 689.1 (m+1), 687.2 (m−1).

EXAMPLE 1208

R=Bis(cyclopropylmethyl)amino; Procedure A, with additional purification via silica gel chromatography. IS-MS, m/z 589.1 (m+1), 587.2 (m−1).

EXAMPLE 1209

R=1-(2-Pyridinyl)ethylamino; Procedure A, with additional purification via silica gel chromatography. IS-MS, m/z 586.1 (m+1), 584.1 (m−1).

TABLE 13

Examples 1301-1310

Compounds of formula I which may be denoted by the following formula I-13

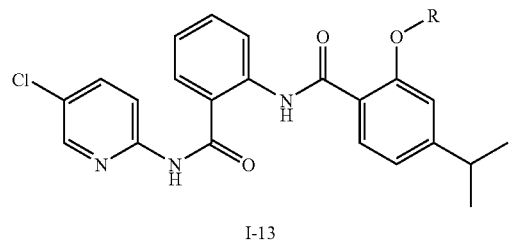

I-13 in which R has the indicated value of R$^1$ were prepared according to the indicated procedure from a requisite corresponding compound of formula I-13 in which R is H and the reagents and conditions appropriate for the indicated procedure or by a procedure otherwise noted.

EXAMPLE 1301

R=3-pyrrolidinyl:

General Procedure H for Alkylation of a Phenol Such as the Compound Described in Example 64-B Using a Resin-Bound Amino-Alcohol A. Preparation of Resin-Bound Amino-Alcohol

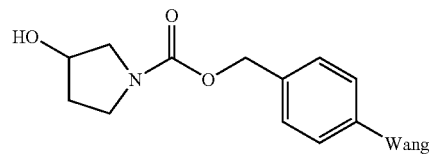

Wang para-nitrophenyl carbonate (Wang-PNP) resin (1 g, 1.4 mmol, 1.4 mmol/g) was weighed into a 20 mL scintillation vial, and 5 mL of 1:1 dichloromethane:NMP was added. 3-Pyrrolidinol (0.366 g, 4.2 mmol) was added, followed by N,N-(diisopropyl)-ethylamine (2 eq), and the vial was capped and placed on an orbital shaker at 200 rpm for 72 h. The reaction was transferred to a tared 30 mL fritted funnel and the resin was washed, alternating with dichloromethane and methanol (8 washes total), then washed with dichloromethane (3×), and dried in the vacuum oven at room temperature.

B. Mitsunobu Alkylation Using Resin-Bound Amino-Alcohol and Removal of Alkylated Product from the Resin The above resin (40.5 mg, 61.0 mmol, 1.508 mmol/g) was weighed into a 3 mL solid phase reaction vessel and the fritted end was capped. $PPh_3$ (19.2 mg, 73.2 mmol) was added as a solution in DMF (0.25 mL), followed by N-(5-chloropyridin-2-yl)-2-(2-hydroxy-4-isopropylbenzoylamino)benzamide (30.0 mg, 73.2 mmol) as a solution in DMF (0.5 mL). DIAD (14.8 mg, 73.2 mmol) was added and the vessel was sealed and heated in a heating block at 60° C. for 72 h. The reaction vessel was drained and the resin was washed with DMF (3×), dichloromethane (3×), THF (2×), water (2×), THF (2×) and dichloromethane (2×). The fritted end of the vessel was capped and phthalic anhydride (45.3 mg, 0.305 mmol, 5 eq) and DMF (1 mL) were added. N,N-(Diisopropyl)-ethylamine (23.7 mL, 0.120 mmol) was added and the vessel capped and placed on a 360° C. rotator for 18 h. The vessel was drained and the resin was washed as before. The vessel was capped on the fritted end and 2 mL of 95:5 TFA:water was added. The vessel was capped and placed back on the rotator for 2 h. The vessel was drained in a 20 mL scintillation vial and the resin was washed with 2 mL of water. The vial was frozen and placed on a lyophilizer for 18 h. The crude residue was purified via silica gel chromatography to give N-(5-chloropyridin-2-yl)-2-[4-isopropyl-2-(3-pyrrolidinyloxy)-benzoylamino]benzamide.

IS-MS, m/z 479.0 (m+1).

EXAMPLE 1302

R=2-Amino-4-methylthiobutyl; Procedure H; IS-MS, m/z 527.0 (m+1).

EXAMPLE 1303

R=2-(1-piperazinyl)ethyl; Procedure H; IS-MS, m/z 522.0 (m+1).

EXAMPLE 1304

R=2-(2-Piperidinyl)ethyl; Procedure H; IS-MS, m/z 521.0 (m+1).

EXAMPLE 1305

R=2-(2-Aminoethoxy)ethyl; Procedure H; IS-MS, m/z 497.0 (m+1).

EXAMPLE 1306

R=2-Aminoethyl; Procedure H; IS-MS, m/z 453.0 (m+1).

EXAMPLE 1307

R=4-Aminobutyl; Procedure H; IS-MS, m/z 481.0 (m+1).

EXAMPLE 1308

R=3-Aminopropyl; Procedure H; IS-MS, m/z 467.0 (m+1).

EXAMPLE 1309

R=4-Piperidinylmethyl; Procedure H; IS-MS, m/z 507.0 (m+1);

EXAMPLE 1310

R=3-piperidinylmethyl; Procedure H, except that the phthalic anhydride addition was omitted and the crude material was purified by SCX solid phase extraction followed be silica gel chromatography. IS-MS, m/z 507.0 (m+1), 505.1 (m−1).

TABLE 14

Examples 1401-1417

Compounds of formula I which may be denoted by the following formula I-14

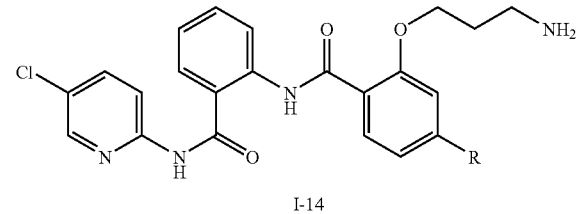

I-14 in which R has the indicated value of $R^2$ were prepared according to the indicated procedure from a requisite corresponding compound of formula $HNR^sR^t$ and the reagents and conditions appropriate for the indicated procedure or by a procedure otherwise noted.

EXAMPLE 1401

R=Piperidin-1-yl; Procedure:

A. 2-[2-(3-tert-Butoxycarbonylaminopropoxy)-4-fluorobenzoylamino]-N-(5-chloropyridin-2-yl)benzamide In a manner substantially aequivalent to Example 201, 2-(3-tert-butoxyaminopropoxy)-4-fluorobenzoic acid (3.29 g, 10.5 mmol) and N-(5-chloropyridin-2-yl)-2-aminobenzamide (2.60 g, 10.5 mmol) gave, after trituration of the crude product with ether, 4.1 g (71.9%) of a white solid.

B. 2-[2-(3-Aminopropoxy)-4-(piperidin-1-yl)benzoylamino]-N-(5-chloropyridin-2-yl)benzamide General Procedure J for the NAS (nuceophilic aromatic substitution) reaction of secondary amines:

The 2-[2-(3-tert-butoxycarbonylaminopropoxy)-4-fluorobenzoylamino]-N-(5-chloropyridin-2-yl)benzamide (0.100 g, 0.184 mmol) was weighed into a 4 mL vial and piperidine (0.5 mL) was added. The capped reaction vessel was heated at 110° C. for 24 h. After cooling, the reaction was diluted with dichloromethane and washed with water and brine, dried, and the solvent was removed in vacuo to give an oil. The crude residue was purified by silica gel chromatography to give 75.9 mg of a viscous oil. The oil was transferred to a 20 mL scintillation vial, 2.5 mL of 95:5 TFA:water was added, and the vial was allowed to stand capped for 2 h. The reaction was diluted with water (2.5 mL), frozen, and lyophilized for 18 h. The crude salt was purified by SCX solid phase chromatography as described in General Procedure A to give 52.8 mg (83.3%) of the title product.

IS-MS, m/z 508.0 (m+1), 506.1 (m−1).

EXAMPLE 1402

R=4-Thiomorpholinyl; Procedure J; IS-MS, m/z 525.9 (m+1), 524.1 (m−1).

EXAMPLE 1403

R=Pyrrolidin-1-yl; Procedure J; IS-MS, m/z 494.0 (m+1), 492.0 (m−1).

EXAMPLE 1404

R=4-(2-Hydroxyethyl)piperidin-1-yl; Procedure J; IS-MS, m/z 524.0 (m+1), 522.0 (m−1).

EXAMPLE 1405

R=4-Hydroxypiperidin-1-yl; Procedure J; IS-MS, m/z 497.1 (m+1), 495.1 (m−1).

EXAMPLE 1406

R=4-Methylpiperazin-1-yl; Procedure J; IS-MS, m/z 523.1 (m+1), 521.0 (m−1).

EXAMPLE 1407

R=(S)-3-(Dimethylamino)pyrrolidin-1-yl; Procedure J; IS-MS, m/z 537.0 (m+1), 535.0 (m−1).

EXAMPLE 1408

R=(S)-3-Aminopyrrolidin-1-yl; Procedure J; IS-MS, m/z 509.0 (m+1), 507.0 (m−1).

EXAMPLE 1409

R=(S)-2-(Methoxymethyl)pyrrolidin-1-yl; Procedure J; IS-MS, m/z 538.0 (m+1), 536.0 (m−1).

EXAMPLE 1410

R=3,4-Didehydropyridin-1-yl; Procedure J; IS-MS, m/z 606.1 (m+1), 604.1 (m−1).

EXAMPLE 1411

R=3-Hydroxypiperidin-1-yl; Procedure J; IS-MS, m/z 624.1 (m+1), 622.2 (m−1).

EXAMPLE 1412

R=3-Carbamoylpiperidin-1-yl; Procedure J; IS-MS, m/z 651.2 (m+1), 649.1 (m−1).

EXAMPLE 1413

R=3-Hydroxypyrrolidin-1-yl; Procedure J; IS-MS, m/z 610.1 (m+1), 608.2 (m−1).

EXAMPLE 1414

R=4-Methylhexahydro-1,4-diazepin-1-yl; Procedure J; IS-MS, m/z 637.2 (m+1), 635.2 (m−1).

EXAMPLE 1415

R=4-Carbamoylpiperidin-1-yl; Procedure J; IS-MS, m/z 651.2 (m+1), 649.2 (m−1).

EXAMPLE 1416

R=3-Methylpiperidin-1-yl; Procedure J; IS-MS, m/z 622.2 (m+1), 620.2 (m−1).

EXAMPLE 1417

R=Hexahydro-1,4-diazepin-1-yl; Procedure J; IS-MS, m/z 622.2 (m+1), 620.1 (m−1).

TABLE 15

Examples 1501-1509

Compounds of formula I which may be denoted by the following formula I-15

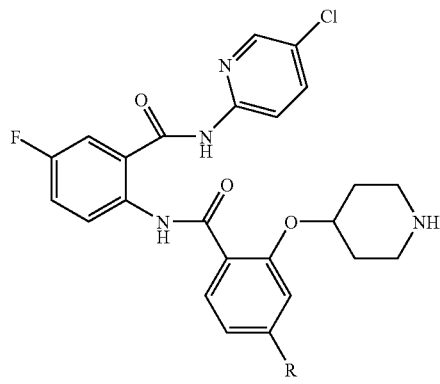

I-15 in which R has the indicated value of $R^2$ were prepared according to the indicated procedure from a requisite corresponding compound of formula $HNR^sR^t$ and the reagents and conditions appropriate for the indicated procedure or by a procedure otherwise noted.

EXAMPLE 1501

R=Piperidin-1-yl; Procedure J, except that DMSO (a volume equal to that of the amine) was added. IS-MS, m/z 552.2 (m+1).

EXAMPLE 1502

R=4-Acetylpiperazin-1-yl; Procedure J, except that DMSO (a volume equal to that of the amine) was added. IS-MS, m/z 595.2 (m+1).

EXAMPLE 1503

R=1-Azetidinyl; Procedure J, except that DMSO (a volume equal to that of the amine) was added. IS-MS, m/z 524.1 (m+1).

EXAMPLE 1504

R=(S)-2-(Methoxymethyl)pyrrolidin-1-yl; Procedure J, except that DMSO (a volume equal to that of the amine) was added. IS-MS, m/z 582.2 (m+1).

EXAMPLE 1505

R=(S)-3-(Acetylamino)pyrrolidin-1-yl; Procedure J, except that DMSO (a volume equal to that of the amine) was added. IS-MS, m/z 595.2 (m+1).

EXAMPLE 1506

R=(R)-2-Carbamoylpyrrolidin-1-yl; Procedure J, except that DMSO (a volume equal to that of the amine) was added. IS-MS, m/z 581.2 (m+1).

EXAMPLE 1507

R=4-Carbamoylpiperidin-1-yl; Procedure J, except that DMSO (a volume equal to that of the amine) was added. IS-MS, m/z 595.5 (m+1).

EXAMPLE 1508

R=4-Thiomorpholinyl; Procedure J, except that DMSO (a volume equal to that of the amine) was added. IS-MS, m/z 570.4 (m+1).

EXAMPLE 1509

R=4-Methylhexahydro-1,4-diazepin-1-yl; Procedure J, except that DMSO (a volume equal to that of the amine) was added. $^1$NMR; IS-MS, m/z 555.2 (m+1), 553.3 (m−1).

Preparation 1601

Preparation of N-(5-Chloropyridin-2-yl)-5-fluoro-2-[4-hydroxy-2-(piperidin-4-yl-oxy)benzoylamino]benzamide

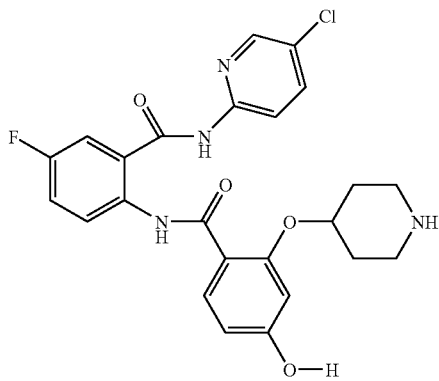

A. Methyl 4-benzyloxy-2-hydroxybenzoate

Methyl 2,4-dihydroxybenzoate (20.0 g, 0.119 mol) was dissolved in DMF (400 mL) and potassium carbonate (17.2 g, 0.125 mol) and benzyl bromide (21.4 g, 0.125 mol) were added using additional DMF (400 mL) to aid the transfer. Potassium iodide (3.0 g) was added, and the reaction was stirred at room temperature under nitrogen for 48 h. The DMF was removed in vacuo and the residue was dissolved in ethyl acetate, washed with water and brine, dried, and the solvent was removed in vacuo to give a white solid which was recrystallized from ethyl acetate:hexane to yield 17.9 g (61.1%) of a white solid.

B. Methyl 4-Benzyloxy-2-(1-tert-butoxycarbonylpiperidin-4-yloxy)benzoate

Methyl 4-benzyloxy-2-(1-tert-butoxycarbonylpiperidin-4-yloxy)benzoate was prepared from methyl 4-benzyloxy-2-hydroxybenzoate and 1-Boc-4-hydroxypiperidine using a procedure similar to that described in Example 21-C. The crude material, in dichloromethane, was filtered and purified by chromatography over silica gel using a preparative high pressure chromatography apparatus, eluting with a gradient of 9:1 to 4:1 to 3:1 hexane:ethyl acetate to give 12.8 g of a white solid.

$^1$NMR Analysis for $C_{25}H_{31}NO_6$: Calcd: C, 68.01; H, 7.08; N, 3.17; Found: C, 67.84; H, 7.12; N, 3.22.

C. Methyl 2-(1-tert-Butoxycarbonylpiperidin-4-yloxy)-4-hydroxybenzoate

The methyl 4-benzyloxy-2-(1-tert-butoxycarbonylpiperidin-4-yloxy)benzoate (12.8 g) was dissolved in EtOH (135 mL). 10% Pd/C catalyst (1.3 g) was added and the reaction was placed under an $H_2$ atmosphere (4.1 bar) for 4 h at room temperature. The catalyst was filtered and the ethanol was removed in vacuo to give 9.15 g (89.7%) of a white foam.

D. Methyl 2-(1-tert-Butoxycarbonylpiperidin-4-yloxy)-4-(methoxymethoxy)benzoate Methyl 2-(1-tert-butoxycarbonylpiperidin-4-yloxy)-4-hydroxybenzoate (9.13 g, 26.0 mmol) was dissolved in DMF. Potassium carbonate (7.19 g, 52.0 mmol) was added, followed by methoxymethyl chloride (2.51 g, 31.2 mmol), and the reaction was stirred at room temperature under a drying tube for 24 h. An additional 1.2 eq of methoxymethyl chloride was added and the reaction stirred an additional 48 h. The DMF was removed in vacuo. The residue was dissolved in ethyl acetate, washed with water, dried, and the solvent was removed in vacuo to give 9.91 g (96.2%) of a viscous oil.

E. 2-(1-tert-Butoxycarbonylpiperidin-4-yloxy)-4-(methoxymethoxy)benzoic Acid In a manner substantially equivalent to Example 21-D, methyl 2-(1-tert-butoxy-carbonylpiperidin-4-yloxy)-4-methoxymethoxy benzoate (9.90 g, 25.0 mmol) gave 8.44 g (88.4%) of the desired product as a viscous oil.

F. 2-[2-(1-tert-Butoxycarbonylpiperidin-4-yloxy)-4-methoxymethoxybenzoyl-amino]-N-(5-chloropyridin-2-yl)-5-fluorobenzamide In a manner substantially equivalent to Example 201, 2-(1-tert-butoxycarbonyl-piperidin-4-yloxy)-4-methoxymethoxybenzoic acid (8.40 g, 22.0 mmol) and 2-amino-N-(5-chloropyridin-2-yl)-5-fluorobenzamide (5.85 g, 22.0 mmol) yielded 6.84 g (49.2%) of the desired product as a white solid.

G. N-(5-Chloropyridin-2-yl)-5-fluoro-2-[4-hydroxy-2-(piperidin-4-yloxy)benzoyl-amino]benzamide 2-[2-(1-tert-Butoxycarbonylpiperidin-4-yloxy)-4-(methoxymethoxy)benzoyl-amino]-N-(5-chloropyridin-2-yl)-5-fluorobenzamide (6.70 g, 10.7 mmol) was suspended in methanol (18 mL). 4 N HCl in dioxane (35 mL) was added and the resulting solution stirred at room temperature under nitrogen for 2 h. The reaction was cooled to 0° C. and cautiously quenched with saturated aqueous sodium bicarbonate. The resulting precipitate was collected and dried in a vacuum oven to give a quantitative yield of the title product as a fine white powder.

IS-MS, m/z 485.1 (m+1), 483.1 (m−1).

TABLE 16

Examples 1602-1611

Compounds of formula I which may be denoted by the following formula I-16

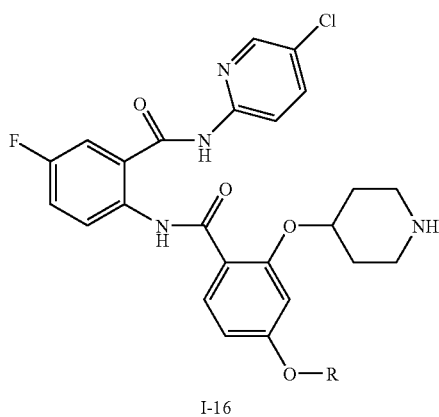

I-16 in which R has the indicated value of $R^q$ were prepared according to the indicated procedure from a requisite alkylating agent and the above described phenol corresponding corresponding to a compound of formula I-16 in which R is hydrogen and the reagents and conditions appropriate for the indicated procedure or by a procedure otherwise noted.

General Procedure K for the Alkylation by Alkyl Halides of Phenols Such as that of Preparation 1601:

Wang-PNP resin (6.85 g, 10.1 mmol, 1.48 mmol/g) was weighed into a 100 mL solid phase reaction vessel and dichloromethane (15 mL) was added. N-(5-Chloro-pyridin-2-yl)-5-fluoro-2-[4-hydroxy-2-(piperidin-4-yloxy)benzoylamino]benzamide (5.16 g, 10.6 mmol) was added in 1-methylpyrrolidin-2-one (15 mL) followed by diisopropylethylamine (2.63 g, 20.3 mmol). The vessel was capped, and placed on a wrist shaker for 24 h. The reaction was poured into a tared fritted funnel, and the resin was washed with dichloromethane and methanol alternately (4 times each), followed by dichloromethane (3×). Drying in the vacuum oven at room temperature gave a quantitative yield of the desired resin (0.981 mmol/g).

The above resin (50 mmol) is weighed into a 4 mL vial and DMF (0.25 mL) was added, followed by sodium methoxide (100 mL, 100.0 mmol, 0.5 N in MeOH). The vial is capped and allowed to stand for 15 min with occasional agitation. The alkyl halide is added (catalytic tetrabutylammonium iodide was added to alkyl chlorides, and 2 eq additional sodium methoxide used for alkyl halides containing acid addition salts of amines) and the capped vial is heated at 60° C. on a 360° rotator for 48 h. The reaction mixture is transferred to a 3 mL solid phase reaction vial. The resin is washed with DMF (2×), dichloromethane (2×), THF (2×), water (2×), THF (2×), and dichloromethane (2×).

After drying briefly in the vacuum oven, 2 mL of 4:1 dichloromethane:TFA is added and the vial is placed on a 360° rotator for 2 h. The reaction is drained into a 20 mL scintillation vial and the resin is washed with 3 mL of dichloromethane. After concentrating overnight under a flow of nitrogen, the residue is taken up in dichloromethane (1 mL) and MeOH (0.25 mL) and the compound purified by SCX solid phase extraction as described in General Procedure A, followed by silica gel chromatography, eluting with a step gradient of 95:5 chloroform:MeOH to 90:10 chloroform:MeOH, to 90:9:1 chloroform:MeOH:(2 N ammonia in MeOH) to 90:5:5 chloroform:MeOH:(2 N ammonia in MeOH) to 90:10:10 chloroform:MeOH:(2 N ammonia in MeOH) to give the desired product.

EXAMPLE 1602

R=2-Methoxyethyl; Procedure K; IS-MS, m/z 543.0 (m+1), 541.0 (m−1).

EXAMPLE 1603

R=2-Amino-2-oxoethyl; Procedure K; IS-MS, m/z 541.9 (m+1), 540.0 (m−1).

EXAMPLE 1604

R=2-Fluoroethyl; Procedure K; IS-MS, m/z 530.9 (m+1), 529.0 (m−1).

EXAMPLE 1605

R=1,2,4-Oxadiazol-3-ylmethyl; Procedure K.

EXAMPLE 1606

R=Propargyl; Procedure K; IS-MS, m/z 522.9 (m+1), 521.0 (m−1).

EXAMPLE 1607

R=2-Ethoxy-2-oxoethyl; Procedure K; IS-MS, m/z 570.9 (m+1), 569.0 (m−1).

EXAMPLE 1608

R=3-Methylbutyl; Procedure K; IS-MS, m/z 555.0 (m+1), 553.0 (m−1).

EXAMPLE 1609

R=Cyclopentyl; Procedure K; IS-MS, m/z 553.0 (m+1), 551.0 (m−1).

EXAMPLE 1610

R=Cycloheptyl; Procedure K; IS-MS, m/z 581.0 (m+), 579.1 (m−1).

EXAMPLE 1611

R=1-Ethylpropyl; Procedure K; IS-MS, m/z 555.0 (m+1), 553.0 (m−1).

What is claimed is:

1. A compound of formula I,

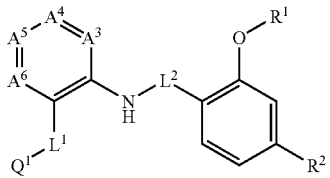

or a pharmaceutically acceptable salt thereof, wherein:

$A^3$, $A^4$, $A^5$ and $A^6$, together with the two carbons to which they are attached, complete a substituted benzene in which $A^3$ is $CR^3$, $A^4$ is $CR^4$, $A^5$ is $CR^5$, and $A^6$ is $CR^6$; wherein $R^3$ is hydrogen, methyl, fluoro, chloro or carboxy;

one of $R^4$ and $R^5$ is hydrogen, (1-4C)alkyl, halo, cyano, trifluoromethyl, trifluoro-methoxy, $R^fO$—, $R^fO_2CCH_2O$—, $HO(CH_2)_aO$— (in which a is 2, 3 or 4), $R^fO_2C$—, $R^fO_2CCH_2$—, nitro or $R^gNH$—;

the other of $R^4$ and $R^5$ is hydrogen; and $R^6$ is hydrogen, methyl, fluoro, chloro or methoxy;

in which $R^f$ is hydrogen, (1-4C)alkyl or benzyl; $R^g$ is hydrogen or $R^hSO_2$—; and $R^h$ is (1-4C)alkyl or dimethylamino;

$L^1$ is —CO—NH— or —SO$_2$—NH— such that -$L^1$-$Q^1$ is —CO—NH-$Q^1$ or —SO$_2$—NH-$Q^1$;

$Q^1$ is $Q^{1C}$ wherein $Q^{1C}$ is pyridyl which may bear one or more amino, nitro, methoxy, methylthio, trifluoromethyl or methyl substituents and may bear one or more halo substituents on carbon which is not bonded to a ring nitrogen); or $L^2$ is carbonyl or methylene;

$R^1$ is —(CH$_2$)$_i$-Q-(CH$_2$)$_j$—NR$^a$R$^b$ wherein:

a) Q is a single bond; the sum of i and j is 2, 3 or 4;
b) Q is oxy; i is 2; and j is 2;
c) Q is —CH(CH$_3$)—, —C(CH$_3$)$_2$—, or —CH(OH)—; i is 1; and j is 1;
d) Q is cyclohexane-1,4-diyl; i is 0; and j is 0;
e) Q is —CH{(CH$_2$)$_2$—SCH$_3$}—; i is 1; and j is 0;
f) Q is —CHR$^c$; i is 0 or 1; j is 1; and R$^b$ and R$^c$ together are —(CH$_2$)$_k$— wherein k is 2 or 3;
g) Q is —CHR$^c$; i is 1 or 2; j is 0; and R$^b$ and R$^c$ together are —(CH$_2$)$_4$—;
h) Q is —CHR$^c$; i is 0; j is 2; and R$^b$ and R$^c$ together are —(CH$_2$)$_2$— or —C(CH$_3$)$_2$—CH$_2$— (wherein the CH$_2$ carbon is bonded to the nitrogen); or
i) Q is —CHR$^c$; i is 1; j is 2; and R$^b$ and R$^c$ together are —(CH$_2$)$_2$—;

wherein, unless defined above, $R^a$ is hydrogen or $R^d$; and $R^b$ is hydrogen or (1-3C) normal alkyl;

or NR$^a$R$^b$ is a cyclic amino group selected from azetidin-1-yl, pyrrolidin-1-yl, 3,4-didehydropyrrolidin-1-yl, thiazolidin-3-yl, piperidin-1-yl, 3,4-didehydropiperidin-1-yl, morpholin-4-yl, thiomorpholin-4-yl, piperazin-1-yl, hexahydroazepin-1-yl, hexahydro-1,4-diazepin-1-yl and octahydroazocin-1-yl (which cyclic group may bear one or more methyl substituents on carbon, or may bear a carbamoyl, hydroxymethyl, methoxymethyl, 2-hydroxyethyl, pyrrolidin-1-ylmethyl or 2-(pyrrolidin-1-yl)ethyl substituent on carbon, or may bear a hydroxy, amino, methylamino, dimethylamino, pyrrolidin-1-yl, piperidin-1-yl, {(1-2C)acyl}amino, or {(1-4C)alkoxy}carbonylamino substituent on a carbon which is not attached to a ring nitrogen, oxygen or sulfur nor double bonded to another carbon, or may bear a (1-3C) alkyl, cyclopentyl, pyrrolidin-1-ylcarbonylmethyl, 2-hydroxyethyl, acetyl, furanylcarbonyl, phenyl {which phenyl may bear a chloro, methyl or methoxy substituent}, pyridinyl, pyrimidinyl or pyrazinyl substituent on a ring nitrogen at the 4-position); or NR$^a$R$^b$ is 1,3,3-trimethyl-6-aza-bicyclo[3.2.1]octan-6-yl or N(CH$_2$R$^w$)$_2$;

$R^d$ is (1-7C)alkyl (which alkyl may bear one or more substituents R$^e$ on a carbon which is not otherwise directly bonded to a nitrogen or oxygen wherein each R$^e$ is independently hydroxy, (1-3C)alkoxy, (1-3C)alkylthio, amino {which amino may bear an acetyl or one or two (1-3C)alkyl groups which may be the same or different} or cyclic amino {which cyclic amino is selected from azetidin-1-yl, pyrrolidin-1-yl, piperidin-1-yl, morpholin-4-yl, thiomorpholin-4-yl and piperazin-1-yl}), or $R^d$ is (3-8C)cycloalkyl (which cycloalkyl may bear one or more methyl substituents and/or may bear one or more hydroxy substituents on a carbon, including a methyl carbon, which is not otherwise directly bonded to a nitrogen or oxygen), or $R^d$ is 3-phenylpropyl, hexahydro-2-oxo-azepin-3-yl, —CH$_2$R$^w$, —CH(CH$_3$)R$^w$, —CH$_2$ CH(OH)R$^w$, —CH$_2$ CH=CHR$^w$, —(CH$_2$)$_2$R$^w$, —CH$_2$ CH(CH$_3$)R$^w$, α-(hydroxymethyl)benzyl, {(1-4C)alkoxy}carbonyl, trifluoroacetyl, —COCH$_2$R$^x$, —COYR$^y$ (in which Y is a single bond, carbonyl or 1,2-ethenediyl) or —CZNH—(CH$_2$)$_z$R$^z$ (in which z is 0, 1, 2 or 3; and Z is O or S); and in which $R^w$ is (1-4C)alkyl, ethynyl, trifluoromethyl, (3-7C)cycloalkyl (which cycloalkyl may bear one or more methyl substituents and/or may bear one or more hydroxy substituents on a carbon, including a methyl carbon, which is not otherwise directly bonded to a nitrogen or oxygen), tetrahydrofuran-2-yl, phenyl (which is unsubstituted or bears one to three substituents independently selected from halo, methyl, trifluoromethyl, methoxy, ethoxy, hydroxy, methylenedioxy, nitro, carboxy, methoxycarbonyl and cyano), or heteroaryl (which heteroaryl is a 5-membered aromatic ring which includes one to three heteroatoms selected from sulfur, oxygen and nitrogen or is a 6-membered aromatic ring which includes one to three nitrogen atoms, wherein the heteroaryl is attached at carbon and may bear one or more methyl substituents on carbon or nitrogen);

$R^x$ is carboxymethyl, dimethylamino, thienyl, pyridinyl or 1-tetrazolyl;

$R^y$ is methyl, phenyl (which may bear a fluoro or methyl substituent), or heteroaryl (which heteroaryl is a 5-membered aromatic ring which includes one to three heteroatoms selected from sulfur, oxygen and nitrogen or is a 6-membered aromatic ring which includes one to three nitrogen atoms, wherein the heteroaryl is attached at carbon and may bear one or more methyl substituents on carbon or nitrogen); and $R^z$ is phenyl (which may bear a fluoro or methyl substituent), thienyl or pyridinyl or (provided z is 2 or 3) $R^z$ is (1-2C)alkoxy, di(1-2C)alkylamino or cyclic amino (which cyclic amino is selected from pyrrolidin-1-yl, piperidin-1-yl, morpholin-4-yl and thiomorpholin-4-yl); or $R^1$ is 4-oxocyclohexyl; and $R^2$ is fluoro, chloro, aminomethyl, 1-aminoethyl, 1-amino-1-methylethyl, —S(O)$_n$—R$''$ (wherein n is 0, 1 or 2), (1-6C)alkyl, phenyl (which may bear a chloro or methoxy substituent at the 4-position), thienyl, —O—R$^q$ or —NR$^s$R$^t$ wherein $R''$ is (1-2C)alkyl;

$R^q$ is (1-6C)alkyl (which alkyl may bear a fluoro or methoxy substituent on a carbon not bound to oxygen), (3-7C)cycloalkyl or —CH$_2$—R$^r$ (in which R$^r$ is ethynyl, cyano, carbamoyl, {(1-2C)alkoxy}carbonyl, phenyl or 1,2,4-triazol-3-yl); and wherein $R^s$ is hydrogen or (1-6C)alkyl and R$^t$ is hydrogen or methyl, or —NR$^s$R$^t$ is a cyclic amino group selected from azetidin-1-yl, pyrrolidin-1-yl, 3,4-didehydropyrrolidin-1-yl, piperidin-1-yl, 3,4-didehydropiperidin-1-yl, morpholin-4-yl, thiomorpholin-4-yl, piperazin-1-yl, and hexahydro-1,4-diazepin-1-yl (which cyclic group may bear one or more methyl substituents on carbon, or may bear a carbamoyl, hydroxymethyl, methoxymethyl, or 2-hydroxyethyl substituent on carbon, or may bear a hydroxy, amino, methylamino, dimethylamino, (1-2C)acylamino, or {(1-4C)alkoxy}carbonylamino substituent on a carbon which is not attached to a ring nitrogen, oxygen or sulfur nor double bonded to another carbon, or may bear a (1-3C)alkyl, acetyl, hydroxyacetyl or acetoxyacetyl substituent on a ring nitrogen at the 4-position);

or —OR$^1$ represents 1-(4-pyridyl)piperidin-4-ylcarbonylamino and $R^2$ is hydrogen.

2. The compound as claimed in claim 1 wherein:

halo is fluoro, chloro, bromo or iodo; (1-2C)acyl is formyl or acetyl; for an alkyl group or the alkyl portion of an alkoxy or alkylthio group: (1-2C)alkyl is methyl or ethyl; (1-3C) normal alkyl is methyl, ethyl or propyl; (1-3C)alkyl is methyl, ethyl, propyl or isopropyl; (1-4C)alkyl is methyl, ethyl, propyl, isopropyl, butyl, isobutyl, or t-butyl; (1-6C)alkyl is methyl, ethyl, propyl, isopropyl, butyl, t-butyl, pentyl or hexyl; (1-7C)alkyl is methyl, ethyl, propyl, isopropyl, butyl, t-butyl, 1-methylpropyl, 2-methylpropyl, pentyl, 2-methyl-butyl, 3-methylbutyl, 1,2-dimethylpropyl, 2,2-dimethylpropyl, hexyl, 3,3-dimethylbutyl, 1,3-dimethylbutyl, 1,2,2-trimethylpropyl, 1-(1-methylethyl)-2-methylpropyl or heptyl; (3-7C)cycloalkyl is cyclopropyl, cyclobutyl, cyclopentyl, cyclohexyl or cycloheptyl; (3-8C)cycloalkyl is cyclopropyl, cyclobutyl, cyclopenylyl, cyclohexyl, cycloheptyl or cyclooctyl.

3. The compound as claimed in claim 1 or 2 wherein:

$R^3$ is hydrogen;

$R^4$ is fluoro, chloro, methoxycarbonyl, carboxy, nitro or amino, and $R^5$ is hydrogen; or $R^4$ is hydrogen, and $R^5$ is hydrogen, fluoro, chloro, iodo or cyano; and $R^6$ is hydrogen.

4. The compound as claimed in claim 3 wherein:

$L^1$ is —CO—NH— such that -L$^1$-Q$^1$ is —CO—NH-Q$^1$;

$Q^{1C}$ is 2-pyridinyl, 5-fluoropyridin-2-yl, 5-chloropyridin-2-yl, 5-methylpyridin-2-yl, 5-trifluoromethylpyridin-2-yl, 3-methylpyridin-2-yl, 3-nitropyridin-2-yl, 3,5-dichloropyridin-2-yl, 4,6-dimethylpyridin-2-yl.

5. The compound as claimed in any one of claims 1-4 wherein:

$R^1$ is —(CH$_2$)$_2$—NR$^a$R$^b$, —(CH$_2$)$_3$—NR$^a$R$^b$, —(CH$_2$)$_4$—NR$^a$R$^b$, —(CH$_2$)$_2$—O—(CH$_2$)$_2$—NR$^a$R$^b$, —CH$_2$—CH(CH$_3$)—CH$_2$—NR$^a$R$^b$, —CH$_2$—C(CH$_3$)$_2$—CH$_2$—NR$^a$R$^b$, —CH$_2$—CH(OH)—CH$_2$—NR$^a$R$^b$, 1,4-cyclohexyl-NR$^a$R$^b$, —CH$_2$—CH{(CH$_2$)$_2$—SCH$_3$}CH$_2$—NR$^a$R$^b$, 3-pyrrolidinyl bearing R$^a$ on the nitrogen, 3-pyrrolidinylmethyl bearing R$^a$ on the nitrogen, 3-piperidinyl bearing a group R$^a$ on the nitrogen, 3-piperidinylmethyl bearing R$^a$ on the nitrogen, 2-piperidinylmethyl bearing R$^a$ on the nitrogen, 2-(2-piperidinyl)ethyl bearing R$^a$ group on the nitrogen, 4-piperidinyl bearing R$^a$ on the nitrogen, 3,3-dimethylpiperidin-4-yl bearing R$^a$ on the nitrogen, or 4-piperidinylmethyl bearing R$^a$ on the nitrogen;

$R^a$ is hydrogen or R$^d$; and R$^b$ is hydrogen, methyl, ethyl or propyl;

or NR$^a$R$^b$ is azetidin-1-yl, pyrrolidin-1-yl, 2-methylpyrrolidin-1-yl, 2-(hydroxymethyl)pyrrolidin-1-yl, 2-(methoxymethyl)pyrrolidin-1-yl, 2-(2-hydroxyethyl)pyrrolidin-1-yl, 2-(pyrrolidin-1-ylmethyl)pyrrolidin-1-yl, 3-hydroxypyrrolidin-1-yl, 2-(dimethylamino)pyrrolidin-1-yl, 3-(acetylamino)pyrrolidin-1-yl, thiazolidin-3-yl, piperidin-1-yl, 2-methylpiperidin-1-yl, 4-methylpiperidin-1-yl, 2,6-dimethylpiperidin-1-yl, 3,5-dimethylpiperidin-1-yl, 3-carbamoylpiperidin-1-yl, 4-carbamoylpiperidin-1-yl, 2-(hydroxymethyl)piperidin-1-yl, 3-(hydroxymethyl)-piperidin-1-yl, 4-(hydroxymethyl)piperidin-1-yl, 2-(2-hydroxyethyl)piperidin-1-yl, 4-(2-hydroxyethyl)piperidin-1-yl, 2-(2-pyrrolidin-1-ylethyl)piperidin-1-yl, 4-hydroxypiperidin-1-yl, 4-(pyrrolidin-1-yl)piperidin-1-yl, 4-(piperidin-1-yl)piperidin-1-yl, 3,4-didehydropiperidin-1-yl, morpholin-4-yl, 3,5-dimethylmorpholin-4-yl, thiomorpholin-4-yl, piperazin-1-yl, 4-methylpiperazin-1-yl, 4-cyclopentylpiperazin-1-yl, 4-(pyrrolidin-1-ylcarbonylmethyl)piperazin-1-yl, 4-(2-hydroxyethyl)piperazin-1-yl, 4-acetylpiperazin-1-yl, 4-(furan-1-ylcarbonyl)piperazin-1-yl, 4-phenylpiperazin-1-yl, 4-(2-chlorophenyl)piperazin-1-yl, 4-(3-chlorophenyl)piperazin-1-yl, 4-(3-methylphenyl)-piperazin-1-yl, 4-(2-methoxyphenyl)piperazin-1-yl, 4-(pyridin-2-yl)piperazin-1-yl, 4-(pyridin-2-yl)piperazin-1-yl, 4-(pyrimidin-2-yl)piperazin-1-yl, 4-(pyrazin-2-yl)-piperazin-1-yl, hexahydroazepin-1-yl, 2,2,5-trimethylhexahydroazepin-1-yl, 3,3,5-trimethylhexahydroazepin-1-yl, 4-methylhexahydro-1,4-diazepin-1-yl, octahydroazocin-1-yl, 1,3,3-trimethyl-6-azabicyclo[3.2.1]octan-6-yl, di(thiophen-2-ylmethyl)amino, di(2-methylbenzyl)amino or di(cyclopropylmethyl)amino; and $R^d$ is methyl, propyl, isopropyl, butyl, t-butyl, pentyl, 2-methylbutyl, 3-methyl-butyl, hexyl, 3,3-dimethylbutyl, 1-(1-methylethyl)-2-methylpropyl, 2-hydroxyethyl, 2-hydroxy-1-methylethyl, 2-hydroxy-1,1-dimethylethyl, 1-hydroxymethyl-2-hydroxyethyl, 3-hydroxypropyl, 3-hydroxy-2-methylpropyl, 4-hydroxybutyl, 1-hydroxymethylpropyl, 3-hydroxy-2,2-dimethylpropyl, 1-hydroxymethyl-2-methylpropyl, 1-hydroxymethyl-2,2-dimethylpropyl, 1-hydroxymethyl-3-methylthiopropyl, 1-hydroxymethyl-3-methylbutyl, 2-methoxyethyl, 2-methylthioethyl, 2-(dimethylamino)ethyl, 1-methyl-2-(dimethylamino)ethyl, 2,2-dimethyl-3-(dimethylamino)propyl, 2-(acetylamino)ethyl, 2-(pyrrolidin-1-yl)ethyl, 2-(piperidin-1-yl)ethyl, cyclopropyl, cyclobutyl, cyclopenylyl, cyclohexyl, cycloheptyl, cyclooctyl, 3-methylcyclohexyl, 4-methylcyclohexyl, trans-4-hydroxycyclohexyl, 1-(hydroxymethyl) cyclopenylyl, 3-phenylpropyl or hexahydro-2-oxoazepin-3-yl, or $R^d$ is —CH$_2$R$^w$, in which R$^w$ is ethynyl, cyclopropyl, tetrahydrofuran-2-yl, phenyl, 2-fluorophenyl, 2-chlorophenyl, 2-methylphenyl, 3-methylphenyl, 4-methylphenyl, 2-methoxyphenyl, 3-methoxyphenyl, 4-methoxyphenyl, 2,3-dimethoxyphenyl, 2,6-dimethoxyphenyl, 2-ethoxyphenyl, 2-hydroxyphenyl, 2-hydroxy-3-methoxyphenyl, 2,3-methylenedioxyphenyl, 2-nitrophenyl, 2-carboxyphenyl, 2-methoxycarbonylphenyl, 2-cyanophenyl, 2-furanyl, 2-thienyl, 3-methylthien-2-yl, 3-thienyl, 2-imidazolyl, 5-methylimidazol-4-yl, 2-thiazolyl, 2-pyridinyl, 3-pyridinyl or 4-pyridinyl, or $R^d$ is —CH(CH$_3$)R$^w$, in which R$^w$ is phenyl or 2-pyridinyl, or $R^d$ is —CH$_2$ CH(OH)R$^w$, in which R$^w$ is methyl, t-butyl or trifluoromethyl, or $R^d$ is —CH$_2$ CH═CHR$^w$, in which R$^w$ is phenyl or 2-furanyl, or $R^d$ is —(CH$_2$)$_2$R$^w$, in which R$^w$ is phenyl or 2-thienyl, or $R^d$ is —CH$_2$ CH(CH$_3$)R$^w$, in which R$^W$ is phenyl, or $R^d$ is α-(hydroxymethyl)benzyl, t-butoxycarbonyl, trifluoroacetyl, or $R^d$ is —COCH$_2$R$^x$, in which R$^x$ is carboxymethyl, dimethylamino, 2-thienyl, 3-thienyl, 2-pyridinyl or 1-tetrazolyl, or $R^d$ is —COR$^y$ in which R$^y$ is methyl, phenyl, 2-fluorophenyl, 3-fluorophenyl, 4-fluorophenyl, 2-methylphenyl, 3-methylphenyl, 4-methylphenyl, 2-thienyl, 3-methylthien-2-yl, 3-thienyl, 1-methylpyrrol-2-yl or 1-methylpyrazol-5-yl, or $R^d$ is —CO—CO—R$^y$ in which R$^y$ is methyl, 2-furanyl or 2-thienyl, or $R^d$ is —CONHR$^z$ in which R$^z$ is 2-fluorophenyl or 4-fluoro-phenyl, or $R^d$ is —CONH—(CH$_2$)$_2$ R$^z$ in which R$^z$ is 2-thienyl, or $R^d$ is —CSNHR$^z$ in which R$^z$ is 2-fluorophenyl, or $R^d$ is —CSNH—CH$_2$—R$^z$ in which R$^z$ is 3-pyridinyl, or $R^d$ is —CSNH—(CH$_2$)$_2$R$^z$ in which R$^z$ is methoxy, or $R^d$ is —CSNH—(CH$_2$)$_3$R$^z$ in which R$^z$ is methoxy, dimethylamino, diethylamino or morpholin-4-yl;

or $R^1$ is 4-oxocyclohexyl.

6. The compound as claimed in any one of claim 5 wherein $R^2$ is fluoro, chloro, 1-aminoethyl, 1-amino-1-methylethyl, methylthio, methylsulfinyl, methylsulfonyl, ethylsulfonyl, isopropyl, t-butyl, 4-chlorophenyl, 4-methoxyphenyl, 3-thienyl, methoxy, 2-fluoroethoxy, 2-methoxyethoxy, isopropoxy, 1-ethylpropoxy, 3-methylbutoxy, cyclopentyloxy, cycloheptyloxy, propargyloxy, 2-amino-2-oxoethoxy, 2-ethoxy-2-oxoethoxy, benzyloxy, 1,2,4-oxadiazol-3-ylmethoxy, dimethylamino, azetidin-1-yl, pyrrolidin-1-yl, (R)-2-carbamoylpyrrolidin-1-yl, (S)-2-(methoxymethyl) pyrrolidin-1-yl, 3-hydroxypyrrolidin-1-yl, 3-aminopyrrolidin-1-yl, (S)-3-aminopyrrolidin-1-yl, (S)-3-(dimethylamino)pyrrolidin-1-yl, 3-(t-butoxycarbonylamino) pyrrolidin-1-yl, (S)-3-(acetylamino)pyrrolidin-1-yl, piperidin-1-yl, 3-methylpiperidin-1-yl, 3-carbamoylpiperidin-1-yl, 4-carbamoylpiperidin-1-yl, 4-(2-hydroxyethyl)piperidin-1-yl, 3-hydroxypiperidin-1-yl, 4-hydroxypiperidin-1-yl, 3,4-didehydropiperidin-1-yl, morpholin-4-yl, thiomorpholin-4-yl, 4-methylpiperazin-1-yl, 4-acetylpiperazin-1-yl, hexahydro-1,4-diazepin-1-yl or 4-methylhexahydro-1,4-diazepin-1-yl.

7. The compound as claimed in any one of claim 6 wherein:
each of $R^3$, $R^5$ and $R^6$ is hydrogen and $R^4$ is methoxycarbonyl; or
each of $R^3$, $R^4$ and $R^6$ is hydrogen and $R^5$ is hydrogen, fluoro or chloro;
$L^1$ is —CO—NH— such that -$L^1$-$Q^1$ is —CO—NH-$Q^1$; and
$Q^1$ is 5-chloropyridin-2-yl, 5-fluoropyridin-2-yl.

8. The compound as claimed in claim 7 wherein:
each of $R^3$, $R^4$ and $R^6$ is hydrogen and $R^5$ is hydrogen or fluoro; and
$Q^1$ is 5-chloropyridin-2-yl.

9. The compound as claimed in any one of claim 8 wherein $R^a$ is hydrogen or methyl, and $R^b$ is hydrogen or methyl; or $R^a$ is hydrogen or methyl, and $R^b$ and $R^c$ together are —(CH$_2$)$_2$—, —(CH$_2$)$_3$—, —(CH$_2$)$_4$— or —C(CH$_3$)$_2$—CH$_2$—.

10. The compound as claimed in claim 9 wherein $R^1$ is 2-aminoethyl, 3-aminopropyl. 4-piperidinyl, 1-methylpiperidin-4-yl or 1-isopropylpiperidin-4-yl.

11. The compound as claimed in claim 10 wherein $R^1$ is 3-aminopropyl or 4-piperidinyl.

12. The compound as claimed in any one of claims 5,7 and 9 wherein $R^2$ is 1-amino-1-methylethyl.

13. The compound as claimed in any one of claims 5,7 and 9 wherein $R^2$ is methylthio, methylsulfinyl, methylsulfonyl or ethylsulfonyl.

14. The compound as claimed in claim 13 wherein $R^2$ is methylsulfinyl or methylsulfonyl.

15. The compound as claimed in any one of claims 5,7 and 9 wherein $R^2$ is methoxy, 2-fluoroethoxy, 2-methoxyethoxy, isopropoxy or propargyloxy.

16. The compound as claimed in claim 15 wherein $R^2$ is 2-fluoroethoxy.

17. The compound as claimed in any one of claims 5,7 and 9 wherein $R^2$ is dimethylamino, azetidin-1-yl, pyrrolidin-1-

1,3-carbamoylpiperidin-1-yl, 4-hydroxypiperidin-1-yl, morpholin-4-yl or 4-methylhexahydro-1,4-diazepin-1-yl.

18. The compound as claimed in claim 17 wherein $R^2$ is dimethylamino, pyrrolidin-1-yl or 4-methylhexahydro-1,4-diazepin-1-yl.

19. The compound as claimed in any one of claim 7 wherein $R^1$ is 4-oxocyclohexyl and $R^2$ is 1-amino-1-methylethyl or 4-methylthexahydro-1,4-diazepin-1-yl.

20. The pharmaceutically acceptable salt of a compound of formula I as claimed in any of claim 1 which is an acid-addition salt made from a basic compound of formula I and an acid which provides a pharmaceutically acceptable anion or a salt which is made from an acidic compound of formula I and a base which provides a pharmaceutically acceptable cation.

21. A pharmaceutical composition comprising in association with a pharmaceutically acceptable carrier, diluent or excipient, a compound of formula I (or a pharmaceutically acceptable salt thereof) as provided in claim 1.

* * * * *

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Chromogenic Substrate for Factor Xa
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 1

Ile Glu Gly Arg
1
```